US007858304B2

(12) United States Patent
Baker et al.

(10) Patent No.: US 7,858,304 B2
(45) **Date of Patent: *Dec. 28, 2010**

(54) GENE EXPRESSION PROFILING IN BIOPSIED TUMOR TISSUES

(75) Inventors: Joffre B. Baker, Montara, CA (US); Maureen T. Cronin, Los Altos, CA (US); Michael C. Kiefer, Clayton, CA (US); Steve Shak, Hillsborough, CA (US); Michael Graham Walker, Sunnyvale, CA (US)

(73) Assignee: Genomic Health, Inc., Redwood City, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 11/450,973

(22) Filed: Jun. 9, 2006

(65) Prior Publication Data

US 2007/0065846 A1 Mar. 22, 2007

Related U.S. Application Data

(63) Continuation of application No. 10/388,360, filed on Mar. 12, 2003, now Pat. No. 7,081,340.

(60) Provisional application No. 60/412,049, filed on Sep. 18, 2002.

(51) Int. Cl.
*C12Q 1/68* (2006.01)
*C07H 21/04* (2006.01)
*C12P 19/34* (2006.01)

(52) U.S. Cl. ........................ 435/6; 536/24.3; 536/23.1; 435/91.2

(58) Field of Classification Search ...................... None
See application file for complete search history.

(56) References Cited

U.S. PATENT DOCUMENTS

| | | | | |
|---|---|---|---|---|
| 4,699,877 | A | 10/1987 | Cline et al. | 435/6 |
| 5,015,568 | A | 5/1991 | Tsujimoto et al. | 435/5 |
| 5,459,251 | A | 10/1995 | Tsujimoto et al. | 536/23.5 |
| 5,563,035 | A | 10/1996 | Weigel | |
| RE35,491 | E | 4/1997 | Cline et al. | 435/6 |
| 5,858,678 | A | 1/1999 | Chinnadurai | 435/7.1 |
| 5,952,179 | A | 9/1999 | Chinnadurai | 435/6 |
| 5,985,553 | A | 11/1999 | King et al. | 435/6 |
| 6,180,333 | B1 | 1/2001 | Giordano | |
| 6,207,452 | B1 | 3/2001 | Govindaswamy | 435/330 |
| 6,271,002 | B1 | 8/2001 | Linsley et al. | 435/91.1 |
| 6,316,208 | B1 | 11/2001 | Roberts et al. | |
| 6,322,986 | B1 | 11/2001 | Ross | 435/6 |
| 6,331,396 | B1 | 12/2001 | Silverman et al. | |
| 6,414,134 | B1 | 7/2002 | Reed | 536/24.5 |
| 6,582,919 | B2 | 6/2003 | Danenberg | 435/6 |
| 6,602,670 | B2 | 8/2003 | Danenberg | 435/6 |
| 6,618,679 | B2 | 9/2003 | Loehrlein et al. | 702/20 |
| 7,081,340 | B2 * | 7/2006 | Baker et al. | 435/6 |
| 2002/0009736 | A1 | 1/2002 | Wang | 435/6 |
| 2003/0073112 | A1 | 4/2003 | Zhang et al. | 435/6 |
| 2003/0104499 | A1 | 6/2003 | Pressman et al. | 435/7.23 |
| 2003/0165952 | A1 | 9/2003 | Linnarsson et al. | 435/6 |
| 2003/0180791 | A1 | 9/2003 | Chinnadurai | 435/6 |
| 2003/0198970 | A1 | 10/2003 | Roberts | 435/6 |
| 2003/0225528 | A1 * | 12/2003 | Baker et al. | 702/19 |
| 2004/0009489 | A1 | 1/2004 | Golub et al. | 435/6 |
| 2004/0133352 | A1 | 7/2004 | Bevilacqua et al. | 702/19 |
| 2004/0209290 | A1 * | 10/2004 | Cobleigh et al. | 435/6 |
| 2006/0286565 | A1 * | 12/2006 | Baker et al. | 435/6 |
| 2007/0059737 | A1 * | 3/2007 | Baker et al. | 435/6 |
| 2007/0065845 | A1 * | 3/2007 | Baker et al. | 435/6 |
| 2007/0141587 | A1 * | 6/2007 | Baker et al. | 435/6 |
| 2007/0141588 | A1 * | 6/2007 | Baker et al. | 435/6 |
| 2007/0141589 | A1 * | 6/2007 | Baker et al. | 435/6 |

FOREIGN PATENT DOCUMENTS

| | | |
|---|---|---|
| EP | 0 108 564 B1 | 5/1988 |
| EP | 1 365 034 | 11/2003 |
| WO | WO 98/33450 | 8/1998 |
| WO | WO 99/02714 | 1/1999 |
| WO | WO 00/50595 | 8/2000 |
| WO | WO 00/55173 | 9/2000 |
| WO | WO 00/55629 A2 | 9/2000 |
| WO | WO 00/60076 | 10/2000 |
| WO | WO 01/04343 | 1/2001 |
| WO | WO 01/25250 | 4/2001 |
| WO | WO 01/40466 | 6/2001 |
| WO | WO 01/40517 A2 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/10436 | 2/2002 |
| WO | WO 02/46467 | 6/2002 |
| WO | WO 02/017852 | 7/2002 |

(Continued)

OTHER PUBLICATIONS

Lucentini, Jack. Gene Association Studies Typically Wrong. 2004. The Scientist vol. 18, pp. 1-4.*

(Continued)

*Primary Examiner*—Stephen Kapushoc
*Assistant Examiner*—Amanda Shaw
(74) *Attorney, Agent, or Firm*—James S. Keddie; Carol L. Francis; Bozicevic, Field & Francis LLP

(57) ABSTRACT

The invention concerns sensitive methods to measure mRNA levels in biopsied tumor tissues, including archived paraffin-embedded biopsy material. The invention also concerns breast cancer gene sets important in the diagnosis and treatment of breast cancer, and methods for assigning the most optimal treatment options to breast cancer patient based upon knowledge derived from gene expression studies.

18 Claims, 9 Drawing Sheets

FOREIGN PATENT DOCUMENTS

| | | |
|---|---|---|
| WO | WO 02/055988 | 7/2002 |
| WO | WO 02/059271 | 8/2002 |
| WO | WO 02/059377 | 8/2002 |
| WO | WO 02/068579 | 9/2002 |
| WO | WO 02/103320 | 12/2002 |
| WO | WO 03/011897 | 2/2003 |
| WO | WO 03/083096 | 10/2003 |

OTHER PUBLICATIONS

Wu, Thomas. Analyzing gene expression data from DNA microarrays to identify candidate genes. 2001. Journal of Pathology. vol. 195 pp. 53-65.*

Miyoshi, Yasuo et al. Association of centrosmal kinase STK15/BTAK mRNA expression with chromosomal instability in human breast cancers. 2001. International Jouranl of Cancer. vol. 92 pp. 370-373.*

The array finder at www.affymetrix.com accessed Jul. 3, 2008 demonstrates that probes for the ESR1 gene are on the HU95A array.*

Unger, Meredith et al. Characterization of adjacent breast tumors using oligonucleotide microarrays. 2001. Breast Cancer Research vol. 3 ages 336-341.*

Gruvberger Sofia et al. Estrogen receptor status in breast cancer is associated with remarkably distinct gene expression patterns. 2001. Breast Cancer Research. vol. 61 pp. 5979-5984.*

Specht, Katja et al. Quantitative gene expression analysis in microdissected archival formalin fixed and paraffin embedded tumor tissue. 2001 American Journal of Pathology. vol. 158 pp. 419-429.*

Sorlie, Therese. Gene expression patterns of breast carcinomas distinguish tumor subclasses with clinical implications. 2001 PNAS vol. 98 pp. 10869-10874.*

The array finder at www.affymetrix.com accessed Jul. 3, 2008 demonstrates that probes for the STK15 gene are on the HU95A array.*

Chan, Eric. Integrating Transcriptomics and Proteomics. 2006. Genomics and Proteomics, available online from www.genpromag.com, pp. 1-6.*

Schmittgen, Thomas, et al. Expression of prostate specific membrane antigen and three alternatively spliced variants of PSMA in prostate cancer patients. 2003 International Jouranl of Cancer. vol. 107 pp. 323-329.*

Lee, Andrew, et al. Invasive lobular and invasive ductal carcinoma of the breast show distinct patterns of vascular endotherlial growth factor expression and angiogenesis. 1998 Journal of Pathology vol. 185 pp. 394-401.*

Brabender, Jan, et al.; *Epidermal Growth Factor Receptor and HER2-neu mRNA Expression in Non-Small Cell Lung Cancer Is Correlated with Survival*, Clinical Cancer Research; vol. 7, Jul. 2001; pp. 1850-1855.

Ding, Chunming, et al.; *A high-throughput gene expression analysis technique using competitive PCR and matrix-assisted laser desorption ionization time-of-flight MS*, PNAS, vol. 100:6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; *BADGE, BeadsArray for the Detection of Gene Expression, a High-Throughput Diagnostic Bioassay*; Genome Research; vol. 11; 2001; pp. 1888-1898.

Affymetrix Inc.: "Affymetrix GeneChip Human Genome U95 Version 2 Set HG-U95A," *GEO, XX, XX*, 1-243 (2002).

Bhattacharjee et al., "Classification of human lung carcinomas by mRNA expression profiling reveals distinct adenocarcinoma subclasses", Proceedings of the National Academy of Sciences of USA, vol. 98, No. 24, pp. 13790-13795 (2001).

Chang, J. et al., "Biologic Markers as Predictors of Clinical Outcome from Systemic Therapy for Primary Operable Breast Cancer," *Journal of Clinical Oncology: Official Journal of the American Society of Clinical Oncology*, vol. 17:(10) 3058-3063 (1999).

Chen-Hsiang Yeang et al., "Molecular Classification of Multiple Tumor Types", Bioinformatics, vol. 17, Suppl. 1, pp. S316-S322 (2001).

Cox, G. et al., "Bcl-2 is an Independent Prognostic Factor and Adds to a Biological Model for Predicting Outcome in Operable Non-Small Cell Lung Cancer," *Lung Cancer*, vol. 34:(3) 417-426 (2001).

Dijkema, I.M. et al., "Influence of p53 and bcl-2 on Proliferative Activity and Treatment Outcome in head and Neck Cancer Patients," *Oral Oncology, Elsevier Science*, vol. 36:(1) 54-60 (2000).

Golub et al., "Molecular Classification of Cancer: Class Discovery and Class Prediction by Gene Expression Monitoring", Science, vol. 286, pp. 531-537 (1999).

Guerin, M. et al., "Structure and Expression of C-ERBB-2 and EGF Receptor Genes in Inflammatory and Non-Inflammatory Breast Cancer: Prognostic Significance," *International Journal of Cancer*, vol. 43 201-208 (1989).

Joensuu, H. et al., "Bcl-2 Protein Expresion and Long-Term Survival in Breast Cancer," *American Journal of Pathology*, vol. 145:(5) 1191-1198 (1994).

Kymionis, G.D., et al., "Can Expression of Apoptosis Genes, bcl-2 and Bax, Predict Survival and Responsiveness to Chemotherapy in Node-Negative Breast Cancer Patients?" *The Journal of Surgical Research*, vol. 99:(2) 161-168 (2001).

Locker, A.P., et al., "Ki67 Immunoreactivity in Breast Carcinoma: Relationships to prognostic Variable and Short time Survival," *European Journal of Surgical Oncology*, vol. 18:(3) 224-229 (1992).

Martin et al., "Linking Gene Expression Patterns to Therapeutic Groups in Breast Cancer", Cancer Research, vol. 60, pp. 2232-2238 (2000).

Murray, P.A. et al., "The Prognostic Significance of Transforming Growth Factors in Human Breast Cancer," *British Journal of Cancer*, vol. 67:(6) 1408-1412 (1993).

Perou et al., "Molecular portraits of human breast tumors", Nature, vol. 406, pp. 747-752 (2000).

Ramaswamy et al., "Multiclass cancer diagnosis using tumor gene expression signatures", Proceedings of the National Academy of Sciences of USA, vol. 98, No. 26, pp. 15149-15154 (2001).

Sens, Mary Ann et al., "Metallothionein Isoform 3 Overexpression is Associated with Breast Cancers Having a Poor Prognosis," *American Journal of Pathology*, vol. 159:(1) 21-26 (2001).

Sorlie et al., "Gene Expression patterns of breast carcinomas distinguish tumor subclass with clinical implications", Proceedings of the National Academy of Sciences of USA, vol. 98, No. 19, pp. 10869-10874 (2001).

Specht K. et al., "Quantitative Gene Expression Analysis in Microdissected Archival Formalin-Fixed and Paraffin-Embedded Tumor Tissue," 158:(2) 419-429 (2001).

Steinbach, Daniel et al., "Clinical Implications of PRAME Gene Expression in Childhood Acute Myeloid Leukemia," *Cancer Genetics and Cytogenetics*, vol. 133:(2) 118-123 (2002).

Veer Van 'T.L.J. et al., "Gene Expression Profiling Predicts Clinical Outcome of Breast Cancer," *Nature, Macmillan Journals Ltd.*, vol. 415:(6871) 530-536 (2002).

West et al., "Predicting the clinical status of human breast cancer by using gene expression profiles", Proceedings of the National Academy of Sciences of USA, vol. 98, No. 20, pp. 11462-11467 (2002).

Yan et al., "Dissecting Complex Epigenetic Alterations in Breast Cancer Using CpG Island Microarrays", Cancer Research, vol. 61, pp. 8375-7380 (2001).

Kreike, B., et al. Local recurrence after breast-conserving therapy in relation to gene expression patterns in a large series of patients. Clinical Cancer Research. 2009, vol. 15, No. 12, pp. 4181-4190.

Paik, S., et al. A multigene assay to predict recurrence of tamoxifen-treated, node-negative breast cancer. The New England Journal of Medicine. 2004, vol. 351, No. 27, pp. 2817-2826.

Paik, S., et al. Gene expression and benefit of chemotherapy in women with node-negative, estrogen receptor-positive breast cancer. Journal of Clinical Oncology. 2006, vol. 24, No. 23, pp. 3726-3734.

Tanaka, T., et al. Centrosomal kinase AIK1 is overexpressed in invasive ductal carcinoma of the breast. Cancer Research. 1999, vol. 59, pp. 2041-2044.

JP Patent Application Serial No. 2003-576654 Office Action, Mar. 1, 2010, Genomic Health, Inc.

JP Patent Application Serial No. 2006-40014 Office Action, Mar. 1, 2010, Genomic Health, Inc.

Ambrosone, C., et al. Polymorphisms in glutathione S-Transferases (GSTM1 and GSTT1) and survival after treatment for breast cancer. Cancer Research. 2001, vol. 61, pp. 7130-7135.
Molino, A., et al. Ki-67 immunostaining in 322 primary breast cancers: Associations with clinical and pathological variables and prognosis. International Journal of Cancer. 1997, vol. 74, pp. 433-437.
Dutta, A., et al., *Proc. Natl. Acad. Sci. USA*—92:5386-5390 (1995).
Winters, Z.E., et al., *European Journal of Cancer*—37(18):2405-2412 (2001).

* cited by examiner

Overall FPET/RT-PCR Flow Chart

GENE EXPRESSION PROFILING IN BIOPSIED TUMOR TISSUES

CROSS-REFERENCE

This application is a continuation of, and claims priority under 35 USC §120 to, U.S. application Ser. No. 10/388,360 filed Mar. 12, 2003, now U.S. Pat. No. 7,081,340, which claims the benefit under 35 U.S.C. 119(e) of the provisional application No. 60/412,049, filed Sep. 18, 2002, the entire disclosures of which are hereby incorporated by reference.

BACKGROUND OF THE INVENTION

Field of the Invention

The present invention relates to gene expression profiling in biopsied tumor tissues. In particular, the present invention concerns sensitive methods to measure mRNA levels in biopsied tumor tissues, including archived paraffin-embedded biopsy material. In addition, the invention provides a set of genes the expression of which is important in the diagnosis and treatment of breast cancer.

Oncologists have a number of treatment options available to them, including different combinations of chemotherapeutic drugs that are characterized as "standard of care," and a number of drugs that do not carry a label claim for a particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

Recently, several groups have published studies concerning the classification of various cancer types by microarray gene expression analysis (see, e.g. Golub et al., *Science* 286:531-537 (1999); Bhattachaijae et al., *Proc. Natl. Acad. Sci. USA* 98:13790-13795 (2001); Chen-Hsiang et al., *Bioinformatics* 17 (Suppl. 1):S316S322 (2001); Ramaswamy et al., *Proc. Natl. Acad. Sci. USA* 98:15149-15154 (2001)). Certain classifications of human breast cancers based on gene expression patterns have also been reported (Martin et aL, *Cancer Res.* 60:2232-2238 (2000); West et aL, *Proc. Natl. Acad. Sci. USA* 98:11462-11467 (2001); Sorlie et aL, *Proc. Natl. Acad. Sci. USA* 98:10869-10874 (2001); Yan et al., *Cancer Res.* 61:8375-8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Hercepting® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as $ErbB2^+$ subgroup, and subgroups characterized by low to absent gene expression of the estrogen receptor (ER) and a few additional transcriptional factors (Perou et al., *Nature* 406:747-752 (2000)) does not reflect the cellular and molecular heterogeneity of breast cancer, and does not allow the design of treatment strategies maximizing patient response.

SUMMARY OF THE INVENTION

The present invention provides (1) sensitive methods to measure mRNA levels in biopsied tumor tissue, (2) a set of approximately 190 genes, the expression of which is important in the diagnosis of breast cancer, and (3) the significance of abnormally low or high expression for the genes identified and included in the gene set, through activation or disruption of biochemical regulatory pathways that influence patient response to particular drugs used or potentially useful in the treatment of breast cancer. These results permit assessment of genomic evidence of the efficacy of more than a dozen relevant drugs.

The present invention accommodates the use of archived paraffin-embedded biopsy material for assay of all markers in the set, and therefore is compatible with the most widely available type of biopsy material. The invention presents an efficient method for extraction of RNA from wax-embedded, fixed tissues, which reduces cost of mass production process for acquisition of this information without sacrificing quality of the analysis. In addition, the invention describes a novel highly effective method for amplifying MRNA copy number, which permits increased assay sensitivity and the ability to monitor expression of large numbers of different genes given the limited amounts of biopsy material. The invention also captures the predictive significance of relationships between expressions of certain markers in the breast cancer marker set. Finally, for each member of the gene set, the invention specifies the oligonucleotide sequences to be used in the test.

In one aspect, the invention concerns a method for predicting clinical outcome for a patient diagnosed with cancer, comprising determining the expression level of one or more genes, or their expression products, selected from the group consisting of p53BP2, cathepsin B, cathepsin L, Ki67/MiB1, and thymidine kinase in a cancer tissue obtained from the patient, normalized against a control gene or genes, and compared to the amount found in a reference cancer tissue set, wherein a poor outcome is predicted if:

(a) the expression level of p53BP2 is in the lower $10^{th}$ percentile; or (b) the expression level of either cathepsin B or cathepsin L is in the upper $10^{th}$ percentile; or (c) the expression level of any either Ki67/MiB1 or thyrnidine kinase is in the upper $10^{th}$ percentile.

Poor clinical outcome can be measured, for example, in terms of shortened survival or increased risk of cancer recurrence, e.g. following surgical removal of the cancer.

In another embodiment, the inventor concerns a method of predicting the likelihood of the recurrence of cancer, following treatment, in a cancer patient, comprising determining the expression level of p27, or its expression product, in a cancer tissue obtained from the patient, normalized against a control gene or genes, and compared to the amount found in a reference cancer tissue set, wherein an expression level in the upper 10th percentile indicates decreased risk of recurrence following treatment.

In another aspect, the invention concerns a method for classifying cancer comprising, determining the expression level of two or more genes selected from the group consisting of Bcl2, hepatocyte nuclear factor 3, ER, ErbB2, and Grb7, or their expression products, in a cancer tissue, normalized against a control gene or genes, and compared to the amount found in a reference cancer tissue set, wherein (i) tumors expressing at least one of Bcl2, hepatocyte nuclear factor 3, and ER, or their expression products, above the mean expression level in the reference tissue set are classified as having a good prognosis for disease free and overall patient survival following treatment; and (ii) tumors expressing elevated levels of ErbB2 and Grb7, or their expression products, at levels ten-fold or more above the mean expression level in the reference tissue set are classified as having poor prognosis of disease free and overall patient survival following treatment.

All types of cancer are included, such as, for example, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer. The foregoing methods are particularly suitable for prognosis/classification of breast cancer.

In all previous aspects, in a specific embodiment, the expression level is determined using RNA obtained from a formalin-fixed, paraffin-embedded tissue sample. While all techniques of gene expression profiling, as well as proteomics techniques, are suitable for use in performing the foregoing aspects of the invention, the gene expression levels are often determined by reverse transcription polymerase chain reaction (RT-PCR).

If the source of the tissue is a formalin-fixed, paraffin embedded tissue sample, the RNA is often fragmented.

The expression data can be further subjected to multivariate analysis, for example using the Cox Proportional Hazards model.

In a further aspect, the invention concerns a method for the preparation of nucleic acid from a fixed, wax-embedded tissue specimen, comprising:

(a) incubating a section of the fixed, wax-embedded tissue specimen at a temperature of about 56° C. to 70° C. in a lysis buffer, in the presence of a protease, without prior dewaxing, to form a lysis solution;

(b) cooling the lysis solution to a temperature where the wax solidifies; and (c) isolating the nucleic acid from the lysis solution.

The lysis buffer may comprise urea, such as 4M urea. In a particular embodiment, incubation in step (a) of the foregoing method is performed at about 65° C.

In another particular embodiment, the protease used in the foregoing method is proteinase K.

In another embodiment, the cooling in step (b) is performed at room temperature.

In a further embodiment, the nucleic acid is isolated after protein removal with 2.5 M $NH_4OAc$.

The nucleic acid can, for example, be total nucleic acid present in the fixed, wax-embedded tissue specimen.

In yet another embodiment, the total nucleic acid is isolated by precipitation from the lysis solution, following protein removal, with 2.5 M $NH_4OAc$. The precipitation may, for example, be performed with isopropanol.

The method described above may further comprise the step of removing DNA from the total nucleic acid, for example by DNAse treatment.

The tissue specimen may, for example, be obtained from a tumor, and the RNA may be obtained from a microdissected portion of the tissue specimen enriched for tumor cells.

All types of tumor are included, such as, without limitation, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer, in particular breast cancer.

The method described above may further comprise the step of subjecting the RNA to gene expression profiling. Thus, the gene expression profile may be completed for a set of genes comprising at least two of the genes listed in Table 1.

Although all methods of gene expression profiling are contemplated, in a particular embodiment, gene expression profiling is performed by RT-PCR which may be preceded by an amplification step.

In another aspect, the invention concerns a method for preparing fragmented RNA for gene expression analysis, comprising the steps of:

(a) mixing the RNA with at least one gene-specific, single-stranded DNA scaffold under conditions such that fragments of the RNA complementary to the DNA scaffold hybridize with the DNA scaffold;

(b) extending the hybridized RNA fragments with a DNA polymerase to form a DNA-DNA duplex; and (c) removing the DNA scaffold from the duplex.

In a specific embodiment, in step (b) of this method, the RNA may be mixed with a mixture of single-stranded DNA templates specific for each gene of interest.

The method can further comprise the step of heat-denaturing and reannealing the duplexed DNA to the DNA scaffold, with or without additional overlapping scaffolds, and further extending the duplexed sense strand with DNA polymerase prior to removal of the scaffold in step (c).

The DNA templates may be, but do not need to be, fully complementary to the gene of interest.

In a particular embodiment, at least one of the DNA templates is complementary to a specific segment of the gene of interest.

In another embodiment, the DNA templates include sequences complementary to polymorphic variants of the same gene.

The DNA template may include one or more dUTP or rNTP sites. In this case. in step (c) the DNA template may be removed by fragmenting the DNA template present in the DNA-DNA duplex formed in step (b) at the dUTP or rNTP sites.

In an important embodiment, the RNA is extracted from fixed, wax-embedded tissue specimens, and purified sufficiently to act as a substrate in an enzyme assay. The RNA purification may, but does not need to, include an oligo-dT based step.

In a further aspect, the invention concerns a method for amplifying RNA fragments in a sample comprising fragmented RNA representing at least one gene of interest, comprising the steps of:

(a) contacting the sample with a pool of single-stranded DNA scaffolds comprising an RNA polymerase promoter at the 5' end under conditions such that the RNA fragments complementary to the DNA scaffolds hybridize with the DNA scaffolds;

(b) extending the hybridized RNA fragments with a DNA polymerase along the DNA scaffolds to form DNA-DNA duplexes;

(c) amplifying the gene or genes of interest by in vitro transcription; and (d) removing the DNA scaffolds from the duplexes.

An exemplary promoter is the T7 RNA polymerase promoter, while an exemplary DNA polymerase is DNA polymerase I.

In step (d) the DNA scaffolds may be removed, for example, by treatment with DNase I.

In a further embodiment, the pool of single-stranded DNA scaffolds comprises partial or complete gene sequences of interest, such as a library of cDNA clones.

In a specific embodiment, the sample represents a whole genome or a fraction thereof. In a preferred embodiment, the genome is the human genome.

In another aspect, the invention concerns a method of preparing a personalized genomics profile for a patient, comprising the steps of:

(a) subjecting RNA extracted from a tissue obtained from the patient to gene expression analysis;

(b) determining the expression level in such tissue of at least two genes selected from the gene set listed in Table 1, wherein the expression level is normalized against a control gene or genes, and is compared to the amount found in a cancer tissue reference set;

(c) and creating a report summarizing the data obtained by the gene expression analysis.

The tissue obtained from the patient may, but does not have to, comprise cancer cells. Just as before, the cancer can, for example, be breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, or brain cancer, breast cancer being particularly preferred.

In a particular embodiment, the RNA is obtained from a microdissected portion of breast cancer tissue enriched for cancer cells. The control gene set may, for example, comprise S-actin, and ribosomal protein LPO.

The report prepared for the use of the patient or the patient's physician, may include the identification of at least one drug potentially beneficial in the treatment of the patient.

Step (b) of the foregoing method may comprise the step of determining the expression level of a gene specifically influencing cellular sensitivity to a drug, where the gene can, for example, be selected from the group consisting of aldehyde dehydrogenase 1A1, aldehyde dehydrogenase 1A3, amphiregulin, ARG, BRK, BCRP, CD9, CD31, CD82/KAI-1, COX2, c-abl, c-kit, c-kit L, CYP1B1, CYP2C9, DHFR, dihydropyrimidine dehydrogenase, EGF, epiregulin, ER-alpha, ErbB-1, ErbB-2, ErbB-3, ErbB-4, ER-beta, farnesyl pyrophosphate synthetase, gamma-GCS (glutamyl cysteine synthetase), GATA3, geranyl geranyl pyrophosphate synthetase, Grb7, GST-alpha, GST-pi, HB-EGF, hsp 27, human chorionic gonadotropin/CGA, IGF-1, IGF-2, IGF1R, KDR, LIV1, Lung Resistance Protein/MVP, Lot1, MDR-1, microsomal epoxide hydrolase, MMP9, MRP1, MRP2, MRP3, MRP4, PAI1, PDGF-A, PDGF-B, PDGF-C, PDGF-D, PGDFR-alpha, PDGFR-beta, PLAGa (pleiomorphic adenoma 1), PREP prolyl endopeptidase, progesterone receptor, pS2/trefoil factor 1, PTEN, PTB1b, RAR-alpha, RAR-beta2, Reduced Folate Carrier, SXR, TGF-alpha, thymidine phosphorylase, thymidine synthase, topoisomerase II-alpha, topoisomerase II-beta, VEGF, XIST, and YB-1.

In another embodiment, step (b) of the foregoing process includes determining the expression level of multidrug resistance factors, such as, for example, gamma-glutamyl-cysteine synthetase (GCS), GST-$\alpha$, GST-$\pi$, MDR-1, MRP1-4, breast cancer resistance protein (BCRP), lung cancer resistance protein (MVP), SXR, or YB-1.

In another embodiment, step (b) of the foregoing process comprises determination of the expression level of eukaryotic translation initiation factor 4E (EIF4E).

In yet another embodiment, step (b) of the foregoing process comprises determination of the expression level of a DNA repair enzyme.

In a further embodiment, step (b) of the foregoing process comprises determination of the expression level of a cell cycle regulator, such as, for example, c-MYC, c-Src, Cyclin D1, Ha-Ras, mdm2. p14ARF, p21WAF1/CI, p16INK4a/p14, p23, p27, p53, PI3K, PKC-epsilon, or PKC-delta.

In a still further embodiment, step (b) of the foregoing process comprises determination of the expression level of a tumor suppressor or a related protein, such as, for example, APC or E-cadherin.

In another embodiment, step (b) of the foregoing method comprises determination of the expression level of a gene regulating apoptosis, such as, for example, p53, BC12, Bc1-x1, Bak, Bax, and related factors, NF$\kappa$-B, CIAP1, CIAP2, survivin, and related factors, p53BP1/ASPP1, or p53BP2/ASPP2.

In yet another embodiment, step (b) of the foregoing process comprises determination of the expression level of a factor that controls cell invasion or angiogenesis, such as, for example, uPA, PAI1, cathepsin B, C, and L, scatter factor (HGF), c-met, KDR, VEGF, or CD31.

In a different embodiment, step (b) of the foregoing method comprises determination of the expression level of a marker for immune or inflammatory cells or processes, such as, for example, Ig light chain $\lambda$, CD18, CD3, CD68. Fas(CD95), or Fas Ligand.

In a further embodiment, step (b) of the foregoing process comprises determination of the expression level of a cell proliferation marker, such as, for example, Ki67/MiB1, PCNA, Pin1, or thymidine kinase.

In a still further embodiment, step (b) of the foregoing process comprises determination of the expression level of a growth factor or growth factor receptor., such as, for example, IGF1, IGF2, IGFBP3, IGF1R, FGF2, CSF-1, CSF-1R/fms, SCF-1, IL6 or IL8.

In another embodiment, step (b) of the foregoing process comprises determination of the expression level of a gene marker that defines a subclass of breast cancer, where the gene marker can, for example, be GRO1 oncogene alpha, Grb7, cytokeratins 5 and 17, retinol binding protein 4, hepatocyte nuclear factor 3, integrin subunit alpha 7, or lipoprotein lipase.

In a still further aspect, the invention concerns a method for predicting the response of a patient diagnosed with breast cancer to 5-fluorouracil (5-FU) or an analog thereof, comprising the steps of:

(a) subjecting RNA extracted from a breast cancer tissue obtained from the patient to gene expression analysis;

(b) determining the expression level in the tissue of thymidylate synthase mRNA, wherein the expression level is normalized against a control gene or genes, and is compared to the amount found in a reference breast cancer tissue set; and (c) predicting patient response based on the normalized thymidylate synthase mRNA level.

Step (d) of the foregoing method can further comprise determining the expression level of dihydropyrimidine phosphorylase.

In another embodiment, step (b) of the method can further comprise determining the expression level of thymidine phosphorylase.

In yet another embodiment, a positive response to 5-FU or an analog thereof is predicted if: (i) normalized thymidylate synthase mRNA level determined in step (b) is at or below the $15^{th}$ percentile; or (ii) the sum of normnalized expression levels of thymidylate synthase and dihydropyrimidine phosphorylase determined in step (b) is at or below the $25^{th}$ percentile; or (iii) the sum of normalized expression levels of thymidylate synthase, dihydropyrimidine phosphorylase, plus thymidine phosphorylase determined in step (b) is at or below the $20^{th}$ percentile.

In a further embodiment, in step (b) of the foregoing method the expression level of c-myc and wild-type p53 is determined. In this case, a positive response to 5-FU or an analog thereof is predicted, if the normalized expression level of c-myc relative to the normalized expression level of wild-type p53 is in the upper $15^{th}$ percentile.

In a still further embodiment, in step (b) of the foregoing method, expression level of NFκB and cIAP2 is determined. In this particular embodiment, resistance to 5-FU or an analog thereof is typically predicted if the normalized expression level of NFκB and cIAP2 is at or above the $10^{th}$ percentile.

In another aspect, the invention concerns a method for predicting the response of a patient diagnosed with breast cancer to methotrexate or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting decreased patient sensitivity to methotrexate or analog if (i) DHFR levels are more than tenfold higher than the average expression level of DHFR in the control gene set, or (ii) the normalized expression levels of members of the reduced folate carrier (RFC) family are below the $10^{th}$ percentile.

In yet another aspect, the invention concerns a method for predicting the response of a patient diagnosed with breast cancer to an anthracycline or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting patient resistance or decreased sensitivity to the anthracycline or analog if (i) the normalized expression level of topoisomerase IIα is below the $10^{th}$ percentile, or (ii) the normalized expression level of topoisomerase IIβ is below the $10^{th}$ percentile, or (iii) the combined normalized topoisomerase IIα or IIβ expression levels are below the $10^{th}$ percentile.

In a different aspect, the invention concerns a method for predicting the response of a patient diagnosed with breast cancer to a docetaxol, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to docetaxol if the normalized expression level of CYP1B1 is in the upper $10^{th}$ percentile.

The invention further concerns a method for predicting the response of a patient diagnosed with breast cancer to cyclophosphamide or an analog thereof, comprising (a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to the cyclophosphamide or analog if the sum of the expression levels of aldehyde dehydrogenase. 1A1 and 1A3 is more than tenfold higher than the average of their combined expression levels in the reference tissue set.

In a further aspect, the invention concerns a method for predicting the response of a patient diagnosed with breast cancer to anti-estrogen therapy, comprising (a) subjecting RNA extracted from a breast cancer tissue obtained from the patient to gene expression analysis, wherein gene expression levels are normalized against a control gene or genes, and compared to the amount found in a reference breast cancer tissue set that contains both specimens negative for and positive for estrogen receptor-α (ERα) and progesterone receptor-α (PRα); and (b) predicting patient response based upon the normalized expression levels of ERα or PRα, and at least one of microsomal epoxide hydrolase, pS2/trefoil factor 1, GATA3 and human chorionic gonadotropin.

In a specific embodiment, lack of response or decreased responsiveness is predicted if (i) the normalized expression level of microsomal epoxide hydrolase is in the upper $10^{th}$ percentile; or (ii) the normalized expression level of pS2/trefoil factor 1, or GATA3 or human chorionic gonaostropin is at or below the corresponding average expression level in said breast cancer tissue set, regardless of the expression level of ERα or PRα in the breast cancer tissue obtained from the patient.

In another aspect, the invention concerns a method for predicting the response of a patient diagnosed with breast cancer to a taxane, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to taxane if (i) no or minimal XIST expression is detected; or (ii) the normalized expression level of GST-π or propyl endopeptidase (PREP) is in the upper $10^{th}$ percentile; or (iii) the normalized expression level of PLAG1 is in the upper $10^{th}$ percentile.

The invention also concerns a method for predicting the response of a patient diagnosed with breast cancer to cisplatin or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting resistance or reduced sensitivity if the normalized expression level of ERCC1 is in the upper $10^{th}$ percentile.

The invention further concerns a method for predicting the response of a patient diagnosed with breast cancer to an ErbB2 or EGFR antagonist, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting patient response based on the normalized expression levels of at least one of Grb7, IGF1R, IGF1 and IGF2.

In particular embodiment, a positive response is predicted if the normalized expression level of Grb7 is in the upper $10^{th}$ percentile, and the expression of IGF1R, IGF1 and IGF2 is not elevated above the $90^{th}$ percentile.

In a further particular embodiment, a decreased responsiveness is predicted if the expression level of at least one of IGF1R, IGF1 and IGF2 is elevated.

In another aspect, the invention concerns a method for predicting the response of a patient diagnosed with breast cancer to a bis-phosphonate drug, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if the breast cancer tissue obtained from the patient expresses mutant Ha-Ras and additionally expresses famesyl pyrophosphate synthetase or geranyl pyrophosphone synthetase at a normalized expression level at or above the $90^{th}$ percentile.

In yet another aspect, the invention concerns a method for predicting the response of a patient diagnosed with breast cancer to treatment with a cyclooxygenase 2 inhibitor, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if the normalized expression level of COX2 in the breast cancer tissue obtained from the patient is at or above the $90^{th}$ percentile.

The invention further concerns a method for predicting the response of a patient diagnosed with breast cancer to an EGF-receptor (EGFR) antagonist, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response to an EGFR antagonist, if (i) the normalized expression level of EGFR is at or above the $10^{th}$ percentile, and (ii) the normalized expression level of at least one of epiregulin, TGF-α, amphiregulin, ErbB3, BRK, CD9, MMP9, CD82, and Lot1is above the $90^{th}$ percentile.

In another aspect, the invention concerns a method for monitoring the response of a patient diagnosed with breast cancer to treatment with an EGFR antagonist, comprising monitoring the expression level of a gene selected from the group consisting of epiregulin, TGFα, amphiregulin, ErbB3, BRK, CD9, MMP9, CD82, and Lot1in the patient during treatment, wherein reduction in the expression level is indicative of positive response to such treatment.

In yet another aspect, the invention concerns a method for predicting the response of a patient diagnosed with breast cancer to a drug targeting a tyrosine kinase selected from the group consisting of ab1, c-kit, PDGFRα, PDGFR-β and ARG, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set;

(b) determining the normalized expression level of a tyrosine kinase selected from the group consisting of ab1, c-kit, PDGFRα, PDGFR-β and ARG, and the cognate ligand of the tyrosine kinase, and if the normalized expression level of the tyrosine kinase is in the upper $10^{th}$ percentile, (c) determining whether the sequence of the tyrosine kinase contains any mutation, wherein a positive response is predicted if (i) the normalized expression level of the tyrosine kinase is in the upper $10^{th}$ percentile, (ii) the sequence of the tyrosine kinase contains an activating mutation, or (iii) the normalized expression level of the tyrosine kinase is normal and the expression level of the ligand is in the upper $10^{th}$ percentile.

Another aspect of the invention is a method for predicting the response of a patient diagnosed with breast cancer to treatment with an anti-angiogenic drug, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if (i) the normalized expression level of VEGF is in the upper $10^{th}$ percentile and (ii) the normalized expression level of KDR or CD31 is in the upper $20^{th}$ percentile.

A further aspect of the invention is a method for predicting the likelihood that a patient diagnosed with breast cancer develops resistance to a drug interacting with the MRP-1 gene coding for the multidrug resistance protein P-glycoprotein, comprising the steps of:

(a) subjecting RNA extracted from a breast cancer tissue obtained from the patient to gene expression analysis to determine the expression level of PTP1b, wherein the expression level is normalized against a control gene or genes, and compared to the amount found in a reference breast cancer tissue set; and (b) concluding that the patient is likely to develop resistance to said drug if the normalized expression level of the MRP-1 gene is above the $90^{th}$ percentile.

The invention further relates to a method for predicting the likelihood that a patient diagnosed with breast cancer develops resistance to a chemotherapeutic drug or toxin used in cancer treatment, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) determining the normalized expression levels of at least one of the following genes: MDR1, SGTα, GSTπ, SXR, BCRP YB-1, and LRP/MVP, wherein the finding of a normalized expression level in the upper $4^{th}$ percentile is an indication that the patient is likely to develop resistance to the drug.

Also included herein is a method for measuring the translational efficiency of VEGF mRNA in a breast cancer tissue sample, comprising determining the expression levels of the VEGF and EIF4E mRNA in the sample, normalized against a control gene or genes, and compared to the amount found in a reference breast cancer tissue set, wherein a higher normalized EIF4E expression level for the same VEGF expression level is indicative of relatively higher translational efficiency for VEGF.

In another aspect, the invention provides a method for predicting the response of a patient diagnosed with breast cancer to a VEGF antagonist, comprising determining the expression level of VEGF and EIF4E mRNA normalized against a control gene or genes, and compared to the amount found in a reference breast cancer tissue set, wherein a VEGF expression level above the $90^{th}$ percentile and an EIF4E expression level above the $50^{th}$ percentile is a predictor of good patient response.

The invention further provides a method for predicting the likelihood of the recurrence of breast cancer in a patient diagnosed with breast cancer, comprising determining the ratio of p53:p21 MRNA expression or p53:mdm2 mRNA expression in a breast cancer tissue obtained from the patient, normalized against a control gene or genes, and compared to the amount found in a reference breast cancer tissue set, wherein an above normal ratio is indicative of a higher risk of recurrence. Typically, a higher risk of recurrence is indicated if the ratio is in the upper $10^{th}$ percentile.

In yet another aspect, the invention concerns a method for predicting the likelihood of the recurrence of breast cancer in a breast cancer patient following surgery, comprising determining the expression level of cyclin D1 in a breast cancer tissue obtained from the patient, normalized against a control gene or genes, and compared to the amount found in a reference breast cancer tissue set, wherein an expression level in the upper $10^{th}$ percentile indicates increased risk of recurrence following surgery. In a particular embodiment of this method, the patient is subjected to adjuvant chemotherapy, if the expression level is in the upper $10^{th}$ percentile.

Another aspect of the invention is a method for predicting the likelihood of the recurrence of breast cancer in a breast cancer patient following surgery, comprising determining the expression level of APC or E-cadherin in a breast cancer tissue obtained from the patient, normalized against a control gene or genes, and compared to the amount found in a reference breast cancer tissue set, wherein an expression level in the upper $5^{th}$ percentile indicates high risk of recurrence following surgery, and heightened risk of shortened survival.

A further aspect of the invention is a method for predicting the response of a patient diagnosed with breast cancer to treatment with a proapoptotic drug comprising determining the expression levels of BC12 and c-MYC in a breast cancer tissue obtained from the patient, normalized against a control gene or genes, and compared to the amount found in a reference breast cancer tissue set, wherein (i) a BC12 expression level in the upper $10^{th}$ percentile in the absence of elevated expression of c-MYC indicates good response, and (ii) a good response is not indicated if the expression level c-MYC is elevated, regardless of the expression level of BC12.

A still further aspect of the invention is a method for predicting treatment outcome for a patient diagnosed with breast cancer, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) determining the normalized expression levels of NFκB and at least one gene selected from the group consisting of cIAP1, cIAP2, XIAP, and Survivin, wherein a poor prognosis is indicated if the expression levels for NFκB and at least one of the genes selected from the group consisting of cIAP1, cIAP2, XIAP, and Survivin is in the upper $5^{th}$ percentile.

The invention further concerns a method for predicting treatment outcome for a patient diagnosed with breast cancer, comprising determining the expression levels of p53BP1 and p53BP2 in a breast cancer tissue obtained from the patient, normalized against a control gene or genes, and compared to the amount found in a reference breast cancer tissue set, wherein a poor outcome is predicted if the expression level of either p53BP 1 or p53BP2 is in the lower $10^{th}$ percentile.

The invention additionally concerns a method for predicting treatment outcome for a patient diagnosed with breast cancer, comprising determining the expression levels of uPA and PAI1 in a breast cancer tissue obtained from the patient, normalized against a control gene or genes, and compared to the amount found in a reference breast cancer tissue set, wherein (i) a poor outcome is predicted if the expression levels of uPA and PAI1 are in the upper $20^{th}$ percentile, and (ii) a decreased risk of recurrence is predicted if the expression levels of uPA and PAI1 are not elevated above the mean observed in the breast cancer reference set. In a particular embodiment, poor outcome is measured in terms of shortened survival or increased risk of cancer recurrence following surgery. In another particular embodiment, uPA and PAI1 are expressed at normal levels, and the patient is subjected to adjuvant chemotherapy following surgery.

Another aspect of the invention is a method for predicting treatment outcome in a patient diagnosed with breast cancer, comprising determining the expression levels of cathepsin B and cathepsin L in a breast cancer tissue obtained from the patient, normalized against a control gene or genes, and compared to the amount found in a reference breast cancer tissue set, wherein a poor outcome is predicted if the expression level of either cathepsin B or cathepsin L is in the upper $10^{th}$ percentile. Just as before, poor treatment outcome may be measured, for example, in terms of shortened survival or increased risk of cancer recurrence.

A further aspect of the invention is a method for devising the treatment of a patient diagnosed with breast cancer, comprising the steps of (a) determining the expression levels of scatter factor and c-met in a breast cancer tissue obtained from the patient, normalized against a control gene or genes, and compared to the amount found in a reference breast cancer tissue set, and (b) suggesting prompt aggressive chemotherapeutic treatment if the expression levels of scatter factor and c-met or the combination of both, are above the $90^{th}$ percentile.

A still further aspect of the invention is a method for predicting treatment outcome for a patient diagnosed with breast cancer, comprising determining the expression levels of VEGF, CD31, and KDR in a breast cancer tissue obtained from the patient, normalized against a control gene or genes, and compared to the amount found in a reference breast cancer tissue set, wherein a poor treatment outcome is predicted if the expression level of any of VEGF, CD31, and KDR is in the upper $10^{th}$ percentile.

Yet another aspect of the invention is a method for predicting treatment outcome for a patient diagnosed with breast cancer, comprising determining the expression levels of Ki67/MiB1, PCNA, Pin1, and thymidine kinase in a breast cancer tissue obtained from the patient, normalized against a control gene or genes, and compared to the amount found in a reference breast cancer tissue set, wherein a poor treatment outcome is predicted if the expression level of any of Ki67/MiB1, PCNA, Pin1, and thymidine kinase is in the upper $10^{th}$ percentile.

The invention further concerns a method for predicting treatment outcome for a patient diagnosed with breast cancer, comprising determining the expression level of soluble and full length CD95 in a breast cancer tissue obtained from the patient, normalized against a control gene or genes, and compared to the amount found in a reference breast cancer tissue set, wherein the presence of soluble CD95 correlates with poor patient survival.

The invention also concerns a method for predicting treatment outcome for a patient diagnosed with breast cancer, comprising determining the expression levels of IGF1, IGF1R and IGFBP3 in a breast cancer tissue obtained from the patient, normalized against a control gene or genes, and compared to the amount found in a reference breast cancer tissue set, wherein a poor treatment outcome is predicted if the sum of the expression levels of IGF1, IGF1R and IGFBP3 is in the upper $10^{th}$ percentile.

The invention additionally concerns a method for classifying breast cancer comprising, determining the expression level of two or more genes selected from the group consisting of Bcl12, hepatocyte nuclear factor 3, LIV1, ER, lipoprotein lipase, retinol binding protein 4, integrin $\alpha$7, cytokeratin 5, cytokeratin 17, GRO oncogen, ErbB2 and Grb7, in a breast cancer tissue, normalized against a control gene or genes, and compared to the amount found in a reference breast cancer tissue set, wherein (i) tumors expressing at least one of Bcl1, hepatocyte nuclear factor 3, LIV1, and ER above the mean expression level in the reference tissue set are classified as having a good prognosis for disease free and overall patient survival following surgical removal; (ii) tumors characterized by elevated expression of at least one of lipoprotein lipase, retinol binding protein 4, integrin $\alpha$7 compared to the reference tissue set are classified as having intermediate prognosis of disease free and overall patient survival following surgical removal; and (iii) tumors expressing either elevated levels of cytokeratins 5 and 17, and GRO oncogen at levels four-fold or greater above the mean expression level in the reference tissue set, or ErbB2 and Grb7 at levels ten-fold or more above the mean expression level in the reference tissue set are classified as having poor prognosis of disease free and overall patient survival following surgical removal.

Another aspect of the invention is a panel of two or more gene specific primers selected from the group consisting of the forward and reverse primers listed in Table 2.

Yet another aspect of the invention is a method for reverse transcription of a fragmented RNA population in RT-PCR amplification, comprising using a multiplicity of gene specific primers as the reverse primers in the amplification reaction. In a particular embodiment, the method uses between two and about 40,000 gene specific primers in the same amplification reaction. In another embodiment, the gene specific primers are about 18 to 24 bases, such as about 20 bases in length. In another embodiment, the Tm of the primers is about 58-60° C. The primers can, for example, be selected from the group consisting of the forward and reverse primers listed in Table 2.

The invention also concerns a method of reverse transcriptase driven first strand cDNA synthesis, comprising using a gene specific primer of about 18 to 24 bases in length and having a Tm optimum between about 58° C. and about 60° C. In a particular embodiment, the first strand cDNA synthesis is followed by PCR DNA amplification, and the primer serves as the reverse primer that drives the PCR amplification. In another embodiment, the method uses a plurality of gene specific primers in the same first strand cDNA synthesis reaction mixture. The number of the gene specific primers can, for example, be between 2 and about 40,000.

In a different aspect, the invention concerns a method of predicting the likelihood of long-term survival of a breast cancer patient without the recurrence of breast cancer, following surgical removal of the primary tumor, comprising determining the expression level of one or more prognostic RNA transcripts or their product in a breast cancer tissue sample obtained from said patient, normalized against the expression level of all RNA transcripts or their products in said breast cancer tissue sample, or of a reference set of RNA transcripts or their products, wherein the prognostic transcript is the transcript of one or more genes selected from the group consisting of: FOXM1, PRAME, Bc12, STK15, CEGP1, Ki-67, GSTM1, CA9, PR, BBC3, NME1, SURV, GATA3, TFRC, YB-1, DPYD, GSTM3, RPS6KB1, Src, Chk1, ID1, ESR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, DIABLO, CDH1, HIF1$\alpha$, IGFBP3, CTSB, and Her2, wherein overexpression of one or more of FOXM1, PRAME, STK15, Ki-67, CA9, NME1, SURV, TFRC, YB-1, RPS6KB1, Src, Chk1, CCNB1, Chk2, CDC25B, CYP3A4, EpCAM, VEGFC, hENT1, BRCA2, EGFR, TK1, VDR, EPHX1, IF1A, Contig51037, CDH1, HIF1$\alpha$, IGFBP3, CTSB, Her2, and pENT1 indicates a decreased likelihood of long-term survival without breast cancer recurrence, and the overexpression of one or more of Bcl2, CEGP1, GSTM1, PR, BBC3, GATA3, DPYD, GSTM3, ID1, ESR1, p27, XIAP, IGF1R, AK055699, P13KC2A, TGFB3, BAGI1, pS2, WISP1, HNF3A, NFKBp65, and DIABLO indicates an increased likelihood of long-term survival without breast cancer recurrence.

In a particular embodiment of this method, the expression level of at least 2, preferably at least 5, more preferably at least 10, most preferably at least 15 prognostic transcipts or their expression products is determined.

When the breast cancer is invasive breast carcinoma, including both estrogen receptor (ER) overexpressing (ER positive) and ER negative tumors, the analysis includes determination of the expression levels of the transcripts of at least two of the following genes, or their expression products: FOXM1, PRAME, Bc12, STK15, CEGP1, Ki-67, GSTM1PR, BBC3, NME1, SURV, GATA3, TFRC, YB-1, DPYD, Src, CA9, Contig51037, RPS6K1 and Her2.

When the breast cancer is ER positive invasive breast carcinoma, the analysis includes dtermination of the expression levels of the transcripts of at least two of the following genes, or their expression products: PRAME, Bc12, FOXM1, DIABLO, EPHX1, HIF1A, VEGFC, Ki-67, IGF1R, VDR, NME1, GSTM3, Contig51037, CDC25B, CTSB, p27, CDH1, and IGFBP3.

Just as before, it is preferred to determine the expression levels of at least 5, more preferably at least 10, most preferably at least 15 genes, or their respective expression products.

In a particular embodiment, the expression level of one or more prognostic RNA transcripts is determined, where RNA may, for example, be obtained from a fixed, wax-embedded breast cancer tissue specimen of the patient. The isolation of RNA can, for example, be carried out following any of the procedures described above or throughout the application, or by any other method known in the art.

In yet another aspect, the invention concerns an array comprising polynucleotides hybridizing to the following genes: FOXM1, PRAME, Bcl2, STK15, CEGP1, Ki-67, GSTM1, PR, BBC3, NME1, SURV, GATA3, TFRC, YB-1, DPYD, CA9, Contig51037, RPS6K1 and Her2, immobilized on a solid surface.

In a particular embodiment, the array comprises polynucleotides hybridizing to the following genes: FOXM1, PRAME, Bcl2, STK15, CEGP1, Ki-67, GSTM1, CA9, PR, BBC3, NME1, SURV, GATA3, TFRC, YB-1, DPYD, GSTM3, RPS6KB1, Src, Chk1, ID1, ESR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, CDH1, HIF1α, IGFBP3, CTSB, Her2 and DIABLO.

In a further aspect, the invention concerns a method of predicting the likelihood of long-term survival of a patient diagnosed with invasive breast cancer, without the recurrence of breast cancer, following surgical removal of the primary tumor, comprising the steps of:

(1) determining the expression levels of the RNA transcripts or the expression products of genes of a gene set selected from the group consisting of (a) Bcl2, cyclinG1, NFKBp65, NME1, EPHX1, TOP2B, DR5, TERC, Src, DIABLO;

(b) Ki67, XIAP, hENT1, TS, CD9, p27, cyclinG1, pS2, NFKBp65, CYP3A4;

(c) GSTM1, XIAP, Ki67, TS, cyclinG1, p27, CYP3A4, pS2, NFKBp65, ErbB3;

(d) PR, NME1, XIAP, upa, cyclinG1, Contig51037, TERC, EPHX1, ALDH1A3, CTSL;

(e) CA9, NME1, TERC, cyclinG1, EPHX1, DPYD, Src, TOP2B, NFKBp65, VEGFC;

(f) TFRC, XIAP, Ki67, TS, cyclinG1, p27, CYP3A4, pS2, ErbB3, NFKBp65;

(g) Bcl2, PRAME, cyclinG1, FOXM1, NFKBp65, TS, XIAP, Ki67, CYP3A4, p27;

(h) FOXM1, cyclinG1, XIAP, Contig51037, PRAME, TS, Ki67, PDGFRa, p27, NFKBp65;

(i) PRAME, FOXM1, cyclinG1, XIAP, Contig51037, TS, Ki6, PDGFRa, p27, NFKBp65;

(j) Ki67, XIAP, PRAME, hiENT1, contig51037, TS, CD9, p27, ErbB3, cyclinG1;

(k) STK15, XIAP, PRAME, PLAUR, p27, CTSL, CD18, PREP, p53, RPS6KB1;

(1) GSTM1, XIAP, PRAME, p27, Contig51037, ErbB3, GSTp, EREG, ID1, PLAUR;

(m) PR, PRAME, NME1, XIAP, PLAUR, cyclinG1, Contig51037, TERC, EPHX1, DR5;

(n) CA9, FOXM1, cyclinG1, XIAP, TS, Ki67, NFKBp65, CYP3A4, GSTM3, p27;

(o) TFRC, XIAP, PRAME, p27, Contig51037, ErbB3, DPYD, TERC, NME1, VEGFC; and (p) CEGP1, PRAME, hENT1, XIAP, Contig51037, ErbB3, DPYD, NFKBp65, ID1, TS in a breast cancer tissue sample obtained from said patient, normalized against the expression levels of all RNA transcripts or their products in said breast cancer tissue sample, or of a reference set of RNA transcripts or their products;

(2) subjecting the data obtained in step (a) to statistical analysis; and (3) determining whether the likelihood of said long-term survival has increased or decreased.

In a still further aspect, the invention concerns a method of predicting the likelihood of long-term survival of a patient diagnosed with estrogen receptor (ER)-positive invasive breast cancer, without the recurrence of breast cancer, following surgical removal of the primary tumor, comprising the steps of:

(1) determining the expression levels of the RNA transcripts or the expression products of genes of a gene set selected from the group consisting of (a) PRAME, p27, IGFBP2, HIF1A, TIMP2, ILT2, CYP3A4, ID1, ESR1, DIABLO;

(b) Contig51037, EPHX1, Ki67, TIMP2, cyclinG1, DPYD, CYP3A4, TP, AIB1, CYP2C8;

(c) Bcl2, hENT1, FOXM1, Contig51037, cyclinG1, Contig46653, PTEN, CYP3A4, TIMP2, AREG;

(d) HIF1A, PRAME, p27, IGFBP2, TIMP2, ILT2, CYP3A4, ID1, ESR1, DIABLO;

(e) IGF1R, PRAME, EPHX1, Contig51037, cyclinG1, Bcl2, NME1, PTEN, TBP, TIMP2;

(f) FOXM1, Contig51037, VEGFC, TBP, HIF1A, DPYD, RAD51C, DCR3, cyclinG1, BAG1;

(g) EPHX1, Contig51037, Ki67, TIMP2, cyclinG1, DPYD, CYP3A4, TP, AIB1, CYP2C8;

(h) Ki67, VEGFC, VDR, GSTM3, p27, upa, ITGA7, rhoC, TERC, Pint;

(i) CDC25B, Contig51037, hENT1, Bcl2, HLAG, TERC, NME1, upa, ID1, CYP;

(j) VEGFC, Ki67, VDR, GSTM3, p27, upa, ITGA7, rhoC, TERC, Pint;

(k) CTSB, PRAME, p27, IGFBP2, EPHX1, CTSL, BAD, DRS, DCR3, XIAP;

(l) DIABLO, Ki67, hENT1, TIMP2, ID1, p27, KRT19, IGFBP2, TS, PDGFB;

(m) p27, PRAME, IGFBP2, HIF1A, TIMP2, ILT2, CYP3A4, ID1, ESR1, DIABLO;

(n) CDH1; PRAME, VEGFC; HIF1A; DPYD, TIMP2, CYP3A4, ESR1, RBP4, p27;

(o) IGFBP3, PRAME, p27, Bcl2, XIAP, ESR1, Ki67, TS, Src, VEGF;

(p) GSTM3, PRAME, p27, IGFBP3, XIAP, FGF2, hENT1, PTEN, ESR1, APC;

(q) hENT1, Bcl2, FOXM1, Contig51037, CyclinG1, Contig46653, PTEN, CYP3A4, TIMP2, AREG;

(r) STK15, VEGFC, PRAME, p27, GCLC, hENT1, ID1, TIMP2, ESR1, MCP1;

(s) NME1, PRAM, p27, IGFBP3, XIAP, PTEN, hENT1, Bcl2, CYP3A4, HLAG;

(t) VDR, Bcl2, p27, hENT1, p53, PI3KC2A, EIF4E, TFRC, MCM3, ID1;

(u) EIF4E, Contig51037, EPHX1, cyclinG1, Bcl2, DRS, TBP, PTEN, NME1, HER2;

(v) CCNB1, PRAME, VEGFC, HIF1A, hENT1, GCLC, TIMP2, ID1, p27, upa;

(w) ID1, PRAME, DIABLO, hENT1, p27, PDGFRa, NME1, BIN1, BRCA1, TP;

(x). FBXO5, PRAME, IGFBP3, p27, GSTM3, hENT1, XIAP, FGF2, TS, PTEN;

(y) GUS, HIA1A, VEGFC, GSTM3, DPYD, hENT1, EBXO5, CA9, CYP, KRT18; and (z) Bclx, Bcl2, hENT1, Contig51037, HLAG, CD9, ID1, BRCA1, BIN1, HBEGF;

(2) subjecting the data obtained in step (1) to statistical analysis; and (3) determining whether the likelihood of said long-term survival has increased or decreased.

In a different aspect, the invention concerns an array comprising polynucleotides hybridizing to a gene set selected from the group consisting of:

(a) Bcl2, cyclinG1, NFKBp65, NME1, EPHX1, TOP2B, DR5, TERC, Src, DIABLO;

(b) Ki67, XIAP, hENT1, TS, CD9, p27, cyclinG1, pS2, NFKBp65, CYP3A4;

(c) GSTM1, XIAP, Ki67, TS, cyclinG1, p27, CYP3A4, pS2, NFKBp65, ErbB3;

(d) PR, NME1, XIAP, upa, cyclinG1, Contig51037, TERC, EPHX1, ALDH1A3, CTSL;

(e) CA9, NME1, TERC, cyclinG1, EPHX1, DPYD, Src, TOP2B, NFKBp65, VEGFC;

(f) TFRC, XIAP, Ki67, TS, cyclinG1, p27, CYP3A4, pS2, ErbB3, NFKBp65;

(g) Bcl2, PRAME, cyclinG1, FOXM1, NFKBp65, TS, XIAP, Ki67, CYP3A4, p27;

(h) FOXM1, cyclinG1, XIAP, Contig51037, PRAME, TS, Ki67, PDGFRa, p27, NFKBp65;

(i) PRAME, FOXM1, cyclinG1, XIAP, Contig51037, TS, Ki6, PDGFRa, p27, NFKBp65;

(j) Ki67, XIAP, PRAME, hENT1, contig51037, TS, CD9, p27, ErbB3, cyclinG1;

(k) STK15, XIAP, PRAME, PLAUR, p27, CTSL, CD18, PREP, p53, RPS6KB1;

(l) GSTM1, XIAP, PRAME, p27, Contig51037, ErbB3, GSTp, EREG, ID1, PLAUR;

(m) PR, PRAME, NME1, XIAP, PLAUR, cyclinG1, Contig51037, TERC, EPHX1, DR5;

(n) CA9, FOXM1, cyclinG1, XIAP, TS, Ki67, NFKBp65, CYP3A4, GSTM3, p27;

(o) TFRC, XIAP, PRAME, p27, Contig51037, ErbB3, DPYD, TERC, NME1, VEGFC; and (p) CEGP1, PRAME, hENT1, XIAP, Contig51037, ErbB3, DPYD, NFKBp65, ID1, TS, immobilized on a solid surface.

In an additional aspect, the invention concerns an array comprising polynucleotides hybridizing to a gene set selected from the group consisting of:

(a) PRAME, p27, IGFBP2, HIF1A, TIMP2, ILT2, CYP3A4, ID1, ESR1, DIABLO;

(b) Contig51037, EPHX1, Ki67, TIMP2, cyclinG1, DPYD, CYP3A4, TP, AIB1, CYP2C8;

(c) Bcl2, hENT1, FOXM1, Contig51037, cyclingl, Contig46653, PTEN, CYP3A4, TIMP2, AREG;

(d) HIF1A, PRAME, p27, IGFBP2, TIMP2, ILT2, CYP3A4, ID1, ESR1, DIABLO;

(e) IGF1R, PRAME, EPHX1, Contig51037, cyclinG1, Bcl2, NME1, PTEN, TBP, TIMP2;

(f) FOXM1, Contig51037, VEGFC, TBP, HIF1A, DPYD, RAD51C, DCR3, cyclinG1, BAG1;

(g) EPHX1, Contig51037, Ki67, TIMP2, cyclinG1, DPYD, CYP3A4, TP, AIB1, CYP2C8;

(h) Ki67, VEGFC, VDR, GSTM3, p27, upa, ITGA7, rhoC, TERC, Pini;

(i) CDC25B, Contig51037, hENT1, Bcl2, HLAG, TERC, NME1, upa, ID1, CYP;

(j) VEGFC, Ki67, VDR, GSTM3, p27, upa, ITGA7, rhoC, TERC, Pini;

(k) CTSB, PRAME, p27, IGFBP2, EPHX1, CTSL, BAD, DR5, DCR3, XIAP;

(l) DIABLO, Ki67, hENT1, TIMP2, ID1, p27, KRT19, IGFBP2, TS, PDGFB;

(m) p27, PRAME, IGFBP2, HIF1A, TIMP2, ILT2, CYP3A4, ID1, ESR1, DIABLO;

(n) CDH1; PRAME, VEGFC; HIF1A; DPYD, TIMP2, CYP3A4, ESR1, RBP4, p27;

(o) IGFBP3, PRAME, p27, Bcl2, XIAP, ESR1, Ki67, TS, Src, VEGF;

(p) GSTM3, PRAME, p27, IGFBP3, XIAP, FGF2, hENT1, PTEN, ESR1, APC;

(q) hENT1, Bcl2, FOXM1, Contig51037, CyclinG1, Contig46653, PTEN, CYP3A4, TIMP2, AREG;

(r) STK15, VEGFC, PRAME, p27, GCLC, hENT1, ID1, TIMP2, ESR1, MCP1;

(s) NME1, PRAM, p27, IGFBP3, XIAP, PTEN, hENT1, Bcl2, CYP3A4, HLAG;

(t) VDR, Bcl2, p27, hENT1, p53, PI3KC2A, EIF4E, TFRC, MCM3, ID1;

(u) EIF4E, Contig51037, EPHX1, cyclinG1, Bcl2, DR5, TBP, PTEN, NME1, HER2;

(v) CCNB1, PRAME, VEGFC, HIF1A, hENT1, GCLC, TIMP2, ID1, p27, upa;

(w) ID1, PRAME, DIABLO, hENT1, p27, PDGFRa, NME1, BIN1, BRCA1, TP;

(x) FBXO5, PRAME, IGFBP3, p27, GSTM3, hENT1, XIAP, FGF2, TS, PTEN;

(y) GUS, HIA1A, VEGFC, GSTM3, DPYD, hENT1, FBXO5, CA9, CYP, KRT18; and (z) Bclx, Bcl2, hENT1, Contig51037, HLAG, CD9, ID1, BRCA1, BIN1, HBEGF, immobilized on a solid surface.

In all aspects, the polynucleotides can be cDNAs ("CDNA arrays") that are typically about 500 to 5000 bases long, although shorter or longer cDNAs can also be used and are within the scope of this invention. Alternatively, the polynucleotids can be oligonucleotides (DNA microarrays), which are typically about 20 to 80 bases long, although shorter and longer oligonucleotides are also suitable and are within the scope of the invention. The solid surface can, for example, be glass or nylon, or any other solid surface typically used in preparing arrays, such as microarrays, and is typically glass.

Figure 1:
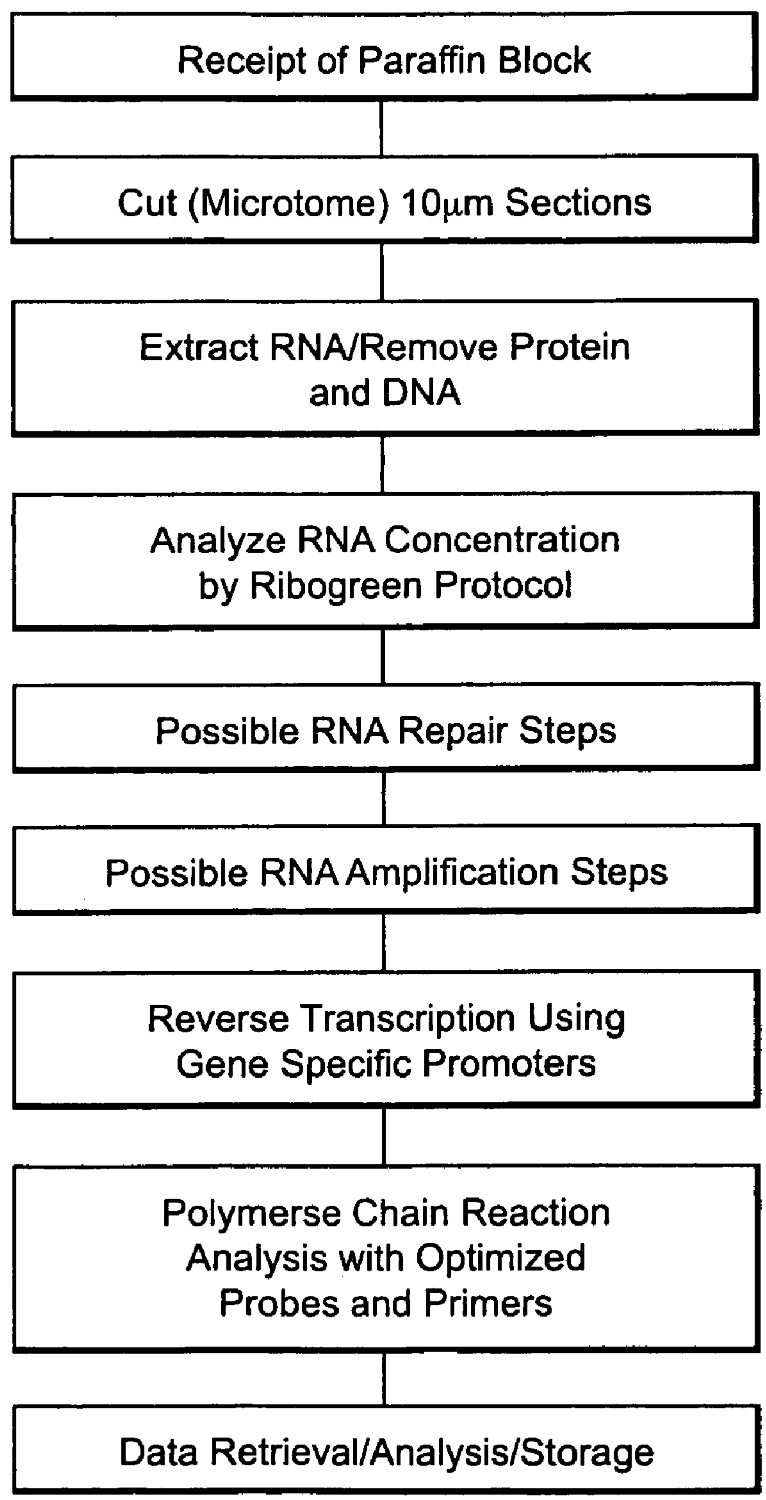
FIG. 1 is a chart illustrating the overall workflow of the process of the invention for measurement of gene expression. In the Figure, FPET stands for "fixed paraffin-embedded tissue," and "RT-PCR" stands for "reverse transcriptase PCR." RNA concentration is determined by using the commercial RiboGreen ™ RNA Quantitation Reagent and Protocol.

Table 1 shows a breast cancer gene list.

Table 2 sets forth amplicon and primer sequences used for amplification of fragmented mRNA.

Table 3 shows the Accession Nos. and SEQ ID NOS of the breast cance genes examined.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "prognosis" is used herein to refer to the prediction of the likelihood of cancer-attributable death or progression, including recurrence, metastatic spread, and drug resistance, of a neoplastic disease, such as breast cancer. The term "prediction" is used herein to refer to the likelihood that a patient will respond either favorably or unfavorably to a drug or set of drugs, and also the extent of those responses. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy.

The term "increased resistance" to a particular drug or treatment option, when used in accordance with the present invention, means decreased response to a standard dose of the drug or to a standard treatment protocol.

The term "decreased sensitivity" to a particular drug or treatment option, when used in accordance with the present invention, means decreased response to a standard dose of the drug or to a standard treatment protocol, where decreased response can be compensated for (at least partially) by increasing the dose of drug, or the intensity of treatment.

"Patient response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. In the context of the present invention, reference to "at least one," "at least two," "at least five," etc. of the genes listed in any particular gene set means any one or any and all combinations of the genes listed.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. Seq ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMang® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor-for each target sequence is used for normalization, and with quantitative comparative PCR using a normalization gene contained within the sample, or a housekeeping gene for RT-PCR. For further details see, e.g. Held et al., *Genome Research* 6:986-994 (1996).

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest are plated, or arrayed, on a microchip. substrate. The arrayed sequences are then hybridized with specific DNA probes from cells or tissues of interest. Just as in the RT-PCR method, the source of MRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue. samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove. non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Ex ression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated-by determining the abundance of individual tags, and identifying the gene corresponding to each tag. For more details see, e.g. Velculescu et al., *Science* 270:484-487 (1995); and Velculescu et al., *Cell* 88:243-51 (1997).

5. Gene Expression Analysis by Massivelv Parallel Signature Sequencinz (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3\times10^6$ microbeads/cm$^2$). The free ends of the cloned templates on each microbead are analyzed simultaneously, using a fluorescence-based signature sequencing method that does not require DNA fragment separation. This method has been shown to simultaneously and accurately-provide, in a single operation, hundreds of thousands of gene signature sequences from a yeast cDNA library.

6. General Description of the mRNA Isolation, Purification and Amplification Methods of the Invention The steps of a representative protocol of the invention, including mRNA isolation, purification, primer extension and amplification are illustrated in FIG. 1. As shown in FIG. 1, this representative process starts with cutting about 10 μm thick sections of paraffin-embedded tumor tissue samples. The RNA is then extracted, and protein and DNA are removed, following the method of the invention described below. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined. The individual steps of this protocol will be discussed in greater detail below.

7. Improved Method for Isolation of Nucleic Acid from Archived Tissue Specimens

As discussed above, in the first step of the method of the invention, total RNA is extracted from the source material of interest, including fixed, paraffin-embedded tissue specimens, and purified sufficiently to act as a substrate in an enzyme assay. Despite the availability of commercial products, and the extensive knowledge available concerning the isolation of nucleic acid, such as RNA, from tissues, isolation of nucleic acid (RNA) from fixed, paraffin-embedded tissue specimens (FPET) is not without difficulty.

In one aspect, the present invention concerns an improved method for the isolation of nucleic acid from archived, e.g. FPET tissue specimens. Measured levels of mRNA species are useful for defining the physiological or pathological status of cells and tissues. RT-PCR (which is discussed above) is one of the most sensitive, reproducible and quantitative methods for this "gene expression profiling". Paraffin-embedded, formalin-fixed tissue is the most widely available material for such studies. Several laboratories have demonstrated that it is possible to successfully use fixed-paraffin-embedded tissue (FPET) as a source of RNA for RT-PCR (Stanta et al., *Biotechniques* 11:304-308 (1991); Stanta et al., *Methods Mol. Biol.* 86:23-26 (1998); Jackson et al., *Lancet* 1:1391 (1989); Jackson et al., *J Clin. Pathol.* 43:499-504 (1999); Finke et al., *Biotechniques* 14:448-453 (1993); Goldsworthy et al., *Mol. Carcinog.* 25:86-91 (1999); Stanta and Bonin, *Biotechniques* 24:271-276 (1998); Godfrey et al., *J Mol. Diagnostics* 2:84 (2000); Specht et al., *J Mol. Med.* 78:B27 (2000); Specht et al., *Am. J Pathol.* 158:419-429 (2001)). This allows gene expression profiling to be carried out on the most commonly available source of human biopsy specimens, and therefore potentially to create new valuable diagnostic and therapeutic information.

The most widely used protocols utilize hazardous organic solvents, such as xylene, or octane (Finke et al., supra) to dewax the tissue in the paraffin blocks before nucleic acid (RNA and/or DNA) extraction. Obligatory organic solvent removal (e.g. with ethanol) and rehydration steps follow, which necessitate multiple manipulations, and addition of substantial total time to the protocol, which can take up to several days. Commercial kits and protocols for RNA extraction from FPET [MasterPure™ Complete DNA and RNA Purification Kit (EPICENTRE®, Madison, Wis; Paraffin Block.RNA Isolation Kit (Ambion, Inc.) and RNeasy™ Mini kit (Qiagen, Chatsworth, Calif.)] use xylene for deparaffinization, in procedures which typically require multiple centrifugations and ethanol buffer changes, and incubations following incubation with xylene.

The present invention provides an improved nucleic acid extraction protocol that produces nucleic acid, in particular RNA, sufficiently intact for gene expression measurements. The key step in the nucleic acid extraction protocol herein is the performance of dewaxing without the use of any organic solvent, thereby eliminating the need for multiple manipulations associated with the removal of the organic solvent, and substantially reducing the total time to the protocol. According to the invention, wax, e.g. paraffin is removed from wax-embedded tissue samples by incubation at 65-75° C. in a lysis buffer that solubilizes the tissue and hydrolyzes the protein, following by cooling to solidify the wax.

Figure 2:
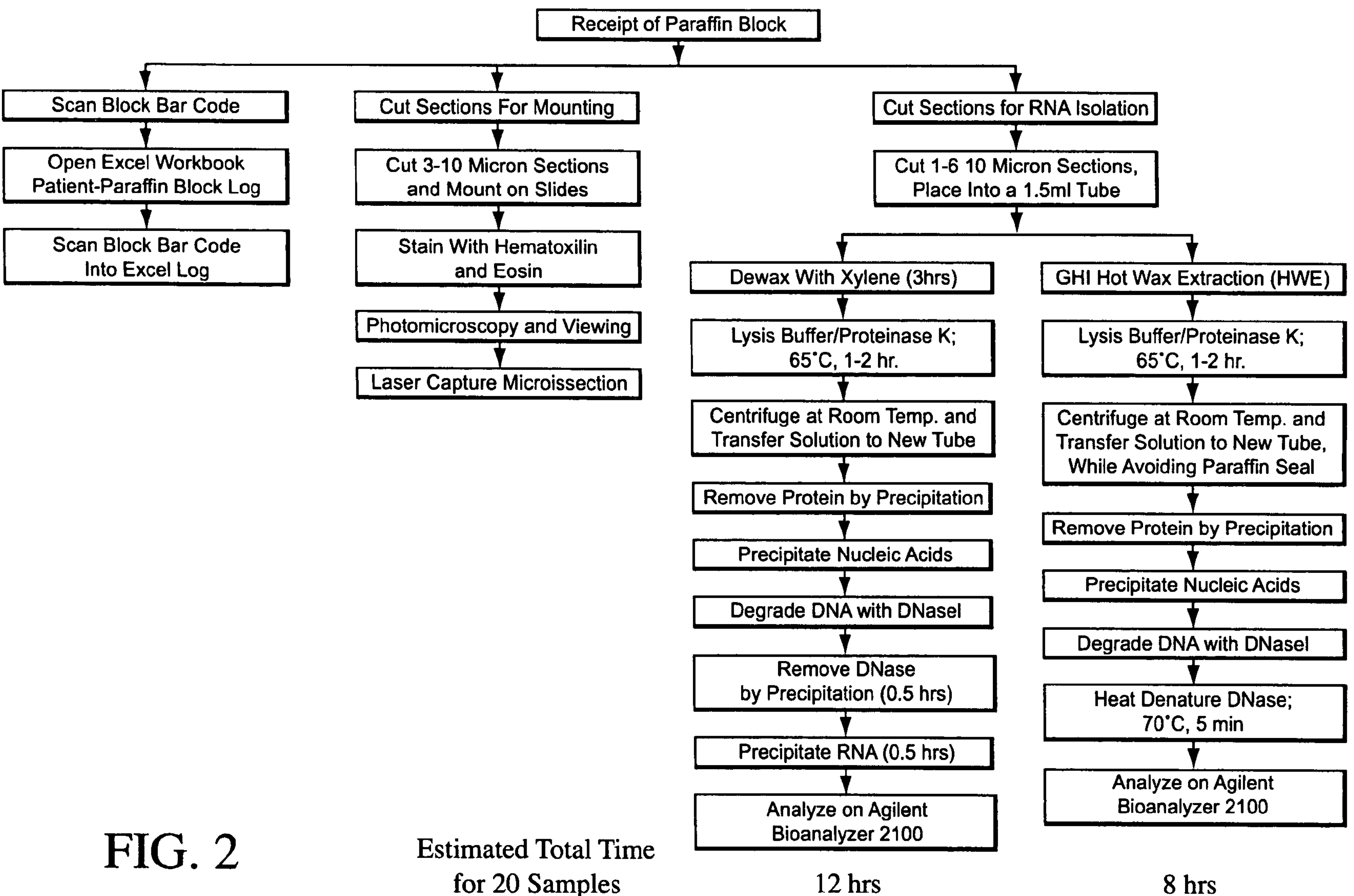
FIG. 2 is a flow chart showing the steps of an RNA extraction method according to the invention alongside a flow chart of a representative commercial method.

FIG. 2 shows a flow chart of an RNA extraction protocol-of the present invention in comparison with a representative commercial method, using xylene to remove wax. The times required for individual steps in the processes and for the overall processes are shown in the chart. As shown, the commercial process requires approximately 50% more time than the process of the invention.

The lysis buffer can be any buffer known for cell lysis. It is, however, preferred that oligo-dT-based methods of selectively purifying polyadenylated MRNA not be used to isolate RNA for the present invention, since the bulk of the mRNA molecules are expected to be fragmented and therefore will not have an intact polyadenylated tail, and will not be recovered or available for subsequent analytical assays. Otherwise, any number of standard nucleic acid purification schemes can be used. These include chaotrope and organic solvent extractions, extraction using glass beads or filters, salting out and precipitation based methods, or any of the purification methods known in the art to recover total RNA or total nucleic acids from a biological source.

Lysis buffers are commercially available, such as, for example, from Qiagen, Epicentre, or Ambion. A preferred group of lysis buffers typically contains urea, and Proteinase K or other protease. Proteinase K is very useful in the isolation of high quality, undamaged DNA or RNA, since most mammalian DNases and RNases are rapidly inactivated by this enzyme, especially in the presence of 0.5- 1% sodium dodecyl sulfate (SDS). This is particularly important in the case of RNA, which is more susceptible to degradation than DNA. While DNases require metal ions for activity, and can therefore be easily inactivated by chelating agents, such as EDTA, there is no similar co-factor requirement for RNases.

Cooling and resultant solidification of the wax permits easy separation of the wax from the total nucleic acid, which can be conveniently precipitated, e.g. by isopropanol. Further processing depends on the intended purpose. If the proposed method of RNA analysis is subject. to bias by contaminating DNA in an extract, the RNA extract can be further treated, e.g. by DNase, post purification to specifically remove DNA while preserving RNA. For example, if the goal is to isolate high quality RNA for subsequent RT-PCR amplification, nucleic acid precipitation is followed by the removal of DNA, usually by DNase treatment. However, DNA can be removed at various stages of nucleic acid isolation, by DNase or other techniques well known in the art.

While the advantages of the nucleic acid extraction protocol of the invention are most apparent for the isolation of RNA from archived, paraffin embedded tissue samples, the wax removal step of the present invention, which does not involve the use of an organic solvent, can also be included in any conventional protocol for the extraction of total nucleic acid (RNA and DNA) or DNA only. All of these aspects are specifically within the scope of the invention.

By using heat followed by cooling to remove paraffin, the process of the present invention saves valuable processing time, and eliminates a series of manipulations, thereby potentially increasing the yield of nucleic acid. Indeed, experimental evidence presented in the examples below, demonstrates that the method of the present invention does not compromise RNA yield.

8. 5'-multiplexed Gene Specific Priming of Reverse Transcription

RT-PCR requires reverse transcription of the test RNA population as a first step. The most commonly used primer for reverse transcription is oligo-dT, which works well when RNA is intact. However, this primer will not be effective when RNA is highly fragmented as is the case in FPE tissues.

The present invention includes the use of gene specific primers, which are roughly 20 bases in length with a Tm optimum between about 58° C. and 60° C. These primers will also serve as the reverse primers that drive PCR DNA amplification.

Figure 9:
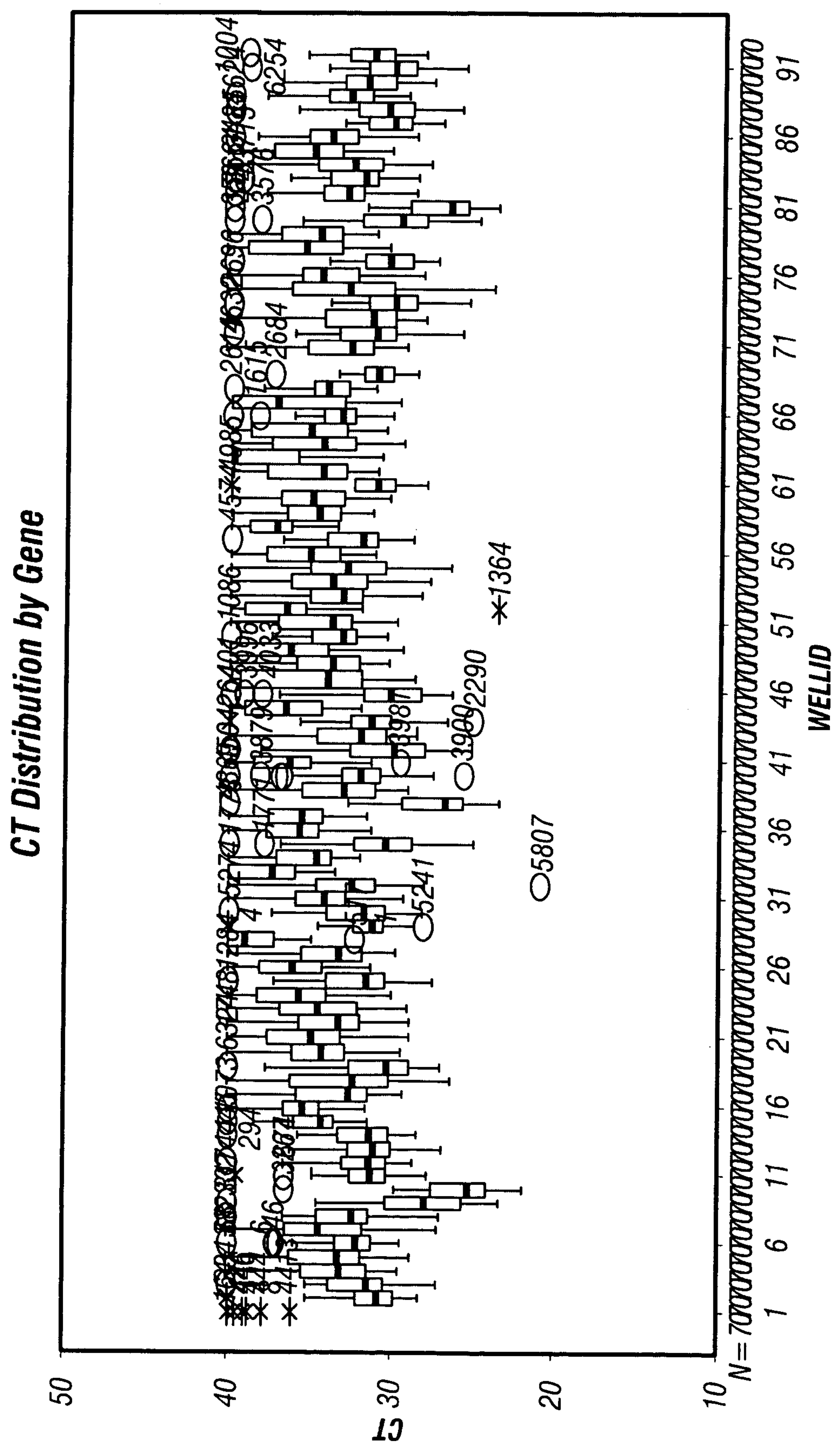
FIG. 9 is a representation of the expression of 92 genes across 70 FPE breast cancer specimens. The y-axis shows expression as cycle threshold times. These genes are a subset of the genes listed in Table 1.

Another aspect of the invention is the inclusion of multiple gene-specific primers in the same reaction mixture. The number of such different primers can vary greatly and can be as low as two and as high as 40,000 or more. Table 2 displays examples of reverse primers that can be successfully used in carrying out the methods of the invention. FIG. 9 shows expression data obtained using this multiplexed gene-specific priming strategy. Specifically, FIG. 9 is a representation of the expression of 92 genes (a subset of genes listed in Table 1) across 70 FPE breast cancer specimens. The y-axis shows expression as cycle threshold times.

An alternative approach is based on the use of random hexamers as primers for cDNA synthesis. However, we have experimentally demonstrated that the method of using a multiplicity of gene-specific primers is superior over the known approach using random hexamers.

9. Preparation of Fraemented mRNA for Expression Profiling Assays

It is of interest to analyze the abundance of specific mRNA species in biological samples, since this expression profile provides an index of the physiological state of that sample. mRNA is notoriously difficult to extract and maintain in its native state, consequently, mRNA recovered from biological sources is often fragmented or somewhat degraded. This is especially true of human tissue specimen which have been chemically fixed and stored for extended periods of time.

In one aspect, the present invention provides a means of preparing the mRNA extracted from various sources, including archived tissue specimens, for expression profiling in a way that its relative abundance is preserved and the mRNA's of interest can be successfully measured. This method is useful as a means of preparing mRNA for analysis by any of the known expression profiling methods, including RT-PCR coupled with 5' exonuclease of reporter probes (TaqMan® type assays), as discussed above, flap endonuclease assays (Cleavase® and Invader® type assays), oligonucleotide hybridization arrays, cDNA hybridization arrays, oligonucleotide ligation assays, 3' single nucleotide extension assays and other assays designed to assess the abundance of specific mRNA sequences in a biological sample.

According to the method of the invention, total RNA is extracted from the source material and sufficiently purified to act as a substrate in an enzyme assay. The extraction procedure, including a new and improved way of removing the wax (e.g. paraffin) used for embedding the tissue samples, has been discussed above. It has also been noted that it is preferred that oligo-dT based methods of selectively purifying polyadenylated mRNA not be used to isolate RNA for this invention since the bulk of the mRNA is expected to be fragmented, will not be polyadenylated and, therefore, will not be recovered and available for subsequent analytical assays if an oligo-dT based method is used.

Figure 3:
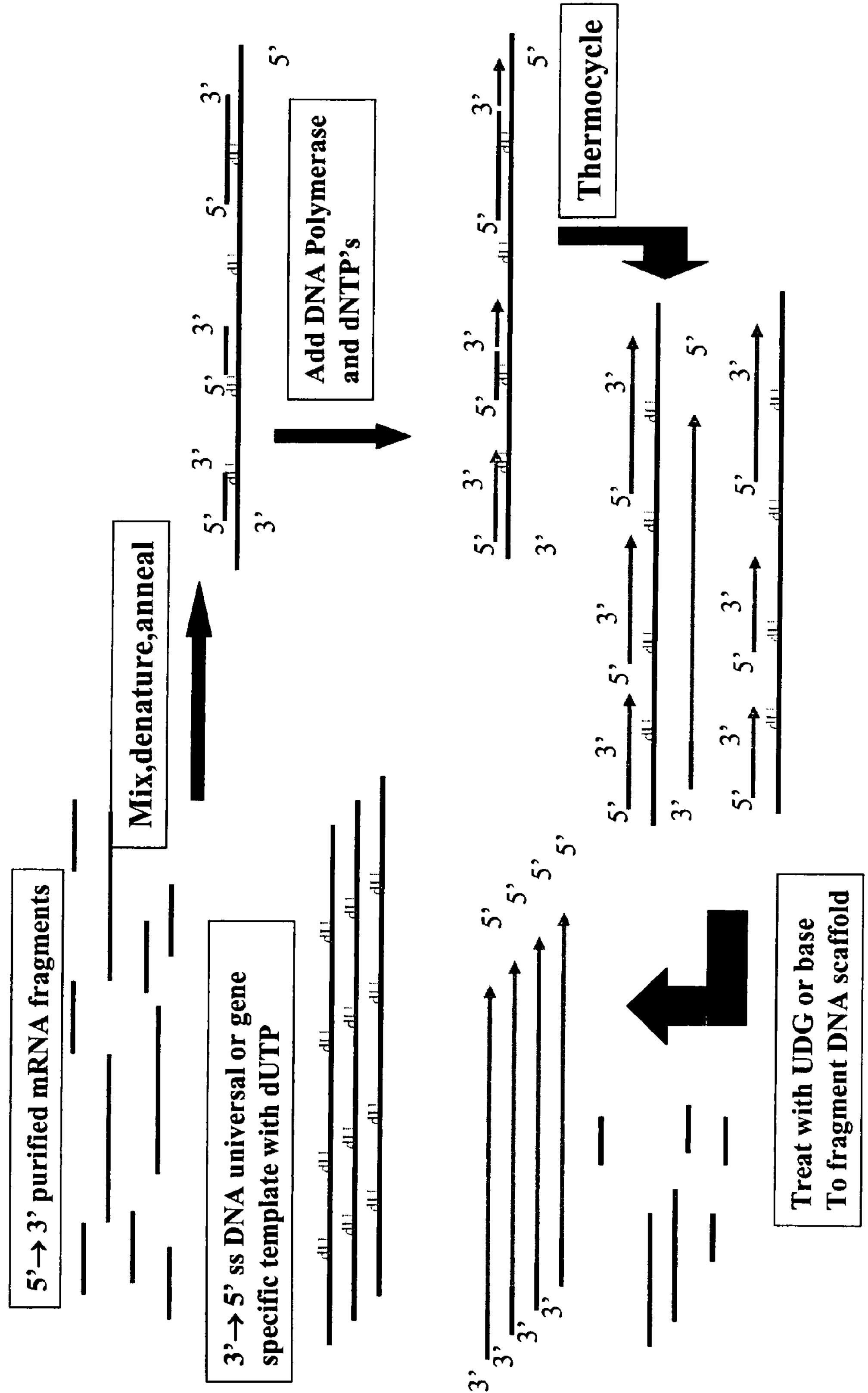
FIG. 3 is a scheme illustrating the steps of an improved method for preparing fragmented mRNA for expression profiling analysis.

A diagram of an improved method for repairing fragmented RNA is shown in FIG. 3. The fragmented RNA purified from the tissue sample is mixed with universal or gene-specific, single-stranded, DNA templates for each mRNA species of interest. These templates may be full length DNA copies of the mRNA derived from cloned gene sources, they may be fragments of the gene representing only the segment of the gene to be assayed, they may be a series of long oligonucleotides representing, either the full length gene or the specific segment(s) of interest. The template can represent either a single consensus sequence or be a mixture of polymorphic variants of the gene. This DNA template, or scaffold, will preferably include one or more dUTP or rNTP sites in its length. This will provide a means of removing the template prior to carrying out subsequent analytical steps to avoid its acting as a substrate or target in later analysis assays. This removal is accomplished by treating the sample with uracil-DNA glycosylase (UDG) and heating it to cause strand breaks where UDG has generated a basic sites. In the case of rNTP's, the sample can be heated in the presence of a basic buffer (pH ~10) to induce strand breaks where rNTP's are located in the template.

The single stranded DNA template is mixed with the purified RNA, the mixture is denatured and annealed so that the RNA fragments complementary to the DNA template effectively become primers that can be extended along the single stranded DNA templates. DNA polymerase I requires a primer for extension but will efficiently use either a DNA or an RNA primer. Therefore in the presence of DNA polymerase I and dNTP's, the fragmented RNA can be extended along the complementary DNA templates. In order to increase the efficiency of the extension, this reaction can be thermally cycled, allowing overlapping templates and extension products to hybridize and extend until the overall population of fragmented RNA becomes represented as double stranded DNA extended from RNA fragment primers.

Following the generation of this "repaired" RNA, the sample should be treated with UDG or heat-treated in a mildly based solution to fragment the DNA template (scaffold) and prevent it from participating in subsequent analytical reactions.

The product resulting from this enzyme extension can then be used as a template in a standard enzyme profiling assay that includes amplification and detectable signal generation such as fluorescent, chemiluminescent, calorimetric or other common read outs from enzyme based assays. For example, for TaqMane® type assays, this double stranded DNA product is added as the template in a standard assay; and, for array hybridization, this product acts as the cDNA template for the cRNA labeling reaction typically used to generate single-stranded, labeled RNA for array hybridization.

This method of preparing template has the advantage of recovering information from mRNA fragments too short to effectively act as templates in standard cDNA generation schemes. In addition, this method acts to preserve the specific locations in mRNA sequences targeted by specific analysis assays. For example, TaqMang® assays rely on a single contiguous sequence in a cDNA copy of mRNA to act as a PCR amplification template targeted by a labeled reporter probe. If mRNA strand breaks occur in this sequence, the assay will not detect that template and will underestimate the quantity of that mRNA in the original sample. This target preparation method minimizes that effect from RNA fragmentation.

The extension product formed in the RNA primer extension assay can be controlled by controlling the input quantity of the single stranded DNA template and by doing limited cycling of the extension reaction. This is important in preserving the relative abundance of the mRNA sequences targeted for analysis.

This method has the added advantage of not requiring parallel preparation for each target sequence since it is easily multiplexed. It is also possible to use large pools of random sequence long oligonucleotides or full libraries of cloned sequences to extend the entire population of mRNA sequences in the sample extract for whole expressed genome analysis rather than targeted gene specific analysis.

10. Amplification of mRNA Species Prior to RT-PCR

Due to the limited amount and poor quality of mRNA that can be isolated from FPET, a new procedure that could accurately amplify mRNAs of interest would be very useful, particularly for real time quantitation of gene expression (TaqMan®) and especially for quantitatively large number (>50) of genes >50 to 10,000.

Figure 4:
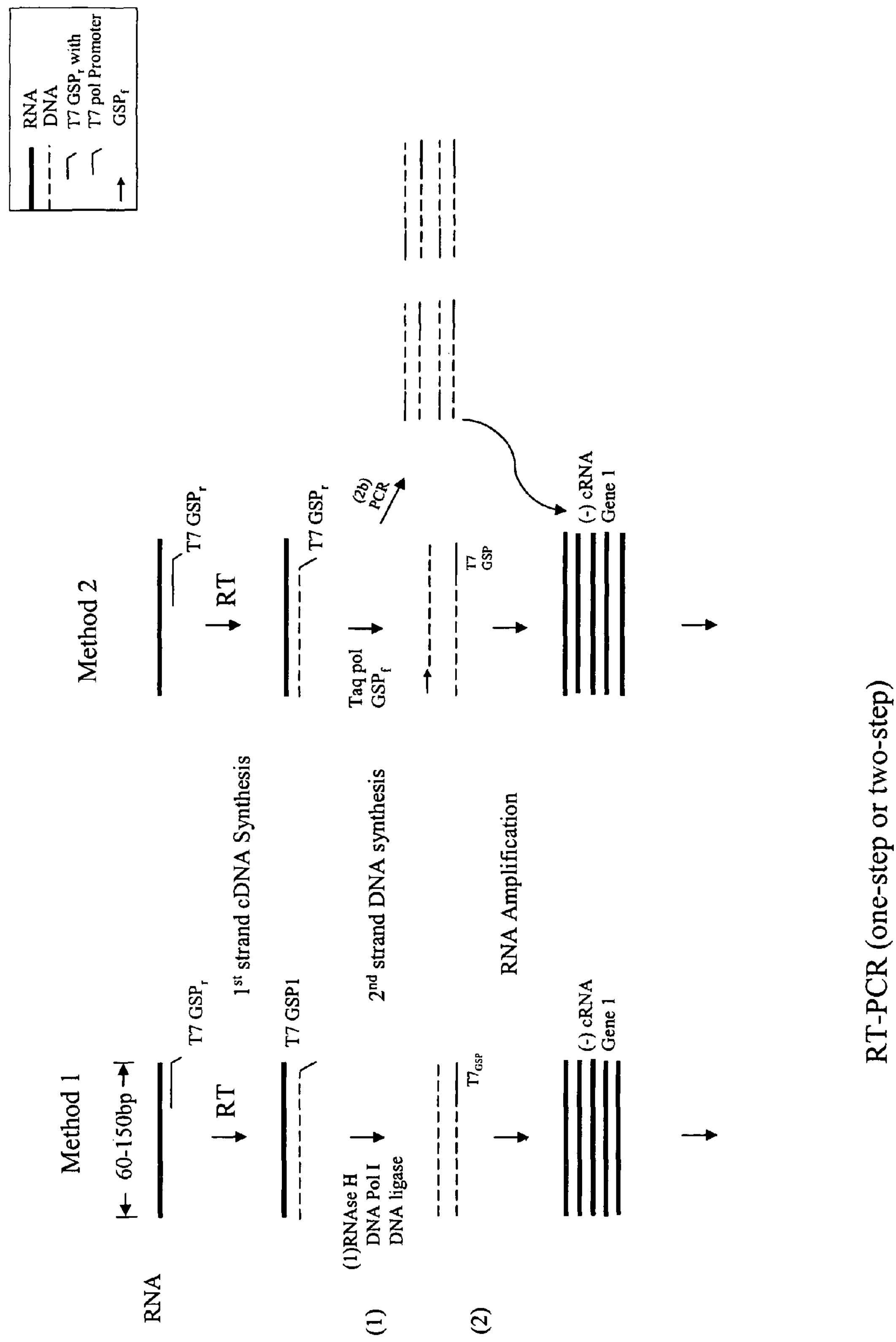
FIG. 4 illustrates methods for amplification of RNA prior to RT-PCR.

Current protocols (e.g. Eberwine, *Biotechniques* 20:584-91 (1996)) are optimized for mRNA amplification from small amount of total or poly $A^+$RNA mainly for microarray analysis. The present invention provides a protocol optimized for amplification of small amounts of fragmented total RNA (average size about 60-150 bps), utilizing gene-specific sequences as primers, as illustrated in FIG. 4.

The amplification procedure of the invention uses a very large number, typically as many as 100-190,000 gene specific primers (GSP's) in one reverse transcription run. Each GSP contains an RNA polymerase promoter, e.g. a T7 DNA-dependent RNA polymerase promoter, at the 5' end for subsequent RNA amplification. GSP's are preferred as primers because of the small size of the RNA. Current protocols utilize dT primers, which would not adequately represent all reverse transcripts of mRNAs due to the small size of the FPET RNA. GSP's can be designed by optimizing usual parameters, such as length, Tm, etc. For example, GSP's can be designed using the Primer Express® (Applied Biosystems), or Primer 3 (MIT) software program. Typically at least 3 sets per gene are designed, and the ones giving the lowest Ct on FPET RNA (best performers) are selected.

Second strand cDNA synthesis is performed by standard procedures (see FIG. 4, Method 1), or by $GSP_f$ primers and Taq pol under PCR conditions (e.g., 95° C., 10 min (Taq activation) then 60° C., 45 sec). The advantages of the latter method are that the second gene specific primer, $SGF_f$ adds additional specificity (and potentially more efficient second strand synthesis) and the option of performing several cycles of PCR, if more starting DNA is necessary for RNA amplification by T7 RNA polymerase. RNA amplification is then performed under standard conditions to generate multiple copies of cRNA, which is then used in a standard TaqMang® reaction.

Although this process is illustrated by using T7-based RNA amplification, a person skilled in the art will understand that other RNA polymerase promoters that do not require a primer, such as T3 or Sp6 can also be used, and are within the scope of the invention.

11. A method of Elongation of Fragmented RNA and Subsequent Ampilication

Figure 5:
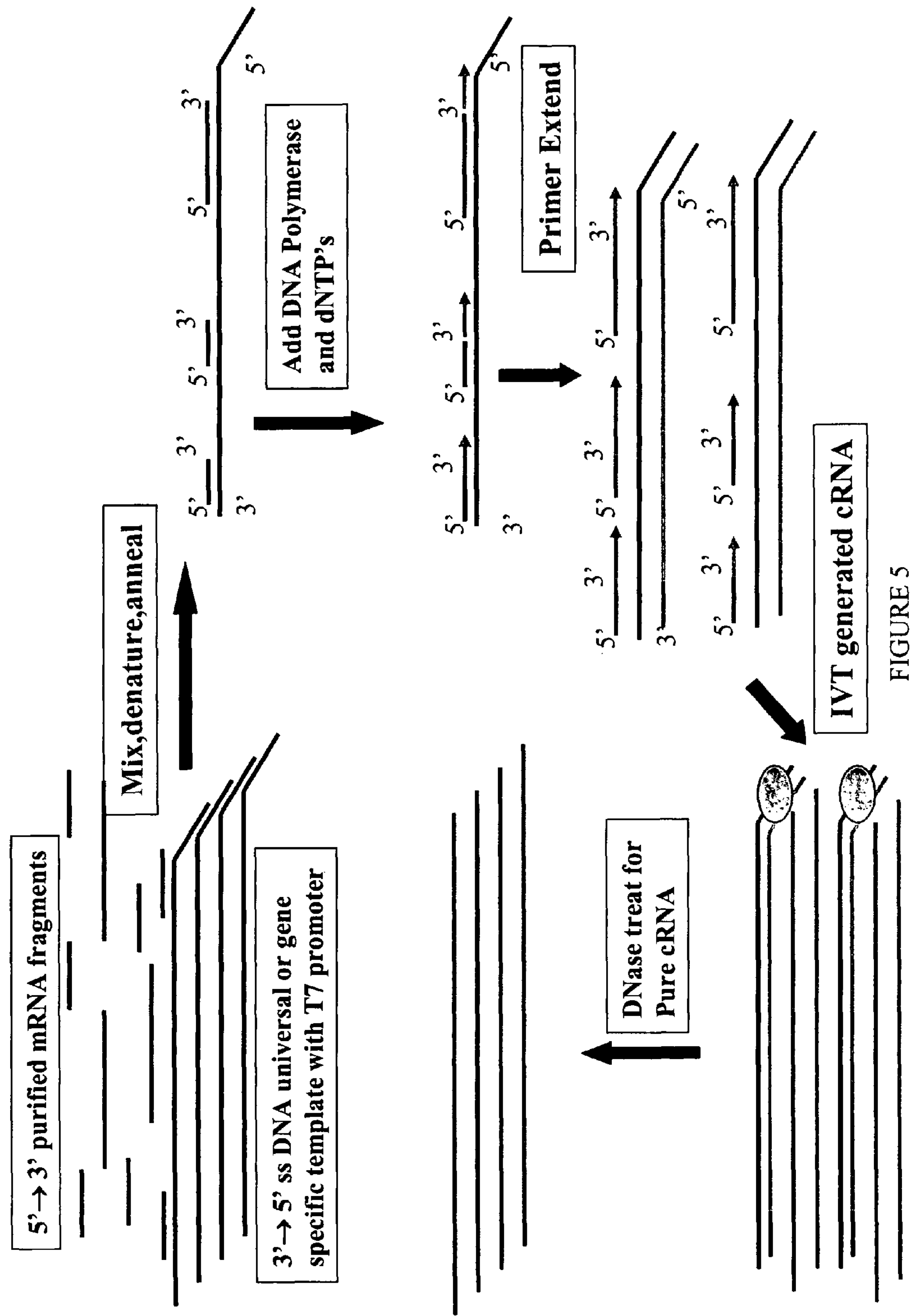
FIG. 5 illustrates an alternative scheme for repair and amplification of fragmented mRNA.

This method, which combines and modifies the inventions described in sections 9 and 10 above, is illustrated in FIG. 5. The procedure begins with elongation of fragmented mRNA. This occurs as described above except that the scaffold DNAs are tagged with the T7 RNA polymerase promoter sequence at their 5' ends, leading to double-stranded DNA extended from RNA fragments. The template sequences need to be removed after in vitro transcription. These templates can include dUTP or rNTP nucleotides, enabling enzymatic removal of the templates as described in section 9, or the templates can be removed by DNaseI treatment.

The template DNA can be a population representing different mRNAs of any number. A high sequence complexity source of DNA templates (scaffolds) can be generated by pooling RNA from a variety of cells or tissues. In one embodiment, these RNAs are converted into double stranded DNA and cloned into phagemids. Single stranded DNA can then be rescued by phagemid growth and single stranded DNA isolation from purified phagemids.

This invention is useful because it increases gene expression profile signals two different ways: both by increasing test mRNA polynucleotide sequence length and by in vitro transcription amplification. An additional advantage is that it eliminates the need to carry out reverse transcription optimization with gene specific primers tagged with the T7 RNA polymerase promoter sequence, and thus, is comparatively fast and economical.

This invention can be used with a variety of different methods to profile gene expression, e.g., RT-PCR or a variety of DNA array methods. Just as in the previous protocol, this approach is illustrated by using a T7 promoter but the invention is not so limited. A person skilled in the art will appreciate, however, that other RNA polymerase promoters, such as T3 or Sp6 can also be used.

12. Breast Cancer Gene Set. Assayed Gene Subsequences and Clinical Application of Gene Expression Data An important aspect of the present invention is to use the measured expression of certain genes by breast cancer tissue to match patients to best drugs or drug combinations, and to provide prognostic information. For this purpose it is necessary to correct for (normalize away) both differences in the amount of RNA assayed and variability in the quality of the RNA used. Therefore, the assay measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor MRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

The breast cancer gene set is shown in Table 1. The gene Accession Numbers, and the SEQ ID NOs for the forward primer, reverse primer and amplicon sequences that can be used for gene amplification, are listed in Table 2. The basis for inclusion of markers, as well as the clinical significance of mRNA level variations with respect to the reference set, is indicated below. Genes are grouped into subsets based on the type of clinical significance indicated by their expression levels: A. Prediction of patient response to drugs used in breast cancer treatment, or to drugs that are approved for other indications and could be used off-label in the treatment of breast cancer. B. Prognostic for survival or recurrence of cancer.

C. Prediction of Patient Response to Therapeutic Drugs

1. Molecules that specifically influence cellular sensitivity to drugs

Table 1 lists 74 genes (shown in italics) that specifically influence cellular sensitivity to potent drugs, which are also listed. Most of the drugs shown are approved and already used to treat breast cancer (e.g., anthracyclines; cyclophosphamide; methotrexate; 5-FU and analogues). Several of the drugs are used to treat breast cancer off-label or are in clinical development phase (e.g., bisphosphonates and anti-VEGF mAb). Several of the drugs have not been widely used to treat breast cancer but are used in other cancers in which the indicated target is expressed (e.g., Celebrex is used to treat familial colon cancer; cisplatin is used to treat ovarian and other cancers.)

Patient response to 5FU is indicated if normalized thymidylate synthase MRNA amount is at or below the $15^{th}$ percentile, or the sum of expression of thymnidylate synthase plus dihydropyrimidine phosphorylase is at or below the $25^{th}$ percentile, or the sum of expression of these mRNAs plus thymidine phosphorylase is at or below the $20^{th}$ percentile. Patients with dihydropyrimidine dehydrogenase below $5^{th}$ percentile are at risk of adverse response to 5FU, or analogs such as Xeloda.

When levels of thymidylate synthase, and dihydropyrimidine dehydrogenase, are within the acceptable range as defined in the preceding paragraph, amplification of c-myc mRNA in the upper 15%, against a background of wild-type p53 [as defined below] predicts a beneficial response to 5FU (see D. Arango et al., *Cancer Res.* 61:4910-4915 (2001)). In the presence of normal levels of thynidylate synthase and dihydropyrimidine dehydrogenase, levels of NFκB and cIAP2 in the upper 10% indicate resistance of breast tumors to the chemotherapeutic drug 5FU.

Patient resistance to anthracyclines is indicated if the normalized mRNA level of topoisomerase IIα is below the $10^{th}$ percentile, or if the topoisomerase IIβ normalized mRNA level is below the $10^{th}$ percentile or if the combined normalized topoisomerase IIα and β signals are below the $10^{th}$ percentile.

Patient sensitivity to methotrexate is compromised if DHFR levels are more than tenfold higher than the average reference set level for this MRNA species, or if reduced folate carrier levels are below $10^{th}$ percentile.

Patients whose tumors express CYPIBI in the upper 10%, have reduced likelihood of responding to docetaxol.

The sum of signals for aldehyde dehydrogenase 1A1 and 1A3, when more than tenfold higher than the reference set average, indicates reduced likelihood of response to cyclophosphamide.

Figure 6:
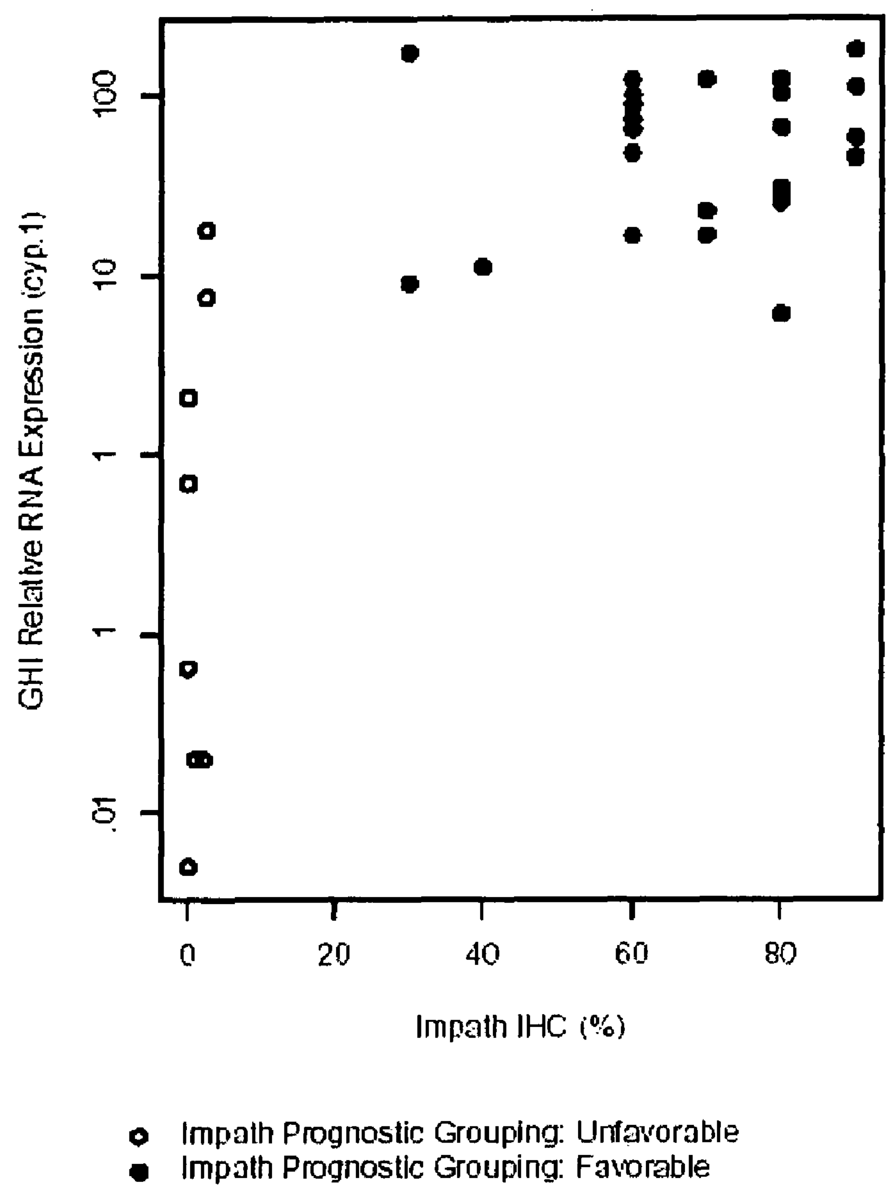
FIG. 6 shows the measurement of estrogen receptor mRNA levels in 40 FPE breast cancer specimens via RT-PCR. Three 10 micron sections were used for each measurement. Each data point represents the average of triplicate measurements.
Figure 7:
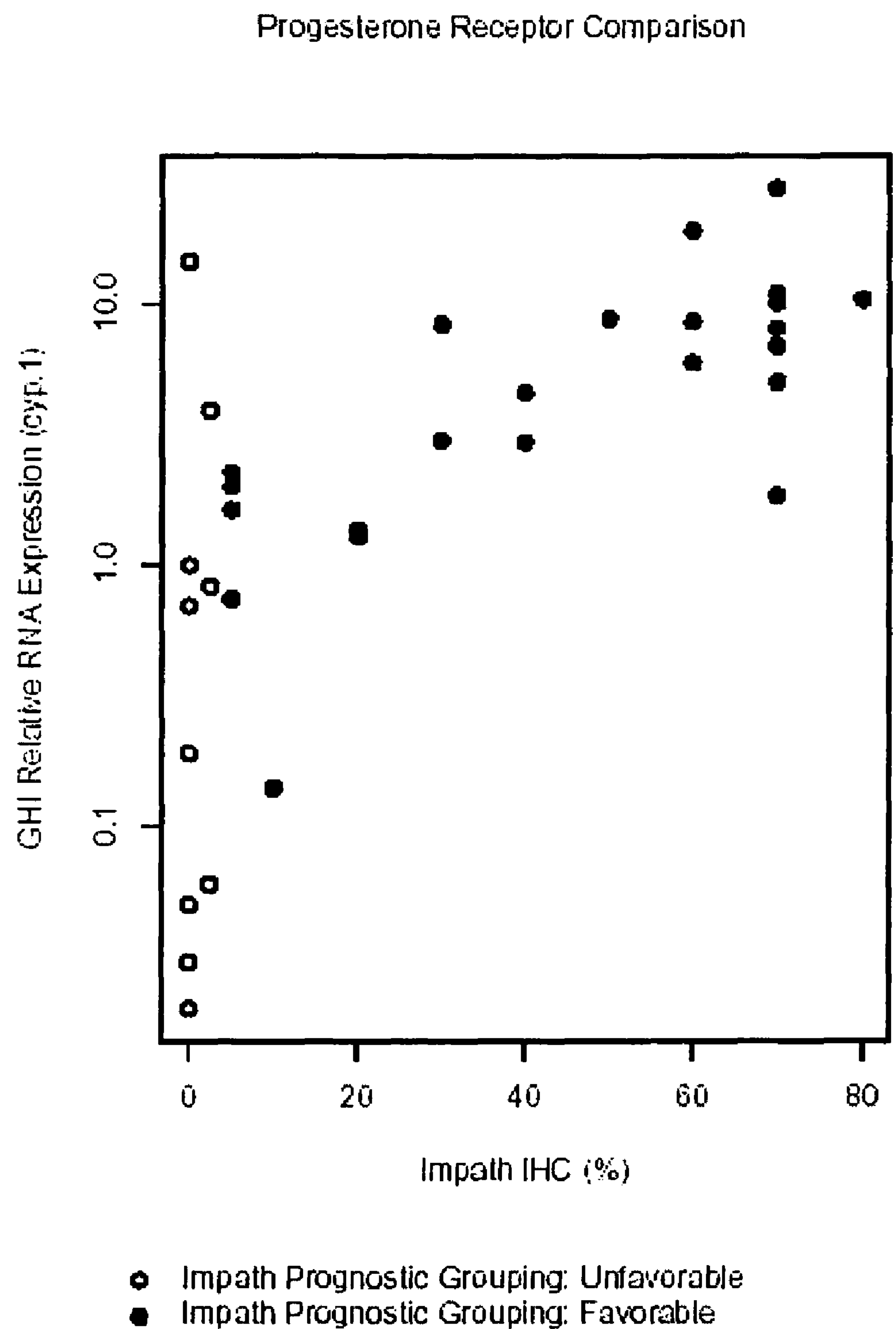
FIG. 7 shows the results of the measurement of progesterone receptor mRNA levels in 40 FPE breast cancer specimens via RT-PCR performed as described in the legend of FIG. 6 above.

Currently, estrogen and progesterone receptor expression as measured by immunohistochemistry is used to select patients for anti-estrogen therapy. We have demonstrated RT-PCR assays for estrogen and progesterone receptor mRNA levels that predict levels of these proteins as determined by a standard clinical diagnostic tests, with high degree of concordance (FIGS. 6 and 7).

Patients whose tumors express ERα or PR mRNA in the upper 70%, are likely to respond to tamoxifen or other anti-estrogens (thus, operationally, lower levels of ERα than this are to defined ERα-negative). However, when the signal for microsomal epoxide hydrolase is in the upper 10% or when mRNAs for pS2/trefoil factor, GATA3 or human chorionic gonadotropin are at or below average levels found in ERα-negative tumors, anti-estrogen therapy will not be beneficial.

Absence of XIST signal compromises the likelihood of response to taxanes, as does elevation of the GST-π or prolyl endopeptidase [PREP] signal in the upper 10%. Elevation of PLAG1 in the upper 10% decreases sensitivity to taxanes.

Expression of ERCC1 mRNA in the upper 10% indicate significant risk of resistance to cisplatin or analogs.

An RT-PCR assay of Her2 mRNA expression predicts Her2 overexpression as measured by a standard diagnostic test, with high degree of concordance (data not shown). Patients whose tumors express Her2 (normalized to cyp.1) in the upper 10% have increased likelihood of beneficial response to treatment with Herceptin or other ErbB2 antagonists. Measurement of expression of Grb7 mRNA serves as a test for HER2 gene amplification, because the Grb7 gene is closely linked to Her2. When Her2 is expression is high as defined above in this paragraph, similarly elevated Grb7 indicates Her2 gene amplification. Overexpression of IGF1R and or IGF1 or IGF2 decreases likelihood of beneficial response to Herceptin and also to EGFR antagonists.

Patients whose tumors express mutant Ha-Ras, and also express farnesyl pyrophosphate synthetase or geranyl pyrophosphonate synthetase mRNAs at levels above the tenth percentile comprise a group that is especially likely to exhibit a beneficial response to bis-phosphonate drugs.

Cox2 is a key control enzyme in the synthesis of prostaglandins. It is frequently expressed at elevated levels in subsets of various types of carcinomas including carcinoma of the breast. Expression of this gene is controlled at the transcriptional level, so RT-PCR serves a valid indicator of the cellular enzyme activity. Nonclinical research has shown that cox2 promotes tumor angiogenesis, suggesting that this enzyme is a promising drug target in solid tumors. Several Cox2 antagonists are marketed products for use in anti-inflammatory conditions. Treatment of familial adenomatous polyposis patients with the cox2 inhibitor Celebrex significantly decreased the number and size of neoplastic polyps. No cox2 inhibitor has yet been approved for treatment of breast cancer, but generally this class of drugs is safe and could be prescribed off-label in breast cancers in which cox2 is over-expressed. Tumors expressing COX2 at levels in the upper ten percentile have increased chance of beneficial response to Celebrex or other cyclooxygenase 2 inhibitors.

The tyrosine kinases ErbB1 [EGFR], ErbB3 [Her3] and ErbB4 [Her4]; also the ligands TGFalpha, amphiregulin, heparin-binding EGF-like growth factor, and epireglin; also BRK, a non-receptor kinase. Several drugs in clinical development block the EGF receptor. ErbB2-4, the indicated ligands, and BRK also increase the activity of the EGFR pathway. Breast cancer patients whose tumors express high levels of EGFR or EGFR and abnormally high levels of the other indicated activators of the EGFR pathway are potential candidates for treatment with an EGFR antagonist.

Patients whose tumors express less than 10% of the average level of EGFR mRNA observed in the reference panel are relatively less likely to respond to EGFR antagonists [such as Iressa, or ImClone 225]. In cases in which the EGFR is above this low range, the additional presence of epiregulin, TGFα, amphiregulin, or ErbB3, or BRK, CD9, MMP9, or Lott at levels above the $90^{th}$ percentile predisposes to response to EGFR antagonists. Epiregulin gene expression, in particular, is a good surrogate marker for EGFR activation, and can be used to not only to predict response to EGFR antagonists, but also to monitor response to EGFR antagonists [taking fine needle biopsies to provide tumor tissue during treatment]. Levels of CD82 above the $90^{th}$ percentile suggest poorer efficacy from EGFR antagonists.

The tyrosine kinases abl, c-kit, PDGFRalpha, PDGFbeta, and ARG; also, the signal transmitting ligands c-kit ligand, PDGFA, B, C and D. The listed tyrosine kinases are all targets of the drug Gleevec™ (imatinib mesylate, Novartis), and the listed ligands stimulate one or more of the listed tyrosine kinases. In the two indications for which Gleevec™ is approved, tyrosine kinase targets (bcr-abl and ckit) are over-expressed and also contain activating mutations. A finding that one of the Gleevec™ target tyrosine kinase targets is expressed in breast cancer tissue will prompt a second stage of analysis wherein the gene will be sequenced to determine whether it is mutated. That a mutation found is an activating mutation can be proved by methods known in the art, such as, for example, by measuring kinase enzyme activity or by measuring phosphorylation status of the particular kinase, relative to the corresponding wild-type kinase. Breast cancer patients whose tumors express high levels of mRNAs encoding Gleevec™ target tyrosine kinases, specifically, in the upper ten percentile, or mRNAs for Gleevec™ target tyrosine kinases in the average range and mRNAs for their cognate growth stimulating ligands in the upper ten percentile, are particularly good candidates for treatment with Gleevec™.

VEGF is a potent and pathologically important angiogenic factor. (See below under Prognostic Indicators.) When VEGF mRNA levels are in the upper ten percentile, aggressive treatment is warranted. Such levels particularly suggest the value of treatment with anti-angiogenic drugs, including VEGF antagonists, such as anti-VEGF antibodies. Additionally, KDR or CD31 mRNA level in the upper 20 percentile further increases likelihood of benefit from VEGF antagonists.

Famesyl pyrophosphatase synthetase and geranyl geranyl pyrophosphatase synthetase. These enzymes are targets of commercialized bisphosphonate drugs, which were developed originally for treatment of osteoporosis but recently have begun to prescribe them off-label in breast cancer. Elevated levels of mRNAs encoding these enzymes in breast cancer tissue, above the $90^{th}$ percentile, suggest use of bisphosphonates as a treatment option.

2. Multidrug Resistance Factors

These factors include 10 Genes: gamma glutamyl cysteine synthetase [GCS]; GST-α; GST-π; MDR-1; MRP1-4; breast cancer resistance protein [BCRP]; lung resistance protein [MVP]; SXR; YB-1.

GCS and both GST-α: and GST-π regulate glutathione levels, which decrease cellular sensitivity to chemotherapeutic drugs and other toxins by reductive derivatization. Glutathione is a necessary cofactor for multi-drug resistant pumps, MDR-1 and the MRPs. MDR1 and MRPs function to actively transport out of cells several important chemotherapeutic drugs used in breast cancer.

GSTs, MDR-1, and MRP-1 have all been studied extensively to determine possible have prognostic or predictive significance in human cancer. However, a great deal of disagreement exists in the literature with respect to these questions. Recently, new members of the MRP family have been identified: MRP-2, MRP-3, MRP-4, BCRP, and lung resistance protein [major vault protein]. These have substrate specificities that overlap with those of MDR-1 and MRP-1. The incorporation of all of these relevant ABC family members as well as glutathione synthetic enzymes into the present invention captures the contribution of this family to drug resistance, in a way that single or double analyte assays cannot.

MRP-1, the gene coding for the multidrug resistance protein.

P-glycoprotein, is not regulated primarily at the transcriptional level. However, p-glycoprotein stimulates the transcription of PTP1b. An embodiment of the present invention is the use of the level of the mRNA for the phosphatase PTP1b as a surrogate measure of MRP-1/p-glycoprotein activity.

The gene SXR is also an activator of multidrug resistance, as it stimulates transcription of certain multidrug resistance factors.

The impact of multidrug resistance factors with respect to chemotherapeutic agents used in breast cancer is as follows. Beneficial response to doxorubicin is compromised when the MRNA levels of either MDR1, GSTα, GSTπ, SXR, BCRP YB-1, or LRP/MVP are in the upper four percentile. Beneficial response to methotrexate is inhibited if mRNA levels of any of MRP1, MRP2, MkP3, or MRP4 or gamma-glutamyl cysteine synthetase are in the upper four percentile.

3. Eukarvotic Translation Initiation Factor 4E [EIF4E]

EIF4E mRNA levels provides evidence of protein expression and so expands the capability of RT-PCR to indicate variation in gene expression. Thus, one claim of the present invention is the use of EIF4E as an added indicator of gene expression of certain genes [e.g., cyclinD1, mdm2, VEGF, and others]. For example, in two tissue specimens containing the same amount of normalized VEGF mRNA, it is likely that the tissue containing the higher normalized level of EIF4E exhibits the greater level of VEGF gene expression.

The background is as follows. A key point in the regulation of MRNA translation is selection of mRNAs by the EIF4G complex to bind to the 43S ribosomal subunit. The protein EIF4E [the m7G CAP-binding protein] is often limiting because more mRNAs than EIF4E copies exist in cells. Highly structured 5'UTRs or highly GC-rich ones are inefficiently translated, and these often code for genes that carry out functions relevant to cancer [e.g., cyclinD1, mdm2, and VEGF]. EIF4E is itself regulated at the transcriptional/mRNA level. Thus, expression of EIF4E provides added indication of increased activity of a number of proteins.

It is also noteworthy that overexpression of EIF4E transforms cultured cells, and hence is an oncogene. Overexpression of EIF4E occurs in several different types of carcinomas but is particularly significant in breast cancer. EIF4E is typically expressed at very low levels in normal breast tissue.

D. Prognostic Indicators

1. DNA Repair Enzymes

Loss of BRCA1 or BRCA2 activity via mutation represents the critical oncogenic step in the most common type[s] of familial breast cancer. The levels of mRNAs of these important enzymes are abnormal in subsets of sporadic breast cancer as well. Loss of signals from either [to within the lower ten percentile] heightens risk of short survival.

2. Cell Cycle Regulators

Cell cycle regulators include 14 genes: c-MYC; c-Src; Cyclin D1; Ha-Ras; mdm2; pl4ARF; p21WAF1/CIP; p16INK4a/p14; p23; p27; p53; PI3K; PKC-epsilon; PKC-delta.

The gene for p53 [TP53] is mutated in a large fraction of breast cancers. Frequently p53 levels are elevated when loss of function mutation occurs. When the mutation is dominant-negative, it creates survival value for the cancer cell because growth is promoted and apoptosis is inhibited. Thousands of different p53 mutations have been found in human cancer, and the functional consequences of many of them are not clear. A large body of academic literature addresses the prognostic and predictive significance of mutated p53 and the results are highly conflicting. The present invention provides a functional genomic measure of p53 activity, as follows. The activated wild type p53 molecule triggers transcription of the cell cycle inhibitor p21. Thus, the ratio of p53 to p21 should be low when p53 is wild-type and activated. When p53 is detectable and the ratio of p53 to p21 is elevated in tumors relative to normal breast, it signifies nonfunctional or dominant negative p53. The cancer literature provides evidence for this as born out by poor prognosis.

Mdm2 is an important p53 regulator. Activated wildtype p53 stimulates transcription of mdm2. The mdm2 protein binds p53 and promotes its proteolytic destruction. Thus, abnormally low levels of mdm2 in the presence of normal or higher levels of p53 indicate that p53 is mutated and inactivated.

One aspect of the present invention is the use of ratios of mRNAs levels p53:p21 and p53:mdm2 to provide a picture of p53 status. Evidence for dominant negative mutation of p53 (as indicated by high p53:p21 and/or high p53:mdm2 mRNA ratios—specifically in the upper ten percentile) presages higher risk of recurrence in breast cancer and therefore weights toward a decision to use chemotherapy in node negative post surgery breast cancer.

Another important cell cycle regulator is p27, which in the activated form blocks cell cycle progression at the level of cdk4. The protein is regulated primarily via phosphorylation/dephosphorylation, rather than at the transcriptional level. However, levels of p27 mRNAs do vary. Therefore a level of p27 mRNA in the upper ten percentile indicates reduced risk of recurrence of breast cancer post surgery.

Cyclin D1 is a principle positive regulator of entry into S phase of the cell cycle. The gene for cyclin D1 is amplified in about 20% of breast cancer patients, and therefore promotes tumor promotes tumor growth in those cases. One aspect of the present invention is use of cyclin D1 mRNA levels for diagnostic purposes in breast cancer. A level of cyclin D1 mRNA in the upper ten percentile suggests high risk of recurrence in breast cancer following surgery and suggests particular benefit of adjuvant chemotherapy.

3. Other Tumor Suppressors and Related Proteins

These include APC and E-cadherin. It has long been known that the tumor suppressor APC is lost in about 50% of colon cancers, with concomitant transcriptional upregulation of E-cadherin, an important cell adhesion molecule and growth suppressor. Recently, it has been found that the APC gene silenced in 15-40% of breast cancers. Likewise, the E-cadherin gene is silenced [via CpG island methylation] in about 30% of breast cancers. An abnormally low level of APC and/or E-cadherin mRNA in the lower 5 percentile suggests high risk of recurrence in breast cancer following surgery and heightened risk of shortened survival.

4. Regulators of Apotosis

These include BC1/BAX family members BC12, Bc1-x1, Bak, Bax and related factors, NFκ-B and related factors, and also p53BP1/ASPP1 and p53BP2/ASPP2.

Bax and Bak are pro-apoptotic and BC12 and Bc1-x1 are anti-apoptotic. Therefore, the ratios of these factors influence the resistance or sensitivity of a cell to toxic (pro-apoptotic) drugs. In breast cancer, unlike other cancers, elevated level of BC12 (in the upper ten percentile) correlates with good outcome. This reflects the fact that BC12 has growth inhibitory activity as well as anti-apoptotic activity, and in breast cancer the significance of the former activity outweighs the significance of the latter. The impact of BC12 is in turn dependent on the status of the growth stimulating transcription factor c-MYC. The gene for c-MYC is amplified in about 20% of breast cancers. When c-MYC message levels are abnormally elevated relative to BC12 (such that this ratio is in the upper ten percentile), then elevated level of BC12 mRNA is no longer a positive indicator.

NFκ-B is another important anti-apoptotic factor. Originally, recognized as a pro-inflammatory transcription factor, it is now clear that it prevents programmed cell death in response to several extracellular toxic factors [such as tumor necrosis factor]. The activity of this transcription factor is regulated principally via phosphorylation/dephosphorylation events. However, levels of NFκ-B nevertheless do vary from cell to cell, and elevated levels should correlate with increased resistance to apoptosis. Importantly for present purposes, NFκ-B, exerts its anti-apoptotic activity largely through its stimulation of transcription of mRNAs encoding certain members of the IAP [inhibitor of apoptosis] family of proteins, specifically cIAP1, cIAP2, XIAP, and Survivin. Thus, abnormally elevated levels of mRNAs for these IAPs and for NFκ-B any in the upper 5 percentile] signify activation of the NFκ-B anti-apoptotic pathway. This suggests high risk of recurrence in breast cancer following chemotherapy and therefore poor prognosis. One embodiment of the present invention is the inclusion in the gene set of the above apoptotic regulators, and the above-outlined use of combinations and ratios of the levels of their mRNAs for prognosis in breast cancer.

The proteins p53BP1 and 2 bind to p53 and promote transcriptional activation of pro-apoptotic genes. The levels of p53BP1 and 2 are suppressed in a significant fraction of breast cancers, correlating with poor prognosis. When either is expressed in the lower tenth percentile poor prognosis is indicated.

5. Factors that Control Cell Invasion and Aniiozenesis

These include uPA, PAI1, cathepsinsB, G and L, scatter factor [HGF], c-met, KDR, VEGF, and CD31. The plasminogen activator uPA and its serpin regulator PAI1 promote breakdown of extracellular matrices and tumor cell invasion. Abnormally elevated levels of both mRNAs in malignant breast tumors (in the upper twenty percentile) signify an increased risk of shortened survival, increased recurrence in breast cancer patients post surgery, and increased importance of receiving adjuvant chemotherapy. On the other hand, node negative patients whose tumors do not express elevated levels of these mRNA species are less likely to have recurrence of this cancer and could more seriously consider whether the benefits of standard chemotherapy justifies the associated toxicity.

Cathepsins B or L, when expressed in the upper ten percentile, predict poor disease-free and overall survival. In particular, cathepsin L predicts short survival in node positive patients.

Scatter factor and its cognate receptor c-met promote cell motility and invasion, cell growth, and angiogenesis. In breast cancer elevated levels of mRNAs encoding these factors should prompt aggressive treatment with chemotherapeutic drugs, when expression of either, or the combination, is above the $90^{th}$ percentile.

VEGF is a central positive regulator of angiogenesis, and elevated levels in solid tumors predict short survival [note many references showing that elevated level of VEGF predicts short survival]. Inhibitors of VEGF therefore slow the growth of solid tumors in animals and humans. VEGF activity is controlled at the level of transcription. VEGF MRNA levels in the upper ten percentile indicate significantly worse than average prognosis. Other markers of vascularization, CD31 [PECAM], and KDR indicate high vessel density in tumors and that the tumor will be particularly malignant and aggressive, and hence that an aggressive therapeutic strategy is warranted.

6. Markers for Immune and Inflammatorv Cells and Processes

These markers include the genes for Immunoglobulin light chain λ, CD18, CD3, CD68, Fas [CD95], and Fas Ligand.

Several lines of evidence suggest that the mechanisms of action of certain drugs used in breast cancer entail activation of the host immune/inflammatory response (For example, Herceptin®). One aspect of the present invention is the inclusion in the gene set of markers for inflammatory and immune cells, and markers that predict tumor resistance to immune surveillance. Immunoglobulin light chain lambda is a marker for immunoglobulin producing cells. CD18 is a marker for all white cells. CD3 is a marker for T-cells. CD68 is a marker for macrophages.

CD95 and Fas ligand are a receptor: ligand pair that mediate one of two major pathways by which cytotoxic T cells and NK cells kill targeted cells. Decreased expression of CD95 and increased expression of Fas Ligand indicates poor prognosis in breast cancer. Both CD95 and Fas Ligand are transmembrane proteins, and need to be membrane anchored to trigger cell death. Certain tumor cells produce a truncated soluble variant of CD95, created as a result of alternative splicing of the CD95 MRNA. This blocks NK cell and cytotoxic T cell Fas Ligand-mediated killing of the tumors cells. Presence of soluble CD95 correlates with poor survival in breast cancer. The gene set includes both soluble and full-length variants of CD95.

7. Cell Proliferation Markers

The gene set includes the cell proliferation markers Ki67/MiB1, PCNA, Pin1, and thymidine kinase. High levels of expression of proliferation markers associate with high histologic grade, and short survival. High levels of thy idine kinase in the upper ten percentile suggest in creased risk of short survival. Pin1 is a prolyl isomerase that stimulates cell growth, in part through the transcriptional activation of the cyclin D1 gene, and levels in the upper ten percentile contribute to a negative prognostic profile.

8. Other Growth Factors and Receptors

This gene set includes IGF1, IGF2, IGFBP3, IGF1R, FGF2, FGFRI, CSF-1R/fms, CSF-1, L6 and IL8. All of these proteins are expressed in breast cancer. Most stimulate tumor growth. However, expression of the growth factor FGF2 correlates with good outcome. Some have anti-apoptotic activity, prominently IGF1. Activation of the IGF1 axis via elevated IGF1, IGF1R, or IGFBP3 (as indicated by the sum of these signals in the upper ten percentile) inhibits tumor cell death and strongly contributes to a poor prognostic profile.

9. Gene Expression Markers that Define Subclasses of Breast Cancer

These include: GRO1 oncogene alpha, Grb7, cytokeratins 5 and 17, retinal binding protein 4, hepatocyte nuclear factor 3, integrin alpha 7, and lipoprotein lipase. These markers subset breast cancer into different cell types that are phenotypically different at the level of gene expression. Tumors expressing signals for Bcl2, hepatocyte nuclear factor 3, LIV1 and ER above the mean have the best prognosis for disease free and overall survival following surgical removal of the cancer. Another category of breast cancer tumor type, characterized by elevated expression of lipoprotein lipase, retinol binding protein 4, and integrin α7, carry intermediate prognosis. Tumors expressing either elevated levels of cytokeratins 5, and 17, GRO oncogene at levels four-fold or greater above the mean, or ErbB2 and Grb7 at levels ten-fold or more above the mean, have worst prognosis.

Although throughout the present description, including the Examples below, various aspects of the invention are explained with reference to gene expression studies, the invention can be performed in a similar manner, and similar results can be reached by applying proteomics techniques that are well known in the art. The proteome is the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry and/or N-terminal sequencing, and (3) analysis of the data using bioinformatics. Proteomics methods are valuable supplements to other methods of gene expression profiling, and can be used, alone or in combination with other methods of the present invention, to detect the products of the gene markers of the present invention.

Further details of the invention will be described in the following non-limiting Examples.

EXAMPLE 1

Isolation of RNA from Formalin-fixed, Paraffin-embedded (FPET) Tissue Specimens A. Protocols I. EPICENTRE(® Xylene Protocol RNA Isolation (1) Cut 1-6 sections (each 10 μm thick) of paraffin-embedded tissue per sample using a clean microtome blade and place into a 1.5 ml eppendorf tube.

(2) To extract paraffin, add 1 ml of xylene and invert the tubes for 10 minutes by rocking on a nutator.

(3) Pellet the sections by centrifugation for 10 minutes at 14,000×g in an eppendorf microcentrifuge.

(4) Remove the xylene, leaving some in the bottom to avoid dislodging the pellet.

(5) Repeat steps 2-4.

(6) Add 1 ml of 100% ethanol and invert for 3 minutes by rocking on the nutator.

(7) Pellet the debris by centrifugation for 10 minutes at 14,000×g in an eppendorf microcentrifuge.

(8) Remove the ethanol, leaving some at the bottom to avoid the pellet.

(9) Repeat steps 6-8 twice.

(10) Remove all of the remaining ethanol.

(11) For each sample, add 2 μl of 50 μg/μl Proteinase K to 300 μl of Tissue and Cell Lysis Solution.

(12) Add 300 μl of Tissue and Cell Lysis Solution containing the Proteinase K to each sample and mix thoroughly.

(13) Incubate at 65° C. for 90 minutes (vortex mixing every 5 minutes). Visually monitor the remaining tissue fragment. If still visible after 30 minutes, add an additional 2 μl of 50 μg/μl Proteinase K and continue incubating at 65° C. until fragment dissolves.

(14) Place the samples on ice for 3-5 minutes and proceed with protein removal and total nucleic acid precipitation.

Protein Removal and Precipitation of Total Nucleic Acid (1) Add 150 μl of MPC Protein Precipitation Reagent to each lysed sample and vortex vigorously for 10 seconds.

(2) Pellet the-debris by centrifugation for 10 minutes at 14,000×g in an eppendorf microcentrifuge.

(3) Transfer the supernatant into clean eppendorf tubes and discard the pellet.

(4) Add 500 μl of isopropanol to the recovered supernatant and thoroughly mix by rocking on the nutator for 3 minutes.

(5) Pellet the RNA/DNA by centrifugation at 4° C. for 10 minutes at 14,000×g in an eppendorf microcentrifuge.

(6) Remove all of the isopropanol with a pipet, being careful not to dislodge the pellet.

Removal of Contaminating DNA from RNA Preparations (1) Prepare 200 μl of DNase I solution for each sample by adding 5 μl RNase-Free DNase I (I U/μl) to 195 μl of 1X DNase Buffer.

(2) Completely resuspended the pelleted RNA in 200 μl of DNase I solution by vortexing.

(3) Incubate the samples at 37° C. for 60 minutes.

(4) Add 200 μl of 2X T and C Lysis Solution to each sample and vortex for 5 seconds.

(5) Add 200 μl of MPC Protein Precipitation Reagent, mix by vortexing for 10 seconds and place on ice for 3-5 minutes.

(6) Pellet the debris by centrifugation for 10 minutes at 14,000×g in an eppendorf microcentrifuge.

(7) Transfer the supernatant -containing the RNA to clean eppendorf tubes and discard the pellet. (Be careful to avoid transferring the pellet.)

(8) Add 500 μl of isopropanol to each supernatant and rock samples on the nutator for 3 minutes.

(9) Pellet the RNA by centrifugation at 4° C. for 10 minutes at 14,000×g in an eppendorf microcentrifuge.

(10) Remove the isopropanol, leaving some at the bottom to avoid dislodging the pellet.

(11) Rinse twice with 1 ml of 75% ethanol. Centrifuge briefly if the RNA pellet is dislodged.

(12) Remove ethanol carefully.

(13) Set under fume hood for about 3 minutes to remove residual ethanol.

(14) Resuspended the RNA in 30 μl of TE Buffer and store at −30° C.

II. Hot Wax/Urea Protocol of the Invention

RNA Isolation (1) Cut 3 sections (each 10 μm thick) of paraffin-embedded tissue using a clean microtome blade and place into a 1.5 ml eppendorf tube.

(2) Add 300 μl of lysis buffer (10 mM Tris 7.5, 0.5% sodium lauroyl sarcosine, 0.1 mM EDTA pH 7.5, 4M Urea) containing 330 μg/ml Proteinase K (added freshly from a 50 μg/μl stock solution) and vortex briefly.

(3) Incubate at 65° C. for 90 minutes (vortex mixing every 5 minutes). Visually monitor the tissue fragment. If still visible after 30 minutes, add an additional 2 μl of 50 μg/μl Proteinase K and continue incubating at 65° C. until fragment dissolves.

(4) Centrifuge for 5 minutes at 14,000×g and transfer upper aqueous phase to new tube, being careful not to disrupt the paraffin seal.

(5) Place the samples on ice for 3-5 minutes and proceed with protein removal and total nucleic acid precipitation.

Protein Removal and Precipitation of Total Nucleic Acid (1) Add 150 μl of 7.5M $NH_4OAc$ to each lysed sample and vortex vigorously for 10 seconds.

(2) Pellet the debris by centrifugation for 10 minutes at 14,000×g in an eppendorf microcentrifuge.

(3) Transfer the supernatant into clean eppendorf tubes and discard the pellet.

(4) Add 500 μl of isopropanol to the recovered supernatant and thoroughly mix by rocking on the nutator for 3 minutes.

(5) Pellet the RNA/DNA by centrifugation at 4° C. for 10 minutes at 14,000×g in an eppendorf microcentrifuge.

(6) Remove all of the isopropanol with a pipet, being careful not to dislodge the pellet.

Removal of Contaminating DNA from RNA Preparations (1) Add 45 μl of 1× DNase I buffer (10 mM Tris-Cl, pH 7,5, 2.5 mM $MgCl_2$, 0.1 mM $CaCl_2$) and 5 μl of RNase-Free DNase I (2U/μl, Ambion) to each sample.

(2) Incubate the samples at 37° C. for 60 minutes. Inactivate the DNaseI by heating at 70° C. for 5 minutes.

B. Results

Experimental evidence demonstrates that the hot RNA extraction protocol of the invention does not compromise RNA yield. Using 19 FPE breast cancer specimens, extracting RNA from three adjacent sections in the same specimens, RNA yields were measured via capillary electrophoresis with fluorescence detection (Agilent Bioanalyzer). Average RNA yields in nanograms and standard deviations with the invented and commercial methods, respectively, were: 139+/−21 versus 141+/−34.

Also, it was found that the urea-containing lysis buffer of the present invention can be substituted for the EPICENTRE® T&C lysis buffer, and the 7.5 M $NH_4OAc$ reagent used for protein precipitation in accordance with the present invention can be substituted for the EPICENTRE® MPC protein precipitation solution with neither significant compromise of RNA yield nor TaqMan® efficiency.

EXAMPLE 2

Amplification of mRNA Species Prior to RT-PCR

The method described in section 10 above was used with RNA isolated from fixed, paraffin-embedded breast cancer tissue. TaqMan® analyses were performed with first strand cDNA generated with the T7-GSP primer (unamplified (T7-GSPr)), T7 amplified RNA (amplified (T7-GSPr)). RNA was amplified according to step 2 of FIG. 4. As a control, TaqMang® was also performed with CDNA generated with an unmodified GSPr (amplified (GSPr)). An equivalent amount of initial template (1 ng/well) was used in each TaqMan(® reaction.

Figure 8:
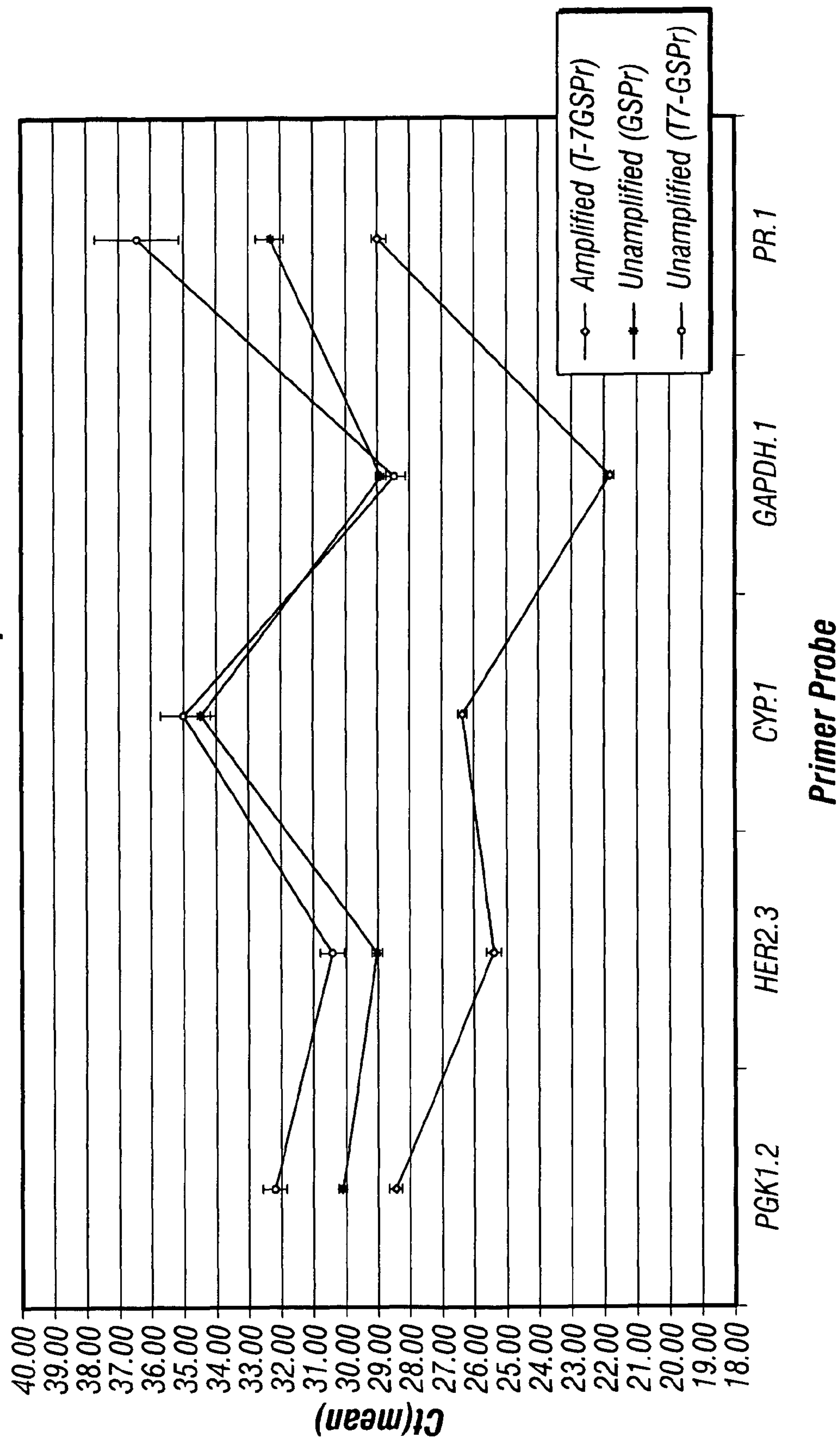
FIG. 8 shows results from an IVT/RT-PCR experiment.

The results are shown in FIG. 8. In vitro transcription increased RT-PCR signal intensity by more than 10 fold, and for certain genes by more than 100 fold relative to controls in which the RT-PCR primers were the same primers used in method 2 for the generation of double-stranded DNA for in vitro transcription (GSP-$T7_r$ and $GSP_f$). Also shown in FIG. 8 are RT-PCR data generated when standard optimized RT-PCR primers (i.e., lacking T7 tails) were used. As shown, compared to this control, the new method yielded substantial increases in RT-PCR signal (from 4 to 64 fold in this experiment).

The new method requires that each T7-GSP sequence be optimized so that the increase in the RT-PCR signal is the same for each gene, relative to the standard optimized RT-PCR (with non-T7 tailed primers).

EXAMPLE 3

A Study of Gene Expression in Premalignant and Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival. A further objective of the study was to compare the molecular profiles in tissue samples of invasive breast cancer with the molecular profiles obtained in ductal carcinoma in situ. The study was further designed to obtain data on the molecular profiles in lobular carcinoma in situ and in paraffin-embedded, fixed tissue samples of invasive lobular carcinoma.

Molecular assays were performed on paraffin-embedded, formalin-fixed primary breast tumor tissues obtained from 202 individual patients diagnosed with breast cancer. All patients underwent surgery with diagnosis of invasive ductal carcinoma of the breast, pure ductal carcinoma in situ (DCIS), lobular carcinoma of the breast, or pure lobular carcinoma in situ (LCIS). Patients were included in the study only if histopathologic assessment, performed as described in the Materials and Methods section, indicated adequate amounts of tumor tissue and homogeneous pathology.

The individuals participating in the study were divided into the following groups:

Group 1 : Pure ductal carcinoma in situ (DCIS); n=18

Group 2 : Invasive ductal carcinoma n=130

Group 3 : Pure lobular carcinoma in situ (LCIS); n=7

Group 4 : Invasive lobular carcinoma n=16

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, all tumor blocks were subjected to the same characterization, as described above, and the block most representative of the pathology was used for analysis.

Gene Expression Analysis mRNA was extracted and purified from fixed, paraffin-embedded tissue samples, and prepared for gene expression analysis as described in chapters 7-11 above. Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 185 cancer-related genes and 7 reference genes. The threshold cycle (CT) values for each patient were normalized based on the median of all genes for that particular patient. Clinical outcome data were available for all patients from a review of registry data and selected patient charts. Outcomes were classified as:

0 died due to breast cancer or to unknown cause or alive with breast cancer recurrence;

1 alive without breast cancer recurrence or died due to a cause other than breast cancer Analysis was Performed by:

1. Analysis of the relationship between normalized gene expression and the binary outcomes of 0 or 1.
2. Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

Analysis of 147 Patients with Invasive Breast Carcinoma by Binary Approach

In the first (binary) approach, analysis was performed on all 146 patients with invasive breast carcinoma. At test was performed on the group of patients classified as 0 or 1 and the p-values for the differences between the groups for each gene were calculated.

The following Table 4 lists the 45 genes for which the p-value for the differences between the groups was <0.05.

TABLE 4

| Gene/ SEQ ID NO: | Mean CT Alive | Mean CT Deceased | t-value | Degrees of freedom | p |
|---|---|---|---|---|---|
| FOXM1 | 33.66 | 32.52 | 3.92 | 144 | 0.0001 |
| PRAME | 35.45 | 33.84 | 3.71 | 144 | 0.0003 |
| Bcl2 | 28.52 | 29.32 | −3.53 | 144 | 0.0006 |
| STK15 | 30.82 | 30.10 | 3.49 | 144 | 0.0006 |
| CEGP1 | 29.12 | 30.86 | −3.39 | 144 | 0.0009 |
| Ki-67 | 30.57 | 29.62 | 3.34 | 144 | 0.0011 |
| GSTM1 | 30.62 | 31.63 | −3.27 | 144 | 0.0014 |
| CA9 | 34.96 | 33.54 | 3.18 | 144 | 0.0018 |
| PR | 29.56 | 31.22 | −3.16 | 144 | 0.0019 |
| BBC3 | 31.54 | 32.10 | −3.10 | 144 | 0.0023 |
| NME1 | 27.31 | 26.68 | 3.04 | 144 | 0.0028 |
| SURV | 31.64 | 30.68 | 2.92 | 144 | 0.0041 |
| GATA3 | 26.06 | 26.99 | −2.91 | 144 | 0.0042 |
| TFRC | 28.96 | 28.48 | 2.87 | 144 | 0.0047 |
| YB-1 | 26.72 | 26.41 | 2.79 | 144 | 0.0060 |
| DPYD | 28.51 | 28.84 | −2.67 | 144 | 0.0084 |
| GSTM3 | 28.21 | 29.03 | −2.63 | 144 | 0.0095 |
| RPS6KB1 | 31.18 | 30.61 | 2.61 | 144 | 0.0099 |
| Src | 27.97 | 27.69 | 2.59 | 144 | 0.0105 |
| Chk1 | 32.63 | 31.99 | 2.57 | 144 | 0.0113 |
| ID1 | 28.73 | 29.13 | −2.48 | 144 | 0.0141 |
| ESR1 | 24.22 | 25.40 | −2.44 | 144 | 0.0160 |
| p27 | 27.15 | 27.51 | −2.41 | 144 | 0.0174 |
| CCNB1 | 31.63 | 30.87 | 2.40 | 144 | 0.0176 |
| XIAP | 30.27 | 30.51 | −2.40 | 144 | 0.0178 |
| Chk2 | 31.48 | 31.11 | 2.39 | 144 | 0.0179 |
| CDC25B | 29.75 | 29.39 | 2.37 | 144 | 0.0193 |
| IGF1R | 28.85 | 29.44 | −2.34 | 144 | 0.0209 |
| AK055699 | 33.23 | 34.11 | −2.28 | 144 | 0.0242 |
| PI3KC2A | 31.07 | 31.42 | −2.25 | 144 | 0.0257 |
| TGFB3 | 28.42 | 28.85 | −2.25 | 144 | 0.0258 |
| BAGI1 | 28.40 | 28.75 | −2.24 | 144 | 0.0269 |
| CYP3A4 | 35.70 | 35.32 | 2.17 | 144 | 0.0317 |
| EpCAM | 28.73 | 28.34 | 2.16 | 144 | 0.0321 |
| VEGFC | 32.28 | 31.82 | 2.16 | 144 | 0.0326 |
| pS2 | 28.96 | 30.60 | −2.14 | 144 | 0.0341 |
| hENT1 | 27.19 | 26.91 | 2.12 | 144 | 0.0357 |
| WISP1 | 31.20 | 31.64 | −2.10 | 144 | 0.0377 |
| HNF3A | 27.89 | 28.64 | −2.09 | 144 | 0.0384 |
| NFKBp65 | 33.22 | 33.80 | −2.08 | 144 | 0.0396 |
| BRCA2 | 33.06 | 32.62 | 2.08 | 144 | 0.0397 |
| EGFR | 30.68 | 30.13 | 2.06 | 144 | 0.0414 |
| TK1 | 32.27 | 31.72 | 2.02 | 144 | 0.0453 |
| VDR | 30.08 | 29.73 | 1.99 | 144 | 0.0488 |

In the foregoing Table 4, lower (negative) t-values indicate higher expression (or lower CTs), associated with better outcomes, and, inversely, higher (positive) t-values indicate higher expression (lower CTs) associated with worse outcomes. Thus, for example, elevated expression of the FOXM1 gene (t-value=3.92, CT mean alive>CT mean deceased) indicates a reduced likelihood of disease free survival. Similarly, elevated expression of the CEGP1 gene (t-value =−3.39; CT mean alive<CT mean deceased) indicates an increased likelihood of disease free survival.

Based on the data set forth in Table 4, the overexpression of any of the following genes in breast cancer indicates a reduced likelihood of survival without cancer recurrence following surgery: FOXM1; PRAME; SKT15, Ki-67; CA9; NME1; SURV; TFRC; YB-1; RPS6KB1; Src; Chk1; CCNB1; Chk2; CDC25B; CYP3A4; EpCAM; VEGFC; hENT1; BRCA2; EGFR; TK1; VDR.

Based on the data set forth in Table 4, the overexpression of any of the following genes in breast cancer indicates a better prognosis for survival without cancer recurrence following surgery: Blc12; CEGP1; GSTM1; PR; BBC3; GATA3; DPYD; GSTM3; ID1; ESR1; p27; XIAP; IGF1R; AK055699; P13KC2A; TGFB3; BAGI1; pS2; WISP1; HNF3A; NFKBp65.

Analysis of 108 ER positive patient by binary approach 108 patients with normalized CT for estrogen receptor (ER) <25.2 (i.e., ER positive patients) were subjected to separate analysis. A t test was performed on the groups of patients classified as 0 or 1 and the p-values for the differences between the groups for each gene were calculated. The following Table 5 lists the 12 genes where the p-value for the differences between the groups was <0.05.

TABLE 5

| Gene/ SEQ ID NO: | Mean CT Alive | Mean CT Deceased | t-value | Degrees of freedom | p |
|---|---|---|---|---|---|
| PRAME | 35.54 | 33.88 | 3.03 | 106 | 0.0031 |
| Bcl2 | 28.24 | 28.87 | −2.70 | 106 | 0.0082 |
| FOXM1 | 33.82 | 32.85 | 2.66 | 106 | 0.089 |
| DIABLO | 30.33 | 30.71 | −2.47 | 106 | 0.0153 |
| EPHX1 | 28.62 | 28.03 | 2.44 | 106 | 0.0163 |
| HIF1A | 29.37 | 28.88 | 2.40 | 106 | 0.0180 |
| VEGFC | 32.39 | 31.69 | 2.39 | 106 | 0.0187 |
| Ki-67 | 30.73 | 29.82 | 2.38 | 106 | 0.0191 |
| IGF1R | 28.60 | 29.18 | −2.37 | 106 | 0.0194 |
| VDR | 30.14 | 29.60 | 2.17 | 106 | 0.0322 |
| NME1 | 27.34 | 26.80 | 2.03 | 106 | 0.0452 |
| GSTM3 | 28.08 | 28.92 | −2.00 | 106 | 0.0485 |

For each gene, a classification algorithm was utilized to identify the best threshold value (CT) for using each gene alone in predicting clinical outcome.

Based on the data set forth in Table 5, overexpression of the following genes in ER-positive cancer is indicative of a reduced likelihood of survival without cancer recurrence following surgery: PRAME; FOXM1; EPHX1; HIF1A; VEGFC; Ki-67; VDR; NME1. Some of these genes (PRAME; FOXM1; VEGFC; Ki-67; VDR; and NME1) were also identified as indicators of poor prognosis in the previous analysis, not limited to ER-positive breast cancer. The overexpression of the remaining genes (EPHX1 and HIF1A) appears to be negative indicator of disease free survival in ER-positive breast cancer only. Based on the data set forth in Table 5, overexpression of the following genes in ER-positive cancer is indicative of a better prognosis for survival without cancer recurrence following surgery: Bcl-2; DIABLO; IGF1R; GSTM3. Of the latter genes, Bcl-2; IGFR1; and GSTM3 have also been identified as indicators of good prognosis in the previous analysis, not limited to ER-positive breast cancer. The overexpression of DIABLO appears to be positive indicator of disease free survival in ER-positive breast cancer only.

Analysis of Multiple Genes and Indicators of Outcome

Two approaches were taken in order to determine whether using multiple genes would provide better discrimination between outcomes.

First, a discrimination analysis was performed using a forward stepwise approach. Models were generated that classified outcome with greater discrimination than was obtained with any single gene alone.

According to a second approach (time-to-event approach), for each gene a Cox Proportional Hazards model (see, e.g. Cox, D. R., and Oakes, D. (1984), *Analysis of Survival Data*, Chapman and Hall, London, N.Y.) was defined with time to recurrence or death as the dependent variable, and the expression level of the gene as the independent variable. The genes that have a p-value<0.05 in the Cox model were identified. For each gene, the Cox model provides the relative risk (RR) of recurrence or death for a unit change in the expression of the gene. One can choose to partition the patients into subgroups at any threshold value of the measured expression (on the CT scale), where all patients with expression values above the threshold have higher risk, and all patients with expression values below the threshold have lower risk, or vice versa, depending on whether the gene is an indicator of good (RR>1.01) or poor (RR<1.01) prognosis. Thus, any threshold value will define subgroups of patients with respectively increased or decreased risk. The results are summarized in the following Tables 6 and 7.

TABLE 6

Cox Model Results for 146 Patients with Invasive Breast Cancer

| Gene | Relative Risk (RR) | SE Relative Risk | p value |
|---|---|---|---|
| FOXM1 | 0.58 | 0.15 | 0.0002 |
| STK15 | 0.51 | 0.20 | 0.0006 |
| PRAME | 0.78 | 0.07 | 0.0007 |
| Bcl2 | 1.66 | 0.15 | 0.0009 |
| CEGP1 | 1.25 | 0.07 | 0.0014 |
| GSTM1 | 1.40 | 0.11 | 0.0014 |
| Ki67 | 0.62 | 0.15 | 0.0016 |
| PR | 1.23 | 0.07 | 0.0017 |
| Contig51037 | 0.81 | 0.07 | 0.0022 |
| NME1 | 0.64 | 0.15 | 0.0023 |
| YB-1 | 0.39 | 0.32 | 0.0033 |
| TFRC | 0.53 | 0.21 | 0.0035 |
| BBC3 | 1.72 | 0.19 | 0.0036 |
| GATA3 | 1.32 | 0.10 | 0.0039 |
| CA9 | 0.81 | 0.07 | 0.0049 |
| SURV | 0.69 | 0.13 | 0.0049 |
| DPYD | 2.58 | 0.34 | 0.0052 |
| RPS6KB1 | 0.60 | 0.18 | 0.0055 |
| GSTM3 | 1.36 | 0.12 | 0.0078 |
| Src.2 | 0.39 | 0.36 | 0.0094 |
| TGFB3 | 1.61 | 0.19 | 0.0109 |
| CDC25B | 0.54 | 0.25 | 0.0122 |
| XIAP | 3.20 | 0.47 | 0.0126 |
| CCNB1 | 0.68 | 0.16 | 0.0151 |
| IGF1R | 1.42 | 0.15 | 0.0153 |
| Chk1 | 0.68 | 0.16 | 0.0155 |
| ID1 | 1.80 | 0.25 | 0.0164 |
| p27 | 1.69 | 0.22 | 0.0168 |
| Chk2 | 0.52 | 0.27 | 0.0175 |
| ESR1 | 1.17 | 0.07 | 0.0196 |
| HNF3A | 1.21 | 0.08 | 0.206 |
| pS2 | 1.12 | 0.05 | 0.0230 |
| BAGI1 | 1.88 | 0.29 | 0.0266 |
| AK055699 | 1.24 | 0.10 | 0.0276 |
| pENT1 | 0.51 | 0.31 | 0.0293 |
| EpCAM | 0.62 | 0.22 | 0.0310 |
| WISP1 | 1.39 | 0.16 | 0.0338 |
| VEGFC | 0.62 | 0.23 | 0.0364 |
| TK1 | 0.73 | 0.15 | 0.0382 |
| NFKBp65 | 1.32 | 0.14 | 0.0384 |
| BRCA2 | 0.66 | 0.20 | 0.0404 |
| CYP3A4 | 0.60 | 0.25 | 0.0417 |
| EGFR | 0.72 | 0.16 | 0.0436 |

TABLE 7

Cox Model Results for 108 Patients wih ER+ Invasive Breast Cancer

| Gene | Relative Risk (RR) | SE Relative Risk | p-value |
|---|---|---|---|
| PRAME | 0.75 | 0.10 | 0.0045 |
| Contig51037 | 0.75 | 0.11 | 0.0060 |
| Blc2 | 2.11 | 0.28 | 0.0075 |
| HIF1A | 0.42 | 0.34 | 0.0117 |
| IGF1R | 1.92 | 0.26 | 0.0117 |
| FOXM1 | 0.54 | 0.24 | 0.0119 |
| EPHX1 | 0.43 | 0.33 | 0.0120 |
| Ki67 | 0.60 | 0.21 | 0.0160 |
| CDC25B | 0.41 | 0.38 | 0.0200 |
| VEGFC | 0.45 | 0.37 | 0.0288 |

TABLE 7-continued

| Cox Model Results for 108 Patients wih ER+ Invasive Breast Cancer | | | |
|---|---|---|---|
| Gene | Relative Risk (RR) | SE Relative Risk | p-value |
| CTSB | 0.32 | 0.53 | 0.0328 |
| DIABLO | 2.91 | 0.50 | 0.0328 |
| p27 | 1.83 | 0.28 | 0.0341 |
| CDH1 | 0.57 | 0.27 | 0.0352 |
| IGFBP3 | 0.45 | 0.40 | 0.0499 |

The binary and time-to-event analyses, with few exceptions, identified the same genes as prognostic markers. For example, comparison of Tables 4 and 6 shows that, with the exception of a single gene, the two analyses generated the same list of top 15 markers (as defined by the smallest p values). Furthermore, when both analyses identified the same gene, they were concordant with respect to the direction (positive or negative sign) of the correlation with survival/recurrence. Overall, these results strengthen the conclusion that the identified markers have significant prognostic value.

For Cox models comprising more than two genes (multivariate models), stepwise entry of each individual gene into the model is performed, where the first gene entered is preselected from among those genes having significant univariate p-values, and the gene selected for entry into the model at each subsequent step is the gene that best improves the fit of the model to the data. This analysis can be performed with any total number of genes. In the analysis the results of which are shown below, stepwise entry was performed for up to 10 genes.

Multivariate analysis is performed using the following equation:

$$RR=\exp[\text{coef}(\text{gene}A)\times Ct(\text{gene}A)+\text{coef}(\text{gene}B)\times Ct(\text{gene}B)+\text{coef}(\text{gene}C)\times Ct(\text{gene}C)+\ldots].$$

In this equation, coefficiencts for genes that are predictors of beneficial outcome are positive numbers and coefficients for genes that are predictors of unfavorable outcome are negative numbers. The "Ct" values in the equation are ΔCts, i.e. reflect the difference between the average normalized Ct value for a population and the normalized Ct measured for the patient in question. The convention used in the present analysis has been that ΔCts below and above the population average have positive signs and negative signs, respectively (reflecting greater or lesser mRNA abundance). The relative risk (RR) calculated by solving this equation will indicate if the patient has an enhanced or reduced chance of long-term survival without cancer recurrence.

Multivariate Gene Analysis of 147 Patients with Invasive Breast Carcinoma (a) A multivariate stepwise analysis, using the Cox Proportional Hazards Model, was performed on the gene expression data obtained for all 146 patients with invasive breast carcinoma. Genes CEGP1, FOXM1, STK15 and PRAME were excluded from this analysis. The following ten-gene sets have been identified by this analysis as having particularly strong predictive value of patient survival without cancer recurrence following surgical removal of primary tumor.

1. Bc12, cyclinG1, NFKBp65, NME1, EPHX1, TOP2B, DRS, TERC, Src, DIABLO;
2. Ki67, XIAP, hENT1, TS, CD9, p27, cyclinG1, pS2, NFKBp65, CYP3A4;
3. GSTM1, XIAP, Ki67, TS, cyclinG1, p27, CYP3A4, pS2, NFKBp65, ErbB3;
4. PR, NME1, XIAP, upa, cyclinG1, Contig51037, TERC, EPHX1, ALDH1A3, CTSL;
5. CA9, NME1, TERC, cyclinG1, EPHX1, DPYD, Src, TOP2B, NFKBp65, VEGFC;
6. TFRC, XIAP, Ki67, TS, cyclinG1, p27, CYP3A4, pS2, ErbB3, NFKBp65.

(b) A multivariate stepwise analysis, using the Cox Proportional Hazards Model, was performed on the gene expression data obtained for all 146 patients with invasive breast carcinoma, using an interrogation set including a reduced number of genes. The following ten-gene sets have been identified by this analysis as having particularly strong predictive value of patient survival without cancer recurrence following surgical removal of primary tumor.

1. Bcl2, PRAME, cyclinG1, FOXM1, NFKBp65, TS, XIAP, Ki67, CYP3A4, p27;
2. FOXM1, cyclinG1, XIAP, Contig51037, PRAME, TS, Ki67, PDGFRa, p27, NFKBp65;
3. PRAME, FOXM1, cyclinG1, XIAP, Contig51037, TS, Ki6, PDGFRa, p27, NFKBp65;
4. Ki67, XIAP, PRAME, hENT1, contig51037, TS, CD9, p27, ErbB3, cyclinG1;
5. STK15, XIAP, PRAME, PLAUR, p27, CTSL, CD18, PREP, p53, RPS6KB1;
6. GSTM1, XIAP, PRAME, p27, Contig51037, ErbB3, GSTp, EREG, ID1, PLAUR;
7. PR; PRAME, NME1, XIAP, PLAUR, cyclinG1, Contig51037, TERC, EPHX1, DR5;
8. CA9, FOXM1, cyclinG1, XIAP, TS, Ki67, NFKBp65, CYP3A4, GSTM3, p27;
9. TFRC, XIAP, PRAME, p27, Contig51037, ErbB3, DPYD, TERC, NME1, VEGFC;
10. CEGP1, PRAME, hENT1, XIAP, Contig51037, ErbB3, DPYD, NFKBp65, ID1, TS.

Multivariate Analysis of Patients with ER Positive Breast Carcinoma

A multivariate stepwise analysis, using the Cox Proportional Hazards Model, was performed on the gene expression data obtained for patients with ER positive invasive breast carcinoma. The following ten-gene sets have been identified by this analysis as having particularly strong predictive value of patient survival without cancer recurrence following surgical removal of primary tumor.

1. PRAME, p27, IGFBP2, HIF1A, TIMP2, ILT2, CYP3A4, ID1, ESR1, DIABLO;
2. Contig51037, EPHX1, Ki67, TIMP2, cyclinG1, DPYD, CYP3A4, TP, AIB1, CYP2C8;
3. Bc12, hENT1, FOXM1, Contig51037, cyclinG1, Contig46653, PTEN, CYP3A4, TIMP2, AREG;
4. HIF1A, PRAME, p27, IGFBP2, TIMP2, ILT2, CYP3A4, ID1, EstR1 ESR1, DIABLO;
5. IGF1R, PRAME, EPHX1, Contig51037, cyclinG1, Bc12, NME1, PTEN, TBP, TIMP2;
6. FOXM1, Contig51037, VEGFC, TBP, HIF1A, DPYD, RAD51C, DCR3, cyclinG1, BAG1;
7. EPHX1, Contig51037, Ki67, TIMP2, cyclinG1, DPYD, CYP3A4, TP, AIB1, CYP2C8;
8. Ki67, VEGFC, VDR, GSTM3, p27, upa, ITGA7, rhoC, TERC, Pin1;
9. CDC25B, Contig51037, hENT1, Bc12, HLAG, TERC, NME1, upa, ID1, CYP;
10. VEGFC, Ki67, VDR, GSTM3, p27, upa, ITGA7, rhoC, TERC, Pin1;
11. CTSB, PRAME, p27, IGFBP2, EPHX1, CTSL, BAD, DRS, DCR3, XIAP;
12. DIABLO, Ki67, hENT1, TIMP2, ID1, p27, KRT19, IGFBP2, TS, PDGFB;

13. p27, PRAME, IGFBP2, HIF1A, TIMP2, ILT2, CYP3A4, ID1, ESR1, DIABLO;
14. CDH1; PRAME, VEGFC; HIF1A; DPYD, TIMP2, CYP3A4, ESR1, RBP4, p27;
15. IGFBP3, PRAME, p27, Bc12, XIAP, EstR1 ESR1, Ki67, TS, Src, VEGF;
16. GSTM3, PRAME, p27, IGFBP3, XIAP, FGF2, hENT1, PTEN, ESR1, APC;
17. hENT1, Bc12, FOXM1, Contig51037, CyclinG1, Contig46653, PTEN, CYP3A4, TIMP2, AREG;
18. STK15, VEGFC, PRAME, p27, GCLC, hENT1, ID1, TIMP2, ESR1, MCP1;
19. NME1, PRAM, p27, IGFBP3, XIAP, PTEN, hENT1, Bc12, CYP3A4, HLAG;
20. VDR, Bc12, p27, hENT1, p53, PI3KC2A, EIF4E, TFRC, MCM3, ID1;
21. EIF4E, Contig51037, EPHX1, cyclinG1, Bc12, DRS, TBP, PTEN, NME1, HER2;
22. CCNB1, PRAME, VEGFC, HIF1A, hENT1, GCLC, TIMP2, ID1, p27, upa;
23. ID1, PRAME, DIABLO, hENT1, p27, PDGFRa, NME1, BIN1, BRCA1, TP;
24. FBXO5, PRAME, IGFBP3, p27, GSTM3, hENT1, XIAP, FGF2, TS, PTEN;
25. GUS, HIA1A, VEGFC, GSTM3, DPYD, hENT1, FBXO5, CA9, CYP, KRT18;
26. Bclx, Bc12, hENT1, Contig51037, HLAG, CD9, ID1, BRCA1, BIN1, HBEGF.

It is noteworthy that many of the foregoing gene sets include genes that alone did not have sufficient predictive value to qualify as prognostic markers under the standards discussed above, but in combination with other genes, their presence provides valuable information about the likelihood of long-term patient survival without cancer recurrence All references cited throughout the disclosure are hereby expressly incorporated by reference.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the diagnosis and treatment of breast cancer, similar genes, gene sets and methods concerning other types of cancer are specifically within the scope herein.

TABLE 1

| | |
|---|---|
| 1. | ADD3 (adducin 3 gamma)* |
| 2. | AKT1/Protein Kinase B |
| 3. | AKT 2 |
| 4. | AKT 3 |
| 5. | Aldehyde dehydrogenase 1A1 |
| 6. | Aldehyde dehydrogenase 1A3 |
| 7. | amphiregulin |
| 8. | APC |
| 9. | ARG |
| 10. | ATM |
| 11. | Bak |
| 12. | Bax |
| 13. | Bcl2 |
| 14. | Bcl-xl |
| 15. | BRK |

TABLE 1-continued

| | |
|---|---|
| 16. | BCRP |
| 17. | BRCA-1 |
| 18. | BRCA-2 |
| 19. | Caspase-3 |
| 20. | Cathepsin B |
| 21. | Cathepsin G |
| 22. | Cathepsin L |
| 23. | CD3 |
| 24. | CD9 |
| 25. | CD18 |
| 26. | CD31 |
| 27. | CD44^ |
| 28. | CD68 |
| 29. | CD82/KAI-1 |
| 30. | Cdc25A |
| 31. | Cdc25B |
| 32. | CGA |
| 33. | COX2 |
| 34. | CSF-1 |
| 35. | CSF-1R/fms |
| 36. | cIAP1 |
| 37. | cIAP2 |
| 38. | c-abl |
| 39. | c-kit |
| 40. | c-kit L |
| 41. | c-met |
| 42. | c-myc |
| 43. | cN-1 |
| 44. | cryptochrome1* |
| 45. | c-Src |
| 46. | Cyclin D1 |
| 47. | CYP1B1 |
| 48. | CYP2C9* |
| 49. | Cytokeratin 5^ |
| 50. | Cytokeratin 17^ |
| 51. | Cytokeratin 18^ |
| 52. | DAP-Kinase-1 |
| 53. | DHFR |
| 54. | DIABLO |
| 55. | Dihydropyrimidine dehydrogenase |
| 56. | EGF |
| 57. | ECadherin/CDH1^ |
| 58. | ELF 3* |
| 59. | Endothelin |
| 60. | Epiregulin |
| 61. | ER-alpha^ |
| 62. | ErbB-1 |
| 63. | ErbB-2^ |
| 64. | ErbB-3 |
| 65. | ErbB-4 |
| 66. | ER-Beta |
| 67. | Eukaryotic Translation Initiation Factor 4B*(EIF4B) |
| 68. | E1F4E |
| 69. | farnesyl pyrolophosphate synthetase |
| 70. | FAS (CD95) |
| 71. | FasL |
| 72. | FGF R 1* |
| 73. | FGF2 [bFGF] |
| 74. | 53BP1 |
| 75. | 53BP2 |
| 76. | GALC (galactosylceramidase)* |
| 77. | Gamma-GCS (glutamyl cysteine synthetase) |
| 78. | GATA3^ |
| 79. | geranyl geranyl pyrophosphate synthetase |
| 80. | G-CSF |
| 81. | GPC3 |
| 82. | gravin* [AK AP258] |
| 83. | GRO1 oncogene alpha^ |
| 84. | Grb7^ |
| 85. | GST-alpha |

TABLE 1-continued

| | |
|---|---|
| 86. | GST-pi^ |
| 87. | Ha-Ras |
| 88. | HB-EGF |
| 89. | HE4-extracellular Proteinase Inhibitor Homologue* |
| 90. | hepatocyte nuclear factor 3^ |
| 91. | HER-2 |
| 92. | HGF/Scatter factor |
| 93. | hIAP1 |
| 94. | hIAP2 |
| 95. | HIF-1 |
| 96. | human kallikrein 10 |
| 97. | MLH1 |
| 98. | hsp 27 |
| 99. | human chorionic gonadotropin/CGA |
| 100. | Human Extracellular Protein S1–5 |
| 101. | Id-1 |
| 102. | Id-2 |
| 103. | Id-3 |
| 104. | IGF-1 |
| 105. | IGF2 |
| 106. | IGF1R |
| 107. | IGFBP3 |
| 108. | interstitial integrin alpha 7 |
| 109. | IL6 |
| 110. | IL8 |
| 111. | IRF-2* |
| 112. | IRF9 Protein |
| 113. | Kalikrein 5 |
| 114. | Kalikrein 6 |
| 115. | KDR |
| 116. | Ki-67/MiB1 |
| 117. | lipoprotein lipase^ |
| 118. | LIV1 |
| 119. | Lung Resistance Protein/MVP |
| 120. | Lot1 |
| 121. | Maspin |
| 122. | MCM2 |
| 123. | MCM3 |
| 124. | MCM7 |
| 125. | MCP-1 |
| 126. | microtubule-associated protein 4 |
| 127. | MCJ |
| 128. | mdm2 |
| 129. | MDR-1 |
| 130. | microsomal epoxide hydrolase |
| 131. | MMP9 |
| 132. | MRP1 |
| 133. | MRP2 |
| 134. | MRP3 |
| 135. | MRP4 |
| 136. | MSN (Moesin)* |
| 137. | mTOR |
| 138. | Muc1/CA 15-3 |
| 139. | NF-kB |
| 140. | P14ARF |
| 141. | P16INK4a/p14 |
| 142. | p21wAF1/CIP1 |
| 143. | p23 |
| 144. | p27 |
| 145. | p311* |
| 146. | p53 |
| 147. | PAI1 |
| 148. | PCNA |
| 149. | PDGF-A |
| 150. | PDGF-B |
| 151. | PDGF-C |
| 152. | PDGF-D |
| 153. | PDGFR-α |
| 154. | PDGFR-β |
| 155. | PI3K |
| 156. | Pin1 |
| 157. | PKC-ϵ |
| 158. | Pkc-δ |
| 159. | PLAG1 (pleiomorphic adenoma 1)* |
| 160. | PREP prolyl endopeptidase*PEP |
| 161. | Progesterone receptor |
| 162. | pS2/trefoil factor 1 |
| 163. | PTEN |
| 164. | PTP1b |
| 165. | RAR-alpha |
| 166. | RAR-beta2 |
| 167. | RCP |
| 168. | Reduced Folate Carrier |
| 169. | Retinol binding protein 4^ |
| 170. | STK15/BTAK |
| 171. | Survivin |
| 172. | SXR |
| 173. | Syk |
| 174. | TGD (thymine-DNA glycosylase)* |
| 175. | TGFalpha |
| 176. | Thymidine Kinase |
| 177. | Thymidine phosphorylase |
| 178. | Thymidylate Synthase |
| 179. | Topoisomerase II-α |
| 180. | Topoisomerase II-β |
| 181. | TRAMP |
| 182. | UPA |
| 183. | VEGF |
| 184. | Vimentin |
| 185. | WTH3 |
| 186. | XAF1 |
| 187. | XIAP |
| 188. | XIST |
| 189. | XPA |
| 190. | YB-1 |

*NCI 60 drug Sens./Resist Marker

^In Cluster Defining tumor subclass Jan. 19, 2002

TABLE 2

| Gene | Accession No. | Forward Primer SEQ ID NO. | Reverse Primer SEQ ID NO. | Amplicon SEQ ID NO. |
|---|---|---|---|---|
| ABCB1 | NM_000927 | 1 | 2 | 3 |
| ABCC1 | NM_004996 | 4 | 5 | 6 |
| ABCC2 | NM_000392 | 7 | 8 | 9 |
| ABCC3 | NM_003786 | 10 | 11 | 12 |
| ABCC4 | NM_005845 | 13 | 14 | 15 |
| ABL1 | NM_005157 | 16 | 17 | 18 |
| ABL2 | NM_005158 | 19 | 20 | 21 |
| ACTB | NM_001101 | 22 | 23 | 24 |
| AKT1 | NM_005163 | 25 | 26 | 27 |
| AKT3 | NM_005465 | 28 | 29 | 30 |
| ALDH1 | NM_000689 | 31 | 32 | 33 |
| ALDH1A3 | NM_000693 | 34 | 35 | 36 |
| APC | NM_000038 | 37 | 38 | 39 |
| AREG | NM_001657 | 40 | 41 | 42 |
| B2M | NM_004048 | 43 | 44 | 45 |
| BAK1 | NM_001188 | 46 | 47 | 48 |
| BAX | NM_004324 | 49 | 50 | 51 |
| BCL2 | NM_000633 | 52 | 53 | 54 |
| BCL2L1 | NM_001191 | 55 | 56 | 57 |
| BIRC3 | NM_001165 | 58 | 59 | 60 |
| BIRC4 | NM_001167 | 61 | 62 | 63 |
| BIRC5 | NM_001168 | 64 | 65 | 66 |
| BRCA1 | NM_007295 | 67 | 68 | 69 |
| BRCA2 | NM_000059 | 70 | 71 | 72 |
| CCND1 | NM_001758 | 73 | 74 | 75 |
| CD3Z | NM_000734 | 76 | 77 | 78 |
| CD68 | NM_001251 | 79 | 80 | 81 |
| CDC25A | NM_001789 | 82 | 83 | 84 |
| CDH1 | NM_004360 | 85 | 86 | 87 |
| CDKN1A | NM_000389 | 88 | 89 | 90 |
| CDKN1B | NM_004064 | 91 | 92 | 93 |

TABLE 2-continued

| Gene | Accession No. | Forward Primer SEQ ID NO. | Reverse Primer SEQ ID NO. | Amplicon SEQ ID NO. |
|---|---|---|---|---|
| CDKN2A | NM_000077 | 94 | 95 | 96 |
| CYP1B1 | NM_000104 | 97 | 98 | 99 |
| DHFR | NM_000791 | 100 | 101 | 102 |
| DPYD | NM_000110 | 103 | 104 | 105 |
| ECGF1 | NM_001953 | 106 | 107 | 108 |
| EGFR | NM_005228 | 109 | 110 | 111 |
| EIF4E | NM_001968 | 112 | 113 | 114 |
| ERBB2 | NM_004448 | 115 | 116 | 117 |
| ERBB3 | NM_001982 | 118 | 119 | 120 |
| ESR1 | NM_000125 | 121 | 122 | 123 |
| ESR2 | NM_001437 | 124 | 125 | 126 |
| GAPD | NM_002046 | 127 | 128 | 129 |
| GATA3 | NM_002051 | 130 | 131 | 132 |
| GRB7 | NM_005310 | 133 | 134 | 135 |
| GRO1 | NM_001511 | 136 | 137 | 138 |
| GSTP1 | NM_000852 | 139 | 140 | 141 |
| GUSB | NM_000181 | 142 | 143 | 144 |
| hHGF | M29145 | 145 | 146 | 147 |
| HNF3A | NM_004496 | 148 | 149 | 150 |
| ID2 | NM_002166 | 151 | 152 | 153 |
| IGF1 | NM_000618 | 154 | 155 | 156 |
| IGFBP3 | NM_000598 | 157 | 158 | 159 |
| ITGA7 | NM_002206 | 160 | 161 | 162 |
| ITGB2 | NM_000211 | 163 | 164 | 165 |
| KDR | NM_002253 | 166 | 167 | 168 |
| KIT | NM_000222 | 169 | 170 | 171 |
| KITLG | NM_000899 | 172 | 173 | 174 |
| KRT17 | NM_000422 | 175 | 176 | 177 |
| KRT5 | NM_000424 | 178 | 179 | 180 |
| LPL | NM_000237 | 181 | 182 | 183 |
| MET | NM_000245 | 184 | 185 | 186 |
| MKI67 | NM_002417 | 187 | 188 | 189 |
| MVP | NM_017458 | 190 | 191 | 192 |
| MYC | NM_002467 | 193 | 194 | 195 |
| PDGFA | NM_002607 | 196 | 197 | 198 |
| PDGFB | NM_002608 | 199 | 200 | 201 |
| PDGFC | NM_016205 | 202 | 203 | 204 |
| PDGFRA | NM_006206 | 205 | 206 | 207 |
| PDGFRB | NM_002609 | 208 | 209 | 210 |
| PGK1 | NM_000291 | 211 | 212 | 213 |
| PGR | NM_000926 | 214 | 215 | 216 |
| PIN1 | NM_006221 | 217 | 218 | 219 |
| PLAU | NM_002658 | 220 | 221 | 222 |
| PPIH | NM_006347 | 223 | 224 | 225 |
| PTEN | NM_000314 | 226 | 227 | 228 |
| PTGS2 | NM_000963 | 229 | 230 | 231 |
| RBP4 | NM_006744 | 232 | 233 | 234 |
| RELA | NM_021975 | 235 | 236 | 237 |
| RPL19 | NM_000981 | 238 | 239 | 240 |
| RPLP0 | NM_001002 | 241 | 242 | 243 |
| SCDGF-B | NM_025208 | 244 | 245 | 246 |
| SERPINE1 | NM_000602 | 247 | 248 | 249 |
| SLC19A1 | NM_003056 | 250 | 251 | 252 |
| TBP | NM_003194 | 253 | 254 | 255 |
| TFF1 | NM_003225 | 256 | 257 | 258 |
| TFRC | NM_003234 | 259 | 260 | 261 |
| TK1 | NM_003258 | 262 | 263 | 264 |
| TNFRSF6 | NM_000043 | 265 | 266 | 267 |
| TNFSF6 | NM_000639 | 268 | 269 | 270 |
| TOP2A | NM_001067 | 271 | 272 | 273 |
| TOP2B | NM_001068 | 274 | 275 | 276 |
| TP53 | NM_000546 | 277 | 278 | 279 |
| TYMS | NM_001071 | 280 | 281 | 282 |
| VEGF | NM_003376 | 283 | 284 | 285 |

TABLE 3

| GENE | ACCESSION NO. | SEQ ID NO: |
|---|---|---|
| AK055699 | AK055699 | 286 |
| BAG1 | NM_004323 | 287 |
| BBC3 | NM_014417 | 288 |

TABLE 3-continued

| GENE | ACCESSION NO. | SEQ ID NO: |
|---|---|---|
| Bcl2 | NM_000633 | 289 |
| BRCA2 | NM_000059 | 290 |
| CA9 | NM_001216 | 291 |
| CCNB1 | NM_031966 | 292 |
| CDC25B | NM_021874 | 293 |
| CEGP1 | NM_020974 | 294 |
| Chk1 | NM_001274 | 295 |
| Chk2 | NM_007194 | 296 |
| CYP3A4 | NM_017460 | 297 |
| DIABLO | NM_019887 | 298 |
| DPYD | NM_000110 | 299 |
| EGFR | NM_005228 | 300 |
| EpCAM | NM_002354 | 301 |
| EPHX1 | NM_000120 | 302 |
| ESR1 | NM_000125 | 303 |
| FOXM1 | NM_021953 | 304 |
| GATA3 | NM_002051 | 305 |
| GSTM1 | NM_000561 | 306 |
| GSTM3 | NM_000849 | 307 |
| hENT1 | NM_004955 | 308 |
| HIF1A | NM_001530 | 309 |
| HNF3A | NM_004496 | 310 |
| ID1 | NM_002165 | 311 |
| IGF1R | NM_000875 | 312 |
| Ki-67 | NM_002417 | 313 |
| NFKBp65 | NM_021975 | 314 |
| NME1 | NM_000269 | 315 |
| p27 | NM_004064 | 316 |
| PI3KC2A | NM_002645 | 317 |
| PR | NM_000926 | 318 |
| PRAME | NM_006115 | 319 |
| pS2 | NM_003225 | 320 |
| RPS6KB1 | NM_003161 | 321 |
| Src | NM_004383 | 322 |
| STK15 | NM_003600 | 323 |
| SURV | NM_001168 | 324 |
| TFRC | NM_003234 | 325 |
| TGFB3 | NM_003239 | 326 |
| TK1 | NM_003258 | 327 |
| VDR | NM_000376 | 328 |
| VEGFC | NM_005429 | 329 |
| WISP1 | NM_003882 | 330 |
| XIAP | NM_001167 | 331 |
| YB-1 | NM_004559 | 332 |
| ITGA7 | NM_002206 | 333 |
| PDGFB | NM_002608 | 334 |
| Upa | NM_002658 | 335 |
| TBP | NM_003194 | 336 |
| PDGFRa | NM_006206 | 337 |
| Pin1 | NM_006221 | 338 |
| CYP | NM_006347 | 339 |
| RBP4 | NM_006744 | 340 |
| BRCA1 | NM_007295 | 341 |
| APC | NM_000038 | 342 |
| GUS | NM_000181 | 343 |
| CD18 | NM_000211 | 344 |
| PTEN | NM_000314 | 345 |
| P53 | NM_000546 | 346 |
| ALDH1A3 | NM_000693 | 347 |
| GSTp | NM_000852 | 348 |
| TOP2B | NM_001068 | 349 |
| TS | NM_001071 | 350 |
| Bclx | NM_001191 | 351 |
| AREG | NM_001657 | 352 |
| TP | NM_001953 | 353 |
| EIF4E | NM_001968 | 354 |
| ErbB3 | NM_001982 | 355 |
| EREG | NM_001432 | 356 |
| GCLC | NM_001498 | 357 |
| CD9 | NM_001769 | 358 |
| HB-EGF | NM_001945 | 359 |
| IGFBP2 | NM_000597 | 360 |
| CTSL | NM_001912 | 361 |
| PREP | NM_002726 | 362 |
| CYP3A4 | NM_017460 | 363 |
| ILT-2 | NM_006669 | 364 |
| MCM3 | NM_002388 | 365 |

TABLE 3-continued

| GENE | ACCESSION NO. | SEQ ID NO: |
|---|---|---|
| KRT19 | NM_002276 | 366 |
| KRT18 | NM_000224 | 367 |
| TIMP2 | NM_003255 | 368 |
| BAD | NM_004322 | 369 |
| CYP2C8 | NM_030878 | 370 |
| DCR3 | NM_016434 | 371 |
| PLAUR | NM_002659 | 372 |
| PI3KC2A | NM_002645 | 373 |
| FGF2 | NM_002006 | 374 |
| HLA-G | NM_002127 | 375 |
| AIB1 | NM_006534 | 376 |
| MCP1 | NM_002982 | 377 |
| Contig46653 | Contig46653 | 378 |
| RhoC | NM_005167 | 379 |
| DR5 | NM_003842 | 380 |
| RAD51C | NM_058216 | 381 |
| BIN1 | NM_004305 | 382 |
| VDR | NM_000376 | 383 |
| TERC | U86046 | 384 |

What is claimed is:

1. A method for predicting the likelihood of long-term survival without the recurrence of breast cancer comprising:

assaying a level of a RNA transcript of STK15 in a tissue sample obtained from a primary ductal or lobular breast tumor of a human patient;

normalizing said level against a level of at least one reference RNA transcript in said tissue sample to provide a normalized STK15 RNA level; and predicting the likelihood of long-term survival of said patient without the recurrence of breast cancer by comparing said normalized STK15 RNA level to gene expression data obtained from reference samples derived from patients with breast cancer, wherein increased normalized STK15 RNA level is negatively correlated with increased likelihood of long-term survival without breast cancer recurrence in said patients with breast cancer.

2. The method of claim 1 further comprising assaying a level of an RNA transcript of one or more genes selected from a group consisting of: Bc12, Ki-67, GSTM1, PR, SURV, ESR1, and BAG1 in said tissue sample, normalized against a level of at least one reference RNA transcript in said tissue sample to provide a normalized RNA level of said one or more genes; and comparing said normalized RNA level of said one or more genes to gene expression data obtained from reference samples derived from patients with breast cancer, wherein increased normalized RNA level of one or more of Ki-67 and SURV negatively correlates with an increased likelihood of long-term survival without breast cancer recurrence, and increased normalized RNA level of one or more of Bc12, GSTM1, PR, ESR1, and BAG1 positively correlates with an increased likelihood of long-term survival without breast cancer recurrence.

3. The method of claim 1 wherein the breast tumor is an invasive breast tumor, and said method further comprises assaying a level of a RNA transcript of one or more genes selected from the group consisting of: FOXM1, PRAME, Bc12, CEGP1, Ki-67, GSTM1, PR, BBC3, NME1, SURV, GATA3, TFRC, YB-1, DPYD, CA9, Contig51037, RPS6K1 and Her2.

4. The method of claim 1 wherein said breast tumor is an estrogen receptor (ER) positive breast tumor.

5. The method of claim 4 further comprising assaying a level of a RNA transcript of one or more genes selected from a group consisting of : PRAME, Bc12, FOXM1, DIABLO, EPHX1, HIF1A, VEGFC, Ki-67, IGF1R, VDR, NME1, GSTM3, Contig51037, CDC25B, CTSB, p27, CDH1, and IGFBP3.

6. The method of claim 2 wherein the levels of 2 or more RNA transcripts is determined.

7. The method of claim 1 wherein said tissue sample is a fixed, wax-embedded tissue specimen.

8. The method of claim 1, wherein said tissue sample is from a fine needle biopsy sample.

9. The method of claim 1, further comprising creating a report based upon said normalized STK15 RNA level.

10. The method of claim 9, wherein said report includes a prediction of the likelihood of long term survival of said patient without the recurrence of cancer.

11. The method of claim 1, wherein said gene expression data is produced using a multivariate analysis using the Cox Proportional Hazards model.

12. The method of claim 1 wherein said assaying is done using RNA obtained from a formalin-fixed paraffin-embedded tissue sample.

13. The method of claim 1 wherein said assaying is done using reverse transcriptase polymerase chain reaction (RT-PCR).

14. The method of claim 1, wherein said assaying is done after a ductal carcinoma has been surgically removed from a breast of said patient.

15. The method of claim 14, wherein said ductal carcinoma is an invasive ductal carcinoma.

16. The method of claim 1, wherein said assaying is done after a lobular carcinoma has been surgically removed from a breast of said patient.

17. The method of claim 16, wherein said lobular carcinoma is an invasive lobular carcinoma.

18. The method of claim 1, wherein said comparing is done by calculating a quantitative score indicating the likelihood of long-term survival without the recurrence of breast cancer of the human patient, wherein said quantitative score is calculated using said normalized STK15 RNA level of the human patient and the negative correlation between increased normalized STK15 RNA level and an increased likelihood of long-term survival without recurrence of breast cancer.

* * * * *

SEQUENCE LISTING

```
<160> NUMBER OF SEQ ID NOS: 384

<210> SEQ ID NO 1
<211> LENGTH: 18
<212> TYPE: DNA
<213> ORGANISM: Homo sapiens

<400> SEQUENCE: 1

gtcccaggag cccatcct                                                 18


<210> SEQ ID NO 2
<211> LENGTH: 19
<212> TYPE: DNA
<213> ORGANISM: Homo sapiens

<400> SEQUENCE: 2

cccggctgtt gtctccata                                                19


<210> SEQ ID NO 3
<211> LENGTH: 68
<212> TYPE: DNA
<213> ORGANISM: Homo sapiens

<400> SEQUENCE: 3

gtcccaggag cccatcctgt ttgactgcag cattgctgag aacattgcct atggagacaa   60

cagccggg                                                            68


<210> SEQ ID NO 4
<211> LENGTH: 18
<212> TYPE: DNA
<213> ORGANISM: Homo sapiens

<400> SEQUENCE: 4

tcatggtgcc cgtcaatg                                                 18


<210> SEQ ID NO 5
<211> LENGTH: 23
<212> TYPE: DNA
<213> ORGANISM: Homo sapiens

<400> SEQUENCE: 5

cgattgtctt tgctcttcat gtg                                           23


<210> SEQ ID NO 6
<211> LENGTH: 79
<212> TYPE: DNA
<213> ORGANISM: Homo sapiens
```

<400> SEQUENCE: 6
tcatggtgcc cgtcaatgct gtgatggcga tgaagaccaa gacgtatcag gtggcccaca 60
tgaagagcaa agacaatcg 79

<210> SEQ ID NO 7
<211> LENGTH: 20
<212> TYPE: DNA
<213> ORGANISM: Homo sapiens

<400> SEQUENCE: 7
aggggatgac ttggacacat 20

<210> SEQ ID NO 8
<211> LENGTH: 20
<212> TYPE: DNA
<213> ORGANISM: Homo sapiens

<400> SEQUENCE: 8
aaaactgcat ggctttgtca 20

<210> SEQ ID NO 9
<211> LENGTH: 65
<212> TYPE: DNA
<213> ORGANISM: Homo sapiens

<400> SEQUENCE: 9
aggggatgac ttggacacat ctgccattcg acatgactgc aattttgaca aagccatgca 60
gtttt 65

<210> SEQ ID NO 10
<211> LENGTH: 22
<212> TYPE: DNA
<213> ORGANISM: Homo sapiens

<400> SEQUENCE: 10
tcatcctggc gatctacttc ct 22

<210> SEQ ID NO 11
<211> LENGTH: 20
<212> TYPE: DNA
<213> ORGANISM: Homo sapiens

<400> SEQUENCE: 11
ccgttgagtg gaatcagcaa 20

<210> SEQ ID NO 12
<211> LENGTH: 91
<212> TYPE: DNA
<213> ORGANISM: Homo sapiens

<400> SEQUENCE: 12
tcatcctggc gatctacttc ctctggcaga acctaggtcc ctctgtcctg gctggagtcg 60
ctttcatggt cttgctgatt ccactcaacg g 91

<210> SEQ ID NO 13
<211> LENGTH: 20
<212> TYPE: DNA
<213> ORGANISM: Homo sapiens

<400> SEQUENCE: 13

```
agcgcctgga atctacaact                                                20


<210> SEQ ID NO 14
<211> LENGTH: 20
<212> TYPE: DNA
<213> ORGANISM: Homo sapiens

<400> SEQUENCE: 14

agagcccctg gagagaagat                                                20


<210> SEQ ID NO 15
<211> LENGTH: 66
<212> TYPE: DNA
<213> ORGANISM: Homo sapiens

<400> SEQUENCE: 15

agcgcctgga atctacaact cggagtccag tgttttccca cttgtcatct tctctccagg    60

ggctct                                                               66


<210> SEQ ID NO 16
<211> LENGTH: 24
<212> TYPE: DNA
<213> ORGANISM: Homo sapiens

<400> SEQUENCE: 16

gcccagagaa ggtctatgaa ctca                                           24


<210> SEQ ID NO 17
<211> LENGTH: 22
<212> TYPE: DNA
<213> ORGANISM: Homo sapiens

<400> SEQUENCE: 17

gtttcaaagg cttggtggat tt                                             22


<210> SEQ ID NO 18
<211> LENGTH: 94
<212> TYPE: DNA
<213> ORGANISM: Homo sapiens

<400> SEQUENCE: 18

gcccagagaa ggtctatgaa ctcatgcgag catgttggca gtggaatccc tctgaccggc    60

cctcctttgc tgaaatccac caagcctttg aaac                                94


<210> SEQ ID NO 19
<211> LENGTH: 21
<212> TYPE: DNA
<213> ORGANISM: Homo sapiens

<400> SEQUENCE: 19

cgcagtgcag ctgagtatct g                                              21


<210> SEQ ID NO 20
<211> LENGTH: 21
<212> TYPE: DNA
<213> ORGANISM: Homo sapiens

<400> SEQUENCE: 20

tgcccagggc tactctcact t                                              21


<210> SEQ ID NO 21
<211> LENGTH: 80
```

<212> TYPE: DNA
<213> ORGANISM: Homo sapiens

<400> SEQUENCE: 21
cgcagtgcag ctgagtatct gctcagcagt ctaatcaatg gcagcttcct ggtgcgagaa 60
agtgagagta gccctgggca 80

<210> SEQ ID NO 22
<211> LENGTH: 21
<212> TYPE: DNA
<213> ORGANISM: Homo sapiens

<400> SEQUENCE: 22
cagcagatgt ggatcagcaa g 21

<210> SEQ ID NO 23
<211> LENGTH: 18
<212> TYPE: DNA
<213> ORGANISM: Homo sapiens

<400> SEQUENCE: 23
gcatttgcgg tggacgat 18

<210> SEQ ID NO 24
<211> LENGTH: 66
<212> TYPE: DNA
<213> ORGANISM: Homo sapiens

<400> SEQUENCE: 24
cagcagatgt ggatcagcaa gcaggagtat gacgagtccg gcccctccat cgtccaccgc 60
aaatgc 66

<210> SEQ ID NO 25
<211> LENGTH: 20
<212> TYPE: DNA
<213> ORGANISM: Homo sapiens

<400> SEQUENCE: 25
cgcttctatg gcgctgagat 20

<210> SEQ ID NO 26
<211> LENGTH: 20
<212> TYPE: DNA
<213> ORGANISM: Homo sapiens

<400> SEQUENCE: 26
tcccggtaca ccacgttctt 20

<210> SEQ ID NO 27
<211> LENGTH: 71
<212> TYPE: DNA
<213> ORGANISM: Homo sapiens

<400> SEQUENCE: 27
cgcttctatg gcgctgagat tgtgtcagcc ctggactacc tgcactcgga gaagaacgtg 60
gtgtaccggg a 71

<210> SEQ ID NO 28
<211> LENGTH: 25
<212> TYPE: DNA
<213> ORGANISM: Homo sapiens

<400> SEQUENCE: 28
ttgtctctgc cttggactat ctaca 25

<210> SEQ ID NO 29
<211> LENGTH: 24
<212> TYPE: DNA
<213> ORGANISM: Homo sapiens

<400> SEQUENCE: 29
ccagcattag attctccaac ttga 24

<210> SEQ ID NO 30
<211> LENGTH: 75
<212> TYPE: DNA
<213> ORGANISM: Homo sapiens

<400> SEQUENCE: 30
ttgtctctgc cttggactat ctacattccg gaaagattgt gtaccgtgat ctcaagttgg 60
agaatctaat gctgg 75

<210> SEQ ID NO 31
<211> LENGTH: 25
<212> TYPE: DNA
<213> ORGANISM: Homo sapiens

<400> SEQUENCE: 31
gaaggagata aggaggatgt tgaca 25

<210> SEQ ID NO 32
<211> LENGTH: 18
<212> TYPE: DNA
<213> ORGANISM: Homo sapiens

<400> SEQUENCE: 32
cgccacggag atccaatc 18

<210> SEQ ID NO 33
<211> LENGTH: 74
<212> TYPE: DNA
<213> ORGANISM: Homo sapiens

<400> SEQUENCE: 33
gaaggagata aggaggatgt tgacaaggca gtgaaggccg caagacaggc ttttcagatt 60
ggatctccgt ggcg 74

<210> SEQ ID NO 34
<211> LENGTH: 21
<212> TYPE: DNA
<213> ORGANISM: Homo sapiens

<400> SEQUENCE: 34
tggtgaacat tgtgccagga t 21

<210> SEQ ID NO 35
<211> LENGTH: 22
<212> TYPE: DNA
<213> ORGANISM: Homo sapiens

<400> SEQUENCE: 35
gaaggcgatc ttgttgatct ga 22

-continued

<210> SEQ ID NO 36
<211> LENGTH: 80
<212> TYPE: DNA
<213> ORGANISM: Homo sapiens

<400> SEQUENCE: 36
tggtgaacat tgtgccagga ttcgggccca cagtgggagc agcaatttct tctcaccctc 60
agatcaacaa gatcgccttc 80

<210> SEQ ID NO 37
<211> LENGTH: 20
<212> TYPE: DNA
<213> ORGANISM: Homo sapiens

<400> SEQUENCE: 37
ggacagcagg aatgtgtttc 20

<210> SEQ ID NO 38
<211> LENGTH: 20
<212> TYPE: DNA
<213> ORGANISM: Homo sapiens

<400> SEQUENCE: 38
acccactcga tttgtttctg 20

<210> SEQ ID NO 39
<211> LENGTH: 69
<212> TYPE: DNA
<213> ORGANISM: Homo sapiens

<400> SEQUENCE: 39
ggacagcagg aatgtgtttc tccatacagg tcacggggag ccaatggttc agaaacaaat 60
cgagtgggt 69

<210> SEQ ID NO 40
<211> LENGTH: 27
<212> TYPE: DNA
<213> ORGANISM: Homo sapiens

<400> SEQUENCE: 40
tgtgagtgaa atgccttcta gtagtga 27

<210> SEQ ID NO 41
<211> LENGTH: 27
<212> TYPE: DNA
<213> ORGANISM: Homo sapiens

<400> SEQUENCE: 41
ttgtggttcg ttatcatact cttctga 27

<210> SEQ ID NO 42
<211> LENGTH: 82
<212> TYPE: DNA
<213> ORGANISM: Homo sapiens

<400> SEQUENCE: 42
tgtgagtgaa atgccttcta gtagtgaacc gtcctcggga gccgactatg actactcaga 60
agagtatgat aacgaaccac aa 82

<210> SEQ ID NO 43
<211> LENGTH: 19
<212> TYPE: DNA

<213> ORGANISM: Homo sapiens

<400> SEQUENCE: 43
gtctcgctcc gtggcctta 19

<210> SEQ ID NO 44
<211> LENGTH: 24
<212> TYPE: DNA
<213> ORGANISM: Homo sapiens

<400> SEQUENCE: 44
cgtgagtaaa cctgaatctt tgga 24

<210> SEQ ID NO 45
<211> LENGTH: 93
<212> TYPE: DNA
<213> ORGANISM: Homo sapiens

<400> SEQUENCE: 45
gtctcgctcc gtggccttag ctgtgctcgc gctactctct ctttctggcc tggaggctat 60
ccagcgtact ccaaagattc aggtttactc acg 93

<210> SEQ ID NO 46
<211> LENGTH: 20
<212> TYPE: DNA
<213> ORGANISM: Homo sapiens

<400> SEQUENCE: 46
ccattcccac cattctacct 20

<210> SEQ ID NO 47
<211> LENGTH: 20
<212> TYPE: DNA
<213> ORGANISM: Homo sapiens

<400> SEQUENCE: 47
gggaacatag acccaccaat 20

<210> SEQ ID NO 48
<211> LENGTH: 66
<212> TYPE: DNA
<213> ORGANISM: Homo sapiens

<400> SEQUENCE: 48
ccattcccac cattctacct gaggccagga cgtctggggt gtggggattg gtgggtctat 60
gttccc 66

<210> SEQ ID NO 49
<211> LENGTH: 18
<212> TYPE: DNA
<213> ORGANISM: Homo sapiens

<400> SEQUENCE: 49
ccgccgtgga cacagact 18

<210> SEQ ID NO 50
<211> LENGTH: 21
<212> TYPE: DNA
<213> ORGANISM: Homo sapiens

<400> SEQUENCE: 50
ttgccgtcag aaaacatgtc a 21

<210> SEQ ID NO 51
<211> LENGTH: 70
<212> TYPE: DNA
<213> ORGANISM: Homo sapiens

<400> SEQUENCE: 51
ccgccgtgga cacagactcc ccccgagagg tctttttccg agtggcagct gacatgtttt 60
ctgacggcaa 70

<210> SEQ ID NO 52
<211> LENGTH: 25
<212> TYPE: DNA
<213> ORGANISM: Homo sapiens

<400> SEQUENCE: 52
cagatggacc tagtacccac tgaga 25

<210> SEQ ID NO 53
<211> LENGTH: 24
<212> TYPE: DNA
<213> ORGANISM: Homo sapiens

<400> SEQUENCE: 53
cctatgattt aagggcattt ttcc 24

<210> SEQ ID NO 54
<211> LENGTH: 73
<212> TYPE: DNA
<213> ORGANISM: Homo sapiens

<400> SEQUENCE: 54
cagatggacc tagtacccac tgagatttcc acgccgaagg acagcgatgg gaaaaatgcc 60
cttaaatcat agg 73

<210> SEQ ID NO 55
<211> LENGTH: 24
<212> TYPE: DNA
<213> ORGANISM: Homo sapiens

<400> SEQUENCE: 55
cttttgtgga actctatggg aaca 24

<210> SEQ ID NO 56
<211> LENGTH: 19
<212> TYPE: DNA
<213> ORGANISM: Homo sapiens

<400> SEQUENCE: 56
cagcggttga agcgttcct 19

<210> SEQ ID NO 57
<211> LENGTH: 70
<212> TYPE: DNA
<213> ORGANISM: Homo sapiens

<400> SEQUENCE: 57
cttttgtgga actctatggg aacaatgcag cagccgagag ccgaaagggc caggaacgct 60
tcaaccgctg 70

<210> SEQ ID NO 58

<211> LENGTH: 24
<212> TYPE: DNA
<213> ORGANISM: Homo sapiens

<400> SEQUENCE: 58
ggatatttcc gtggctctta ttca 24

<210> SEQ ID NO 59
<211> LENGTH: 25
<212> TYPE: DNA
<213> ORGANISM: Homo sapiens

<400> SEQUENCE: 59
cttctcatca aggcagaaaa atctt 25

<210> SEQ ID NO 60
<211> LENGTH: 86
<212> TYPE: DNA
<213> ORGANISM: Homo sapiens

<400> SEQUENCE: 60
ggatatttcc gtggctctta ttcaaactct ccatcaaatc ctgtaaactc cagagcaaat 60
caagattttt ctgccttgat gagaag 86

<210> SEQ ID NO 61
<211> LENGTH: 23
<212> TYPE: DNA
<213> ORGANISM: Homo sapiens

<400> SEQUENCE: 61
gcagttggaa gacacaggaa agt 23

<210> SEQ ID NO 62
<211> LENGTH: 21
<212> TYPE: DNA
<213> ORGANISM: Homo sapiens

<400> SEQUENCE: 62
tgcgtggcac tattttcaag a 21

<210> SEQ ID NO 63
<211> LENGTH: 77
<212> TYPE: DNA
<213> ORGANISM: Homo sapiens

<400> SEQUENCE: 63
gcagttggaa gacacaggaa agtatcccca aattgcagat ttatcaacgg cttttatctt 60
gaaaatagtg ccacgca 77

<210> SEQ ID NO 64
<211> LENGTH: 20
<212> TYPE: DNA
<213> ORGANISM: Homo sapiens

<400> SEQUENCE: 64
tgttttgatt cccgggctta 20

<210> SEQ ID NO 65
<211> LENGTH: 24
<212> TYPE: DNA
<213> ORGANISM: Homo sapiens

<400> SEQUENCE: 65
caaagctgtc agctctagca aaag 24

<210> SEQ ID NO 66
<211> LENGTH: 80
<212> TYPE: DNA
<213> ORGANISM: Homo sapiens

<400> SEQUENCE: 66
tgttttgatt cccgggctta ccaggtgaga agtgagggag gaagaaggca gtgtcccttt 60
tgctagagct gacagctttg 80

<210> SEQ ID NO 67
<211> LENGTH: 20
<212> TYPE: DNA
<213> ORGANISM: Homo sapiens

<400> SEQUENCE: 67
tcagggggct agaaatctgt 20

<210> SEQ ID NO 68
<211> LENGTH: 20
<212> TYPE: DNA
<213> ORGANISM: Homo sapiens

<400> SEQUENCE: 68
ccattccagt tgatctgtgg 20

<210> SEQ ID NO 69
<211> LENGTH: 65
<212> TYPE: DNA
<213> ORGANISM: Homo sapiens

<400> SEQUENCE: 69
tcagggggct agaaatctgt tgctatgggc ccttcaccaa catgcccaca gatcaactgg 60
aatgg 65

<210> SEQ ID NO 70
<211> LENGTH: 20
<212> TYPE: DNA
<213> ORGANISM: Homo sapiens

<400> SEQUENCE: 70
agttcgtgct ttgcaagatg 20

<210> SEQ ID NO 71
<211> LENGTH: 20
<212> TYPE: DNA
<213> ORGANISM: Homo sapiens

<400> SEQUENCE: 71
aaggtaagct gggtctgctg 20

<210> SEQ ID NO 72
<211> LENGTH: 70
<212> TYPE: DNA
<213> ORGANISM: Homo sapiens

<400> SEQUENCE: 72
agttcgtgct ttgcaagatg gtgcagagct ttatgaagca gtgaagaatg cagcagaccc 60
agcttacctt 70

<210> SEQ ID NO 73
<211> LENGTH: 21
<212> TYPE: DNA
<213> ORGANISM: Homo sapiens

<400> SEQUENCE: 73
gcatgttcgt ggcctctaag a 21

<210> SEQ ID NO 74
<211> LENGTH: 22
<212> TYPE: DNA
<213> ORGANISM: Homo sapiens

<400> SEQUENCE: 74
cggtgtagat gcacagcttc tc 22

<210> SEQ ID NO 75
<211> LENGTH: 69
<212> TYPE: DNA
<213> ORGANISM: Homo sapiens

<400> SEQUENCE: 75
gcatgttcgt ggcctctaag atgaaggaga ccatcccccct gacggccgag aagctgtgca 60
tctacaccg 69

<210> SEQ ID NO 76
<211> LENGTH: 20
<212> TYPE: DNA
<213> ORGANISM: Homo sapiens

<400> SEQUENCE: 76
agatgaagtg gaaggcgctt 20

<210> SEQ ID NO 77
<211> LENGTH: 21
<212> TYPE: DNA
<213> ORGANISM: Homo sapiens

<400> SEQUENCE: 77
tgcctctgta atcggcaact g 21

<210> SEQ ID NO 78
<211> LENGTH: 65
<212> TYPE: DNA
<213> ORGANISM: Homo sapiens

<400> SEQUENCE: 78
agatgaagtg gaaggcgctt ttcaccgcgg ccatcctgca ggcacagttg ccgattacag 60
aggca 65

<210> SEQ ID NO 79
<211> LENGTH: 18
<212> TYPE: DNA
<213> ORGANISM: Homo sapiens

<400> SEQUENCE: 79
tggttcccag ccctgtgt 18

<210> SEQ ID NO 80
<211> LENGTH: 19
<212> TYPE: DNA
<213> ORGANISM: Homo sapiens -continued

<400> SEQUENCE: 80
ctcctccacc ctgggttgt 19

<210> SEQ ID NO 81
<211> LENGTH: 74
<212> TYPE: DNA
<213> ORGANISM: Homo sapiens

<400> SEQUENCE: 81
tggttcccag ccctgtgtcc acctccaagc ccagattcag attcgagtca tgtacacaac 60
ccagggtgga ggag 74

<210> SEQ ID NO 82
<211> LENGTH: 20
<212> TYPE: DNA
<213> ORGANISM: Homo sapiens

<400> SEQUENCE: 82
tcttgctggc tacgcctctt 20

<210> SEQ ID NO 83
<211> LENGTH: 21
<212> TYPE: DNA
<213> ORGANISM: Homo sapiens

<400> SEQUENCE: 83
ctgcattgtg gcacagttct g 21

<210> SEQ ID NO 84
<211> LENGTH: 71
<212> TYPE: DNA
<213> ORGANISM: Homo sapiens

<400> SEQUENCE: 84
tcttgctggc tacgcctctt ctgtccctgt tagacgtcct ccgtccatat cagaactgtg 60
ccacaatgca g 71

<210> SEQ ID NO 85
<211> LENGTH: 21
<212> TYPE: DNA
<213> ORGANISM: Homo sapiens

<400> SEQUENCE: 85
tgagtgtccc ccggtatctt c 21

<210> SEQ ID NO 86
<211> LENGTH: 21
<212> TYPE: DNA
<213> ORGANISM: Homo sapiens

<400> SEQUENCE: 86
cagccgcttt cagattttca t 21

<210> SEQ ID NO 87
<211> LENGTH: 81
<212> TYPE: DNA
<213> ORGANISM: Homo sapiens

<400> SEQUENCE: 87
tgagtgtccc ccggtatctt ccccgccctg ccaatcccga tgaaattgga aattttattg 60

-continued

```
atgaaaatct gaaagcggct g                                               81


<210> SEQ ID NO 88
<211> LENGTH: 21
<212> TYPE: DNA
<213> ORGANISM: Homo sapiens

<400> SEQUENCE: 88

tggagactct cagggtcgaa a                                               21


<210> SEQ ID NO 89
<211> LENGTH: 22
<212> TYPE: DNA
<213> ORGANISM: Homo sapiens

<400> SEQUENCE: 89

ggcgtttgga gtggtagaaa tc                                              22


<210> SEQ ID NO 90
<211> LENGTH: 65
<212> TYPE: DNA
<213> ORGANISM: Homo sapiens

<400> SEQUENCE: 90

tggagactct cagggtcgaa aacggcggca gaccagcatg acagatttct accactccaa     60

acgcc                                                                 65


<210> SEQ ID NO 91
<211> LENGTH: 21
<212> TYPE: DNA
<213> ORGANISM: Homo sapiens

<400> SEQUENCE: 91

cggtggacca cgaagagtta a                                               21


<210> SEQ ID NO 92
<211> LENGTH: 19
<212> TYPE: DNA
<213> ORGANISM: Homo sapiens

<400> SEQUENCE: 92

ggctcgcctc ttccatgtc                                                  19


<210> SEQ ID NO 93
<211> LENGTH: 66
<212> TYPE: DNA
<213> ORGANISM: Homo sapiens

<400> SEQUENCE: 93

cggtggacca cgaagagtta acccgggact tggagaagca ctgcagagac atggaagagg     60

cgagcc                                                                66


<210> SEQ ID NO 94
<211> LENGTH: 19
<212> TYPE: DNA
<213> ORGANISM: Homo sapiens

<400> SEQUENCE: 94

gcggaaggtc cctcagaca                                                  19


<210> SEQ ID NO 95
<211> LENGTH: 23
```

```
<212> TYPE: DNA
<213> ORGANISM: Homo sapiens

<400> SEQUENCE: 95

tctaagtttc ccgaggtttc tca                                               23


<210> SEQ ID NO 96
<211> LENGTH: 70
<212> TYPE: DNA
<213> ORGANISM: Homo sapiens

<400> SEQUENCE: 96

gcggaaggtc cctcagacat ccccgattga aagaaccaga gaggctctga gaaacctcgg       60

gaaacttaga                                                              70


<210> SEQ ID NO 97
<211> LENGTH: 22
<212> TYPE: DNA
<213> ORGANISM: Homo sapiens

<400> SEQUENCE: 97

ccagctttgt gcctgtcact at                                                22


<210> SEQ ID NO 98
<211> LENGTH: 20
<212> TYPE: DNA
<213> ORGANISM: Homo sapiens

<400> SEQUENCE: 98

gggaatgtgg tagcccaaga                                                   20


<210> SEQ ID NO 99
<211> LENGTH: 71
<212> TYPE: DNA
<213> ORGANISM: Homo sapiens

<400> SEQUENCE: 99

ccagctttgt gcctgtcact attcctcatg ccaccactgc caacacctct gtcttgggct       60

accacattcc c                                                            71


<210> SEQ ID NO 100
<211> LENGTH: 27
<212> TYPE: DNA
<213> ORGANISM: Homo sapiens

<400> SEQUENCE: 100

ttgctataac taagtgcttc tccaaga                                           27


<210> SEQ ID NO 101
<211> LENGTH: 22
<212> TYPE: DNA
<213> ORGANISM: Homo sapiens

<400> SEQUENCE: 101

gtggaatggc agctcactgt ag                                                22


<210> SEQ ID NO 102
<211> LENGTH: 73
<212> TYPE: DNA
<213> ORGANISM: Homo sapiens

<400> SEQUENCE: 102
```

-continued

```
ttgctataac taagtgcttc tccaagaccc caactgagtc cccagcacct gctacagtga      60

gctgccattc cac                                                         73


<210> SEQ ID NO 103
<211> LENGTH: 19
<212> TYPE: DNA
<213> ORGANISM: Homo sapiens

<400> SEQUENCE: 103

aggacgcaag gagggtttg                                                   19


<210> SEQ ID NO 104
<211> LENGTH: 21
<212> TYPE: DNA
<213> ORGANISM: Homo sapiens

<400> SEQUENCE: 104

gatgtccgcc gagtccttac t                                                21


<210> SEQ ID NO 105
<211> LENGTH: 87
<212> TYPE: DNA
<213> ORGANISM: Homo sapiens

<400> SEQUENCE: 105

aggacgcaag gagggtttgt cactggcaga ctcgagactg taggcactgc catggcccct      60

gtgctcagta aggactcggc ggacatc                                          87


<210> SEQ ID NO 106
<211> LENGTH: 24
<212> TYPE: DNA
<213> ORGANISM: Homo sapiens

<400> SEQUENCE: 106

ctatatgcag ccagagatgt gaca                                             24


<210> SEQ ID NO 107
<211> LENGTH: 24
<212> TYPE: DNA
<213> ORGANISM: Homo sapiens

<400> SEQUENCE: 107

ccacgagttt cttactgaga atgg                                             24


<210> SEQ ID NO 108
<211> LENGTH: 82
<212> TYPE: DNA
<213> ORGANISM: Homo sapiens

<400> SEQUENCE: 108

ctatatgcag ccagagatgt gacagccacc gtggacagcc tgccactcat cacagcctcc      60

attctcagta agaaactcgt gg                                               82


<210> SEQ ID NO 109
<211> LENGTH: 20
<212> TYPE: DNA
<213> ORGANISM: Homo sapiens

<400> SEQUENCE: 109

tgtcgatgga cttccagaac                                                  20
```

<210> SEQ ID NO 110
<211> LENGTH: 19
<212> TYPE: DNA
<213> ORGANISM: Homo sapiens

<400> SEQUENCE: 110
attgggacag cttggatca 19

<210> SEQ ID NO 111
<211> LENGTH: 62
<212> TYPE: DNA
<213> ORGANISM: Homo sapiens

<400> SEQUENCE: 111
tgtcgatgga cttccagaac cacctgggca gctgccaaaa gtgtgatcca agctgtccca 60
at 62

<210> SEQ ID NO 112
<211> LENGTH: 23
<212> TYPE: DNA
<213> ORGANISM: Homo sapiens

<400> SEQUENCE: 112
gatctaagat ggcgactgtc gaa 23

<210> SEQ ID NO 113
<211> LENGTH: 25
<212> TYPE: DNA
<213> ORGANISM: Homo sapiens

<400> SEQUENCE: 113
ttagattccg ttttctcctc ttctg 25

<210> SEQ ID NO 114
<211> LENGTH: 82
<212> TYPE: DNA
<213> ORGANISM: Homo sapiens

<400> SEQUENCE: 114
gatctaagat ggcgactgtc gaaccggaaa ccacccctac tcctaatccc ccgactacag 60
aagaggagaa aacggaatct aa 82

<210> SEQ ID NO 115
<211> LENGTH: 20
<212> TYPE: DNA
<213> ORGANISM: Homo sapiens

<400> SEQUENCE: 115
cggtgtgaga agtgcagcaa 20

<210> SEQ ID NO 116
<211> LENGTH: 19
<212> TYPE: DNA
<213> ORGANISM: Homo sapiens

<400> SEQUENCE: 116
cctctcgcaa gtgctccat 19

<210> SEQ ID NO 117
<211> LENGTH: 70
<212> TYPE: DNA
<213> ORGANISM: Homo sapiens -continued

<400> SEQUENCE: 117
cggtgtgaga agtgcagcaa gccctgtgcc cgagtgtgct atggtctggg catggagcac 60
ttgcgagagg 70

<210> SEQ ID NO 118
<211> LENGTH: 23
<212> TYPE: DNA
<213> ORGANISM: Homo sapiens

<400> SEQUENCE: 118
cggttatgtc atgccagata cac 23

<210> SEQ ID NO 119
<211> LENGTH: 24
<212> TYPE: DNA
<213> ORGANISM: Homo sapiens

<400> SEQUENCE: 119
gaactgagac ccactgaaga aagg 24

<210> SEQ ID NO 120
<211> LENGTH: 81
<212> TYPE: DNA
<213> ORGANISM: Homo sapiens

<400> SEQUENCE: 120
cggttatgtc atgccagata cacacctcaa aggtactccc tcctcccggg aaggcaccct 60
ttcttcagtg ggtctcagtt c 81

<210> SEQ ID NO 121
<211> LENGTH: 19
<212> TYPE: DNA
<213> ORGANISM: Homo sapiens

<400> SEQUENCE: 121
cgtggtgccc ctctatgac 19

<210> SEQ ID NO 122
<211> LENGTH: 19
<212> TYPE: DNA
<213> ORGANISM: Homo sapiens

<400> SEQUENCE: 122
ggctagtggg cgcatgtag 19

<210> SEQ ID NO 123
<211> LENGTH: 68
<212> TYPE: DNA
<213> ORGANISM: Homo sapiens

<400> SEQUENCE: 123
cgtggtgccc ctctatgacc tgctgctgga gatgctggac gcccaccgcc tacatgcgcc 60
cactagcc 68

<210> SEQ ID NO 124
<211> LENGTH: 20
<212> TYPE: DNA
<213> ORGANISM: Homo sapiens

<400> SEQUENCE: 124
tggtccatcg ccagttatca 20

<210> SEQ ID NO 125
<211> LENGTH: 23
<212> TYPE: DNA
<213> ORGANISM: Homo sapiens

<400> SEQUENCE: 125
tgttctagcg atcttgcttc aca 23

<210> SEQ ID NO 126
<211> LENGTH: 76
<212> TYPE: DNA
<213> ORGANISM: Homo sapiens

<400> SEQUENCE: 126
tggtccatcg ccagttatca catctgtatg cggaacctca aaagagtccc tggtgtgaag 60
caagatcgct agaaca 76

<210> SEQ ID NO 127
<211> LENGTH: 24
<212> TYPE: DNA
<213> ORGANISM: Homo sapiens

<400> SEQUENCE: 127
catccatgac aactttggta tcgt 24

<210> SEQ ID NO 128
<211> LENGTH: 21
<212> TYPE: DNA
<213> ORGANISM: Homo sapiens

<400> SEQUENCE: 128
cagtcttctg ggtggcagtg a 21

<210> SEQ ID NO 129
<211> LENGTH: 74
<212> TYPE: DNA
<213> ORGANISM: Homo sapiens

<400> SEQUENCE: 129
catccatgac aactttggta tcgtggaagg actcatgacc acagtccatg ccatcactgc 60
cacccagaag actg 74

<210> SEQ ID NO 130
<211> LENGTH: 23
<212> TYPE: DNA
<213> ORGANISM: Homo sapiens

<400> SEQUENCE: 130
caaaggagct cactgtggtg tct 23

<210> SEQ ID NO 131
<211> LENGTH: 26
<212> TYPE: DNA
<213> ORGANISM: Homo sapiens

<400> SEQUENCE: 131
gagtcagaat ggcttattca cagatg 26

<210> SEQ ID NO 132
<211> LENGTH: 75
<212> TYPE: DNA

<213> ORGANISM: Homo sapiens

<400> SEQUENCE: 132
caaaggagct cactgtggtg tctgtgttcc aaccactgaa tctggacccc atctgtgaat 60
aagccattct gactc 75

<210> SEQ ID NO 133
<211> LENGTH: 20
<212> TYPE: DNA
<213> ORGANISM: Homo sapiens

<400> SEQUENCE: 133
ccatctgcat ccatcttgtt 20

<210> SEQ ID NO 134
<211> LENGTH: 20
<212> TYPE: DNA
<213> ORGANISM: Homo sapiens

<400> SEQUENCE: 134
ggccaccagg gtattatctg 20

<210> SEQ ID NO 135
<211> LENGTH: 67
<212> TYPE: DNA
<213> ORGANISM: Homo sapiens

<400> SEQUENCE: 135
ccatctgcat ccatcttgtt tgggctcccc acccttgaga agtgcctcag ataataccct 60
ggtggcc 67

<210> SEQ ID NO 136
<211> LENGTH: 23
<212> TYPE: DNA
<213> ORGANISM: Homo sapiens

<400> SEQUENCE: 136
cgaaaagatg ctgaacagtg aca 23

<210> SEQ ID NO 137
<211> LENGTH: 20
<212> TYPE: DNA
<213> ORGANISM: Homo sapiens

<400> SEQUENCE: 137
tcaggaacag ccaccagtga 20

<210> SEQ ID NO 138
<211> LENGTH: 73
<212> TYPE: DNA
<213> ORGANISM: Homo sapiens

<400> SEQUENCE: 138
cgaaaagatg ctgaacagtg acaaatccaa ctgaccagaa gggaggagga agctcactgg 60
tggctgttcc tga 73

<210> SEQ ID NO 139
<211> LENGTH: 20
<212> TYPE: DNA
<213> ORGANISM: Homo sapiens

<400> SEQUENCE: 139
gagaccctgc tgtcccagaa 20

<210> SEQ ID NO 140
<211> LENGTH: 23
<212> TYPE: DNA
<213> ORGANISM: Homo sapiens

<400> SEQUENCE: 140
ggttgtagtc agcgaaggag atc 23

<210> SEQ ID NO 141
<211> LENGTH: 76
<212> TYPE: DNA
<213> ORGANISM: Homo sapiens

<400> SEQUENCE: 141
gagaccctgc tgtcccagaa ccagggaggc aagaccttca ttgtgggaga ccagatctcc 60
ttcgctgact acaacc 76

<210> SEQ ID NO 142
<211> LENGTH: 20
<212> TYPE: DNA
<213> ORGANISM: Homo sapiens

<400> SEQUENCE: 142
cccactcagt agccaagtca 20

<210> SEQ ID NO 143
<211> LENGTH: 20
<212> TYPE: DNA
<213> ORGANISM: Homo sapiens

<400> SEQUENCE: 143
cacgcaggtg gtatcagtct 20

<210> SEQ ID NO 144
<211> LENGTH: 73
<212> TYPE: DNA
<213> ORGANISM: Homo sapiens

<400> SEQUENCE: 144
cccactcagt agccaagtca caatgtttgg aaaacagccc gtttacttga gcaagactga 60
taccacctgc gtg 73

<210> SEQ ID NO 145
<211> LENGTH: 24
<212> TYPE: DNA
<213> ORGANISM: Homo sapiens

<400> SEQUENCE: 145
catcaaatgt cagccctgga gttc 24

<210> SEQ ID NO 146
<211> LENGTH: 26
<212> TYPE: DNA
<213> ORGANISM: Homo sapiens

<400> SEQUENCE: 146
ttcctgtagg tctttacccc gatagc 26

<210> SEQ ID NO 147

<211> LENGTH: 85
<212> TYPE: DNA
<213> ORGANISM: Homo sapiens

<400> SEQUENCE: 147
catcaaatgt cagccctgga gttccatgat accacacgaa cacagctttt tgccttcgag 60
ctatcggggt aaagacctac aggaa 85

<210> SEQ ID NO 148
<211> LENGTH: 24
<212> TYPE: DNA
<213> ORGANISM: Homo sapiens

<400> SEQUENCE: 148
tccaggatgt taggaactgt gaag 24

<210> SEQ ID NO 149
<211> LENGTH: 22
<212> TYPE: DNA
<213> ORGANISM: Homo sapiens

<400> SEQUENCE: 149
gcgtgtctgc gtagtagctg tt 22

<210> SEQ ID NO 150
<211> LENGTH: 73
<212> TYPE: DNA
<213> ORGANISM: Homo sapiens

<400> SEQUENCE: 150
tccaggatgt taggaactgt gaagatggaa gggcatgaaa ccagcgactg gaacagctac 60
tacgcagaca cgc 73

<210> SEQ ID NO 151
<211> LENGTH: 23
<212> TYPE: DNA
<213> ORGANISM: Homo sapiens

<400> SEQUENCE: 151
aacgactgct actccaagct caa 23

<210> SEQ ID NO 152
<211> LENGTH: 22
<212> TYPE: DNA
<213> ORGANISM: Homo sapiens

<400> SEQUENCE: 152
ggatttccat cttgctcacc tt 22

<210> SEQ ID NO 153
<211> LENGTH: 76
<212> TYPE: DNA
<213> ORGANISM: Homo sapiens

<400> SEQUENCE: 153
aacgactgct actccaagct caaggagctg gtgcccagca tcccccagaa caagaaggtg 60
agcaagatgg aaatcc 76

<210> SEQ ID NO 154
<211> LENGTH: 21
<212> TYPE: DNA
<213> ORGANISM: Homo sapiens

<400> SEQUENCE: 154
tccggagctg tgatctaagg a 21

<210> SEQ ID NO 155
<211> LENGTH: 20
<212> TYPE: DNA
<213> ORGANISM: Homo sapiens

<400> SEQUENCE: 155
cggacagagc gagctgactt 20

<210> SEQ ID NO 156
<211> LENGTH: 76
<212> TYPE: DNA
<213> ORGANISM: Homo sapiens

<400> SEQUENCE: 156
tccggagctg tgatctaagg aggctggaga tgtattgcgc acccctcaag cctgccaagt 60
cagctcgctc tgtccg 76

<210> SEQ ID NO 157
<211> LENGTH: 17
<212> TYPE: DNA
<213> ORGANISM: Homo sapiens

<400> SEQUENCE: 157
acgcaccggg tgtctga 17

<210> SEQ ID NO 158
<211> LENGTH: 24
<212> TYPE: DNA
<213> ORGANISM: Homo sapiens

<400> SEQUENCE: 158
tgccctttct tgatgatgat tatc 24

<210> SEQ ID NO 159
<211> LENGTH: 68
<212> TYPE: DNA
<213> ORGANISM: Homo sapiens

<400> SEQUENCE: 159
acgcaccggg tgtctgatcc caagttccac cccctccatt caaagataat catcatcaag 60
aaagggca 68

<210> SEQ ID NO 160
<211> LENGTH: 22
<212> TYPE: DNA
<213> ORGANISM: Homo sapiens

<400> SEQUENCE: 160
ccattcaccc tgtgtaacag ga 22

<210> SEQ ID NO 161
<211> LENGTH: 21
<212> TYPE: DNA
<213> ORGANISM: Homo sapiens

<400> SEQUENCE: 161
ccgaccctct aggttaaggc a 21

-continued

<210> SEQ ID NO 162
<211> LENGTH: 68
<212> TYPE: DNA
<213> ORGANISM: Homo sapiens

<400> SEQUENCE: 162
ccattcaccc tgtgtaacag gaccccaagg acctgcctcc ccggaagtgc cttaacctag 60
agggtcgg 68

<210> SEQ ID NO 163
<211> LENGTH: 20
<212> TYPE: DNA
<213> ORGANISM: Homo sapiens

<400> SEQUENCE: 163
cgtcaggacc caccatgtct 20

<210> SEQ ID NO 164
<211> LENGTH: 24
<212> TYPE: DNA
<213> ORGANISM: Homo sapiens

<400> SEQUENCE: 164
ggttaattgg tgacatcctc aaga 24

<210> SEQ ID NO 165
<211> LENGTH: 81
<212> TYPE: DNA
<213> ORGANISM: Homo sapiens

<400> SEQUENCE: 165
cgtcaggacc caccatgtct gccccatcac gcggccgaga catggcttgg ccacagctct 60
tgaggatgtc accaattaac c 81

<210> SEQ ID NO 166
<211> LENGTH: 23
<212> TYPE: DNA
<213> ORGANISM: Homo sapiens

<400> SEQUENCE: 166
caaacgctga catgtacggt cta 23

<210> SEQ ID NO 167
<211> LENGTH: 18
<212> TYPE: DNA
<213> ORGANISM: Homo sapiens

<400> SEQUENCE: 167
gctcgttggc gcactctt 18

<210> SEQ ID NO 168
<211> LENGTH: 88
<212> TYPE: DNA
<213> ORGANISM: Homo sapiens

<400> SEQUENCE: 168
caaacgctga catgtacggt ctatgccatt cctcccccgc atcacatcca ctggtattgg 60
cagttggagg aagagtgcgc caacgagc 88

<210> SEQ ID NO 169
<211> LENGTH: 25

<212> TYPE: DNA
<213> ORGANISM: Homo sapiens

<400> SEQUENCE: 169
gaggcaactg cttatggctt aatta 25

<210> SEQ ID NO 170
<211> LENGTH: 18
<212> TYPE: DNA
<213> ORGANISM: Homo sapiens

<400> SEQUENCE: 170
ggcactcggc ttgagcat 18

<210> SEQ ID NO 171
<211> LENGTH: 75
<212> TYPE: DNA
<213> ORGANISM: Homo sapiens

<400> SEQUENCE: 171
gaggcaactg cttatggctt aattaagtca gatgcggcca tgactgtcgc tgtaaagatg 60
ctcaagccga gtgcc 75

<210> SEQ ID NO 172
<211> LENGTH: 18
<212> TYPE: DNA
<213> ORGANISM: Homo sapiens

<400> SEQUENCE: 172
gtccccggga tggatgtt 18

<210> SEQ ID NO 173
<211> LENGTH: 25
<212> TYPE: DNA
<213> ORGANISM: Homo sapiens

<400> SEQUENCE: 173
gatcagtcaa gctgtctgac aattg 25

<210> SEQ ID NO 174
<211> LENGTH: 79
<212> TYPE: DNA
<213> ORGANISM: Homo sapiens

<400> SEQUENCE: 174
gtccccggga tggatgtttt gccaagtcat tgttggataa gcgagatggt agtacaattg 60
tcagacagct tgactgatc 79

<210> SEQ ID NO 175
<211> LENGTH: 21
<212> TYPE: DNA
<213> ORGANISM: Homo sapiens

<400> SEQUENCE: 175
cgaggattgg ttcttcagca a 21

<210> SEQ ID NO 176
<211> LENGTH: 22
<212> TYPE: DNA
<213> ORGANISM: Homo sapiens

<400> SEQUENCE: 176

-continued actctgcacc agctcactgt tg 22

<210> SEQ ID NO 177
<211> LENGTH: 73
<212> TYPE: DNA
<213> ORGANISM: Homo sapiens

<400> SEQUENCE: 177
cgaggattgg ttcttcagca agacagagga actgaaccgc gaggtggcca ccaacagtga 60
gctggtgcag agt 73

<210> SEQ ID NO 178
<211> LENGTH: 20
<212> TYPE: DNA
<213> ORGANISM: Homo sapiens

<400> SEQUENCE: 178
tcagtggaga aggagttgga 20

<210> SEQ ID NO 179
<211> LENGTH: 20
<212> TYPE: DNA
<213> ORGANISM: Homo sapiens

<400> SEQUENCE: 179
tgccatatcc agaggaaaca 20

<210> SEQ ID NO 180
<211> LENGTH: 69
<212> TYPE: DNA
<213> ORGANISM: Homo sapiens

<400> SEQUENCE: 180
tcagtggaga aggagttgga ccagtcaaca tctctgttgt cacaagcagt gtttcctctg 60
gatatggca 69

<210> SEQ ID NO 181
<211> LENGTH: 26
<212> TYPE: DNA
<213> ORGANISM: Homo sapiens

<400> SEQUENCE: 181
gtacaagaga gaaccagact ccaatg 26

<210> SEQ ID NO 182
<211> LENGTH: 18
<212> TYPE: DNA
<213> ORGANISM: Homo sapiens

<400> SEQUENCE: 182
gtgtagcccg cggacact 18

<210> SEQ ID NO 183
<211> LENGTH: 87
<212> TYPE: DNA
<213> ORGANISM: Homo sapiens

<400> SEQUENCE: 183
gtacaagaga gaaccagact ccaatgtcat tgtggtggac tggctgtcac gggctcagga 60
gcattaccca gtgtccgcgg gctacac 87

-continued

<210> SEQ ID NO 184
<211> LENGTH: 22
<212> TYPE: DNA
<213> ORGANISM: Homo sapiens

<400> SEQUENCE: 184
gacatttcca gtcctgcagt ca 22

<210> SEQ ID NO 185
<211> LENGTH: 20
<212> TYPE: DNA
<213> ORGANISM: Homo sapiens

<400> SEQUENCE: 185
ctccgatcgc acacatttgt 20

<210> SEQ ID NO 186
<211> LENGTH: 86
<212> TYPE: DNA
<213> ORGANISM: Homo sapiens

<400> SEQUENCE: 186
gacatttcca gtcctgcagt caatgcctct ctgccccacc ctttgttcag tgtggctggt 60
gccacgacaa atgtgtgcga tcggag 86

<210> SEQ ID NO 187
<211> LENGTH: 24
<212> TYPE: DNA
<213> ORGANISM: Homo sapiens

<400> SEQUENCE: 187
gttttggagg aaatgtgttc ttca 24

<210> SEQ ID NO 188
<211> LENGTH: 26
<212> TYPE: DNA
<213> ORGANISM: Homo sapiens

<400> SEQUENCE: 188
ttctctaata cactgccgtc ttaagg 26

<210> SEQ ID NO 189
<211> LENGTH: 101
<212> TYPE: DNA
<213> ORGANISM: Homo sapiens

<400> SEQUENCE: 189
gttttggagg aaatgtgttc ttcagtgcac agaatgcagc aaaacagcca tctgataaat 60
gctctgcaag ccctccctta agacggcagt gtattagaga a 101

<210> SEQ ID NO 190
<211> LENGTH: 22
<212> TYPE: DNA
<213> ORGANISM: Homo sapiens

<400> SEQUENCE: 190
acgagaacga gggcatctat gt 22

<210> SEQ ID NO 191
<211> LENGTH: 22
<212> TYPE: DNA
<213> ORGANISM: Homo sapiens -continued

<400> SEQUENCE: 191
gcatgtaggt gcttccaatc ac 22

<210> SEQ ID NO 192
<211> LENGTH: 75
<212> TYPE: DNA
<213> ORGANISM: Homo sapiens

<400> SEQUENCE: 192
acgagaacga gggcatctat gtgcaggatg tcaagaccgg aaaggtgcgc gctgtgattg 60
gaagcaccta catgc 75

<210> SEQ ID NO 193
<211> LENGTH: 21
<212> TYPE: DNA
<213> ORGANISM: Homo sapiens

<400> SEQUENCE: 193
tccctccact cggaaggact a 21

<210> SEQ ID NO 194
<211> LENGTH: 22
<212> TYPE: DNA
<213> ORGANISM: Homo sapiens

<400> SEQUENCE: 194
cggttgttgc tgatctgtct ca 22

<210> SEQ ID NO 195
<211> LENGTH: 84
<212> TYPE: DNA
<213> ORGANISM: Homo sapiens

<400> SEQUENCE: 195
tccctccact cggaaggact atcctgctgc caagagggtc aagttggaca gtgtcagagt 60
cctgagacag atcagcaaca accg 84

<210> SEQ ID NO 196
<211> LENGTH: 19
<212> TYPE: DNA
<213> ORGANISM: Homo sapiens

<400> SEQUENCE: 196
ttgttggtgt gccctggtg 19

<210> SEQ ID NO 197
<211> LENGTH: 21
<212> TYPE: DNA
<213> ORGANISM: Homo sapiens

<400> SEQUENCE: 197
tgggttctgt ccaaacactg g 21

<210> SEQ ID NO 198
<211> LENGTH: 67
<212> TYPE: DNA
<213> ORGANISM: Homo sapiens

<400> SEQUENCE: 198
ttgttggtgt gccctggtgc cgtggtggcg gtcactccct ctgctgccag tgtttggaca 60
gaaccca 67

<210> SEQ ID NO 199
<211> LENGTH: 20
<212> TYPE: DNA
<213> ORGANISM: Homo sapiens

<400> SEQUENCE: 199
actgaaggag acccttggag 20

<210> SEQ ID NO 200
<211> LENGTH: 20
<212> TYPE: DNA
<213> ORGANISM: Homo sapiens

<400> SEQUENCE: 200
taaataaccc tgcccacaca 20

<210> SEQ ID NO 201
<211> LENGTH: 62
<212> TYPE: DNA
<213> ORGANISM: Homo sapiens

<400> SEQUENCE: 201
actgaaggag acccttggag cctaggggca tcggcaggag agtgtgtggg cagggttatt 60
ta 62

<210> SEQ ID NO 202
<211> LENGTH: 28
<212> TYPE: DNA
<213> ORGANISM: Homo sapiens

<400> SEQUENCE: 202
agttactaaa aaataccacg aggtcctt 28

<210> SEQ ID NO 203
<211> LENGTH: 21
<212> TYPE: DNA
<213> ORGANISM: Homo sapiens

<400> SEQUENCE: 203
gtcggtgagt gatttgtgca a 21

<210> SEQ ID NO 204
<211> LENGTH: 79
<212> TYPE: DNA
<213> ORGANISM: Homo sapiens

<400> SEQUENCE: 204
agttactaaa aaataccacg aggtccttca gttgagacca aagaccggtg tcaggggatt 60
gcacaaatca ctcaccgac 79

<210> SEQ ID NO 205
<211> LENGTH: 20
<212> TYPE: DNA
<213> ORGANISM: Homo sapiens

<400> SEQUENCE: 205
gggagtttcc aagagatgga 20

<210> SEQ ID NO 206
<211> LENGTH: 20
<212> TYPE: DNA

<213> ORGANISM: Homo sapiens

<400> SEQUENCE: 206
cttcaaccac cttcccaaac 20

<210> SEQ ID NO 207
<211> LENGTH: 72
<212> TYPE: DNA
<213> ORGANISM: Homo sapiens

<400> SEQUENCE: 207
gggagtttcc aagagatgga ctagtgcttg gtcgggtctt ggggtctgga gcgtttggga 60
aggtggttga ag 72

<210> SEQ ID NO 208
<211> LENGTH: 23
<212> TYPE: DNA
<213> ORGANISM: Homo sapiens

<400> SEQUENCE: 208
aggtgtcatc catcaacgtc tct 23

<210> SEQ ID NO 209
<211> LENGTH: 20
<212> TYPE: DNA
<213> ORGANISM: Homo sapiens

<400> SEQUENCE: 209
tcccgatcac aatgcacatg 20

<210> SEQ ID NO 210
<211> LENGTH: 90
<212> TYPE: DNA
<213> ORGANISM: Homo sapiens

<400> SEQUENCE: 210
aggtgtcatc catcaacgtc tctgtgaacg cagtgcagac tgtggtccgc cagggtgaga 60
acatcaccct catgtgcatt gtgatcggga 90

<210> SEQ ID NO 211
<211> LENGTH: 24
<212> TYPE: DNA
<213> ORGANISM: Homo sapiens

<400> SEQUENCE: 211
agagccagtt gctgtagaac tcaa 24

<210> SEQ ID NO 212
<211> LENGTH: 21
<212> TYPE: DNA
<213> ORGANISM: Homo sapiens

<400> SEQUENCE: 212
ctgggcctac acagtccttc a 21

<210> SEQ ID NO 213
<211> LENGTH: 74
<212> TYPE: DNA
<213> ORGANISM: Homo sapiens

<400> SEQUENCE: 213
agagccagtt gctgtagaac tcaaatctct gctgggcaag gatgttctgt tcttgaagga 60

-continued

```
ctgtgtaggc ccag                                                  74


<210> SEQ ID NO 214
<211> LENGTH: 26
<212> TYPE: DNA
<213> ORGANISM: Homo sapiens

<400> SEQUENCE: 214

gaaatgactg catcgttgat aaaatc                                     26


<210> SEQ ID NO 215
<211> LENGTH: 19
<212> TYPE: DNA
<213> ORGANISM: Homo sapiens

<400> SEQUENCE: 215

tgccagcctg acagcactt                                             19


<210> SEQ ID NO 216
<211> LENGTH: 78
<212> TYPE: DNA
<213> ORGANISM: Homo sapiens

<400> SEQUENCE: 216

gaaatgactg catcgttgat aaaatccgca gaaaaaactg cccagcatgt cgccttagaa 60

agtgctgtca ggctggca                                              78


<210> SEQ ID NO 217
<211> LENGTH: 20
<212> TYPE: DNA
<213> ORGANISM: Homo sapiens

<400> SEQUENCE: 217

gatcaacggc tacatccaga                                            20


<210> SEQ ID NO 218
<211> LENGTH: 20
<212> TYPE: DNA
<213> ORGANISM: Homo sapiens

<400> SEQUENCE: 218

tgaactgtga ggccagagac                                            20


<210> SEQ ID NO 219
<211> LENGTH: 68
<212> TYPE: DNA
<213> ORGANISM: Homo sapiens

<400> SEQUENCE: 219

gatcaacggc tacatccaga agatcaagtc gggagaggag gactttgagt ctctggcctc 60

acagttca                                                         68


<210> SEQ ID NO 220
<211> LENGTH: 19
<212> TYPE: DNA
<213> ORGANISM: Homo sapiens

<400> SEQUENCE: 220

gtggatgtgc cctgaagga                                             19


<210> SEQ ID NO 221
```

<211> LENGTH: 20
<212> TYPE: DNA
<213> ORGANISM: Homo sapiens

<400> SEQUENCE: 221
ctgcggatcc agggtaagaa 20

<210> SEQ ID NO 222
<211> LENGTH: 70
<212> TYPE: DNA
<213> ORGANISM: Homo sapiens

<400> SEQUENCE: 222
gtggatgtgc cctgaaggac aagccaggcg tctacacgag agtctcacac ttcttaccct 60
ggatccgcag 70

<210> SEQ ID NO 223
<211> LENGTH: 27
<212> TYPE: DNA
<213> ORGANISM: Homo sapiens

<400> SEQUENCE: 223
tggacttcta gtgatgagaa agattga 27

<210> SEQ ID NO 224
<211> LENGTH: 22
<212> TYPE: DNA
<213> ORGANISM: Homo sapiens

<400> SEQUENCE: 224
cactgcgaga tcaccacagg ta 22

<210> SEQ ID NO 225
<211> LENGTH: 84
<212> TYPE: DNA
<213> ORGANISM: Homo sapiens

<400> SEQUENCE: 225
tggacttcta gtgatgagaa agattgagaa tgttcccaca ggccccaaca ataagcccaa 60
gctacctgtg gtgatctcgc agtg 84

<210> SEQ ID NO 226
<211> LENGTH: 25
<212> TYPE: DNA
<213> ORGANISM: Homo sapiens

<400> SEQUENCE: 226
tggctaagtg aagatgacaa tcatg 25

<210> SEQ ID NO 227
<211> LENGTH: 25
<212> TYPE: DNA
<213> ORGANISM: Homo sapiens

<400> SEQUENCE: 227
tgcacatatc attacaccag ttcgt 25

<210> SEQ ID NO 228
<211> LENGTH: 81
<212> TYPE: DNA
<213> ORGANISM: Homo sapiens

<400> SEQUENCE: 228

-continued tggctaagtg aagatgacaa tcatgttgca gcaattcact gtaaagctgg aaagggacga 60
actggtgtaa tgatatgtgc a 81

<210> SEQ ID NO 229
<211> LENGTH: 23
<212> TYPE: DNA
<213> ORGANISM: Homo sapiens

<400> SEQUENCE: 229
tctgcagagt tggaagcact cta 23

<210> SEQ ID NO 230
<211> LENGTH: 21
<212> TYPE: DNA
<213> ORGANISM: Homo sapiens

<400> SEQUENCE: 230
gccgaggctt ttctaccaga a 21

<210> SEQ ID NO 231
<211> LENGTH: 79
<212> TYPE: DNA
<213> ORGANISM: Homo sapiens

<400> SEQUENCE: 231
tctgcagagt tggaagcact ctatggtgac atcgatgctg tggagctgta tcctgccctt 60
ctggtagaaa agcctcggc 79

<210> SEQ ID NO 232
<211> LENGTH: 24
<212> TYPE: DNA
<213> ORGANISM: Homo sapiens

<400> SEQUENCE: 232
acgacacgta tgccgtacag tact 24

<210> SEQ ID NO 233
<211> LENGTH: 18
<212> TYPE: DNA
<213> ORGANISM: Homo sapiens

<400> SEQUENCE: 233
ccgggaaaac acgaagga 18

<210> SEQ ID NO 234
<211> LENGTH: 86
<212> TYPE: DNA
<213> ORGANISM: Homo sapiens

<400> SEQUENCE: 234
acgacacgta tgccgtacag tactcctgcc gcctcctgaa cctcgatggc acctgtgctg 60
acagctactc cttcgtgttt tcccgg 86

<210> SEQ ID NO 235
<211> LENGTH: 19
<212> TYPE: DNA
<213> ORGANISM: Homo sapiens

<400> SEQUENCE: 235
ctgccgggat ggcttctat 19

<210> SEQ ID NO 236
<211> LENGTH: 22
<212> TYPE: DNA
<213> ORGANISM: Homo sapiens

<400> SEQUENCE: 236
ccaggttctg gaaactgtgg at 22

<210> SEQ ID NO 237
<211> LENGTH: 68
<212> TYPE: DNA
<213> ORGANISM: Homo sapiens

<400> SEQUENCE: 237
ctgccgggat ggcttctatg aggctgagct ctgcccggac cgctgcatcc acagtttcca 60
gaacctgg 68

<210> SEQ ID NO 238
<211> LENGTH: 20
<212> TYPE: DNA
<213> ORGANISM: Homo sapiens

<400> SEQUENCE: 238
ccacaagctg aaggcagaca 20

<210> SEQ ID NO 239
<211> LENGTH: 21
<212> TYPE: DNA
<213> ORGANISM: Homo sapiens

<400> SEQUENCE: 239
gcgtgcttcc ttggtcttag a 21

<210> SEQ ID NO 240
<211> LENGTH: 85
<212> TYPE: DNA
<213> ORGANISM: Homo sapiens

<400> SEQUENCE: 240
ccacaagctg aaggcagaca aggcccgcaa gaagctcctg gctgaccagg ctgaggcccg 60
caggtctaag accaaggaag cacgc 85

<210> SEQ ID NO 241
<211> LENGTH: 24
<212> TYPE: DNA
<213> ORGANISM: Homo sapiens

<400> SEQUENCE: 241
ccattctatc atcaacgggt acaa 24

<210> SEQ ID NO 242
<211> LENGTH: 23
<212> TYPE: DNA
<213> ORGANISM: Homo sapiens

<400> SEQUENCE: 242
tcagcaagtg ggaaggtgta atc 23

<210> SEQ ID NO 243
<211> LENGTH: 75
<212> TYPE: DNA
<213> ORGANISM: Homo sapiens

<400> SEQUENCE: 243
ccattctatc atcaacgggt acaaacgagt cctggccttg tctgtggaga cggattacac 60
cttcccactt gctga 75

<210> SEQ ID NO 244
<211> LENGTH: 20
<212> TYPE: DNA
<213> ORGANISM: Homo sapiens

<400> SEQUENCE: 244
tatcgaggca ggtcatacca 20

<210> SEQ ID NO 245
<211> LENGTH: 20
<212> TYPE: DNA
<213> ORGANISM: Homo sapiens

<400> SEQUENCE: 245
taacgcttgg catcatcatt 20

<210> SEQ ID NO 246
<211> LENGTH: 74
<212> TYPE: DNA
<213> ORGANISM: Homo sapiens

<400> SEQUENCE: 246
tatcgaggca ggtcatacca tgaccggaag tcaaaagttg acctggatag gctcaatgat 60
gatgccaagc gtta 74

<210> SEQ ID NO 247
<211> LENGTH: 19
<212> TYPE: DNA
<213> ORGANISM: Homo sapiens

<400> SEQUENCE: 247
ccgcaacgtg gttttctca 19

<210> SEQ ID NO 248
<211> LENGTH: 21
<212> TYPE: DNA
<213> ORGANISM: Homo sapiens

<400> SEQUENCE: 248
tgctgggttt ctcctcctgt t 21

<210> SEQ ID NO 249
<211> LENGTH: 81
<212> TYPE: DNA
<213> ORGANISM: Homo sapiens

<400> SEQUENCE: 249
ccgcaacgtg gttttctcac cctatggggt ggcctcggtg ttggccatgc tccagctgac 60
aacaggagga gaaacccagc a 81

<210> SEQ ID NO 250
<211> LENGTH: 25
<212> TYPE: DNA
<213> ORGANISM: Homo sapiens

<400> SEQUENCE: 250

-continued

```
tcaagaccat catcactttc attgt                                           25


<210> SEQ ID NO 251
<211> LENGTH: 27
<212> TYPE: DNA
<213> ORGANISM: Homo sapiens

<400> SEQUENCE: 251

ggatcaggaa gtacacggag tataact                                         27


<210> SEQ ID NO 252
<211> LENGTH: 96
<212> TYPE: DNA
<213> ORGANISM: Homo sapiens

<400> SEQUENCE: 252

tcaagaccat catcactttc attgtctcgg acgtgcgggg cctgggcctc ccggtccgca     60

agcagttcca gttatactcc gtgtacttcc tgatcc                               96


<210> SEQ ID NO 253
<211> LENGTH: 19
<212> TYPE: DNA
<213> ORGANISM: Homo sapiens

<400> SEQUENCE: 253

gcccgaaacg ccgaatata                                                  19


<210> SEQ ID NO 254
<211> LENGTH: 23
<212> TYPE: DNA
<213> ORGANISM: Homo sapiens

<400> SEQUENCE: 254

cgtggctctc ttatcctcat gat                                             23


<210> SEQ ID NO 255
<211> LENGTH: 65
<212> TYPE: DNA
<213> ORGANISM: Homo sapiens

<400> SEQUENCE: 255

gcccgaaacg ccgaatataa tcccaagcgg tttgctgcgg taatcatgag gataagagag     60

ccacg                                                                 65


<210> SEQ ID NO 256
<211> LENGTH: 19
<212> TYPE: DNA
<213> ORGANISM: Homo sapiens

<400> SEQUENCE: 256

gccctcccag tgtgcaaat                                                  19


<210> SEQ ID NO 257
<211> LENGTH: 25
<212> TYPE: DNA
<213> ORGANISM: Homo sapiens

<400> SEQUENCE: 257

cgtcgatggt attaggatag aagca                                           25


<210> SEQ ID NO 258
<211> LENGTH: 86
```

<212> TYPE: DNA
<213> ORGANISM: Homo sapiens

<400> SEQUENCE: 258
gccctcccag tgtgcaaata agggctgctg tttcgacgac accgttcgtg gggtcccctg 60
gtgcttctat cctaatacca tcgacg 86

<210> SEQ ID NO 259
<211> LENGTH: 27
<212> TYPE: DNA
<213> ORGANISM: Homo sapiens

<400> SEQUENCE: 259
caagctagat cagcattctc taacttg 27

<210> SEQ ID NO 260
<211> LENGTH: 25
<212> TYPE: DNA
<213> ORGANISM: Homo sapiens

<400> SEQUENCE: 260
cacatgactg ttatcgccat ctact 25

<210> SEQ ID NO 261
<211> LENGTH: 99
<212> TYPE: DNA
<213> ORGANISM: Homo sapiens

<400> SEQUENCE: 261
caagctagat cagcattctc taacttgttt ggtggagaac cattgtcata tacccggttc 60
agcctggctc ggcaagtaga tggcgataac agtcatgtg 99

<210> SEQ ID NO 262
<211> LENGTH: 22
<212> TYPE: DNA
<213> ORGANISM: Homo sapiens

<400> SEQUENCE: 262
cacaggaaca acagcatctt tc 22

<210> SEQ ID NO 263
<211> LENGTH: 20
<212> TYPE: DNA
<213> ORGANISM: Homo sapiens

<400> SEQUENCE: 263
agataagccc ctgggatcca 20

<210> SEQ ID NO 264
<211> LENGTH: 75
<212> TYPE: DNA
<213> ORGANISM: Homo sapiens

<400> SEQUENCE: 264
cacaggaaca acagcatctt tcaccaagat gggtggcacc aaccttgctg ggacttggat 60
cccaggggct tatct 75

<210> SEQ ID NO 265
<211> LENGTH: 21
<212> TYPE: DNA
<213> ORGANISM: Homo sapiens

<400> SEQUENCE: 265
ggattgctca acaaccatgc t 21

<210> SEQ ID NO 266
<211> LENGTH: 24
<212> TYPE: DNA
<213> ORGANISM: Homo sapiens

<400> SEQUENCE: 266
ggcattaaca cttttggacg ataa 24

<210> SEQ ID NO 267
<211> LENGTH: 91
<212> TYPE: DNA
<213> ORGANISM: Homo sapiens

<400> SEQUENCE: 267
ggattgctca acaaccatgc tgggcatctg gaccctccta cctctggttc ttacgtctgt 60
tgctagatta tcgtccaaaa gtgttaatgc c 91

<210> SEQ ID NO 268
<211> LENGTH: 24
<212> TYPE: DNA
<213> ORGANISM: Homo sapiens

<400> SEQUENCE: 268
gcactttggg attctttcca ttat 24

<210> SEQ ID NO 269
<211> LENGTH: 24
<212> TYPE: DNA
<213> ORGANISM: Homo sapiens

<400> SEQUENCE: 269
gcatgtaaga agaccctcac tgaa 24

<210> SEQ ID NO 270
<211> LENGTH: 80
<212> TYPE: DNA
<213> ORGANISM: Homo sapiens

<400> SEQUENCE: 270
gcactttggg attctttcca ttatgattct ttgttacagg caccgagaat gttgtattca 60
gtgagggtct tcttacatgc 80

<210> SEQ ID NO 271
<211> LENGTH: 20
<212> TYPE: DNA
<213> ORGANISM: Homo sapiens

<400> SEQUENCE: 271
aatccaaggg ggagagtgat 20

<210> SEQ ID NO 272
<211> LENGTH: 20
<212> TYPE: DNA
<213> ORGANISM: Homo sapiens

<400> SEQUENCE: 272
gtacagattt tgcccgagga 20

<210> SEQ ID NO 273
<211> LENGTH: 72
<212> TYPE: DNA
<213> ORGANISM: Homo sapiens

<400> SEQUENCE: 273
aatccaaggg ggagagtgat gacttccata tggactttga ctcagctgtg gctcctcggg 60
caaaatctgt ac 72

<210> SEQ ID NO 274
<211> LENGTH: 21
<212> TYPE: DNA
<213> ORGANISM: Homo sapiens

<400> SEQUENCE: 274
tgtggacatc ttcccctcag a 21

<210> SEQ ID NO 275
<211> LENGTH: 18
<212> TYPE: DNA
<213> ORGANISM: Homo sapiens

<400> SEQUENCE: 275
ctagcccgac cggttcgt 18

<210> SEQ ID NO 276
<211> LENGTH: 66
<212> TYPE: DNA
<213> ORGANISM: Homo sapiens

<400> SEQUENCE: 276
tgtggacatc ttcccctcag acttccctac tgagccacct tctctgccac gaaccggtcg 60
ggctag 66

<210> SEQ ID NO 277
<211> LENGTH: 20
<212> TYPE: DNA
<213> ORGANISM: Homo sapiens

<400> SEQUENCE: 277
ctttgaaccc ttgcttgcaa 20

<210> SEQ ID NO 278
<211> LENGTH: 18
<212> TYPE: DNA
<213> ORGANISM: Homo sapiens

<400> SEQUENCE: 278
cccgggacaa agcaaatg 18

<210> SEQ ID NO 279
<211> LENGTH: 68
<212> TYPE: DNA
<213> ORGANISM: Homo sapiens

<400> SEQUENCE: 279
ctttgaaccc ttgcttgcaa taggtgtgcg tcagaagcac ccaggacttc catttgcttt 60
gtcccggg 68

<210> SEQ ID NO 280
<211> LENGTH: 18
<212> TYPE: DNA

<213> ORGANISM: Homo sapiens

<400> SEQUENCE: 280
gcctcggtgt gcctttca 18

<210> SEQ ID NO 281
<211> LENGTH: 19
<212> TYPE: DNA
<213> ORGANISM: Homo sapiens

<400> SEQUENCE: 281
cgtgatgtgc gcaatcatg 19

<210> SEQ ID NO 282
<211> LENGTH: 65
<212> TYPE: DNA
<213> ORGANISM: Homo sapiens

<400> SEQUENCE: 282
gcctcggtgt gcctttcaac atcgccagct acgccctgct cacgtacatg attgcgcaca 60
tcacg 65

<210> SEQ ID NO 283
<211> LENGTH: 20
<212> TYPE: DNA
<213> ORGANISM: Homo sapiens

<400> SEQUENCE: 283
ctgctgtctt gggtgcattg 20

<210> SEQ ID NO 284
<211> LENGTH: 18
<212> TYPE: DNA
<213> ORGANISM: Homo sapiens

<400> SEQUENCE: 284
gcagcctggg accacttg 18

<210> SEQ ID NO 285
<211> LENGTH: 71
<212> TYPE: DNA
<213> ORGANISM: Homo sapiens

<400> SEQUENCE: 285
ctgctgtctt gggtgcattg gagccttgcc ttgctgctct acctccacca tgccaagtgg 60
tcccaggctg c 71

<210> SEQ ID NO 286
<211> LENGTH: 1947
<212> TYPE: DNA
<213> ORGANISM: Homo sapiens

<400> SEQUENCE: 286
ttttccccag atatggggtt ctattcagcc atagataatc tagacagagg atttcagaat 60
gaaaggaaaa atgtgtggag attagtccta gttcattctg agggccgact aagtggctca 120
gccagcttct tactccatct gcagttcata ctgccaaaga gctcccactt ccaaatcccc 180
agtgacttta tggagaagat tctgcattaa attgtctttc gaatgatggg gaagcaaggc 240 ataaatatgcg atgatgagga gaaagtagac cagtgaggtg attgcaagac taacaaggag 300
actcaatggg aagtttttct ttcttttaga tattgctttt gaagtagatg gtaaaatttt 360

-continued

```
tgtcatcctt cttgtatttt ttgtacccca agttacaatt tttcttcttc cttgtaaata    420
atttaaacag tatttatttt tgtaaggcat aactagaaac taaaatatat tctaaaaaat    480
tcattattct gaacaaagtg atcaaattag aatacatatt tttcaacagt ggtagagctt    540
ttaatatatg tttattgaaa gttatctata atacttgcac cagtgttgaa aaaagttaac    600
atgtaggcaa gagcaatatg tttgtctcaa ggatttttcc atggtttcct cagtgatggt    660
gtcctggaat tattcaggtg gtgaccatca ctggtctaag tttgtgtgca gggttttcag    720
acgtgttttt gtgaaacttg gtagaaccat ggctaataaa gaggacagtg ttgtcagggt    780
ccatctgccc tccatagaaa aatgtctctg gctcataaaa tgagactccc tcagggacta    840
aatatgaact gacagcagta actctgatac agaataatct aaattgcatc aaatggcctt    900
aattcagagt ttgttaggct tatcagtatg ttgcttttaa ttggggtggg aaagtagagg    960
gagagaaagc aagacattta ttaagcacct cgtatgtgcc aggcactatg ctaagcactt   1020
tacataagtt aggattaatc cctgcaagaa tcctataaag aatgttacta gcatttacac   1080
ttcccaaatg aaggtaccaa agctcaaacg caatgttgtg aagctgtttc cttcagattt   1140
aggttatgtg ggatgatgtg ggattgaaga ggaaagaaag gtgggattat ccccctagga   1200
agactttcag gcctgacttc ataggaattc atccatctta tcatgtggag tttatctcac   1260
cctgctgttg caggatgcta tttgcatgtg tccccaggtg atgtttttc tttggggagt    1320
aggggtttgg cttcctcatt catccctctt gctaaaagag gagatagttg atgttgcatc   1380
taaagatgct ataagacaat gaaagtttga tgttgtacat acctacaagt accatttttg   1440
tgcatgatta cactccactg acatcttcca agtactgcat gtgattgaat aagaaacaag   1500
aaagtgacca caccaaagcc tccctggctg gtgtacaggg atcaggtcca cagtggtaca   1560
gattcaacca ccacccaggg agtgcttgca gactctgcat agatgttgct gcatgcgtcc   1620
catgtgcctg tcagaatggc agtgtttaat tctcttgaaa gaaagttatt tgctcactat   1680
ccccagcctc aaggagccaa ggaagagtca ttcacatgga aggtccgggt ctggtcagcc   1740
actctgactt ttctaccaca ttaaattctc cattacatct cactattggt aatggcttaa   1800
gtgtaaagag ccatgatgtg tatattaagc tatgtgccac atatttattt ttagactctc   1860
cacagcattc atgtcaatat gggattaatg cctaaacttt gtaaatattg tacagtttgt   1920
aaatcaatga ataaaggttt tgagtgt                                       1947
```

<210> SEQ ID NO 287
<211> LENGTH: 1311
<212> TYPE: DNA
<213> ORGANISM: Homo sapiens

<400> SEQUENCE: 287

```
tagtcgggcg gggttgtgag acgccgcgct cagcttccat cgctgggcgg tcaacaagtg     60
cgggcctggc tcagcgcggg ggggcgcgga gaccgcgagg cgaccgggag cggctgggtt    120
cccggctgcg cgcccttcgg ccaggccggg agccgcgcca gtcggagccc ccggcccagc    180
gtggtccgcc tccctctcgg cgtccacctg cccggagtac tgccagcggg catgaccgac    240
ccaccagggg cgccgccgcc ggcgctcgca ggccgcggat gaagaagaaa acccggcgcc    300
gctcgacccg gagcgaggag ttgacccgga gcgaggagtt gaccctgagt gaggaagcga    360
cctggagtga agaggcgacc cagagtgagg aggcgaccca gggcgaagag atgaatcgga    420
gccaggaggt gacccgggac gaggagtcga cccggagcga ggaggtgacc agggaggaaa    480
```

-continued

```
tggcggcagc tgggctcacc gtgactgtca cccacagcaa tgagaagcac gaccttcatg    540

ttacctccca gcagggcagc agtgaaccag ttgtccaaga cctggcccag gttgttgaag    600

aggtcatagg ggttccacag tcttttcaga aactcatatt taagggaaaa tctctgaagg    660

aaatggaaac accgttgtca gcacttggaa tacaagatgg ttgccgggtc atgttaattg    720

ggaaaaagaa cagtccacag gaagaggttg aactaaagaa gttgaaacat ttggagaagt    780

ctgtggagaa gatagctgac cagctggaag agttgaataa agagcttact ggaatccagc    840

agggttttct gcccaaggat ttgcaagctg aagctctctg caaacttgat aggagagtaa    900

aagccacaat agagcagttt atgaagatct tggaggagat tgacacactg atcctgccag    960

aaaatttcaa agacagtaga ttgaaaagga aaggcttggt aaaaaaggtt caggcattcc   1020

tagccgagtg tgacacagtg gagcagaaca tctgccagga gactgagcgg ctgcagtcta   1080

caaactttgc cctggccgag tgaggtgtag cagaaaaagg ctgtgctgcc ctgaagaatg   1140

gcgccaccag ctctgccgtc tctggatcgg aatttacctg atttcttcag ggctgctggg   1200

ggcaactggc catttgccaa ttttcctact ctcacactgg ttctcaatga aaaatagtgt   1260

ctttgtgatt tgagtaaagc tcctattctg tttttcacaa aaaaaaaaaa a            1311
```

<210> SEQ ID NO 288
<211> LENGTH: 582
<212> TYPE: DNA
<213> ORGANISM: Homo sapiens

<400> SEQUENCE: 288

```
atggcccgcg cacgccagga gggcagctcc ccggagcccg tagagggcct ggcccgcgac     60

ggcccgcgcc ccttcccgct cggccgcctg gtgccctcgg cagtgtcctg cggcctctgc    120

gagcccggcc tggctgccgc ccccgccgcc cccaccctgc tgcccgctgc ctacctctgc    180

gcccccaccg ccccacccgc cgtcaccgcc gccctggggg gttcccgctg gcctgggggt    240

ccccgcagcc ggccccgagg cccgcgcccg gacggtcctc agccctcgct ctcgctggcg    300

gagcagcacc tggagtcgcc cgtgcccagc gccccggggg ctctggcggg cggtcccacc    360

caggcggccc cgggagtccg cggggaggag gaacagtggg cccgggagat cggggcccag    420

ctgcggcgga tggcggacga cctcaacgca cagtacgagc ggcggagaca agaggagcag    480

cagcggcacc gcccctcacc ctggagggtc ctgtacaatc tcatcatggg actcctgccc    540

ttacccaggg gccacagagc cccgagatg gagcccaatt ag                        582
```

<210> SEQ ID NO 289
<211> LENGTH: 6030
<212> TYPE: DNA
<213> ORGANISM: Homo sapiens

<400> SEQUENCE: 289

```
gttggccccc gttacttttc ctctgggaaa tatggcgcac gctgggagaa cagggtacga     60

taaccgggag atagtgatga agtacatcca ttataagctg tcgcagaggg gctacgagtg    120

ggatgcggga gatgtgggcg ccgcgccccc gggggccgcc cccgcgccgg gcatcttctc    180

ctcgcagccc gggcacacgc cccatacagc cgcatcccgg gacccggtcg ccaggacctc    240

gccgctgcag accccggctg cccccggcgc cgccgcgggg cctgcgctca gcccggtgcc    300

acctgtggtc cacctgaccc tccgccaggc cggcgacgac ttctcccgcc gctaccgccg    360

cgacttcgcc gagatgtcca ggcagctgca cctgacgccc ttcaccgcgc ggggacgctt    420

tgccacggtg gtggaggagc tcttcaggga cggggtgaac tgggggagga ttgtggcctt    480
```

```
ctttgagttc ggtggggtca tgtgtgtgga gagcgtcaac cgggagatgt cgcccctggt    540
ggacaacatc gccctgtgga tgactgagta cctgaaccgg cacctgcaca cctggatcca    600
ggataacgga ggctgggatg cctttgtgga actgtacggc cccagcatgc ggcctctgtt    660
tgatttctcc tggctgtctc tgaagactct gctcagtttg gccctggtgg gagcttgcat    720
caccctgggt gcctatctgg gccacaagtg aagtcaacat gcctgcccca aacaaatatg    780
caaaaggttc actaaagcag tagaaataat atgcattgtc agtgatgttc catgaaacaa    840
agctgcaggc tgtttaagaa aaaataacac acatataaac atcacacaca cagacagaca    900
cacacacaca caacaattaa cagtcttcag gcaaaacgtc gaatcagcta tttactgcca    960
aagggaaata tcatttattt tttacattat taagaaaaaa agatttattt atttaagaca   1020
gtcccatcaa aactcctgtc tttggaaatc cgaccactaa ttgccaagca ccgcttcgtg   1080
tggctccacc tggatgttct gtgcctgtaa acatagattc gctttccatg ttgttggccg   1140
gatcaccatc tgaagagcag acggatggaa aaaggacctg atcattgggg aagctggctt   1200
tctggctgct ggaggctggg gagaaggtgt tcattcactt gcatttcttt gccctggggg   1260
ctgtgatatt aacagaggga gggttcctgt ggggggaagt ccatgcctcc ctggcctgaa   1320
gaagagactc tttgcatatg actcacatga tgcatacctg gtgggaggaa aagagttggg   1380
aacttcagat ggacctagta cccactgaga tttccacgcc gaaggacagc gatgggaaaa   1440
atgcccttaa atcataggaa agtatttttt taagctacca attgtgccga gaaaagcatt   1500
ttagcaattt atacaatatc atccagtacc ttaagccctg attgtgtata ttcatatatt   1560
ttggatacgc accccccaac tcccaatact ggctctgtct gagtaagaaa cagaatcctc   1620
tggaacttga ggaagtgaac atttcggtga cttccgcatc aggaaggcta gagttaccca   1680
gagcatcagg ccgccacaag tgcctgcttt taggagaccg aagtccgcag aacctgcctg   1740
tgtcccagct tggaggcctg gtcctggaac tgagccgggg ccctcactgg cctcctccag   1800
ggatgatcaa cagggcagtg tggtctccga atgtctggaa gctgatggag ctcagaattc   1860
cactgtcaag aaagagcagt agaggggtgt ggctgggcct gtcaccctgg ggccctccag   1920
gtaggcccgt tttcacgtgg agcatgggag ccacgaccct tcttaagaca tgtatcactg   1980
tagagggaag gaacagaggc cctgggccct tcctatcaga aggacatggt gaaggctggg   2040
aacgtgagga gaggcaatgg ccacggccca ttttggctgt agcacatggc acgttggctg   2100
tgtggccttg gcccacctgt gagtttaaag caaggcttta aatgactttg gagagggtca   2160
caaatcctaa aagaagcatt gaagtgaggt gtcatggatt aattgacccc tgtctatgga   2220
attacatgta aaacattatc ttgtcactgt agtttggttt tatttgaaaa cctgacaaaa   2280
aaaaagttcc aggtgtggaa tatgggggtt atctgtacat cctggggcat taaaaaaaaa   2340
atcaatggtg gggaactata aagaagtaac aaaagaagtg acatcttcag caaataaact   2400
aggaaatttt tttttcttcc agtttagaat cagccttgaa acattgatgg aataactctg   2460
tggcattatt gcattatata ccatttatct gtattaactt tggaatgtac tctgttcaat   2520
gtttaatgct gtggttgata tttcgaaagc tgctttaaaa aaatacatgc atctcagcgt   2580
tttttgttt ttaattgtat ttagttatgg cctatacact atttgtgagc aaaggtgatc   2640
gttttctgtt tgagattttt atctcttgat tcttcaaaag cattctgaga aggtgagata   2700
agccctgagt ctcagctacc taagaaaaac ctggatgtca ctggccactg aggagctttg   2760
tttcaaccaa gtcatgtgca tttccacgtc aacagaattg tttattgtga cagttatatc   2820
```

-continued

```
tgttgtccct ttgaccttgt ttcttgaagg tttcctcgtc cctgggcaat tccgcattta   2880

attcatggta ttcaggatta catgcatgtt tggttaaacc catgagattc attcagttaa   2940

aaatccagat ggcaaatgac cagcagattc aaatctatgg tggtttgacc tttagagagt   3000

tgctttacgt ggcctgtttc aacacagacc cacccagagc cctcctgccc tccttccgcg   3060

ggggctttct catggctgtc cttcagggtc ttcctgaaat gcagtggtgc ttacgctcca   3120

ccaagaaagc aggaaacctg tggtatgaag ccagacctcc ccggcgggcc tcagggaaca   3180

gaatgatcag acctttgaat gattctaatt tttaagcaaa atattatttt atgaaaggtt   3240

tacattgtca aagtgatgaa tatggaatat ccaatcctgt gctgctatcc tgccaaaatc   3300

attttaatgg agtcagtttg cagtatgctc cacgtggtaa gatcctccaa gctgctttag   3360

aagtaacaat gaagaacgtg gacgctttta atataaagcc tgttttgtct tctgttgttg   3420

ttcaaacggg attcacagag tatttgaaaa atgtatatat attaagaggt cacggggggct   3480

aattgctggc tggctgcctt ttgctgtggg gttttgttac ctggttttaa taacagtaaa   3540

tgtgcccagc ctcttggccc cagaactgta cagtattgtg gctgcacttg ctctaagagt   3600

agttgatgtt gcattttcct tattgttaaa aacatgttag aagcaatgaa tgtatataaa   3660

agcctcaact agtcattttt ttctcctctt ctttttttttc attatatcta attattttgc   3720

agttgggcaa cagagaacca tccctatttt gtattgaaga gggattcaca tctgcatctt   3780

aactgctctt tatgaatgaa aaaacagtcc tctgtatgta ctcctcttta cactggccag   3840

ggtcagagtt aaatagagta tatgcacttt ccaaattggg gacaagggct ctaaaaaaag   3900

ccccaaaagg agaagaacat ctgagaacct cctcggccct cccagtccct cgctgcacaa   3960

atactccgca agagaggcca gaatgacagc tgacagggtc tatggccatc gggtcgtctc   4020

cgaagatttg gcaggggcag aaaactctgg caggcttaag atttggaata aagtcacaga   4080

atcaaggaag cacctcaatt tagttcaaac aagacgccaa cattctctcc acagctcact   4140

tacctctctg tgttcagatg tggccttcca tttatatgtg atctttgttt tattagtaaa   4200

tgcttatcat ctaaagatgt agctctggcc cagtgggaaa aattaggaag tgattataaa   4260

tcgagaggag ttataataat caagattaaa tgtaaataat cagggcaatc ccaacacatg   4320

tctagctttc acctccagga tctattgagt gaacagaatt gcaaatagtc tctatttgta   4380

attgaactta tcctaaaaca aatagtttat aaatgtgaac ttaaactcta attaattcca   4440

actgtacttt taaggcagtg gctgttttta gactttctta tcacttatag ttagtaatgt   4500

acacctactc tatcagagaa aaacaggaaa ggctcgaaat acaagccatt ctaaggaaat   4560

tagggagtca gttgaaattc tattctgatc ttattctgtg gtgtcttttg cagcccagac   4620

aaatgtggtt acacactttt taagaaatac aattctacat tgtcaagctt atgaaggttc   4680

caatcagatc tttattgtta ttcaatttgg atctttcagg gatttttttt ttaaattatt   4740

atgggacaaa ggacatttgt tggaggggtg ggagggagga acaattttta aatataaaac   4800

attcccaagt ttggatcagg gagttggaag ttttcagaat aaccagaact aagggtatga   4860

aggacctgta ttggggtcga tgtgatgcct ctgcgaagaa ccttgtgtga caaatgagaa   4920

acattttgaa gtttgtggta cgacctttag attccagaga catcagcatg gctcaaagtg   4980

cagctccgtt tggcagtgca atggtataaa tttcaagctg gatatgtcta atgggtattt   5040

aaacaataaa tgtgcagttt taactaacag gatatttaat gacaaccttc tggttggtag   5100

ggacatctgt ttctaaatgt ttattatgta caatacagaa aaaaatttta taaaattaag   5160

caatgtgaaa ctgaattgga gagtgataat acaagtcctt tagtcttacc cagtgaatca   5220
```

```
ttctgttcca tgtctttgga caaccatgac cttggacaat catgaaatat gcatctcact   5280
ggatgcaaag aaaatcagat ggagcatgaa tggtactgta ccggttcatc tggactgccc   5340
cagaaaaata acttcaagca aacatcctat caacaacaag gttgttctgc ataccaagct   5400
gagcacagaa gatgggaaca ctggtggagg atggaaaggc tcgctcaatc aagaaaattc   5460
tgagactatt aataaataag actgtagtgt agatactgag taaatccatg cacctaaacc   5520
ttttggaaaa tctgccgtgg gccctccaga tagctcattt cattaagttt ttccctccaa   5580
ggtagaattt gcaagagtga cagtggattg catttctttt ggggaagctt tcttttggtg   5640
gttttgttta ttataccttc ttaagttttc aaccaaggtt tgcttttgtt ttgagttact   5700
ggggttattt ttgttttaaa taaaaataag tgtacaataa gtgtttttgt attgaaagct   5760
tttgttatca agattttcat acttttacct tccatggctc tttttaagat tgatactttt   5820
aagaggtggc tgatattctg caacactgta cacataaaaa atacggtaag gatactttac   5880
atggttaagg taaagtaagt ctccagttgg ccaccattag ctataatggc actttgtttg   5940
tgttgttgga aaaagtcaca ttgccattaa actttccttg tctgtctagt taatattgtg   6000
aagaaaaata aagtacagtg tgagatactg                                    6030
```

<210> SEQ ID NO 290
<211> LENGTH: 10987
<212> TYPE: DNA
<213> ORGANISM: Homo sapiens

<400> SEQUENCE: 290

```
ggtggcgcga gcttctgaaa ctaggcggca gaggcggagc cgctgtggca ctgctgcgcc     60
tctgctgcgc ctcgggtgtc ttttgcggcg gtgggtcgcc gccgggagaa gcgtgagggg    120
acagatttgt gaccggcgcg gtttttgtca gcttactccg gccaaaaaag aactgcacct    180
ctggagcgga cttatttacc aagcattgga ggaatatcgt aggtaaaaat gcctattgga    240
tccaaagaga ggccaacatt ttttgaaatt tttaagacac gctgcaacaa agcagattta    300
ggaccaataa gtcttaattg gtttgaagaa ctttcttcag aagctccacc ctataattct    360
gaacctgcag aagaatctga acataaaaac aacaattacg aaccaaacct atttaaaact    420
ccacaaagga aaccatctta taatcagctg gcttcaactc caataatatt caaagagcaa    480
gggctgactc tgccgctgta ccaatctcct gtaaaagaat tagataaatt caaattagac    540
ttaggaagga atgttcccaa tagtagacat aaaagtcttc gcacagtgaa aactaaaatg    600
gatcaagcag atgatgtttc ctgtccactt ctaaattctt gtcttagtga aagtcctgtt    660
gttctacaat gtacacatgt aacaccacaa agagataagt cagtggtatg tgggagtttg    720
tttcatacac caaagtttgt gaagggtcgt cagacaccaa aacatatttc tgaaagtcta    780
ggagctgagg tggatcctga tatgtcttgg tcaagttctt tagctacacc acccaccctt    840
agttctactg tgctcatagt cagaaatgaa gaagcatctg aaactgtatt tcctcatgat    900
actactgcta atgtgaaaag ctatttttcc aatcatgatg aaagtctgaa gaaaaatgat    960
agatttatcg cttctgtgac agacagtgaa aacacaaatc aaagagaagc tgcaagtcat   1020
ggatttggaa aaacatcagg gaattcattt aaagtaaata gctgcaaaga ccacattgga   1080
aagtcaatgc caaatgtcct agaagatgaa gtatatgaaa cagttgtaga tacctctgaa   1140
gaagatagtt tttcattatg tttttctaaa tgtagaacaa aaaatctaca aaaagtaaga   1200
actagcaaga ctaggaaaaa aattttccat gaagcaaacg ctgatgaatg tgaaaaatct   1260
```

-continued

```
aaaaaccaag tgaaagaaaa atactcattt gtatctgaag tggaaccaaa tgatactgat   1320
ccattagatt caaatgtagc acatcagaag ccctttgaga gtggaagtga caaaatctcc   1380
aaggaagttg taccgtcttt ggcctgtgaa tggtctcaac taaccctttc aggtctaaat   1440
ggagcccaga tggagaaaat accoctattg catatttctt catgtgacca aaatatttca   1500
gaaaaagacc tattagacac agagaacaaa agaaagaaag attttcttac ttcagagaat   1560
tctttgccac gtatttctag cctaccaaaa tcagagaagc cattaaatga ggaaacagtg   1620
gtaaataaga gagatgaaga gcagcatctt gaatctcata cagactgcat tcttgcagta   1680
aagcaggcaa tatctggaac ttctccagtg gcttcttcat ttcagggtat caaaaagtct   1740
atattcagaa taagagaatc acctaaagag actttcaatg caagtttttc aggtcatatg   1800
actgatccaa actttaaaaa agaaactgaa gcctctgaaa gtggactgga aatacatact   1860
gtttgctcac agaaggagga ctccttatgt ccaaatttaa ttgataatgg aagctggcca   1920
gccaccacca cacagaattc tgtagctttg aagaatgcag gtttaatatc cactttgaaa   1980
aagaaaacaa ataagtttat ttatgctata catgatgaaa cattttataa aggaaaaaaa   2040
ataccgaaag accaaaaatc agaactaatt aactgttcag cccagtttga agcaaatgct   2100
tttgaagcac cacttacatt tgcaaatgct gattcaggtt tattgcattc ttctgtgaaa   2160
agaagctgtt cacagaatga ttctgaagaa ccaactttgt ccttaactag ctcttttggg   2220
acaattctga ggaaatgttc tagaaatgaa acatgttcta ataatacagt aatctctcag   2280
gatcttgatt ataaagaagc aaaatgtaat aaggaaaaac tacagttatt tattacccca   2340
gaagctgatt ctctgtcatg cctgcaggaa ggacagtgtg aaaatgatcc aaaaagcaaa   2400
aaagtttcag atataaaaga agaggtcttg gctgcagcat gtcacccagt acaacattca   2460
aaagtggaat acagtgatac tgactttcaa tcccagaaaa gtcttttata tgatcatgaa   2520
aatgccagca ctcttatttt aactcctact tccaaggatg ttctgtcaaa cctagtcatg   2580
atttctagag gcaaagaatc atacaaaatg tcagacaagc tcaaaggtaa caattatgaa   2640
tctgatgttg aattaaccaa aaatattccc atggaaaaga atcaagatgt atgtgcttta   2700
aatgaaaatt ataaaaacgt tgagctgttg ccacctgaaa aatacatgag agtagcatca   2760
ccttcaagaa aggtacaatt caaccaaaac acaaatctaa gagtaatcca aaaaaatcaa   2820
gaagaaacta cttcaatttc aaaaataact gtcaatccag actctgaaga acttttctca   2880
gacaatgaga ataattttgt cttccaagta gctaatgaaa ggaataatct tgctttagga   2940
aatactaagg aacttcatga aacagacttg acttgtgtaa acgaacccat tttcaagaac   3000
tctaccatgg ttttatatgg agacacaggt gataaacaag caacccaagt gtcaattaaa   3060
aaagatttgg tttatgttct tgcagaggag aacaaaaata gtgtaaagca gcatataaaa   3120
atgactctag gtcaagattt aaaatcggac atctccttga atatagataa aataccagaa   3180
aaaaataatg attacatgaa caaatgggca ggactcttag gtccaatttc aaatcacagt   3240
tttggaggta gcttcagaac agcttcaaat aaggaaatca agctctctga acataacatt   3300
aagaagagca aaatgttctt caaagatatt gaagaacaat atcctactag tttagcttgt   3360
gttgaaattg taaatacctt ggcattagat aatcaaaaga aactgagcaa gcctcagtca   3420
attaatactg tatctgcaca tttacagagt agtgtagttg tttctgattg taaaaatagt   3480
catataaccc ctcagatgtt attttccaag caggatttta attcaaacca taatttaaca   3540
cctagccaaa aggcagaaat tacagaactt tctactatat tagaagaatc aggaagtcag   3600
tttgaattta ctcagtttag aaaaccaagc tacatattgc agaagagtac atttgaagtg   3660
```

-continued

```
cctgaaaacc agatgactat cttaaagacc acttctgagg aatgcagaga tgctgatctt   3720
catgtcataa tgaatgcccc atcgattggt caggtagaca gcagcaagca atttgaaggt   3780
acagttgaaa ttaaacggaa gtttgctggc ctgttgaaaa atgactgtaa caaaagtgct   3840
tctggttatt taacagatga aaatgaagtg gggtttaggg gcttttattc tgctcatggc   3900
acaaaactga atgtttctac tgaagctctg caaaaagctg tgaaactgtt tagtgatatt   3960
gagaatatta gtgaggaaac ttctgcagag gtacatccaa taagtttatc ttcaagtaaa   4020
tgtcatgatt ctgttgtttc aatgtttaag atagaaaatc ataatgataa aactgtaagt   4080
gaaaaaaata ataaatgcca actgatatta caaaataata ttgaaatgac tactggcact   4140
tttgttgaag aaattactga aaattacaag agaaatactg aaaatgaaga taacaaatat   4200
actgctgcca gtagaaattc tcataactta gaatttgatg gcagtgattc aagtaaaaat   4260
gatactgttt gtattcataa agatgaaacg gacttgctat ttactgatca gcacaacata   4320
tgtcttaaat tatctggcca gtttatgaag gagggaaaca ctcagattaa agaagatttg   4380
tcagatttaa ctttttgga agttgcgaaa gctcaagaag catgtcatgg taatacttca   4440
aataaagaac agttaactgc tactaaaacg gagcaaaata taaaagattt tgagacttct   4500
gatacatttt ttcagactgc aagtgggaaa aatattagtg tcgccaaaga gtcatttaat   4560
aaaattgtaa atttctttga tcagaaacca gaagaattgc ataacttttc cttaaattct   4620
gaattacatt ctgacataag aaagaacaaa atggacattc taagttatga ggaaacagac   4680
atagttaaac acaaaatact gaaagaaagt gtcccagttg gtactggaaa tcaactagtg   4740
accttccagg gacaacccga acgtgatgaa aagatcaaag aacctactct gttgggtttt   4800
catacagcta gcgggaaaaa agttaaaatt gcaaaggaat ctttggacaa agtgaaaaac   4860
ctttttgatg aaaaagagca aggtactagt gaaatcacca gttttagcca tcaatgggca   4920
aagaccctaa agtacagaga ggcctgtaaa gaccttgaat tagcatgtga gaccattgag   4980
atcacagctg ccccaaagtg taaagaaatg cagaattctc tcaataatga taaaaacctt   5040
gtttctattg agactgtggt gccacctaag ctcttaagtg ataatttatg tagacaaact   5100
gaaaatctca aaacatcaaa aagtatcttt ttgaaagtta aagtacatga aaatgtagaa   5160
aaagaaacag caaaaagtcc tgcaacttgt tacacaaatc agtcccctta ttcagtcatt   5220
gaaaattcag ccttagcttt ttacacaagt tgtagtagaa aaacttctgt gagtcagact   5280
tcattacttg aagcaaaaaa atggcttaga gaaggaatat ttgatggtca accagaaaga   5340
ataaatactg cagattatgt aggaaattat ttgtatgaaa ataattcaaa cagtactata   5400
gctgaaaatg acaaaaatca tctctccgaa aaacaagata cttatttaag taacagtagc   5460
atgtctaaca gctattccta ccattctgat gaggtatata atgattcagg atatctctca   5520
aaaaataaac ttgattctgg tattgagcca gtattgaaga atgttgaaga tcaaaaaaac   5580
actagttttt ccaaagtaat atccaatgta aaagatgcaa atgcataccc acaaactgta   5640
aatgaagata tttgcgttga ggaacttgtg actagctctt caccctgcaa aaataaaaat   5700
gcagccatta aattgtccat atctaatagt aataattttg aggtagggcc acctgcattt   5760
aggatagcca gtggtaaaat cgtttgtgtt tcacatgaaa caattaaaaa agtgaaagac   5820
atatttacag acagtttcag taaagtaatt aaggaaaaca acgagaataa atcaaaaatt   5880
tgccaaacga aaattatggc aggttgttac gaggcattgg atgattcaga ggatattctt   5940
cataactctc tagataatga tgaatgtagc acgcattcac ataaggtttt tgctgacatt   6000
```

-continued

```
cagagtgaag aaattttaca acataaccaa aatatgtctg gattggagaa agtttctaaa   6060
atatcacctt gtgatgttag tttggaaact tcagatatat gtaaatgtag tatagggaag   6120
cttcataagt cagtctcatc tgcaaatact tgtgggattt ttagcacagc aagtggaaaa   6180
tctgtccagg tatcagatgc ttcattacaa aacgcaagac aagtgttttc tgaaatagaa   6240
gatagtacca agcaagtctt ttccaaagta ttgtttaaaa gtaacgaaca ttcagaccag   6300
ctcacaagag aagaaaatac tgctatacgt actccagaac atttaatatc ccaaaaaggc   6360
ttttcatata atgtggtaaa ttcatctgct ttctctggat ttagtacagc aagtggaaag   6420
caagtttcca ttttagaaag ttccttacac aaagttaagg gagtgttaga ggaatttgat   6480
ttaatcagaa ctgagcatag tcttcactat tcacctacgt ctagacaaaa tgtatcaaaa   6540
atacttcctc gtgttgataa gagaaaccca gagcactgtg taaactcaga aatggaaaaa   6600
acctgcagta aagaatttaa attatcaaat aacttaaatg ttgaaggtgg ttcttcagaa   6660
aataatcact ctattaaagt ttctccatat ctctctcaat ttcaacaaga caaacaacag   6720
ttggtattag gaaccaaagt ctcacttgtt gagaacattc atgttttggg aaaagaacag   6780
gcttcaccta aaaacgtaaa aatggaaatt ggtaaaactg aaactttttc tgatgttcct   6840
gtgaaaacaa atatagaagt ttgttctact tactccaaag attcagaaaa ctactttgaa   6900
acagaagcag tagaaattgc taaagctttt atggaagatg atgaactgac agattctaaa   6960
ctgccaagtc atgccacaca ttctcttttt acatgtcccg aaaatgagga aatggttttg   7020
tcaaattcaa gaattggaaa aagaagagga gagcccctta tcttagtggg agaaccctca   7080
atcaaaagaa acttattaaa tgaatttgac aggataatag aaaatcaaga aaaatcctta   7140
aaggcttcaa aaagcactcc agatggcaca ataaaagatc gaagattgtt tatgcatcat   7200
gtttctttag agccgattac ctgtgtaccc tttcgcacaa ctaaggaacg tcaagagata   7260
cagaatccaa attttaccgc acctggtcaa gaatttctgt ctaaatctca tttgtatgaa   7320
catctgactt tggaaaaatc ttcaagcaat ttagcagttt caggacatcc attttatcaa   7380
gtttctgcta caagaaatga aaaaatgaga cacttgatta ctacaggcag accaaccaaa   7440
gtctttgttc caccttttaa aactaaatca cattttcaca gagttgaaca gtgtgttagg   7500
aatattaact tggaggaaaa cagacaaaag caaaacattg atggacatgg ctctgatgat   7560
agtaaaaata agattaatga caatgagatt catcagttta acaaaaacaa ctccaatcaa   7620
gcagcagctg taactttcac aaagtgtgaa gaagaacctt tagatttaat tacaagtctt   7680
cagaatgcca gagatataca ggatatgcga attaagaaga aacaaaggca acgcgtcttt   7740
ccacagccag gcagtctgta tcttgcaaaa acatccactc tgcctcgaat ctctctgaaa   7800
gcagcagtag gaggccaagt tccctctgcg tgttctcata aacagctgta tacgtatggc   7860
gtttctaaac attgcataaa aattaacagc aaaaatgcag agtcttttca gtttcacact   7920
gaagattatt ttggtaagga aagtttatgg actggaaaag gaatacagtt ggctgatggt   7980
ggatggctca taccctccaa tgatggaaag gctggaaaag aagaatttta tagggctctg   8040
tgtgacactc caggtgtgga tccaaagctt atttctagaa tttgggttta taatcactat   8100
agatggatca tatggaaact ggcagctatg gaatgtgcct ttcctaagga atttgctaat   8160
agatgcctaa gcccagaaag ggtgcttctt caactaaaat acagatatga tacggaaatt   8220
gatagaagca gaagatcggc tataaaaaag ataatggaaa gggatgacac agctgcaaaa   8280
acacttgttc tctgtgtttc tgacataatt tcattgagcg caaatatatc tgaaacttct   8340
agcaataaaa ctagtagtgc agatacccaa aaagtggcca ttattgaact tacagatggg   8400
```

```
tggtatgctg ttaaggccca gttagatcct cccctcttag ctgtcttaaa gaatggcaga   8460
ctgacagttg gtcagaagat tattcttcat ggagcagaac tggtgggctc tcctgatgcc   8520
tgtacacctc ttgaagcccc agaatctctt atgttaaaga tttctgctaa cagtactcgg   8580
cctgctcgct ggtataccaa acttggattc tttcctgacc ctagaccttt tcctctgccc   8640
ttatcatcgc ttttcagtga tggaggaaat gttggttgtg ttgatgtaat tattcaaaga   8700
gcatacccta tacagtggat ggagaagaca tcatctggat tatacatatt tcgcaatgaa   8760
agagaggaag aaaaggaagc agcaaaatat gtggaggccc aacaaaagag actagaagcc   8820
ttattcacta aaattcagga ggaatttgaa gaacatgaag aaaacacaac aaaaccatat   8880
ttaccatcac gtgcactaac aagacagcaa gttcgtgctt tgcaagatgg tgcagagctt   8940
tatgaagcag tgaagaatgc agcagaccca gcttaccttg agggttattt cagtgaagag   9000
cagttaagag ccttgaataa tcacaggcaa atgttgaatg ataagaaaca agctcagatc   9060
cagttggaaa ttaggaaggc catggaatct gctgaacaaa aggaacaagg tttatcaagg   9120
gatgtcacaa ccgtgtggaa gttgcgtatt gtaagctatt caaaaaaaga aaaagattca   9180
gttatactga gtatttggcg tccatcatca gatttatatt ctctgttaac agaaggaaag   9240
agatacagaa tttatcatct tgcaacttca aaatctaaaa gtaaatctga aagagctaac   9300
atacagttag cagcgacaaa aaaaactcag tatcaacaac taccggtttc agatgaaatt   9360
ttatttcaga tttaccagcc acgggagccc cttcacttca gcaaattttt agatccagac   9420
tttcagccat cttgttctga ggtggaccta ataggatttg tcgtttctgt tgtgaaaaaa   9480
acaggacttg cccctttcgt ctatttgtca gacgaatgtt acaatttact ggcaataaag   9540
ttttggatag accttaatga ggacattatt aagcctcata tgttaattgc tgcaagcaac   9600
ctccagtggc gaccagaatc caaatcaggc cttcttactt tatttgctgg agatttttct   9660
gtgttttctg ctagtccaaa agagggccac tttcaagaga cattcaacaa aatgaaaaat   9720
actgttgaga atattgacat actttgcaat gaagcagaaa acaagcttat gcatatactg   9780
catgcaaatg atcccaagtg gtccacccca actaaagact gtacttcagg gccgtacact   9840
gctcaaatca ttcctggtac aggaaacaag cttctgatgt cttctcctaa ttgtgagata   9900
tattatcaaa gtcctttatc actttgtatg gccaaaagga agtctgtttc cacacctgtc   9960
tcagcccaga tgacttcaaa gtcttgtaaa ggggagaaag agattgatga ccaaaagaac  10020
tgcaaaaaga gaagagcctt ggatttcttg agtagactgc ctttacctcc acctgttagt  10080
cccatttgta catttgtttc tccggctgca cagaaggcat ttcagccacc aaggagttgt  10140
ggcaccaaat acgaaacacc cataaagaaa aaagaactga attctcctca gatgactcca  10200
tttaaaaaat tcaatgaaat ttctcttttg gaaagtaatt caatagctga cgaagaactt  10260
gcattgataa atacccaagc tcttttgtct ggttcaacag gagaaaaaca atttatatct  10320
gtcagtgaat ccactaggac tgctcccacc agttcagaag attatctcag actgaaacga  10380
cgttgtacta catctctgat caaagaacag gagagttccc aggccagtac ggaagaatgt  10440
gagaaaaata agcaggacac aattacaact aaaaaatata tctaagcatt tgcaaaggcg  10500
acaataaatt attgacgctt aacctttcca gtttataaga ctggaatata atttcaaacc  10560
acacattagt acttatgttg cacaatgaga aaagaaatta gtttcaaatt tacctcagcg  10620
tttgtgtatc gggcaaaaat cgttttgccc gattccgtat tggtatactt ttgcttcagt  10680
tgcatatctt aaaactaaat gtaatttatt aactaatcaa gaaaaacatc tttggctgag  10740
```

ctcggtggct catgcctgta atcccaacac tttgagaagc tgaggtggga ggagtgcttg 10800
aggccaggag ttcaagacca gcctgggcaa catagggaga cccccatctt tacgaagaaa 10860
aaaaaaaagg ggaaaagaaa atcttttaaa tctttggatt tgatcactac aagtattatt 10920
ttacaatcaa caaaatggtc atccaaactc aaacttgaga aaatatcttg ctttcaaatt 10980
gacacta 10987

<210> SEQ ID NO 291
<211> LENGTH: 1552
<212> TYPE: DNA
<213> ORGANISM: Homo sapiens

<400> SEQUENCE: 291
gcccgtacac accgtgtgct gggacacccc acagtcagcc gcatggctcc cctgtgcccc 60
agcccctggc tccctctgtt gatcccggcc cctgctccag gcctcactgt gcaactgctg 120
ctgtcactgc tgcttctgat gcctgtccat ccccagaggt tgccccggat gcaggaggat 180 tccccccttgg gaggaggctc ttctggggaa gatgacccac tgggcgagga ggatctgccc 240
agtgaagagg attcacccag agaggaggat ccacccggag aggaggatct acctggagag 300
gaggatctac ctggagagga ggatctacct gaagttaagc ctaaatcaga agaagagggc 360
tccctgaagt tagaggatct acctactgtt gaggctcctg gagatcctca agaaccccag 420
aataatgccc acagggacaa agaaggggat gaccagagtc attggcgcta tggaggcgac 480
ccgccctggc cccgggtgtc cccagcctgc gcgggccgct tccagtcccc ggtggatatc 540
cgcccccagc tcgccgcctt ctgcccggcc ctgcgccccc tggaactcct gggcttccag 600
ctcccgccgc tcccagaact gcgcctgcgc aacaatggcc acagtgtgca actgaccctg 660
cctcctgggc tagagatggc tctgggtccc gggcgggagt accgggctct gcagctgcat 720
ctgcactggg gggctgcagg tcgtccgggc tcggagcaca ctgtggaagg ccaccgtttc 780
cctgccgaga tccacgtggt tcacctcagc accgcctttg ccagagttga cgaggccttg 840
gggcgcccgg gaggcctggc cgtgttggcc gcctttctgg aggagggccc ggaagaaaac 900
agtgcctatg agcagttgct gtctcgcttg gaagaaatcg ctgaggaagg ctcagagact 960
caggtcccag gactggacat atctgcactc ctgccctctg acttcagccg ctacttccaa 1020
tatgaggggt ctctgactac accgccctgt gcccagggtg tcatctggac tgtgtttaac 1080
cagacagtga tgctgagtgc taagcagctc cacaccctct ctgacaccct gtggggacct 1140
ggtgactctc ggctacagct gaacttccga gcgacgcagc ctttgaatgg gcgagtgatt 1200
gaggcctcct tccctgctgg agtggacagc agtcctcggg ctgctgagcc agtccagctg 1260
aattcctgcc tggctgctgg tgacatccta gccctggttt ttggcctcct ttttgctgtc 1320
accagcgtcg cgttccttgt gcagatgaga aggcagcaca gaaggggaac caaagggggt 1380
gtgagctacc gcccagcaga ggtagccgag actggagcct agaggctgga tcttggagaa 1440
tgtgagaagc cagccagagg catctgaggg ggagccggta actgtcctgt cctgctcatt 1500
atgccacttc cttttaactg ccaagaaatt ttttaaaata aatatttata at 1552

<210> SEQ ID NO 292
<211> LENGTH: 1578
<212> TYPE: DNA
<213> ORGANISM: Homo sapiens

<400> SEQUENCE: 292
acgaacaggc caataaggag ggagcagtgc ggggtttaaa tctgaggcta ggctggctct 60

```
tctcggcgtg ctgcggcgga acggctgttg gtttctgctg gttgtaggtc cttggctggt    120

cgggcctccg gtgttctgct tctccccgct gagctgctgc ctggtgaaga ggaagccatg    180

gcgctccgag tcaccaggaa ctcgaaaatt aatgctgaaa ataaggcgaa gatcaacatg    240

gcaggcgcaa agcgcgttcc tacggcccct gctgcaacct ccaagcccgg actgaggcca    300

agaacagctc ttggggacat tggtaacaaa gtcagtgaac aactgcaggc caaaatgcct    360

atgaagaagg aagcaaaacc ttcagctact ggaaaagtca ttgataaaaa actaccaaaa    420

cctcttgaaa aggtacctat gctggtgcca gtgccagtgt ctgagccagt gccagagcca    480

gaacctgagc cagaacctga gcctgttaaa gaagaaaaac tttcgcctga gcctattttg    540

gttgatactg cctctccaag cccaatggaa acatctggat gtgcccctgc agaagaagac    600

ctgtgtcagg ctttctctga tgtaattctt gcagtaaatg atgtggatgc agaagatgga    660

gctgatccaa acctttgtag tgaatatgtg aaagatattt atgcttatct gagacaactt    720

gaggaagagc aagcagtcag accaaaatac ctactgggtc gggaagtcac tggaaacatg    780

agagccatcc taattgactg gctagtacag gttcaaatga aattcaggtt gttgcaggag    840

accatgtaca tgactgtctc cattattgat cggttcatgc agaataattg tgtgcccaag    900

aagatgctgc agctggttgg tgtcactgcc atgtttattg caagcaaata tgaagaaatg    960

taccctccag aaattggtga ctttgctttt gtgactgaca acacttatac taagcaccaa   1020

atcagacaga tggaaatgaa gattctaaga gctttaaact ttggtctggg tcggcctcta   1080

cctttgcact tccttcggag agcatctaag attggagagg ttgatgtcga gcaacatact   1140

ttggccaaat acctgatgga actaactatg ttggactatg acatggtgca ctttcctcct   1200

tctcaaattg cagcaggagc tttttgctta gcactgaaaa ttctggataa tggtgaatgg   1260

acaccaactc tacaacatta cctgtcatat actgaagaat ctcttcttcc agttatgcag   1320

cacctggcta agaatgtagt catggtaaat caaggactta caaagcacat gactgtcaag   1380

aacaagtatg ccacatcgaa gcatgctaag atcagcactc taccacagct gaattctgca   1440

ctagttcaag atttagccaa ggctgtggca aaggtgtaac ttgtaaactt gagttggagt   1500

actatattta caaataaaat tggcaccatg tgccatctgt aaaaaaaaaa aaaaaaaaaa   1560

aaaaaaaaaa aaaaaaa                                                  1578
```

<210> SEQ ID NO 293
<211> LENGTH: 3195
<212> TYPE: DNA
<213> ORGANISM: Homo sapiens

<400> SEQUENCE: 293

```
agaggcttcc ctggctggtg cctgagcccg gcgtccctcg ccccccgccc tccccgcatc     60

cctctcctcc ctcgcgcctg gccctgtggc tcttcctccc tccctccttc cccccccccc    120

cacccctcgc ccgctgcctc cctcggccca gccagctgtg ccggcgtttg ttggctgccc    180

tgcgcccggc cctccagcca gccttctgcc ggccccgccg cgatggaggt gccccagccg    240

gagcccgcgc caggctcggc tctcagtcca gcaggcgtgt gcggtggcgc ccagcgtccg    300

ggccacctcc cgggcctcct gctgggatct catggcctcc tggggtcccc ggtgcgggcg    360

gccgcttcct cgccggtcac caccctcacc cagaccatgc acgacctcgc cgggctcggc    420

agccgcagcc gcctgacgca cctatccctg tctcgacggg catccgaatc ctccctgtcg    480

tctgaatcct ccgaatcttc tgatgcaggt ctctgcatgg attcccccag ccctatggac    540
```

-continued

```
ccccacatgg cggagcagac gtttgaacag gccatccagg cagccagccg gatcattcga    600
aacgagcagt ttgccatcag acgcttccag tctatgccgg tgaggctgct gggccacagc    660
cccgtgcttc ggaacatcac caactcccag gcgcccgacg gccggaggaa gagcgaggcg    720
ggcagtggag ctgccagcag ctctggggaa gacaaggaga atgtgcgctt ctggaaggcc    780
ggggtgggag ctctccggga agaggagggg gcatgctggg gtggttccct ggcatgtgag    840
gaccctcctc tcccatcttg gctgcaggat ggatttgtct tcaagatgcc atggaagccc    900
acacatccca gctccaccca tgctctggca gagtgggcca gccgcaggga agcctttgcc    960
cagagaccca gctcggcccc cgacctgatg tgtctcagtc ctgaccggaa gatggaagtg   1020
gaggagctca gccccctggc cctaggtcgc ttctctctga cccctgcaga gggggatact   1080
gaggaagatg atggatttgt ggacatccta gagagtgact taaaggatga tgatgcagtt   1140
cccccaggca tggagagtct cattagtgcc ccactggtca agaccttgga aaaggaagag   1200
gaaaaggacc tcgtcatgta cagcaagtgc cagcggctct tccgctctcc gtccatgccc   1260
tgcagcgtga tccggcccat cctcaagagg ctggagcggc cccaggacag ggacacgccc   1320
gtgcagaata agcggaggcg gagcgtgacc cctcctgagg agcagcagga ggctgaggaa   1380
cctaaagccc gcgtcctccg ctcaaaatca ctgtgtcacg atgagatcga gaacctcctg   1440
gacagtgacc accgagagct gattggagat tactctaagg ccttcctcct acagacagta   1500
gacggaaagc accaagacct caagtacatc tcaccagaaa cgatggtggc cctattgacg   1560
ggcaagttca gcaacatcgt ggataagttt gtgattgtag actgcagata cccctatgaa   1620
tatgaaggcg ggcacatcaa gactgcggtg aacttgcccc tggaacgcga cgccgagagc   1680
ttcctactga agagccccat cgcgccctgt agcctggaca agagagtcat cctcattttc   1740
cactgtgaat tctcatctga gcgtgggccc cgcatgtgcc gtttcatcag ggaacgagac   1800
cgtgctgtca acgactaccc cagcctctac taccctgaga tgtatatcct gaaaggcggc   1860
tacaaggagt tcttccctca gcacccgaac ttctgtgaac cccaggacta ccggcccatg   1920
aaccacgagg ccttcaagga tgagctaaag accttccgcc tcaagactcg cagctgggct   1980
ggggagcgga gccggcggga gctctgtagc cggctgcagg accagtgagg ggcctgcgcc   2040
agtcctgcta cctcccttgc ctttcgaggc ctgaagccag ctgccctatg ggcctgccgg   2100
gctgagggcc tgctggaggc ctcaggtgct gtccatggga aagatggtgt ggtgtcctgc   2160
ctgtctgccc cagcccagat tcccctgtgt catcccatca ttttccatat cctggtgccc   2220
cccacccctg gaagagccca gtctgttgag ttagttaagt tgggttaata ccagcttaaa   2280
ggcagtattt tgtgtcctcc aggagcttct tgtttccttg ttagggttaa cccttcatct   2340
tcctgtgtcc tgaaacgctc ctttgtgtgt gtgtcagctg aggctgggga gagccgtggt   2400
ccctgaggat gggtcagagc taaactcctt cctggcctga gagtcagctc tctgccctgt   2460
gtacttcccg ggccagggct gcccctaatc tctgtaggaa ccgtggtatg tctgccatgt   2520
tgcccctttc tcttttcccc tttcctgtcc caccatacga gcacctccag cctgaacaga   2580
agctcttact ctttcctatt tcagtgttac ctgtgtgctt ggtctgtttg actttacgcc   2640
catctcagga cacttccgta gactgtttag gttcccctgt caaatatcag ttacccactc   2700
ggtcccagtt ttgttgcccc agaaagggat gttattatcc ttgggggctc ccagggcaag   2760
ggttaaggcc tgaatcatga gcctgctgga agcccagccc ctactgctgt gaaccctggg   2820
gcctgactgc tcagaacttg ctgctgtctt gttgcggatg gatggaaggt tggatggatg   2880
ggtggatggc cgtggatggc cgtggatgcg cagtgccttg catacccaaa ccaggtggga   2940
```

```
gcgttttgtt gagcatgaca cctgcagcag gaatatatgt gtgcctattt gtgtggacaa   3000

aaatatttac acttagggtt tggagctatt caagaggaaa tgtcacagaa gcagctaaac   3060

caaggactga gcaccctctg gattctgaat ctcaagatgg gggcagggct gtgcttgaag   3120

gccctgctga gtcatctgtt agggccttgg ttcaataaag cactgagcaa gttgagaaaa   3180

aaaaaaaaaa aaaaa                                                    3195
```

```
<210> SEQ ID NO 294
<211> LENGTH: 3737
<212> TYPE: DNA
<213> ORGANISM: Homo sapiens

<400> SEQUENCE: 294

ggcgtccgcg cacacctccc cgcgccgccg ccgccaccgc ccgcactccg ccgcctctgc     60

ccgcaaccgc tgagccatcc atgggggtcg cgggccgcaa ccgtcccggg gcggcctggg    120

cggtgctgct gctgctgctg ctgctgccgc cactgctgct gctggcgggg gccgtcccgc    180

cgggtcgggg ccgtgccgcg gggccgcagg aggatgtaga tgagtgtgcc caagggctag    240

atgactgcca tgccgacgcc ctgtgtcaga acacacccac ctcctacaag tgctcctgca    300

agcctggcta ccaaggggaa ggcaggcagt gtgaggacat cgatgaatgt ggaaatgagc    360

tcaatggagg ctgtgtccat gactgtttga atattccagg caattatcgt tgcacttgtt    420

ttgatggctt catgttggct catgacggtc ataattgtct tgatgtggac gagtgcctgg    480

agaacaatgg cggctgccag catacctgtg tcaacgtcat ggggagctat gagtgctgct    540

gcaaggaggg gtttttcctg agtgacaatc agcacacctg cattcaccgc tcggaagagg    600

gcctgagctg catgaataag gatcacggct gtagtcacat ctgcaaggag gccccaaggg    660

gcagcgtcgc ctgtgagtgc aggcctggtt ttgagctggc caagaaccag agagactgca    720

tcttgacctg taaccatggg aacggtgggt gccagcactc ctgtgacgat acagccgatg    780

gcccagagtg cagctgccat ccacagtaca agatgcacac agatgggagg agctgccttg    840

agcgagagga cactgtcctg gaggtgacag agagcaacac cacatcagtg gtggatgggg    900

ataaacgggt gaaacggcgg ctgctcatgg aaacgtgtgc tgtcaacaat ggaggctgtg    960

accgcacctg taaggatact tcgacaggtg tccactgcag ttgtcctgtt ggattcactc   1020

tccagttgga tgggaagaca tgtaaagata ttgatgagtg ccagacccgc aatggaggtt   1080

gtgatcattt ctgcaaaaac atcgtgggca gttttgactg cggctgcaag aaaggattta   1140

aattattaac agatgagaag tcttgccaag atgtggatga gtgctctttg gataggacct   1200

gtgaccacag ctgcatcaac caccctggca catttgcttg tgcttgcaac cgagggtaca   1260

ccctgtatgg cttcacccac tgtggagaca ccaatgagtg cagcatcaac aacggaggct   1320

gtcagcaggt ctgtgtgaac acagtgggca gctatgaatg ccagtgccac cctgggtaca   1380

agctccactg gaataaaaaa gactgtgtgg aagtgaaggg gctcctgccc acaagtgtgt   1440

caccccgtgt gtccctgcac tgcggtaaga gtggtggagg agacgggtgc ttcctcagat   1500

gtcactctgg cattcacctc tcttcagatg tcaccaccat caggacaagt gtaaccttta   1560

agctaaatga aggcaagtgt agtttgaaaa atgctgagct gtttcccgag ggtctgcgac   1620

cagcactacc agagaagcac agctcagtaa aagagagctt ccgctacgta aaccttacat   1680

gcagctctgg caagcaagtc ccaggagccc ctggccgacc aagcacccct aaggaaatgt   1740

ttatcactgt tgagtttgag cttgaaacta accaaaagga ggtgacagct tcttgtgacc   1800
```

-continued

```
tgagctgcat cgtaaagcga accgagaagc ggctccgtaa agccatccgc acgctcagaa   1860

aggccgtcca cagggagcag tttcacctcc agctctcagg catgaacctc gacgtggcta   1920

aaaagcctcc cagaacatct gaacgccagg cagagtcctg tggagtgggc cagggtcatg   1980

cagaaaacca atgtgtcagt tgcagggctg ggacctatta tgatggagca cgagaacgct   2040

gcattttatg tccaaatgga accttccaaa atgaggaagg acaaatgact tgtgaaccat   2100

gcccaagacc aggaaattct ggggccctga agaccccaga agcttggaat atgtctgaat   2160

gtggaggtct gtgtcaacct ggtgaatatt ctgcagatgg ctttgcacct tgccagctct   2220

gtgccctggg cacgttccag cctgaagctg gtcgaacttc ctgcttcccc tgtggaggag   2280

gccttgccac caaacatcag ggagctactt cctttcagga ctgtgaaacc agagttcaat   2340

gttcacctgg acatttctac aacaccacca ctcaccgatg tattcgttgc ccagtgggaa   2400

cataccagcc tgaatttgga aaaaataatt gtgtttcttg cccaggaaat actacgactg   2460

actttgatgg ctccacaaac ataacccagt gtaaaaacag aagatgtgga ggggagctgg   2520

gagatttcac tgggtacatt gaatccccaa actacccagg caattaccca gccaacaccg   2580

agtgtacgtg gaccatcaac ccaccccccca agcgccgcat cctgatcgtg gtccctgaga   2640

tcttcctgcc catagaggac gactgtgggg actatctggt gatgcggaaa acctcttcat   2700

ccaattctgt gacaacatat gaaacctgcc agacctacga acgccccatc gccttcacct   2760

ccaggtcaaa gaagctgtgg attcagttca agtccaatga agggaacagc gctagagggt   2820

tccaggtccc atacgtgaca tatgatgagg actaccagga actcattgaa gacatagttc   2880

gagatggcag gctctatgca tctgagaacc atcaggaaat acttaaggat aagaaactta   2940

tcaaggctct gtttgatgtc ctggcccatc cccagaacta tttcaagtac acagcccagg   3000

agtcccgaga gatgtttcca agatcgttca tccgattgct acgttccaaa gtgtccaggt   3060

ttttgagacc ttacaaatga ctcagcccac gtgccactca atacaaatgt tctgctatag   3120

ggttggtggg acagagctgt cttccttctg catgtcagca cagtcgggta ttgctgcctc   3180

ccgtatcagt gactcattag agttcaattt ttatagataa tacagatatt ttggtaaatt   3240

gaacttggtt tttctttccc agcatcgtgg atgtagactg agaatggctt tgagtggcat   3300

cagcttctca ctgctgtggg cggatgtctt ggatagatca cgggctggct gagctggact   3360

ttggtcagcc taggtgagac tcacctgtcc ttctggggtc ttactcctcc tcaaggagtc   3420

tgtagtggaa aggaggccac agaataagct gcttattctg aaacttcagc ttcctctagc   3480

ccggccctct ctaagggagc cctctgcact cgtgtgcagg ctctgaccag gcagaacagg   3540

caagagggga gggaaggaga cccctgcagg ctccctccac ccaccttgag acctgggagg   3600

actcagtttc tccacagcct tctccagcct gtgtgataca agtttgatcc caggaacttg   3660

agttctaagc agtgctcgtg aaaaaaaaaa gcagaaagaa ttagaaataa ataaaaacta   3720

agcacttctg gagacat                                                  3737
```

<210> SEQ ID NO 295
<211> LENGTH: 2042
<212> TYPE: DNA
<213> ORGANISM: Homo sapiens

<400> SEQUENCE: 295

```
ggggccagtc gttcgccgga aagcatttgt ctcccacctc atcataacaa caattaattt     60

cctctggggc ctgaggaggg cagaatttca accttcggtg tgcttgggag tggcgattgt    120

gatttacacg acaaaatgcc gaggtgctcg gtggagtcat ggcagtgccc tttgtggaag    180
```

-continued

```
actgggactt ggtgcaaacc ctgggagaag gtgcctatgg agaagttcaa cttgctgtga    240
atagagtaac tgaagaagca gtcgcagtga agattgtaga tatgaagcgt gccgtagact    300
gtccagaaaa tattaagaaa gagatctgta tcaataaaat gctaaatcat gaaaatgtag    360
taaaattcta tggtcacagg agagaaggca atatccaata tttatttctg gagtactgta    420
gtggaggaga gctttttgac agaatagagc cagacatagg catgcctgaa ccagatgctc    480
agagattctt ccatcaactc atggcagggg tggtttatct gcatggtatt ggaataactc    540
acagggatat taaaccagaa aatcttctgt tggatgaaag ggataacctc aaaatctcag    600
actttggctt ggcaacagta tttcggtata ataatcgtga gcgtttgttg aacaagatgt    660
gtggtacttt accatatgtt gctccagaac ttctgaagag aagagaattt catgcagaac    720
cagttgatgt ttggtcctgt ggaatagtac ttactgcaat gctcgctgga gaattgccat    780
gggaccaacc cagtgacagc tgtcaggagt attctgactg gaaagaaaaa aaaacatacc    840
tcaacccttg gaaaaaaatc gattctgctc ctctagctct gctgcataaa atcttagttg    900
agaatccatc agcaagaatt accattccag acatcaaaaa agatagatgg tacaacaaac    960
ccctcaagaa aggggcaaaa aggccccgag tcacttcagg tggtgtgtca gagtctccca   1020
gtggattttc taagcacatt caatccaatt tggacttctc tccagtaaac agtgcttcta   1080
gtgaagaaaa tgtgaagtac tccagttctc agccagaacc ccgcacaggt ctttccttat   1140
gggataccag cccctcatac attgataaat tggtacaagg gatcagcttt tcccagccca   1200
catgtcctga tcatatgctt ttgaatagtc agttacttgg caccccagga tcctcacaga   1260
acccctggca gcggttggtc aaaagaatga cacgattctt taccaaattg gatgcagaca   1320
aatcttatca atgcctgaaa gagacttgtg agaagttggg ctatcaatgg aagaaaagtt   1380
gtatgaatca ggttactata tcaacaactg ataggagaaa caataaactc attttcaaag   1440
tgaatttgtt agaaatggat gataaaatat tggttgactt ccggctttct aagggtgatg   1500
gattggagtt caagagacac ttcctgaaga ttaaagggaa gctgattgat attgtgagca   1560
gccagaaggt ttggcttcct gccacatgat cggaccatcg gctctgggga atcctggtga   1620
atatagtgct gctatgttga cattattctt cctagagaag attatcctgt cctgcaaact   1680
gcaaatagta gttcctgaag tgttcacttc cctgtttatc caaacatctt ccaatttatt   1740
ttgtttgttc ggcatacaaa taatacctat atcttaattg taagcaaaac tttggggaaa   1800
ggatgaatag aattcatttg attatttctt catgtgtgtt tagtatctga atttgaaact   1860
catctggtgg aaaccaagtt tcaggggaca tgagttttcc agcttttata cacacgtatc   1920
tcatttttat caaaacattt tgtttaattc aaaaagtaca tatttcttcc atgttgattt   1980
aattctaaga tgaaccaata aagacataat tcttgcaaaa aaaaaaaaaa aaaaaaaaaa   2040
aa                                                                  2042
```

<210> SEQ ID NO 296
<211> LENGTH: 2547
<212> TYPE: DNA
<213> ORGANISM: Homo sapiens

<400> SEQUENCE: 296

```
cttacaaggt acagtcctct gctcaggggg gccaggaggg tcttataggc atcattcacc     60
agggtcgaat gcttctctga gaagtccttt tcagtctgag acctctggct gaagaaatct    120
gggtggacaa gacgctgcag ttgctggtac ctgtgctgga gcttcgctgt atcaactctg    180
```

-continued

```
aaggaacggt tgcagtccat aaggctgaag tagtctcgag tggggtcagg tgcctgcagc    240
gctcggcact gtgggcagaa gaacctgtcc tcccgcccgg ggccccatgg gccgccgcag    300
ttccaacagc ggggataatt gcttcccgcc tgcgacgcag catcgcagct tagcggtctc    360
cttctgggaa cccctgtcgg ccaaaacccc cacacccgga gcaaagcccc ggctctcccc    420
cgccacatct ggccggcggc ctatctagcc gtggtcactc gtggggaaaa gcaaagagag    480
cgtctaacca gactaatgtt gctgattggc tggggagtcg agggggcggg atcacccgag    540
gggaacccgg gttctaagtt ccgctctccc ttctaaacta caactcccag gaggcattga    600
ggcggcgcct gacggccaca tctgctgctc ctcattggtc cggcggcagg ggagggggtt    660
ttgattggct gagggtggag tttgtatctg caggtttagc gccactctgc tggctgaggc    720
tgcggagagt gtgcggctcc aggtgggctc acgcggtcgt gatgtctcgg gagtcggatg    780
ttgaggctca gcagtctcat ggcagcagtg cctgttcaca gccccatggc agcgttaccc    840
agtcccaagg ctcctcctca cagtcccagg gcatatccag ctcctctacc agcacgatgc    900
caaactccag ccagtcctct cactccagct ctgggacact gagctcctta gagacagtgt    960
ccactcagga actctattct attcctgagg accaagaacc tgaggaccaa gaacctgagg   1020
agcctacccc tgcccccctgg gctcgattat gggcccttca ggatggattt gccaatcttg   1080
aatgtgtgaa tgacaactac tggtttggga gggacaaaag ctgtgaatat tgctttgatg   1140
aaccactgct gaaaagaaca gataaatacc gaacatacag caagaaacac tttcggattt   1200
tcagggaagt gggtcctaaa aactcttaca ttgcatacat agaagatcac agtggcaatg   1260
gaacctttgt aaatacagag cttgtaggga aaggaaaacg ccgtcctttg aataacaatt   1320
ctgaaattgc actgtcacta agcagaaata aagtttttgt ctttttttgat ctgactgtag   1380
atgatcagtc agtttatcct aaggcattaa gagatgaata catcatgtca aaaactcttg   1440
gaagtggtgc ctgtggagag gtaaagctgg ctttcgagag gaaaacatgt aagaaagtag   1500
ccataaagat catcagcaaa aggaagtttg ctattggttc agcaagagag gcagacccag   1560
ctctcaatgt tgaaacagaa atagaaattt tgaaaaagct aaatcatcct tgcatcatca   1620
agattaaaaa ctttttttgat gcagaagatt attatattgt tttggaattg atggaagggg   1680
gagagctgtt tgacaaagtg gtggggaata aacgcctgaa agaagctacc tgcaagctct   1740
atttttacca gatgctcttg gctgtgcagt accttcatga aaacggtatt atacaccgtg   1800
acttaaagcc agagaatgtt ttactgtcat ctcaagaaga ggactgtctt ataaagatta   1860
ctgattttgg gcactccaag attttgggag agacctctct catgagaacc ttatgtggaa   1920
cccccaccta cttggcgcct gaagttcttg tttctgttgg gactgctggg tataaccgtg   1980
ctgtggactg ctggagttta ggagttattc tttttatctg ccttagtggg tatccacctt   2040
tctctgagca taggactcaa gtgtcactga aggatcagat caccagtgga aaatacaact   2100
tcattcctga agtctgggca gaagtctcag agaaagctct ggaccttgtc aagaagttgt   2160
tggtagtgga tccaaaggca cgttttacga cagaagaagc cttaagacac ccgtggcttc   2220
aggatgaaga catgaagaga aagtttcaag atcttctgtc tgaggaaaat gaatccacag   2280
ctctacccca ggttctagcc cagccttcta ctagtcgaaa gcggccccgt gaaggggaag   2340
ccgagggtgc cgagaccaca aagcgcccag ctgtgtgtgc tgctgtgttg tgaactccgt   2400
ggtttgaaca cgaaagaaat gtaccttctt tcactctgtc atctttcttt tctttgagtc   2460
tgttttttta tagtttgtat tttaattatg ggaataattg ctttttcaca gtcactgatg   2520
tacaattaaa aacctgatgg aacctgg                                       2547
```

<210> SEQ ID NO 297
<211> LENGTH: 2768
<212> TYPE: DNA
<213> ORGANISM: Homo sapiens

<400> SEQUENCE: 297

```
cactgctgtg cagggcagga aagctccatg cacatagccc agcaaagagc aacacagagc     60
tgaaaggaag actcagagga gagagataag taaggaaagt agtgatggct ctcatcccag    120
acttggccat ggaaacctgg cttctcctgg ctgtcagcct ggtgctcctc tatctatatg    180
gaacccattc acatggactt tttaagaagc ttggaattcc agggcccaca cctctgcctt    240
ttttgggaaa tattttgtcc taccataagg gcttttgtat gtttgacatg gaatgtcata    300
aaaagtatgg aaaagtgtgg ggcttttatg atggtcaaca gcctgtgctg gctatcacag    360
atcctgacat gatcaaaaca gtgctagtga aagaatgtta ttctgtcttc acaaaccgga    420
ggccttttgg tccagtggga tttatgaaaa gtgccatctc tatagctgag gatgaagaat    480
ggaagagatt acgatcattg ctgtctccaa ccttcaccag tggaaaactc aaggagatgg    540
tccctatcat tgcccagtat ggagatgtgt tggtgagaaa tctgaggcgg gaagcagaga    600
caggcaagcc tgtcaccttg aaagacgtct ttggggccta cagcatggat gtgatcacta    660
gcacatcatt tggagtgaac atcgactctc tcaacaatcc acaagacccc tttgtggaaa    720
acaccaagaa gcttttaaga tttgattttt tggatccatt ctttctctca ataacagtct    780
ttccattcct catcccaatt cttgaagtat taaatatctg tgtgtttcca agagaagtta    840
caaatttttt aagaaaatct gtaaaaagga tgaaagaaag tcgcctcgaa gatacacaaa    900
agcaccgagt ggatttcctt cagctgatga ttgactctca gaattcaaaa gaaactgagt    960
cccacaaagc tctgtccgat ctggagctcg tggcccaatc aattatcttt atttttgctg   1020
gctatgaaac cacgagcagt gttctctcct tcattatgta tgaactggcc actcaccctg   1080
atgtccagca gaaactgcag gaggaaattg atgcagtttt acccaataag gcaccaccca   1140
cctatgatac tgtgctacag atggagtatc ttgacatggt ggtgaatgaa acgctcagat   1200
tattcccaat tgctatgaga cttgagaggg tctgcaaaaa agatgttgag atcaatggga   1260
tgttcattcc caaagggggtg gtggtgatga ttccaagcta tgctcttcac cgtgacccaa   1320
agtactggac agagcctgag aagttcctcc ctgaaagatt cagcaagaag aacaaggaca   1380
acatagatcc ttacatatac acaccctttg gaagtggacc cagaaactgc attggcatga   1440
ggtttgctct catgaacatg aaacttgctc taatcagagt ccttcagaac ttctccttca   1500
aaccttgtaa agaaacacag atcccccctga aattaagctt aggaggactt cttcaaccag   1560
aaaaacccgt tgttctaaag gttgagtcaa gggatggcac cgtaagtgga gcctgaattt   1620
tcctaaggac ttctgctttg ctcttcaaga aatctgtgcc tgagaacacc agagacctca   1680
aattactttg tgaatagaac tctgaaatga agatgggctt catccaatgg actgcataaa   1740
taaccgggga ttctgtacat gcattgagct ctctcattgt ctgtgtagag tgttatactt   1800
gggaatataa aggaggtgac caaatcagtg tgaggaggta gatttggctc ctctgcttct   1860
cacgggacta tttccaccac ccccagttag caccattaac tcctcctgag ctctgataag   1920
agaatcaaca tttctcaata atttcctcca caaattatta atgaaaataa gaattatttt   1980
gatggctcta acaatgacat ttatatcaca tgttttctct ggagtattct ataagtttta   2040
tgttaaatca ataaagacca ctttacaaaa gtattatcag atgctttcct gcacattaag   2100
```

-continued

```
gagaaatcta tagaactgaa tgagaaccaa caagtaaata tttttggtca ttgtaatcac   2160

tgttggcgtg gggcctttgt cagaactaga atttgattat taacataggt gaaagttaat   2220

ccactgtgac tttgcccatt gtttagaaag aatattcata gtttaattat gccttttttg   2280

atcaggcaca gtggctcacg cctgtaatcc tagcagtttg ggaggctgag ccgggtggat   2340

cgcctgaggt caggagttca agacaagcct ggcctacatg gttgaaaccc catctctact   2400

aaaaatacac aaattagcta ggcatggtgg actcgcctgt aatctcacta cacaggaggc   2460

tgaggcagga gaatcacttg aacctgggag gcggatgttg aagtgagctg agattgcacc   2520

actgcactcc agtctgggtg agagtgagac tcagtcttaa aaaaatatgc ctttttgaag   2580

cacgtacatt ttgtaacaaa gaactgaagc tcttattata ttattagttt tgatttaatg   2640

ttttcagccc atctcctttc atatttctgg gagacagaaa acatgtttcc ctacacctct   2700

tgcattccat cctcaacacc caactgtctc gatgcaatga acacttaata aaaaacagtc   2760

gattggtc                                                             2768
```

```
<210> SEQ ID NO 298
<211> LENGTH: 1358
<212> TYPE: DNA
<213> ORGANISM: Homo sapiens

<400> SEQUENCE: 298

ggcgtccgcg cgctgcacaa tggcggctct gaagagttgg ctgtcgcgca gcgtaacttc     60

attcttcagg tacagacagt gtttgtgtgt tcctgttgtg gctaacttta agaagcggtg    120

tttctcagaa ttgataagac catggcacaa aactgtgacg attggctttg gagtaaccct    180

gtgtgcggtt cctattgcac agaaatcaga gcctcattcc cttagtagtg aagcattgat    240

gaggagagca gtgtctttgg taacagatag cacctctacc tttctctctc agaccacata    300

tgcgttgatt gaagctatta ctgaatatac taaggctgtt tataccttaa cttctcttta    360

ccgacaatat acaagtttac ttgggaaaat gaattcagag gaggaagatg aagtgtggca    420

ggtgatcata ggagccagag ctgagatgac ttcaaaacac caagagtact tgaagctgga    480

aaccacttgg atgactgcag ttggtctttc agagatggca gcagaagctg catatcaaac    540

tggcgcagat caggcctcta taaccgccag gaatcacatt cagctggtga aactgcaggt    600

ggaagaggtg caccagctct cccggaaagc agaaaccaag ctggcagaag cacagataga    660

agagctccgt cagaaaacac aggaggaagg ggaggagcgg gctgagtcgg agcaggaggc    720

ctacctgcgt gaggattgag ggcctgagca cactgccctg tctccccact cagtggggaa    780

agcaggggca gatgccaccc tgcccagggt tggcatgact gtctgtgcac cgagaagagg    840

cggcaggtcc tgccctggcc aatcaggcga gacgcctttg tgagctgtga gtgcctcctg    900

tggtctcagg cttgcgctgg acctggttct tagcccttgg gcactgcacc ctgtttaaca    960

tttcacccca ctctgtacag ctgctcttac ccattttttt tacctcacac ccaaagcatt   1020

ttgcctacct gggtcagaga gaggagtcct ttttgtcatg cccttaagtt cagcaactgt   1080

ttaacctgtt ttcagtctta tttacgtcgt caaaaatgat ttagtacttg ttccctctgt   1140

tgggatgcca gttgtggcag ggggagggga acctgtccag tttgtacgat ttctttgtat   1200

gtatttctga tgtgttctct gatctgcccc cactgtcctg tgaggacagc tgaggccaag   1260

gagtgaaaaa cctattacta ctaagagaag gggtgcagag tgtttacctg gtgctctcaa   1320

caggacttaa catcaacagg acttaacaca gaaaaaaa                           1358
```

<210> SEQ ID NO 299
<211> LENGTH: 4407
<212> TYPE: DNA
<213> ORGANISM: Homo sapiens

<400> SEQUENCE: 299

```
tttcgactcg cgctccggct gctgtcactt ggctctctgg ctggagcttg aggacgcaag     60
gagggtttgt cactggcaga ctcgagactg taggcactgc catggcccct gtgctcagta    120
aggactcggc ggacatcgag agtatcctgg ctttaaatcc tcgaacacaa actcatgcaa    180
ctctgtgttc cacttcggcc aagaaattag acaagaaaca ttggaaaaga aatcctgata    240
agaactgctt taattgtgag aagctggaga ataattttga tgacatcaag cacacgactc    300
ttggtgagcg aggagctctc cgagaagcaa tgagatgcct gaaatgtgca gatgccccgt    360
gtcagaagag ctgtccaact aatcttgata ttaaatcatt catcacaagt attgcaaaca    420
agaactatta tggagctgct aagatgatat tttctgacaa cccacttggt ctgacttgtg    480
gaatggtatg tccaacctct gatctatgtg taggtggatg caatttatat gccactgaag    540
agggacccat taatattggt ggattgcagc aatttgctac tgaggtattc aaagcaatga    600
gtatcccaca gatcagaaat ccttcgctgc ctcccccaga aaaaatgtct gaagcctatt    660
ctgcaaagat tgctcttttt ggtgctgggc ctgcaagtat aagttgtgct tcctttttgg    720
ctcgattggg gtactctgac atcactatat ttgaaaaaca agaatatgtt ggtggtttaa    780
gtacttctga aattcctcag ttccggctgc cgtatgatgt agtgaatttt gagattgagc    840
taatgaagga ccttggtgta aagataattt gcggtaaaag cctttcagtg aatgaaatga    900
ctcttagcac tttgaaagaa aaaggctaca aagctgcttt cattggaata ggtttgccag    960
aacccaataa agatgccatc ttccaaggcc tgacgcagga ccaggggttt tatacatcca   1020
aagacttttt gccacttgta gccaaaggca gtaaagcagg aatgtgcgcc tgtcactctc   1080
cattgccatc gatacgggga gtcgtgattg tacttggagc tggagacact gccttcgact   1140
gtgcaacatc tgctctacgt tgtggagctc gccgagtgtt catcgtcttc agaaaaggct   1200
ttgttaatat aagagctgtc cctgaggaga tggagcttgc taaggaagaa aagtgtgaat   1260
ttctgccatt cctgtcccca cggaaggtta tagtaaaagg tgggagaatt gttgctatgc   1320
agtttgttcg gacagagcaa gatgaaactg gaaaatggaa tgaagatgaa gatcagatgg   1380
tccatctgaa agccgatgtg gtcatcagtg cctttggttc agttctgagt gatcctaaag   1440
taaaagaagc cttgagccct ataaaattta acagatgggg tctcccagaa gtagatccag   1500
aaactatgca aactagtgaa gcatgggtat ttgcaggtgg tgatgtcgtt ggtttggcta   1560
acactacagt ggaatcggtg aatgatggaa agcaagcttc ttggtacatt cacaaatacg   1620
tacagtcaca atatggagct tccgtttctg ccaagcctga actacccctc ttttacactc   1680
ctattgatct ggtggacatt agtgtagaaa tggccggatt gaagtttata aatcctttttg   1740
gtcttgctag cgcaactcca gccaccagca catcaatgat tcgaagagct tttgaagctg   1800
gatggggttt tgccctcacc aaaactttct ctcttgataa ggacattgtg acaaatgttt   1860
cccccagaat catccgggga accacctctg gccccatgta tggccctgga caaagctcct   1920
ttctgaatat tgagctcatc agtgagaaaa cggctgcata ttggtgtcaa agtgtcactg   1980
aactaaaggc tgacttccca gacaacattg tgattgctag cattatgtgc agttacaata   2040
aaaatgactg gacggaactt gccaagaagt ctgaggattc tggagcagat gccctggagt   2100
taaatttatc atgtccacat ggcatgggag aaagaggaat gggcctggcc tgtgggcagg   2160
```

-continued

```
atccagagct ggtgcggaac atctgccgct gggttaggca agctgttcag attccttttt   2220
ttgccaagct gaccccaaat gtcactgata ttgtgagcat cgcaagagct gcaaaggaag   2280
gtggtgccaa tggcgttaca gccaccaaca ctgtctcagg tctgatggga ttaaaatctg   2340
atggcacacc ttggccagca gtggggattg caaagcgaac tacatatgga ggagtgtctg   2400
ggacagcaat cagacctatt gctttgagag ctgtgacctc cattgctcgt gctctgcctg   2460
gatttcccat tttggctact ggtggaattg actctgctga aagtggtctt cagtttctcc   2520
atagtggtgc ttccgtcctc caggtatgca gtgccattca gaatcaggat ttcactgtga   2580
tcgaagacta ctgcactggc ctcaaagccc tgctttatct gaaaagcatt gaagaactac   2640
aagactggga tggacagagt ccagctactg tgagtcacca gaaagggaaa ccagttccac   2700
gtatagctga actcatggac aagaaactgc caagttttgg accttatctg gaacagcgca   2760
agaaaatcat agcagaaaac aagattagac tgaaagaaca aaatgtagct tttcaccac   2820
ttaagagaag ctgttttatc cccaaaaggc ctattcctac catcaaggat gtaataggaa   2880
aagcactgca gtaccttgga acatttggtg aattgagcaa cgtagagcaa gttgtggcta   2940
tgattgatga agaaatgtgt atcaactgtg gtaaatgcta catgacctgt aatgattctg   3000
gctaccaggc tatacagttt gatccagaaa cccacctgcc caccataacc gacacttgta   3060
caggctgtac tctgtgtctc agtgtttgcc ctattgtcga ctgcatcaaa atggtttcca   3120
ggacaacacc ttatgaacca aagagaggcg tacccttatc tgtgaatccg gtgtgttaag   3180
gtgatttgtg aaacagttgc tgtgaacttt catgtcacct acatatgctg atctcttaaa   3240
atcatgatcc ttgtgttcag ctctttccaa attaaaacaa atatacattt tctaaataaa   3300
aatatgtaat ttcaaaatac atttgtaagt gtaaaaaatg tctcatgtca atgaccattc   3360
aattagtggc ataaaataga ataattcttt tctgaggata gtagttaaat aactgtgtgg   3420
cagttaattg gatgttcact gccagttgtc ttatgtgaaa aattaacttt ttgtgtggca   3480
attagtgtga cagtttccaa attgccctat gctgtgctcc atatttgatt tctaattgta   3540
agtgaaatta agcattttga aacaaagtac tctttaacat acaagaaaat gtatccaagg   3600
aaacatttta tcaataaaaa ttacctttaa ttttaatgct gtttctaaga aaatgtagtt   3660
agctccataa agtacaaatg aagaaagtca aaaattattt gctatggcag gataagaaag   3720
cctaaaattg agtttgtgga ctttattaag taaaatcccc ttcgctgaaa ttgcttattt   3780
ttggtgttgg atagaggata gggagaatat ttactaacta aataccattc actactcatg   3840
cgtgagatgg gtgtacaaac tcatcctctt ttaatggcat ttctctttaa actatgttcc   3900
taaccaaatg agatgatagg atagatcctg gttaccactc ttttactgtg cacatatggg   3960
ccccggaatt ctttaatagt caccttcatg attatagcaa ctaatgtttg aacaaagctc   4020
aaagtatgca atgcttcatt attcaagaat gaaaaatata atgttgataa tatatattaa   4080
gtgtgccaaa tcagtttgac tactctctgt tttagtgttt atgtttaaaa gaaatatatt   4140
ttttgttatt attagataat atttttgtat ttctctattt tcataatcag taaatagtgt   4200
catataaact catttatctc ctcttcatgg catcttcaat atgaatctat aagtagtaaa   4260
tcagaaagta acaatctatg gcttatttct atgacaaatt caagagctag aaaaataaaa   4320
tgtttcatta tgcactttta gaaatgcata tttgccacaa aacctgtatt actgaataat   4380
atcaaataaa atatcataaa gcatttt                                       4407
```

<210> SEQ ID NO 300
<211> LENGTH: 5532

-continued

<212> TYPE: DNA
<213> ORGANISM: Homo sapiens

<400> SEQUENCE: 300

```
gccgcgctgc gccggagtcc cgagctagcc ccggcgccgc cgccgcccag accggacgac     60
aggccacctc gtcggcgtcc gcccgagtcc ccgcctcgcc gccaacgcca caaccaccgc    120
gcacggcccc ctgactccgt ccagtattga tcgggagagc cggagcgagc tcttcgggga    180
gcagcgatgc gaccctccgg gacggccggg gcagcgctcc tggcgctgct ggctgcgctc    240
tgcccggcga gtcgggctct ggaggaaaag aaagtttgcc aaggcacgag taacaagctc    300
acgcagttgg gcacttttga agatcatttt ctcagcctcc agaggatgtt caataactgt    360
gaggtggtcc ttgggaattt ggaaattacc tatgtgcaga ggaattatga tctttccttc    420
ttaaagacca tccaggaggt ggctggttat gtcctcattg ccctcaacac agtggagcga    480
attcctttgg aaaacctgca gatcatcaga ggaaatatgt actacgaaaa ttcctatgcc    540
ttagcagtct tatctaacta tgatgcaaat aaaaccggac tgaaggagct gcccatgaga    600
aatttacagg aaatcctgca tggcgccgtg cggttcagca acaaccctgc cctgtgcaac    660
gtggagagca tccagtggcg ggacatagtc agcagtgact ttctcagcaa catgtcgatg    720
gacttccaga accacctggg cagctgccaa aagtgtgatc caagctgtcc caatgggagc    780
tgctggggtg caggagagga gaactgccag aaactgacca aaatcatctg tgcccagcag    840
tgctccgggc gctgccgtgg caagtccccc agtgactgct gccacaacca gtgtgctgca    900
ggctgcacag gcccccggga gagcgactgc ctggtctgcc gcaaattccg agacgaagcc    960
acgtgcaagg acacctgccc cccactcatg ctctacaacc ccaccacgta ccagatggat   1020
gtgaaccccg agggcaaata cagctttggt gccacctgcg tgaagaagtg tccccgtaat   1080
tatgtggtga cagatcacgg ctcgtgcgtc cgagcctgtg gggccgacag ctatgagatg   1140
gaggaagacg gcgtccgcaa gtgtaagaag tgcgaagggc cttgccgcaa agtgtgtaac   1200
ggaataggta ttggtgaatt taaagactca ctctccataa atgctacgaa tattaaacac   1260
ttcaaaaact gcacctccat cagtggcgat ctccacatcc tgccggtggc atttaggggt   1320
gactccttca cacatactcc tcctctggat ccacaggaac tggatattct gaaaaccgta   1380
aaggaaatca cagggttttt gctgattcag gcttggcctg aaaacaggac ggacctccat   1440
gcctttgaga acctagaaat catacgcggc aggaccaagc aacatggtca gttttctctt   1500
gcagtcgtca gcctgaacat aacatccttg ggattacgct ccctcaagga gataagtgat   1560
ggagatgtga taatttcagg aaacaaaaat ttgtgctatg caaatacaat aaactggaaa   1620
aaactgtttg ggacctccgg tcagaaaacc aaaattataa gcaacagagg tgaaaacagc   1680
tgcaaggcca caggccaggt ctgccatgcc ttgtgctccc ccgagggctg ctggggcccg   1740
gagcccaggg actgcgtctc ttgccggaat gtcagccgag gcagggaatg cgtggacaag   1800
tgcaagcttc tggagggtga gccaagggag tttgtggaga actctgagtg catacagtgc   1860
cacccagagt gcctgcctca ggccatgaac atcacctgca caggacgggg accagacaac   1920
tgtatccagt gtgcccacta cattgacggc ccccactgcg tcaagacctg cccggcagga   1980
gtcatgggag aaaacaacac cctggtctgg aagtacgcag acgccggcca tgtgtgccac   2040
ctgtgccatc caaactgcac ctacggatgc actgggccag gtcttgaagg ctgtccaacg   2100
aatgggccta agatcccgtc catcgccact gggatggtgg gggccctcct cttgctgctg   2160
gtggtggccc tggggatcgg cctcttcatg cgaaggcgcc acatcgttcg gaagcgcacg   2220
```

-continued

```
ctgcggaggc tgctgcagga gagggagctt gtggagcctc ttacacccag tggagaagct   2280
cccaaccaag ctctcttgag gatcttgaag gaaactgaat tcaaaaagat caaagtgctg   2340
ggctccggtg cgttcggcac ggtgtataag ggactctgga tcccagaagg tgagaaagtt   2400
aaaattcccg tcgctatcaa ggaattaaga gaagcaacat ctccgaaagc caacaaggaa   2460
atcctcgatg aagcctacgt gatggccagc gtggacaacc cccacgtgtg ccgcctgctg   2520
ggcatctgcc tcacctccac cgtgcaactc atcacgcagc tcatgccctt cggctgcctc   2580
ctggactatg tccgggaaca caaagacaat attggctccc agtacctgct caactggtgt   2640
gtgcagatcg caaagggcat gaactacttg gaggaccgtc gcttggtgca ccgcgacctg   2700
gcagccagga acgtactggt gaaaacaccg cagcatgtca agatcacaga ttttgggctg   2760
gccaaactgc tgggtgcgga agagaaagaa taccatgcag aaggaggcaa agtgcctatc   2820
aagtggatgg cattggaatc aattttacac agaatctata cccaccagag tgatgtctgg   2880
agctacgggg tgaccgtttg ggagttgatg acctttggat ccaagccata tgacggaatc   2940
cctgccagcg agatctcctc catcctggag aaaggagaac gcctccctca gccacccata   3000
tgtaccatcg atgtctacat gatcatggtc aagtgctgga tgatagacgc agatagtcgc   3060
ccaaagttcc gtgagttgat catcgaattc tccaaaatgg cccgagaccc ccagcgctac   3120
cttgtcattc aggggggatga aagaatgcat ttgccaagtc ctacagactc caacttctac   3180
cgtgccctga tggatgaaga agacatggac gacgtggtgg atgccgacga gtacctcatc   3240
ccacagcagg gcttcttcag cagcccctcc acgtcacgga ctcccctcct gagctctctg   3300
agtgcaacca gcaacaattc caccgtggct tgcattgata gaaatgggct gcaaagctgt   3360
cccatcaagg aagacagctt cttgcagcga tacagctcag accccacagg cgccttgact   3420
gaggacagca tagacgacac cttcctccca gtgcctgaat acataaacca gtccgttccc   3480
aaaaggcccg ctggctctgt gcagaatcct gtctatcaca atcagcctct gaaccccgcg   3540
cccagcagag acccacacta ccaggacccc cacagcactg cagtgggcaa ccccgagtat   3600
ctcaacactg tccagcccac ctgtgtcaac agcacattcg acagccctgc ccactgggcc   3660
cagaaaggca gccaccaaat tagcctggac aaccctgact accagcagga cttctttccc   3720
aaggaagcca agccaaatgg catctttaag ggctccacag ctgaaaatgc agaataccta   3780
agggtcgcgc cacaaagcag tgaatttatt ggagcatgac cacggaggat agtatgagcc   3840
ctaaaaatcc agactctttc gatacccagg accaagccac agcaggtcct ccatcccaac   3900
agccatgccc gcattagctc ttagacccac agactggttt tgcaacgttt acaccgacta   3960
gccaggaagt acttccacct cgggcacatt ttgggaagtt gcattccttt gtcttcaaac   4020
tgtgaagcat ttacagaaac gcatccagca agaatattgt ccctttgagc agaaatttat   4080
ctttcaaaga ggtatatttg aaaaaaaaaa aaaaagtata tgtgaggatt tttattgatt   4140
ggggatcttg gagtttttca ttgtcgctat tgatttttac ttcaatgggc tcttccaaca   4200
aggaagaagc ttgctggtag cacttgctac cctgagttca tccaggccca actgtgagca   4260
aggagcacaa gccacaagtc ttccagagga tgcttgattc cagtggttct gcttcaaggc   4320
ttccactgca aaacactaaa gatccaagaa ggccttcatg gccccagcag gccggatcgg   4380
tactgtatca agtcatggca ggtacagtag gataagccac tctgtccctt cctgggcaaa   4440
gaagaaacgg aggggatgaa ttcttcctta gacttacttt tgtaaaaatg tccccacggt   4500
acttactccc cactgatgga ccagtggttt ccagtcatga gcgttagact gacttgtttg   4560
tcttccattc cattgttttg aaactcagta tgccgcccct gtcttgctgt catgaaatca   4620
```

-continued

```
gcaagagagg atgacacatc aaataataac tcggattcca gcccacattg gattcatcag   4680

catttggacc aatagcccac agctgagaat gtggaatacc taaggataac accgcttttg   4740

ttctcgcaaa aacgtatctc ctaatttgag gctcagatga aatgcatcag gtcctttggg   4800

gcatagatca gaagactaca aaaatgaagc tgctctgaaa tctcctttag ccatcacccc   4860

aaccccccaa aattagtttg tgttacttat ggaagatagt tttctccttt tacttcactt   4920

caaaagcttt ttactcaaag agtatatgtt ccctccaggt cagctgcccc caaacccccct   4980

ccttacgctt tgtcacacaa aaagtgtctc tgccttgagt catctattca agcacttaca   5040

gctctggcca caacagggca ttttacaggt gcgaatgaca gtagcattat gagtagtgtg   5100

aattcaggta gtaaatatga aactagggtt tgaaattgat aatgctttca caacatttgc   5160

agatgtttta gaaggaaaaa agttccttcc taaaataatt tctctacaat tggaagattg   5220

gaagattcag ctagttagga gcccattttt tcctaatctg tgtgtgccct gtaacctgac   5280

tggttaacag cagtcctttg taaacagtgt tttaaactct cctagtcaat atccacccca   5340

tccaatttat caaggaagaa atggttcaga aaatattttc agcctacagt tatgttcagt   5400

cacacacaca tacaaaatgt tccttttgct tttaaagtaa tttttgactc ccagatcagt   5460

cagagcccct acagcattgt taagaaagta tttgattttt gtctcaatga aaataaaact   5520

atattcattt cc                                                        5532
```

<210> SEQ ID NO 301
<211> LENGTH: 1528
<212> TYPE: DNA
<213> ORGANISM: Homo sapiens

<400> SEQUENCE: 301

```
cggcgagcga gcaccttcga cgcggtccgg ggaccccctc gtcgctgtcc tcccgacgcg     60

gacccgcgtg ccccaggcct cgcgctgccc ggccggctcc tcgtgtccca ctcccggcgc    120

acgccctccc gcgagtcccg ggcccctccc gcgcccctct tctcggcgcg cgcgcagcat    180

ggcgcccccg caggtcctcg cgttcgggct tctgcttgcc gcggcgacgg cgacttttgc    240

cgcagctcag gaagaatgtg tctgtgaaaa ctacaagctg gccgtaaact gctttgtgaa    300

taataatcgt caatgccagt gtacttcagt tggtgcacaa aatactgtca tttgctcaaa    360

gctggctgcc aaatgtttgg tgatgaaggc agaaatgaat ggctcaaaac ttgggagaag    420

agcaaaacct gaaggggccc tccagaacaa tgatgggctt tatgatcctg actgcgatga    480

gagcgggctc tttaaggcca agcagtgcaa cggcacctcc acgtgctggt gtgtgaacac    540

tgctggggtc agaagaacag acaaggacac tgaaataacc tgctctgagc gagtgagaac    600

ctactggatc atcattgaac taaaacacaa agcaagagaa aaaccttatg atagtaaaag    660

tttgcggact gcacttcaga aggagatcac aacgcgttat caactggatc caaaatttat    720

cacgagtatt ttgtatgaga ataatgttat cactattgat ctggttcaaa attcttctca    780

aaaaactcag aatgatgtgg acatagctga tgtggcttat tattttgaaa aagatgttaa    840

aggtgaatcc ttgtttcatt ctaagaaaat ggacctgaca gtaaatgggg aacaactgga    900

tctggatcct ggtcaaactt taatttatta tgttgatgaa aaagcacctg aattctcaat    960

gcagggtcta aaagctggtg ttattgctgt tattgtggtt gtggtgatag cagttgttgc   1020

tggaattgtt gtgctggtta tttccagaaa gaagagaatg gcaaagtatg agaaggctga   1080

gataaaggag atgggtgaga tgcataggga actcaatgca taactatata atttgaagat   1140
```

```
tatagaagaa gggaaatagc aaatggacac aaattacaaa tgtgtgtgcg tgggacgaag   1200

acatctttga aggtcatgag tttgttagtt taacatcata tatttgtaat agtgaaacct   1260

gtactcaaaa tataagcagc ttgaaactgg ctttaccaat cttgaaattt gaccacaagt   1320

gtcttatata tgcagatcta atgtaaaatc cagaacttgg actccatcgt taaaattatt   1380

tatgtgtaac attcaaatgt gtgcattaaa tatgcttcca cagtaaaatc tgaaaaactg   1440

atttgtgatt gaaagctgcc tttctattta cttgagtctt gtacatacat actttttat    1500

gagctatgaa ataaaacatt ttaaactg                                      1528


<210> SEQ ID NO 302
<211> LENGTH: 1856
<212> TYPE: DNA
<213> ORGANISM: Homo sapiens

<400> SEQUENCE: 302

ctgacttggc aggactgtgc aattgtcaga aggccgtggg gagtgggggc cagtgcctgc     60

agcctgccct gcctctctca caggcccctta gagcatcgcc aggtgcagag ctccacagct   120

ctctttccca aggagtaatc agagggtgag aacgtggagc ctggtggaca ggtgaaagca   180

ctgggatctt tctgcccaga aaggggaaag ttgcacattt atatcctaga gggaagcgac   240

agcagtgctt ctccctgtgc tgaggtacag gagccatgtg gctagaaatc ctcctcactt   300

cagtgctggg ctttgccatc tactggttca tctcccggga caaagaggaa actttgccac   360

ttgaagatgg gtggtggggg ccaggcacga ggtccgcagc cagggaggac gacagcatcc   420

gcccttcaa ggtggaaacg tcagatgagg agatccacga cttacaccag aggatcgata    480

agttccgttt caccccacct ttggaggaca gctgcttcca ctatggcttc aactccaact   540

acctgaagaa agtcatctcc tactggcgga atgaatttga ctggaagaag caggtggaga   600

ttctcaacag ataccctcac ttcaagacta agattgaagg gctggacatc cacttcatcc   660

acgtgaagcc cccccagctg cccgcaggcc ataccccgaa gcccttgctg atggtgcacg   720

gctggcccgg ctctttctac gagttttata agatcatccc actcctgact gaccccaaga   780

accatggcct gagcgatgag cacgtttttg aagtcatctg cccttccatc cctggctatg   840

gcttctcaga ggcatcctcc aagaaggggt tcaactcggt ggccaccgcc aggatctttt   900

acaagctgat gctgcggctg ggcttccagg aattctacat tcaaggaggg gactgggggt   960

ccctgatctg cactaatatg gcccagctgg tgcccagcca cgtgaaaggc ctgcacttga  1020

acatggcttt ggttttaagc aacttctcta ccctgaccct cctcctggga cagcgtttcg  1080

ggaggtttct tggcctcact gagagggatg tggagctgct gtaccccgtc aaggagaagg  1140

tattctacag cctgatgagg gagagcggct acatgcacat ccagtgcacc aagcctgaca  1200

ccgtaggctc tgctctgaat gactctcctg tgggtctggc tgcctatatt ctagagaagt  1260

tttccacctg gaccaatacg gaattccgat acctggagga tggaggcctg gaaaggaagt  1320

tctccctgga cgacctgctg accaacgtca tgctctactg gacaacaggc accatcatct  1380

cctcccagcg cttctacaag gagaacctgg gacagggctg gatgacccag aagcatgagc  1440

ggatgaaggt ctatgtgccc actggcttct ctgccttccc ttttgagcta ttgcacacgc  1500

ctgaaaagtg ggtgaggttc aagtacccaa agctcatctc ctattcctac atggttcgtg  1560

ggggccactt tgcggccttt gaggagccgg agctgctcgc ccaggacatc cgcaagttcc  1620

tgtcggtgct ggagcggcaa tgacccaccc ctctcccccc gcctgccacc tccccccaca  1680

agtgccctcc aggcttttct tggggaagat accccttttc tgaggaatga gtttgcctcc  1740
```

```
gtcccctgcc catgctggga gcccacgctc accccctcac ccctccaagc tcactcccca   1800

acccccaact ccgtgtggta agcaacatgg ctttgatgat aaacgacttt actcta       1856
```

<210> SEQ ID NO 303
<211> LENGTH: 6450
<212> TYPE: DNA
<213> ORGANISM: Homo sapiens

<400> SEQUENCE: 303

```
gagttgtgcc tggagtgatg tttaagccaa tgtcagggca aggcaacagt ccctggccgt     60

cctccagcac ctttgtaatg catatgagct cgggagacca gtacttaaag ttggaggccc    120

gggagcccag gagctggcgg agggcgttcg tcctgggagc tgcacttgct ccgtcgggtc    180

gccggcttca ccggaccgca ggctcccggg gcagggccgg ggccagagct cgcgtgtcgg    240

cgggacatgc gctgcgtcgc ctctaacctc gggctgtgct ctttttccag gtggcccgcc    300

ggtttctgag ccttctgccc tgcggggaca cggtctgcac cctgcccgcg gccacggacc    360

atgaccatga ccctccacac caaagcatct gggatggccc tactgcatca gatccaaggg    420

aacgagctgg agcccctgaa ccgtccgcag ctcaagatcc ccctggagcg gcccctgggc    480

gaggtgtacc tggacagcag caagcccgcc gtgtacaact accccgaggg cgccgcctac    540

gagttcaacg ccgcggccgc cgccaacgcg caggtctacg gtcagaccgg cctcccctac    600

ggccccgggt ctgaggctgc ggcgttcggc tccaacggcc tgggggggttt ccccccactc    660

aacagcgtgt ctccgagccc gctgatgcta ctgcacccgc cgccgcagct gtcgcctttc    720

ctgcagcccc acggccagca ggtgccctac tacctggaga acgagcccag cggctacacg    780

gtgcgcgagg ccggcccgcc ggcattctac aggccaaatt cagataatcg acgccagggt    840

ggcagagaaa gattggccag taccaatgac aagggaagta tggctatgga atctgccaag    900

gagactcgct actgtgcagt gtgcaatgac tatgcttcag gctaccatta tggagtctgg    960

tcctgtgagg gctgcaaggc cttcttcaag agaagtattc aaggacataa cgactatatg   1020

tgtccagcca ccaaccagtg caccattgat aaaaacagga ggaagagctg ccaggcctgc   1080

cggctccgca aatgctacga agtgggaatg atgaaaggtg ggatacgaaa agaccgaaga   1140

ggagggagaa tgttgaaaca caagcgccag agagatgatg gggagggcag gggtgaagtg   1200

gggtctgctg gagacatgag agctgccaac ctttggccaa gcccgctcat gatcaaacgc   1260

tctaagaaga acagcctggc cttgtccctg acggccgacc agatggtcag tgccttgttg   1320

gatgctgagc cccccatact ctattccgag tatgatccta ccagaccctt cagtgaagct   1380

tcgatgatgg gcttactgac caacctggca gacagggagc tggttcacat gatcaactgg   1440

gcgaagaggg tgccaggctt tgtggatttg accctccatg atcaggtcca ccttctagaa   1500

tgtgcctggc tagagatcct gatgattggt ctcgtctggc gctccatgga gcacccagtg   1560

aagctactgt ttgctcctaa cttgctcttg gacaggaacc agggaaaatg tgtagagggc   1620

atggtggaga tcttcgacat gctgctggct acatcatctc ggttccgcat gatgaatctg   1680

cagggagagg agtttgtgtg cctcaaatct attattttgc ttaattctgg agtgtacaca   1740

tttctgtcca gcaccctgaa gtctctggaa gagaaggacc atatccaccg agtcctggac   1800

aagatcacag acactttgat ccacctgatg gccaaggcag gcctgaccct gcagcagcag   1860

caccagcggc tggcccagct cctcctcatc ctctcccaca tcaggcacat gagtaacaaa   1920

ggcatggagc atctgtacag catgaagtgc aagaacgtgg tgcccctcta tgacctgctg   1980
```

-continued

```
ctggagatgc tggacgccca ccgcctacat gcgcccacta gccgtggagg ggcatccgtg   2040
gaggagacgg accaaagcca cttggccact gcgggctcta cttcatcgca ttccttgcaa   2100
aagtattaca tcacgggggga ggcagagggt ttccctgcca cagtctgaga gctccctggc   2160
tcccacacgg ttcagataat ccctgctgca ttttaccctc atcatgcacc actttagcca   2220
aattctgtct cctgcataca ctccggcatg catccaacac caatggcttt ctagatgagt   2280
ggccattcat ttgcttgctc agttcttagt ggcacatctt ctgtcttctg ttgggaacag   2340
ccaaagggat tccaaggcta aatctttgta acagctctct ttcccccttg ctatgttact   2400
aagcgtgagg attcccgtag ctcttcacag ctgaactcag tctatgggtt ggggctcaga   2460
taactctgtg catttaagct acttgtagag acccaggcct ggagagtaga cattttgcct   2520
ctgataagca ctttttaaat ggctctaaga ataagccaca gcaaagaatt taaagtggct   2580
cctttaattg gtgacttgga gaaagctagg tcaagggttt attatagcac cctcttgtat   2640
tcctatggca atgcatcctt ttatgaaagt ggtacacctt aaagctttta tatgactgta   2700
gcagagtatc tggtgattgt caattcactt cccccctatag gaatacaagg ggccacacag   2760
ggaaggcaga tcccctagtt ggccaagact tattttaact tgatacactg cagattcaga   2820
gtgtcctgaa gctctgcctc tggctttccg gtcatgggtt ccagttaatt catgcctccc   2880
atggacctat ggagagcaac aagttgatct tagttaagtc tccctatatg agggataagt   2940
tcctgatttt tgtttttatt tttgtgttac aaaagaaagc cctccctccc tgaacttgca   3000
gtaaggtcag cttcaggacc tgttccagtg ggcactgtac ttggatcttc ccggcgtgtg   3060
tgtgccttac acaggggtga actgttcact gtggtgatgc atgatgaggg taaatggtag   3120
ttgaaaggag caggggccct ggtgttgcat ttagccctgg ggcatggagc tgaacagtac   3180
ttgtgcagga ttgttgtggc tactagagaa caagagggaa agtagggcag aaactggata   3240
cagttctgag cacagccaga cttgctcagg tggccctgca caggctgcag ctacctagga   3300
acattccttg cagaccccgc attgcctttg ggggtgccct gggatccctg gggtagtcca   3360
gctcttattc atttcccagc gtggccctgg ttggaagaag cagctgtcaa gttgtagaca   3420
gctgtgttcc tacaattggc ccagcaccct ggggcacggg agaagggtgg ggaccgttgc   3480
tgtcactact caggctgact ggggcctggt cagattacgt atgcccttgg tggtttagag   3540
ataatccaaa atcagggttt ggtttgggga agaaaatcct ccccccttcct cccccgcccc   3600
gttccctacc gcctccactc ctgccagctc atttccttca atttcctttg acctataggc   3660
taaaaaagaa aggctcattc cagccacagg gcagccttcc ctgggccttt gcttctctag   3720
cacaattatg ggttacttcc tttttcttaa caaaaaagaa tgtttgattt cctctgggtg   3780
accttattgt ctgtaattga aaccctattg agaggtgatg tctgtgttag ccaatgaccc   3840
aggtagctgc tcgggcttct cttggtatgt cttgtttgga aaagtggatt tcattcattt   3900
ctgattgtcc agttaagtga tcaccaaagg actgagaatc tgggagggca aaaaaaaaaa   3960
aaaaagtttt tatgtgcact taaatttggg gacaatttta tgtatctgtg ttaaggatat   4020
gcttaagaac ataattcttt tgttgctgtt tgtttaagaa gcaccttagt ttgtttaaga   4080
agcaccttat atagtataat atatattttt ttgaaattac attgcttgtt tatcagacaa   4140
ttgaatgtag taattctgtt ctggatttaa tttgactggg ttaacatgca aaaaccaagg   4200
aaaaatattt agtttttttt tttttttttg tatacttttc aagctacctt gtcatgtata   4260
cagtcattta tgcctaaagc ctggtgatta ttcatttaaa tgaagatcac atttcatatc   4320
aacttttgta tccacagtag acaaaatagc actaatccag atgcctattg ttggatattg   4380
```

-continued

```
aatgacagac aatcttatgt agcaaagatt atgcctgaaa aggaaaatta ttcagggcag   4440
ctaattttgc ttttaccaaa atatcagtag taatattttt ggacagtagc taatgggtca   4500
gtgggttctt tttaatgttt atacttagat tttcttttaa aaaaattaaa ataaaacaaa   4560
aaaaatttct aggactagac gatgtaatac cagctaaagc caaacaatta tacagtggaa   4620
ggttttacat tattcatcca atgtgtttct attcatgtta agatactact acatttgaag   4680
tgggcagaga acatcagatg attgaaatgt tcgcccaggg gtctccagca actttggaaa   4740
tctctttgta tttttacttg aagtgccact aatggacagc agatattttc tggctgatgt   4800
tggtattggg tgtaggaaca tgatttaaaa aaaaaactct tgcctctgct ttcccccact   4860
ctgaggcaag ttaaaatgta aaagatgtga tttatctggg gggctcaggt atggtgggga   4920
agtggattca ggaatctggg gaatggcaaa tatattaaga agagtattga aagtatttgg   4980
aggaaaatgg ttaattctgg gtgtgcacca aggttcagta gagtccactt ctgccctgga   5040
gaccacaaat caactagctc catttacagc catttctaaa atggcagctt cagttctaga   5100
gaagaaagaa caacatcagc agtaaagtcc atggaatagc tagtggtctg tgtttctttt   5160
cgccattgcc tagcttgccg taatgattct ataatgccat catgcagcaa ttatgagagg   5220
ctaggtcatc caaagagaag accctatcaa tgtaggttgc aaaatctaac ccctaaggaa   5280
gtgcagtctt tgatttgatt tccctagtaa ccttgcagat atgtttaacc aagccatagc   5340
ccatgccttt tgagggctga acaaataagg gacttactga taatttactt ttgatcacat   5400
taaggtgttc tcaccttgaa atcttataca ctgaaatggc cattgattta ggccactggc   5460
ttagagtact ccttcccctg catgacactg attacaaata ctttcctatt catactttcc   5520
aattatgaga tggactgtgg gtactgggag tgatcactaa caccatagta atgtctaata   5580
ttcacaggca gatctgcttg ggaagctag ttatgtgaaa ggcaaataaa gtcatacagt   5640
agctcaaaag gcaaccataa ttctctttgg tgcaagtctt gggagcgtga tctagattac   5700
actgcaccat tcccaagtta atcccctgaa aacttactct caactggagc aaatgaactt   5760
tggtcccaaa tatccatctt ttcagtagcg ttaattatgc tctgtttcca actgcatttc   5820
ctttccaatt gaattaaagt gtggcctcgt ttttagtcat ttaaaattgt tttctaagta   5880
attgctgcct ctattatggc acttcaattt tgcactgtct tttgagattc aagaaaaatt   5940
tctattcatt tttttgcatc caattgtgcc tgaactttta aaatatgtaa atgctgccat   6000
gttccaaacc catcgtcagt gtgtgtgttt agagctgtgc accctagaaa caacatactt   6060
gtcccatgag caggtgcctg agacacagac ccctttgcat tcacagagag gtcattggtt   6120
atagagactt gaattaataa gtgacattat gccagtttct gttctctcac aggtgataaa   6180
caatgctttt tgtgcactac atactcttca gtgtagagct cttgttttat gggaaaaggc   6240
tcaaatgcca aattgtgttt gatggattaa tatgcccttt tgccgatgca tactattact   6300
gatgtgactc ggttttgtcg cagctttgct ttgtttaatg aaacacactt gtaaacctct   6360
tttgcacttt gaaaaagaat ccagcgggat gctcgagcac ctgtaaacaa ttttctcaac   6420
ctatttgatg ttcaaataaa gaattaaact                                    6450
```

<210> SEQ ID NO 304
<211> LENGTH: 3336
<212> TYPE: DNA
<213> ORGANISM: Homo sapiens
<220> FEATURE:
<221> NAME/KEY: unsure
<222> LOCATION: (0)...(0)

<223> OTHER INFORMATION: n = A, T, C or G

<400> SEQUENCE: 304

```
cggcggcgac tgcagtctgg agggtccaca cttgtgattc tcaatggaga gtgaaaacgc     60
agattcataa tgaaagctag cccccgtcgg ccactgattc tcaaaagacg gaggctgccc    120
cttcctgttc aaaatgcccc aagtgaaaca tcagaggagg aacctaagag atcccctgcc    180
caacaggagt ctaatcaagc agaggcctcc aaggaagtgg cggagtccaa ctcttgcaag    240
tttccagctg ggatcaagat tattaaccac cccaccatgc ccaacacgca agtagtggcc    300
atccccaaca atgctaatat tcacagcatc atcacagcac tgactgccaa gggaaaagag    360
agtggcagta gtgggcccaa caaattcatc ctcatcagct gtgggggagc cccaactcag    420
cctccaggac tccggcctca aacccaaacc agctatgatg ccaaaaggac agaagtgacc    480
ctggagacct tgggaccaaa acctgcagct agggatgtga atcttcctag accacctgga    540
gccctttgcg agcagaaacg ggagacctgt gcagatggtg aggcagcagg ctgcactatc    600
aacaatagcc tatccaacat ccagtggctt cgaaagatga gttctgatgg actgggctcc    660
cgcagcatca agcaagagat ggaggaaaag gagaattgtc acctggagca gcgacaggtt    720
aaggttgagg agccttcgag accatcagcg tcctggcaga actctgtgtc tgagcggcca    780
ccctactctt acatggccat gatacaattc gccatcaaca gcactgagag gaagcgcatg    840
actttgaaag acatctatac gtggattgag gaccactttc cctactttaa gcacattgcc    900
aagccaggct ggaagaactc catccgccac aacctttccc tgcacgacat gtttgtccgg    960
gagacgtctg ccaatggcaa ggtctccttc tggaccattc accccagtgc caaccgctac   1020
ttgacattgg accaggtgtt taagccactg gacccagggt ctccacaatt gcccgagcac   1080
ttggaatcac agcagaaacg accgaatcca gagctccgcc ggaacatgac catcaaaacc   1140
gaactccccc tgggcgcacg gcggaagatg aagccactgc taccacgggt cagctcatac   1200
ctggtaccta tccagttccc ggtgaaccag tcactggtgt tgcagccctc ggtgaaggtg   1260
ccattgcccc tggcggcttc cctcatgagc tcagagcttg cccgccatag caagcgagtc   1320
cgcattgccc ccaaggtgct gctagctgag gaggggatag ctcctctttc ttctgcagga   1380
ccagggaaag aggagaaact cctgtttgga gaagggtttt ctcctttgct tccagttcag   1440
actatcaagg aggaagaaat ccagcctggg gaggaaatgc cacacttagc gagacccatc   1500
aaagtggaga gccctccctt ggaagagtgg ccctccccgg ccccatcttt caaagaggaa   1560
tcatctcact cctgggagga ttcgtcccaa tctcccaccc caagacccaa gaagtcctac   1620
agtgggctta ggtccccaac ccggtgtgtc tcggaaatgc ttgtgattca acacagggag   1680
aggagggaga ggagccggtc tcggaggaaa cagcatctac tgcctccctg tgtggatgag   1740
ccggagctgc tcttctcaga ggggcccagt acttcccgct gggccgcaga gctcccgttc   1800
ccagcagact cctctgaccc tgcctcccag ctcagctact cccaggaagt gggaggacct   1860
tttaagacac ccattaagga aacgctgccc atctcctcca ccccgagcaa atctgtcctc   1920
cccagaaccc ctgaatcctg gaggctcacg cccccagcca aagtaggggg actggatttc   1980
agcccagtac aaacctccca gggtgcctct gacccccttgc ctgacccccct ggggctgatg   2040
gatctcagca ccactccctt gcaaagtgct cccccccttg aatcaccgca aaggctcctc   2100
agttcagaac ccttagacct catctccgtc ccctttggca actcttctcc ctcagatata   2160
gacgtcccca agccaggctc cccggagcca caggtttctg gccttgcagc caatcgttct   2220
ctgacagaag gcctggtcct ggacacaatg aatgacagcc tcagcaagat cctgctggac   2280
```

atcagctttc ctggcctgga cgaggaccca ctgggccctg acaacatcaa ctggtcccag 2340
tttattcctg agctacagta gagccctgcc cttgcccctg tgctcaagct gtccaccatc 2400
ccgggcactc caaggctcag tgcaccccaa gcctctgagt gaggacagca ggcagggact 2460
gttctgctcc tcatagctcc ctgctgcctg attatgcaaa agtagcagtc acaccctagc 2520
cactgctggg accttgtgtt ccccaagagt atctgattcc tctgctgtcc ctgccaggag 2580
ctgaagggtg ggaacaacaa aggcaatggt gaaaagagat taggaacccc ccagcctgtt 2640
tccattctct gcccagcagt ctcttacctt ccctgatctt tgcagggtgg tccgtgtaaa 2700
tagtataaat tctccaaatt atcctctaat tataaatgta agcttatttc cttagatcat 2760
tatccagaga ctgccagaag gtgggtagga tgacctgggg tttcaattga cttctgttcc 2820
ttgcttttag ttttgataga agggaagacc tgcagtgcac ggtttcttcc aggctgaggt 2880
acctggatct tgggttcttc actgcaggga cccagacaag tggatctgct tgccagagtc 2940
ctttttgccc ctccctgcca cctccccgtg tttccaagtc agctttcctg caagaagaaa 3000
tcctggttaa aaaagtcttt tgtattgggt caggagttga atttggggtg ggaggatgga 3060
tgcaactgaa gcagagtgtg ggtgcccaga tgtgcgctat tagatgtttc tctgataatg 3120
tccccaatca taccagggag actggcattg acgagaactc aggtggaggc ttgagaaggc 3180
cgaaagggcc cctgacctgc ctggcttcct tagcttgccc ctcagctttg caaagagcca 3240
ccctaggccc cagctgaccg catgggtgtg agccagcttg agaacactaa ctactcaata 3300
aaagcgaagg tggaccnaaa aaaaaaaaaa aaaaaa 3336

<210> SEQ ID NO 305
<211> LENGTH: 2365
<212> TYPE: DNA
<213> ORGANISM: Homo sapiens

<400> SEQUENCE: 305
tcccagcctt cccatccccc caccgaaagc aaatcattca acgacccccg accctccgac 60
ggcaggagcc ccccgacctc ccaggcggac cgcccttccc tccccgcgcg ggttccgggc 120
ccggcgagag ggcgcgacga cagccgaggc catggaggtg acggcggacc agccgcgctg 180
ggtgagccac caccaccccg ccgtgctcaa cgggcagcac ccggacacgc accacccggg 240
cctcagccac tcctacatgg acgcggcgca gtacccgctg ccggaggagg tggatgtgct 300
ttttaacatc gacggtcaag gcaaccacgt cccgccctac tacggaaact cggtcagggc 360
cacggtgcag aggtaccctc cgacccacca cgggagccag gtgtgccgcc cgcctctgct 420
tcatggatcc ctaccctggc tggacggcgg caaagccctg ggcagccacc acaccgcctc 480
cccctggaat ctcagcccct tctccaagac gtccatccac cacggctccc cggggcccct 540
ctccgtctac cccccggcct cgtcctcctc cttgtcgggg ggccacgcca gcccgcacct 600
cttcaccttc ccgcccaccc cgccgaagga cgtctccccg gacccatcgc tgtccacccc 660
aggctcggcc ggctcggccc ggcaggacga gaaagagtgc ctcaagtacc aggtgcccct 720
gcccgacagc atgaagctgg agtcgtccca ctcccgtggc agcatgaccg ccctgggtgg 780
agcctcctcg tcgacccacc accccatcac cacctacccg ccctacgtgc ccgagtacag 840
ctccggactc ttccccccca gcagcctgct gggcggctcc cccaccggct tcggatgcaa 900
gtccaggccc aaggcccggt ccagcacagg cagggagtgt gtgaactgtg gggcaacctc 960
gaccccactg tggcggcgag atggcacggg acactacctg tgcaacgcct gcgggctcta 1020

-continued

```
tcacaaaatg aacggacaga accggcccct cattaagccc aagcgaaggc tgtctgcagc   1080

caggagagca gggacgtcct gtgcgaactg tcagaccacc acaaccacac tctggaggag   1140

gaatgccaat ggggaccctg tctgcaatgc ctgtgggctc tactacaagc ttcacaatat   1200

taacagaccc ctgactatga agaaggaagg catccagacc agaaaccgaa aaatgtctag   1260

caaatccaaa aagtgcaaaa aagtgcatga ctcactggag gacttcccca agaacagctc   1320

gtttaacccg gccgccctct ccagacacat gtcctccctg agccacatct cgcccttcag   1380

ccactccagc cacatgctga ccacgcccac gccgatgcac ccgccatcca gcctgtcctt   1440

tggaccacac cacccctcca gcatggtcac cgccatgggt tagagccctg ctcgatgctc   1500

acagggcccc cagcgagagt ccctgcagtc cctttcgact tgcatttttg caggagcagt   1560

atcatgaagc ctaaacgcga tggatatatg tttttgaagg cagaaagcaa aattatgttt   1620

gccactttgc aaaggagctc actgtggtgt ctgtgttcca accactgaat ctggacccca   1680

tctgtgaata agccattctg actcatatcc cctatttaac agggtctcta gtgctgtgaa   1740

aaaaaaaaat cctgaacatt gcatataact tatattgtaa gaaatactgt acaatgactt   1800

tattgcatct gggtagctgt aaggcatgaa ggatgccaag aagtttaagg aatatgggag   1860

aaatagtgtg gaaattaaga agaaactagg tctgatattc aaatggacaa actgccagtt   1920

ttgtttcctt tcactggcca cagttgtttg atgcattaaa agaaaataaa aaaaagaaaa   1980

aagagaaaag aaaaaaaaag aaaaaagttg taggcgaatc atttgttcaa agctgttggc   2040

cctctgcaaa ggaaatacca gttctgggca atcagtgtta ccgttcacca gttgccattg   2100

agggtttcag agagcctttt tctaggccta catgctttgt gaacaagtcc ctgtaattgt   2160

tgtttgtatg tataattcaa agcaccaaaa taagaaaaga tgtagattta tttcatcata   2220

ttatacagac cgaactgttg tataaattta tttactgcta gtcttaagaa ctgctttctt   2280

tcgtttgttt gtttcaatat tttccttctc tctcaatttt cggttgaata aactagatta   2340

cattcagttg gcaaaaaaaa aaaaa                                         2365
```

<210> SEQ ID NO 306
<211> LENGTH: 1117
<212> TYPE: DNA
<213> ORGANISM: Homo sapiens

<400> SEQUENCE: 306

```
gcaccaacca gcaccatgcc catgatactg gggtactggg acatccgcgg gctggcccac     60

gccatccgcc tgctcctgga atacacagac tcaagctatg aggaaaagaa gtacacgatg    120

ggggacgctc ctgattatga cagaagccag tggctgaatg aaaaattcaa gctgggcctg    180

gactttccca atctgcccta cttgattgat ggggctcaca agatcaccca gagcaacgcc    240

atcttgtgct acattgcccg caagcacaac ctgtgtgggg agacagaaga ggagaagatt    300

cgtgtggaca ttttggagaa ccagaccatg gacaaccata tgcagctggg catgatctgc    360

tacaatccag aatttgagaa actgaagcca aagtacttgg aggaactccc tgaaaagcta    420

aagctctact cagagtttct ggggaagcgg ccatggtttg caggaaacaa gatcactttt    480

gtagattttc tcgtctatga tgtccttgac ctccaccgta tatttgagcc caactgcttg    540

gacgccttcc caaatctgaa ggacttcatc tcccgctttg agggcttgga gaagatctct    600

gcctacatga agtccagccg cttcctccca agacctgtgt tctcaaagat ggctgtctgg    660

ggcaacaagt agggccttga aggcaggagg tgggagtgag gagcccatac tcagcctgct    720

gcccaggctg tgcagcgcag ctggactctg catcccagca cctgcctcct cgttcctttc    780
```

-continued

```
tcctgtttat tcccatcttt actcccaaga cttcattgtc cctcttcact ccccctaaac    840

ccctgtccca tgcaggccct ttgaagcctc agctacccac tatccttcgt gaacatcccc    900

tcccatcatt acccttccct gcactaaagc cagcctgacc ttccttcctg ttagtggttg    960

tgtctgcttt aaagcctgcc tggcccctcg cctgtggagc tcagccccga gctgtccccg   1020

tgttgcatga aggagcagca ttgactggtt tacaggccct gctcctgcag catggtccct   1080

gcctaggcct acctgatgga agtaaagcct caaccac                            1117
```

<210> SEQ ID NO 307
<211> LENGTH: 1266
<212> TYPE: DNA
<213> ORGANISM: Homo sapiens

<400> SEQUENCE: 307

```
ctcggaagcc cgtcaccatg tcgtgcgagt cgtctatggt tctcgggtac tgggatattc     60

gtgggctggc gcacgccatc cgcctgctcc tggagttcac ggatacctct tatgaggaga    120

aacggtacac gtgcggggaa gctcctgact atgatcgaag ccaatggctg gatgtgaaat    180

tcaagctaga cctggacttt cctaatctgc cctacctcct ggatgggaag aacaagatca    240

cccagagcaa tgccatcttg cgctacatcg ctcgcaagca caacatgtgt ggtgagactg    300

aagaagaaaa gattcgagtg gacatcatag agaaccaagt aatggatttc cgcacacaac    360

tgataaggct ctgttacagc tctgaccacg aaaaactgaa gcctcagtac ttggaagagc    420

tacctggaca actgaaacaa ttctccatgt ttctgtggaa attctcatgg tttgccgggg    480

aaaagctcac ctttgtggat ttctcacct atgatatctt ggatcagaac cgtatatttg    540

accccaagtg cctggatgag ttcccaaacc tgaaggcttt catgtgccgt tttgaggctt    600

tggagaaaat cgctgcctac ttacagtctg atcagttctg caagatgccc atcaacaaca    660

agatggccca gtggggcaac aagcctgtat gctgagcagg aggcagactt gcagagcttg    720

ttttgtttca tcctgtccgt aaggggtcag cgctcttgct ttgctctttt caatgaatag    780

cacttatgtt actggtgtcc agctgagttt ctcttgggta taaaggctaa aagggaaaaa    840

ggatatgtgg agaatcatca agatatgaat tgaatcgctg cgatactgtg gcatttccct    900

actccccaac tgagttcaag ggctgtaggt tcatgcccaa gccctgagag tgggtactag    960

aaaaaacgag attgcacagt tggagagagc aggtgtgtta aatggactgg agtccctgtg   1020

aagactgggt gaggataaca caagtaaaac tgtggtactg atggacttaa ccggagttcg   1080

gaaaccgtcc tgtgtacaca tgggagttta gtgtgataaa ggcagtattt cagactggtg   1140

ggctagccaa tagagttggc aattgcttat tgaaactcat taaaaataat agagccccac   1200

ttgacactat tcactaaaat taatctggaa tttaaggccc aacattaaac acaaagctgt   1260

attgat                                                              1266
```

<210> SEQ ID NO 308
<211> LENGTH: 2162
<212> TYPE: DNA
<213> ORGANISM: Homo sapiens

<400> SEQUENCE: 308

```
gggctgcgct gtccagctgt ggctatggcc ccagccccga gatgaggagg gagagaacta     60

ggggcccgca ggcctgggaa tttccgtccc ccaccaagtc cggatgctca ctccaaagtc    120

tcagcaggcc cctgagggag ggagctgtca gccagggaaa accgagaaca ccatcaccat    180
```

-continued

```
gacaaccagt caccagcctc aggacagata caaagctgtc tggcttatct tcttcatgct    240
gggtctggga acgctgctcc cgtggaattt tttcatgacg gccactcagt atttcacaaa    300
ccgcctggac atgtcccaga atgtgtcctt ggtcactgct gaactgagca aggacgccca    360
ggcgtcagcc gcccctgcag caccccttgcc tgagcggaac tctctcagtg ccatcttcaa    420
caatgtcatg accctatgtg ccatgctgcc cctgctgtta ttcacctacc tcaactcctt    480
cctgcatcag aggatccccc agtccgtacg gatcctgggc agcctggtgg ccatcctgct    540
ggtgtttctg atcactgcca tcctggtgaa ggtgcagctg gatgctctgc ccttctttgt    600
catcaccatg atcaagatcg tgctcattaa ttcatttggt gccatcctgc agggcagcct    660
gtttggtctg gctggccttc tgcctgccag ctacacggcc cccatcatga gtggccaggg    720
cctagcaggc ttctttgcct ccgtggccat gatctgcgct attgccagtg gctcggaact    780
atcagaaagt gccttcggct actttatcac agcctgtgct gttatcattt tgaccatcat    840
ctgttacctg ggcctgcccc gcctggaatt ctaccgctac taccagcagc tcaagcttga    900
aggacccggg gagcaggaga ccaagttgga cctcattagc aaaggagagg agccaagagc    960
aggcaaagag gaatctggag tttcagtctc caactctcag cccaccaatg aaagccactc   1020
tatcaaagcc atcctgaaaa atatctcagt cctggctttc tctgtctgct tcatcttcac   1080
tatcaccatt gggatgtttc cagccgtgac tgttgaggtc aagtccagca tcgcaggcag   1140
cagcacctgg gaacgttact tcattcctgt gtcctgtttc ttgactttca atatctttga   1200
ctggttgggc cggagcctca cagctgtatt catgtggcct gggaaggaca gccgctggct   1260
gccaagcctg gtgctggccc ggctggtgtt tgtgccactg ctgctgctgt gcaacattaa   1320
gccccgccgc tacctgactg tggtcttcga gcacgatgcc tggttcatct tcttcatggc   1380
tgcctttgcc ttctccaacg gctacctcgc cagcctctgc atgtgcttcg ggcccaagaa   1440
agtgaagcca gctgaggcag agaccgcagg agccatcatg gccttcttcc tgtgtctggg   1500
tctggcactg gggcctgttt tctccttcct gttccgggca attgtgtgac aaaggatgga   1560
cagaaggact gcctgcctcc ctccctgtct gcctcctgcc ccttccttct gccaggggtg   1620
atcctgagtg gtctggcggt tttttcttct aactgacttc tgctttccac ggcgtgtgct   1680
gggcccggat ctccaggccc tggggaggga gcctctggac ggacagtggg gacattgtgg   1740
gtttggggct cagagtcgag ggacggggtg tagcctcggc atttgcttga gtttctccac   1800
tcttggctct gactgatccc tgcttgtgca ggccagtgga ggctcttggg cttggagaac   1860
acgtgtgtct ctgtgtatgt gtctgtgtgt ctgcgtccgt gtctgtcaga ctgtctgcct   1920
gtcctggggt ggctaggagc tgggtctgac cgttgtatgg tttgacctga tatactccat   1980
tctcccctgc gcctcctcct ctgtgttttt tccatgtccc cctcccaact ccccatgccc   2040
agtttttacc catcatgcac cctgtacagt tgccacgtta ctgccttttt taaaaatata   2100
tttgacagaa accaggtgcc ttcagaggct ctctgattta aataaacctt tcttgttttt   2160
tt                                                                  2162
```

<210> SEQ ID NO 309
<211> LENGTH: 3933
<212> TYPE: DNA
<213> ORGANISM: Homo sapiens

<400> SEQUENCE: 309

```
cacgaggcag cactctcttc gtcgcttcgg ccagtgtgtc gggctgggcc ctgacaagcc     60
acctgaggag aggctcggag ccgggcccgg accccggcga ttgccgcccg cttctctcta    120
```

-continued

```
gtctcacgag gggtttcccg cctcgcaccc ccacctctgg acttgccttt ccttctcttc    180
tccgcgtgtg gagggagcca gcgcttaggc cggagcgagc ctgggggccg cccgccgtga    240
agacatcgcg gggaccgatt caccatggag ggcgccggcg gcgcgaacga caagaaaaag    300
ataagttctg aacgtcgaaa agaaaagtct cgagatgcag ccagatctcg gcgaagtaaa    360
gaatctgaag tttttatga gcttgctcat cagttgccac ttccacataa tgtgagttcg    420
catcttgata aggcctctgt gatgaggctt accatcagct atttgcgtgt gaggaaactt    480
ctggatgctg gtgatttgga tattgaagat gacatgaaag cacagatgaa ttgcttttat    540
ttgaaagcct tggatggttt tgttatggtt ctcacagatg atggtgacat gatttacatt    600
tctgataatg tgaacaaata catgggatta actcagtttg aactaactgg acacagtgtg    660
tttgatttta ctcatccatg tgaccatgag gaaatgagag aaatgcttac acacagaaat    720
ggccttgtga aaaagggtaa agaacaaaac acacagcgaa gctttttct cagaatgaag    780
tgtaccctaa ctagccgagg aagaactatg aacataaagt ctgcaacatg gaaggtattg    840
cactgcacag gccacattca cgtatatgat accaacagta accaacctca gtgtgggtat    900
aagaaaccac ctatgacctg cttggtgctg atttgtgaac ccattcctca cccatcaaat    960
attgaaattc ctttagatag caagactttc ctcagtcgac acagcctgga tatgaaattt   1020
tcttattgtg atgaaagaat taccgaattg atgggatatg agccagaaga acttttaggc   1080
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttacgttgtg agtggtatta ttcagcacga cttgattttc   1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc caacgaaaaa ttacagaata taaatttggc aatgtctcca   1620
ttacccaccg ctgaaacgcc aaagccactt cgaagtagtg ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgtttttat gtggatagtg atatggtcaa tgaattcaag   1860
ttggaattgg tagaaaaact ttttgctgaa gacacagaag caaagaaccc attttctact   1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aaatattgat tgcatctcca tctcctaccc acatacataa agaaactact   2220
agtgccacat catcaccata tagagatact caaagtcgga cagcctcacc aaacagagca   2280
ggaaaaggag tcatagaaca gacagaaaaa tctcatccaa gaagccctaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
```

-continued

```
ggaattggaa cattattaca gcagccagac gatcatgcag ctactacatc actttcttgg   2520

aaacgtgtaa aaggatgcaa atctagtgaa cagaatggaa tggagcaaaa gacaattatt   2580

ttaataccct ctgatttagc atgtagactg ctggggcaat caatggatga aagtggatta   2640

ccacagctga ccagttatga ttgtgaagtt aatgctccta tacaaggcag cagaaaccta   2700

ctgcagggtg aagaattact cagagctttg gatcaagtta actgagcttt ttcttaattt   2760

cattcctttt tttggacact ggtggctcac tacctaaagc agtctattta tattttctac   2820

atctaatttt agaagcctgg ctacaatact gcacaaactt ggttagttca atttttgatc   2880

ccctttctac ttaatttaca ttaatgctct tttttagtat gttctttaat gctggatcac   2940

agacagctca ttttctcagt tttttggtat ttaaaccatt gcattgcagt agcatcattt   3000

taaaaaatgc accttttat ttatttattt ttggctaggg agtttatccc tttttcgaat   3060

tatttttaag aagatgccaa tataattttt gtaagaaggc agtaaccttt catcatgatc   3120

ataggcagtt gaaaaatttt tacacctttt ttttcacatt ttacataaat aataatgctt   3180

tgccagcagt acgtggtagc cacaattgca caatatattt tcttaaaaaa taccagcagt   3240

tactcatgga atatattctg cgtttataaa actagttttt aagaagaaat tttttttggc   3300

ctatgaaatt gttaaacctg gaacatgaca ttgttaatca tataataatg attcttaaat   3360

gctgtatggt ttattattta aatgggtaaa gccatttaca taatatagaa agatatgcat   3420

atatctagaa ggtatgtggc atttatttgg ataaaattct caattcagag aaatcatctg   3480

atgtttctat agtcactttg ccagctcaaa agaaaacaat accctatgta gttgtggaag   3540

tttatgctaa tattgtgtaa ctgatattaa acctaaatgt tctgcctacc ctgttggtat   3600

aaagatattt tgagcagact gtaaacaaga aaaaaaaaat catgcattct tagcaaaatt   3660

gcctagtatg ttaatttgct caaaatacaa tgtttgattt tatgcacttt gtcgctatta   3720

acatcctttt tttcatgtag atttcaataa ttgagtaatt ttagaagcat tattttagga   3780

atatatagtt gtcacagtaa atatcttgtt ttttctatgt acattgtaca aatttttcat   3840

tccttttgct ctttgtggtt ggatctaaca ctaactgtat tgttttgtta catcaaataa   3900

acatcttctg tggaaaaaaa aaaaaaaaaa aaa                                 3933
```

<210> SEQ ID NO 310
<211> LENGTH: 2872
<212> TYPE: DNA
<213> ORGANISM: Homo sapiens

<400> SEQUENCE: 310

```
tccaggaatc gatagtgcat tcgtgcgcgc ggccgcccgt cgcttcgcac agggctggat     60

ggttgtattg ggcagggtgg ctccaggatg ttaggaactg tgaagatgga agggcatgaa    120

accagcgact ggaacagcta ctacgcagac acgcaggagg cctactcctc ggtcccggtc    180

agcaacatga actcaggcct gggctccatg aactccatga acacctacat gaccatgaac    240

accatgacta cgagcggcaa catgaccccg gcgtccttca acatgtccta tgccaacccg    300

gccttagggg ccggcctgag tcccggcgca gtagccggca tgccgggggg ctcggcgggc    360

gccatgaaca gcatgactgc ggccggcgtg acggccatgg gtacggcgct gagcccgagc    420

ggcatgggcg ccatgggtgc gcagcaggcg gcctccatga tgaatggcct gggcccctac    480

gcggccgcca tgaacccgtg catgagcccc atggcgtacg cgccgtccaa cctgggccgc    540

agccgcgcgg gcggcggcgg cgacgccaag acgttcaagc gcagttaccc gcacgccaag    600

ccgccctact cgtacatctc gctcatcacc atggccatcc agcgggcgcc cagcaagatg    660
```

-continued

```
ctcacgctga gcgagatcta ccagtggatc atggacctct tcccctatta ccggcagaac     720
cagcagcgct ggcagaactc catccgccac tcgctgtcct tcaatgactg cttcgtcaag     780
gtggcacgct ccccggacaa gccgggcaag ggctcctact ggacgctgca cccggactcc     840
ggcaacatgt tcgagaacgg ctgctacttg cgccgccaga agcgcttcaa gtgcgagaag     900
cagccggggg ccggcggcgg gggcgggagc ggaagcgggg gcagcggcgc caagggcggc     960
cctgagagcc gcaaggaccc ctctggcgcc tctaacccca gcgccgactc gcccctccat    1020
cggggtgtgc acgggaagac cggccagcta gagggcgcgc cggcccccggg cccggccgcc   1080
agcccccaga ctctggacca cagtggggcg acggcgacag gggggcgcctc ggagttgaag   1140
actccagcct cctcaactgc gccccccata agctccgggc ccggggcgct ggcctctgtg    1200
cccgcctctc acccggcaca cggcttggca ccccacgagt cccagctgca cctgaaaggg    1260
gacccccact actccttcaa ccacccgttc tccatcaaca acctcatgtc ctcctcggag    1320
cagcagcata agctggactt caaggcatac gaacaggcac tgcaatactc gccttacggc    1380
tctacgttgc ccgccagcct gcctctaggc agcgcctcgg tgaccaccag gagccccatc    1440
gagccctcag ccctggagcc ggcgtactac caaggtgtgt attccagacc cgtcctaaac    1500
acttcctagc tcccgggact gggggggtttg tctggcatag ccatgctggt agcaagagag   1560
aaaaaatcaa cagcaaacaa aaccacacaa accaaaccgt caacagcata ataaaatcca    1620
acaactattt ttatttcatt tttcatgcac aaccttgccc ccagtgcaaa agactgttac    1680
tttattattg tattcaaaat tcattgtgta tattactaca aagacggccc caaaccaatt    1740
tttttcctgc gaagtttaat gatccacaag tgtatatatg aaattctcct ccttccttgc    1800
ccccctctct ttcttccctc ttggccctcc agacattcta gtttgtggag ggttatttaa    1860
aaaacaaaaa ggaagatggt caagtttgta aaatatttgt ttgtgctttt ccccccctcct   1920
tacctgaccc cctacgagtt tacaggcttg tggcaatact cttaaccata agaattgaaa    1980
tggtgaagaa acaagtatac actagaggct cttaaaagta ttgaaaagac aatactgctg    2040
ttatatagca agacataaac agattataaa catcagagcc atttgcttct cagtttacat    2100
ttctgataca tgcagatagc agatgtcttt aaatgaaata catgtatatt gtgtatggac    2160
ttaattatgc acatgctcag atgtgtagac atcctccgta tatttacata acatatagag    2220
gtaatagata ggtgatatac gtgatacgtt ctcaagagtt gcttgaccga aagttacaag    2280
gaccccaacc cctttgctct ctacccacag atggccctgg gaacaatcct caggaattgc    2340
cctcaagaac tcgcttcttt gctttgagag tgccatggtc atgtcattct gaggtacata    2400
acacataaat tagtttctat gagtgtatac catttaaaga ttttttcagt aaagggaata    2460
ttacatgttg ggaggaggag ataagttata gggagctgga tttcaaacgg tggtccaaga    2520
ttcaaaaatc ctattgatag tggccatttt aatcattgcc atcgtgtgct tgtttcatcc    2580
agtgttatgc actttccaca gttggtgtta gtatagccag agggtttcat tattatttct    2640
ctttgctttc tcaatgttaa tttattgcat ggtttattct ttttctttac agctgaaatt    2700
gctttaaatg atggttaaaa ttacaaatta aattgggaat ttttatcaat gtgattgtaa    2760
ttaaaaatat tttgatttaa ataacaaaaa taataccaga ttttaagccg cggaaaatgt    2820
tcttgatcat ttgcagttaa ggactttaaa taaatcaaat gttaacaaaa aa            2872
```

<210> SEQ ID NO 311
<211> LENGTH: 926
<212> TYPE: DNA

-continued

<213> ORGANISM: Homo sapiens

<400> SEQUENCE: 311

```
ggggcccatt ctgtttcagc cagtcgccaa gaatcatgaa agtcgccagt ggcagcaccg     60
ccaccgccgc cgcgggcccc agctgcgcgc tgaaggccgg caagacagcg agcggtgcgg    120
gcgaggtggt gcgctgtctg tctgagcaga gcgtggccat ctcgcgctgc cggggcgccg    180
gggcgcgcct gcctgccctg ctggacgagc agcaggtaaa cgtgctgctc tacgacatga    240
acggctgtta ctcacgcctc aaggagctgg tgcccaccct gccccagaac cgcaaggtga    300
gcaaggtgga gattctccag cacgtcatcg actacatcag ggaccttcag ttggagctga    360
actcggaatc cgaagttggg acccccgggg gccgagggct gccggtccgg gctccgctca    420
gcaccctcaa cggcgagatc agcgccctga cggccgaggc ggcatgcgtt cctgcggacg    480
atcgcatctt gtgtcgctga agcgcctccc ccagggaccg gcggaccccca gccatccagg    540
gggcaagagg aattacgtgc tctgtgggtc tcccccaacg cgcctcgccg gatctgaggg    600
agaacaagac cgatcggcgg ccactgcgcc cttaactgca tccagcctgg ggctgaggct    660
gaggcactgg cgaggagagg gcgctcctct ctgcacacct actagtcacc agagacttta    720
gggggtggga ttccactcgt gtgtttctat tttttgaaaa gcagacattt taaaaaatgg    780
tcacgtttgg tgcttctcag atttctgagg aaattgcttt gtattgtata ttacaatgat    840
caccgactga gaatattgtt ttacaatagt tctgtggggc tgttttttttg ttattaaaca    900
aataatttag atggtgaaaa aaaaaa                                         926
```

<210> SEQ ID NO 312
<211> LENGTH: 4989
<212> TYPE: DNA
<213> ORGANISM: Homo sapiens

<400> SEQUENCE: 312

```
tttttttttt ttttgagaaa gggaatttca tcccaaataa aaggaatgaa gtctggctcc     60
ggaggagggt ccccgacctc gctgtggggg ctcctgtttc tctccgccgc gctctcgctc    120
tggccgacga gtggagaaat ctgcgggcca ggcatcgaca tccgcaacga ctatcagcag    180
ctgaagcgcc tggagaactg cacggtgatc gagggctacc tccacatcct gctcatctcc    240
aaggccgagg actaccgcag ctaccgcttc cccaagctca cggtcattac cgagtacttg    300
ctgctgttcc gagtggctgg cctcgagagc ctcggagacc tcttccccaa cctcacggtc    360
atccgcggct ggaaactctt ctacaactac gccctggtca tcttcgagat gaccaatctc    420
aaggatattg ggctttacaa cctgaggaac attactcggg gggccatcag gattgagaaa    480
aatgctgacc tctgttacct ctccactgtg gactggtccc tgatcctgga tgcggtgtcc    540
aataactaca ttgtggggaa taagcccccca aaggaatgtg gggacctgtg tccagggacc    600
atggaggaga agccgatgtg tgagaagacc accatcaaca atgagtacaa ctaccgctgc    660
tggaccacaa accgctgcca gaaaatgtgc ccaagcacgt gtgggaagcg ggcgtgcacc    720
gagaacaatg agtgctgcca ccccgagtgc ctgggcagct gcagcgcgcc tgacaacgac    780
acggcctgtg tagcttgccg ccactactac tatgccggtg tctgtgtgcc tgcctgcccg    840
cccaacacct acaggtttga gggctggcgc tgtgtggacc gtgacttctg cgccaacatc    900
ctcagcgccg agagcagcga ctccgagggg tttgtgatcc acgacggcga gtgcatgcag    960
gagtgcccct cgggcttcat ccgcaacggc agccagagca tgtactgcat cccttgtgaa   1020
ggtccttgcc cgaaggtctg tgaggaagaa aagaaaacaa agaccattga ttctgttact   1080
```

-continued

```
tctgctcaga tgctccaagg atgcaccatc ttcaagggca atttgctcat taacatccga   1140
cgggggaata acattgcttc agagctggag aacttcatgg ggctcatcga ggtggtgacg   1200
ggctacgtga agatccgcca ttctcatgcc ttggtctcct tgtccttcct aaaaaacctt   1260
cgcctcatcc taggagagga gcagctagaa gggaattact ccttctacgt cctcgacaac   1320
cagaacttgc agcaactgtg ggactgggac caccgcaacc tgaccatcaa agcagggaaa   1380
atgtactttg ctttcaatcc caaattatgt gtttccgaaa tttaccgcat ggaggaagtg   1440
acggggacta aagggcgcca aagcaaaggg gacataaaca ccaggaacaa cggggagaga   1500
gcctcctgtg aaagtgacgt cctgcatttc acctccacca ccacgtcgaa gaatcgcatc   1560
atcataacct ggcaccggta ccggcccct gactacaggg atctcatcag cttcaccgtt   1620
tactacaagg aagcaccctt taagaatgtc acagagtatg atgggcagga tgcctgcggc   1680
tccaacagct ggaacatggt ggacgtggac ctcccgccca acaaggacgt ggagcccggc   1740
atcttactac atgggctgaa gccctggact cagtacgccg tttacgtcaa ggctgtgacc   1800
ctcaccatgg tggagaacga ccatatccgt ggggccaaga gtgagatctt gtacattcgc   1860
accaatgctt cagttccttc cattcccttg gacgttcttt cagcatcgaa ctcctcttct   1920
cagttaatcg tgaagtggaa ccctccctct ctgcccaacg gcaacctgag ttactacatt   1980
gtgcgctggc agcggcagcc tcaggacggc tacctttacc ggcacaatta ctgctccaaa   2040
gacaaaatcc ccatcaggaa gtatgccgac ggcaccatcg acattgagga ggtcacagag   2100
aaccccaaga ctgaggtgtg tggtggggag aaagggcctt gctgcgcctg ccccaaaact   2160
gaagccgaga agcaggccga gaaggaggag gctgaatacc gcaaagtctt tgagaatttc   2220
ctgcacaact ccatcttcgt gcccagacct gaaaggaagc ggagagatgt catgcaagtg   2280
gccaacacca ccatgtccag ccgaagcagg aacaccacgg ccgcagacac ctacaacatc   2340
accgacccgg aagagctgga gacagagtac cctttctttg agagcagagt ggataacaag   2400
gagagaactg tcatttctaa ccttcggcct ttcacattgt accgcatcga tatccacagc   2460
tgcaaccacg aggctgagaa gctgggctgc agcgcctcca acttcgtctt tgcaaggact   2520
atgcccgcag aaggagcaga tgacattcct gggccagtga cctgggagcc aaggcctgaa   2580
aactccatct ttttaaagtg gccggaacct gagaatccca atggattgat tctaatgtat   2640
gaaataaaat acggatcaca agttgaggat cagcgagaat gtgtgtccag acaggaatac   2700
aggaagtatg gaggggccaa gctaaaccgg ctaaacccgg ggaactacac agcccggatt   2760
caggccacat ctctctctgg gaatgggtcg tggacagatc ctgtgttctt ctatgtccag   2820
gccaaaacag gatatgaaaa cttcatccat ctgatcatcg ctctgcccgt cgctgtcctg   2880
ttgatcgtgg gagggttggt gattatgctg tacgtcttcc atagaaagag aaataacagc   2940
aggctgggga atggagtgct gtatgcctct gtgaacccgg agtacttcag cgctgctgat   3000
gtgtacgttc ctgatgagtg ggaggtggct cgggagaaga tcaccatgag ccgggaactt   3060
gggcaggggt cgtttgggat ggtctatgaa ggagttgcca agggtgtggt gaaagatgaa   3120
cctgaaacca gagtggccat taaaacagtg aacgaggccg caagcatgcg tgagaggatt   3180
gagtttctca acgaagcttc tgtgatgaag gagttcaatt gtcaccatgt ggtgcgattg   3240
ctgggtgtgg tgtcccaagg ccagccaaca ctggtcatca tggaactgat gacacggggc   3300
gatctcaaaa gttatctccg gtctctgagg ccagaaatgg agaataatcc agtcctagca   3360
cctccaagcc tgagcaagat gattcagatg gccggagaga ttgcagacgg catggcatac   3420
```

-continued

```
ctcaacgcca ataagttcgt ccacagagac cttgctgccc ggaattgcat ggtagccgaa   3480
gatttcacag tcaaaatcgg agattttggt atgacgcgag atatctatga gacagactat   3540
taccggaaag gaggcaaagg gctgctgccc gtgcgctgga tgtctcctga gtccctcaag   3600
gatggagtct tcaccactta ctcggacgtc tggtccttcg ggtcgtcct ctgggagatc    3660
gccacactgg ccgagcagcc ctaccagggc ttgtccaacg agcaagtcct tcgcttcgtc   3720
atggagggcg gccttctgga caagccagac aactgtcctg acatgctgtt tgaactgatg   3780
cgcatgtgct ggcagtataa ccccaagatg aggccttcct tcctggagat catcagcagc   3840
atcaaagagg agatggagcc tggcttccgg gaggtctcct tctactacag cgaggagaac   3900
aagctgcccg agccggagga gctggacctg gagccagaga acatggagag cgtccccctg   3960
gacccctcgg cctcctcgtc ctccctgcca ctgcccgaca gacactcagg acacaaggcc   4020
gagaacggcc ccggccctgg ggtgctggtc ctccgcgcca gcttcgacga gagacagcct   4080
tacgcccaca tgaacggggg ccgcaagaac gagcgggcct tgccgctgcc ccagtcttcg   4140
acctgctgat ccttggatcc tgaatctgtg caaacagtaa cgtgtgcgca cgcgcagcgg   4200
ggtggggggg gagagagagt tttaacaatc cattcacaag cctcctgtac ctcagtggat   4260
cttcagttct gcccttgctg cccgcgggag acagcttctc tgcagtaaaa cacatttggg   4320
atgttccttt tttcaatatg caagcagctt tttattccct gcccaaaccc ttaactgaca   4380
tgggccttta agaaccttaa tgacaacact taatagcaac agagcacttg agaaccagtc   4440
tcctcactct gtccctgtcc ttccctgttc tccctttctc tctcctctct gcttcataac   4500
ggaaaaataa ttgccacaag tccagctggg aagccctttt tatcagtttg aggaagtggc   4560
tgtccctgtg gccccatcca accactgtac acacccgcct gacaccgtgg gtcattacaa   4620
aaaaacacgt ggagatggaa atttttacct ttatctttca cctttctagg gacatgaaat   4680
ttacaaaggg ccatcgttca tccaaggctg ttaccatttt aacgctgcct aattttgcca   4740
aaatcctgaa ctttctccct catcggcccg gcgctgattc ctcgtgtccg gaggcatggg   4800
tgagcatggc agctggttgc tccatttgag agacacgctg gcgacacact ccgtccatcc   4860
gactgcccct gctgtgctgc tcaaggccac aggcacacag gtctcattgc ttctgactag   4920
attattattt gggggaactg gacacaatag gtctttctct cagtgaaggt ggggagaagc   4980
tgaaccggc                                                           4989
```

<210> SEQ ID NO 313
<211> LENGTH: 12515
<212> TYPE: DNA
<213> ORGANISM: Homo sapiens

<400> SEQUENCE: 313

```
ctaccgggcg gaggtgagcg cggcgccggc tcctcctgcg gcggactttg ggtgcgactt     60
gacgagcggt ggttcgacaa gtggccttgc gggccggatc gtcccagtgg aagagttgta    120
aatttgcttc tggccttccc ctacggatta tacctggcct tcccctacgg attatactca    180
acttactgtt tagaaaatgt ggcccacgag acgcctggtt actatcaaaa ggagcggggt    240
cgacggtccc cactttcccc tgagcctcag cacctgcttg tttggaaggg gtattgaatg    300
tgacatccgt atccagcttc ctgttgtgtc aaaacaacat tgcaaaattg aaatccatga    360
gcaggaggca atattacata atttcagttc cacaaatcca acacaagtaa atgggtctgt    420
tattgatgag cctgtacggc taaaacatgg agatgtaata actattattg atcgttcctt    480
caggtatgaa aatgaaagtc ttcagaatgg aaggaagtca actgaatttc caagaaaaat    540
```

-continued

```
acgtgaacag gagccagcac gtcgtgtctc aagatctagc ttctcttctg accctgatga    600
gaaagctcaa gattccaagg cctattcaaa aatcactgaa ggaaaagttt caggaaatcc    660
tcaggtacat atcaagaatg tcaaagaaga cagtaccgca gatgactcaa aagacagtgt    720
tgctcaggga acaactaatg ttcattcctc agaacatgct ggacgtaatg gcagaaatgc    780
agctgatccc atttctgggg attttaaaga aatttccagc gttaaattag tgagccgtta    840
tggagaattg aagtctgttc ccactacaca atgtcttgac aatagcaaaa aaaatgaatc    900
tccctttttgg aagctttatg agtcagtgaa gaaagagttg gatgtaaaat cacaaaaaga    960
aaatgtccta cagtattgta gaaaatctgg attacaaact gattacgcaa cagagaaaga   1020
aagtgctgat ggtttacagg gggagaccca actgttggtc tcgcgtaagt caagaccaaa   1080
atctggtggg agcggccacg ctgtggcaga gcctgcttca cctgaacaag agcttgacca   1140
gaacaagggg aagggaagag acgtggagtc tgttcagact cccagcaagg ctgtgggcgc   1200
cagctttcct ctctatgagc cggctaaaat gaagacccct gtacaatatt cacagcaaca   1260
aaattctcca caaaaacata agaacaaaga cctgtatact actggtagaa gagaatctgt   1320
gaatctgggt aaaagtgaag gcttcaaggc tggtgataaa actcttactc ccaggaagct   1380
ttcaactaga aatcgaacac cagctaaagt tgaagatgca gctgactctg ccactaagcc   1440
agaaaatctc tcttccaaaa ccagaggaag tattcctaca gatgtggaag ttctgcctac   1500
ggaaactgaa attcacaatg agccattttt aactctgtgg ctcactcaag ttgagaggaa   1560
gatccaaaag gattccctca gcaagcctga gaaattgggc actacagctg gacagatgtg   1620
ctctgggtta cctggtctta gttcagttga tatcaacaac tttggtgatt ccattaatga   1680
gagtgaggga atacctttga aaagaaggcg tgtgtccttt ggtgggcacc taagacctga   1740
actatttgat gaaaacttgc ctcctaatac gcctctcaaa aggggagaag ccccaaccaa   1800
aagaaagtct ctggtaatgc acactccacc tgtcctgaag aaaatcatca aggaacagcc   1860
tcaaccatca ggaaaacaag agtcaggttc agaaatccat gtggaagtga aggcacaaag   1920
cttggttata agccctccag ctcctagtcc taggaaaact ccagttgcca gtgatcaacg   1980
ccgtaggtcc tgcaaaacag cccctgcttc cagcagcaaa tctcagacag aggttcctaa   2040
gagaggagga gaaagagtgg caacctgcct tcaaaagaga gtgtctatca gccgaagtca   2100
acatgatatt ttacagatga tatgttccaa aagaagaagt ggtgcttcgg aagcaaatct   2160
gattgttgca aaatcatggg cagatgtagt aaaacttggt gcaaaacaaa cacaaactaa   2220
agtcataaaa catggtcctc aaaggtcaat gaacaaaagg caaagaagac ctgctactcc   2280
aaagaagcct gtgggcgaag ttcacagtca atttagtaca ggccacgcaa actctccttg   2340
taccataata atagggaaag ctcatactga aaaagtacat gtgcctgctc gaccctacag   2400
agtgctcaac aacttcattt ccaaccaaaa aatggacttt aaggaagatc tttcaggaat   2460
agctgaaatg ttcaagaccc cagtgaagga gcaaccgcag ttgacaagca catgtcacat   2520
cgctatttca aattcagaga atttgcttgg aaaacagttt caaggaactg attcaggaga   2580
agaacctctg ctccccacct cagagagttt tggaggaaat gtgttcttca gtgcacagaa   2640
tgcagcaaaa cagccatctg ataaatgctc tgcaagccct cccttaagac ggcagtgtat   2700
tagagaaaat ggaaacgtag caaaaacgcc caggaacacc tacaaaatga cttctctgga   2760
gacaaaaact tcagatactg agacagagcc ttcaaaaaca gtatccactg taaacaggtc   2820
aggaaggtct acagagttca ggaatataca gaagctacct gtggaaagta agagtgaaga   2880
```

-continued

```
aacaaataca gaaattgttg agtgcatcct aaaaagaggt cagaaggcaa cactactaca   2940
acaaaggaga gaaggagaga tgaaggaaat agaaagacct tttgagacat ataaggaaaa   3000
tattgaatta aaagaaaacg atgaaaagat gaaagcaatg aagagatcaa gaacttgggg   3060
gcagaaatgt gcaccaatgt ctgacctgac agacctcaag agcttgcctg atacagaact   3120
catgaaagac acggcacgtg gccagaatct cctccaaacc caagatcatg ccaaggcacc   3180
aaagagtgag aaaggcaaaa tcactaaaat gccctgccag tcattacaac cagaaccaat   3240
aaacacccca acacacacaa aacaacagtt gaaggcatcc ctggggaaag taggtgtgaa   3300
agaagagctc ctagcagtcg gcaagttcac acggacgtca ggggagacca cgcacacgca   3360
cagagagcca gcaggagatg gcaagagcat cagaacgttt aaggagtctc caaagcagat   3420
cctggaccca gcagcccgtg taactggaat gaagaagtgg ccaagaacgc ctaaggaaga   3480
ggcccagtca ctagaagacc tggctggctt caaagagctc ttccagacac caggtccctc   3540
tgaggaatca atgactgatg agaaaactac caaaatagcc tgcaaatctc caccaccaga   3600
atcagtggac actccaacaa gcacaaagca atggcctaag agaagtctca ggaaagcaga   3660
tgtagaggaa gaattcttag cactcaggaa actaacacca tcagcaggga aagccatgct   3720
tacgcccaaa ccagcaggag gtgatgagaa agacattaaa gcatttatgg gaactccagt   3780
gcagaaactg gacctggcag gaactttacc tggcagcaaa agacagctac agactcctaa   3840
ggaaaaggcc caggctctag aagacctggc tggctttaaa gagctcttcc agactcctgg   3900
tcacaccgag gaattagtgg ctgctggtaa aaccactaaa ataccctgcg actctccaca   3960
gtcagaccca gtggacaccc caacaagcac aaagcaacga cccaagagaa gtatcaggaa   4020
agcagatgta gagggagaac tcttagcgtg caggaatcta atgccatcag caggcaaagc   4080
catgcacacg cctaaaccat cagtaggtga agagaaagac atcatcatat ttgtgggaac   4140
tccagtgcag aaactggacc tgacagagaa cttaaccggc agcaagagac ggccacaaac   4200
tcctaaggaa gaggcccagg ctctggaaga cctgactggc tttaaagagc tcttccagac   4260
ccctggtcat actgaagaag cagtggctgc tggcaaaact actaaaatgc cctgcgaatc   4320
ttctccacca gaatcagcag acaccccaac aagcacaaga aggcagccca agacaccttt   4380
ggagaaaagg gacgtacaga aggagctctc agccctgaag aagctcacac agacatcagg   4440
ggaaaccaca cacacagata aagtaccagg aggtgaggat aaaagcatca acgcgtttag   4500
ggaaactgca aaacagaaac tggacccagc agcaagtgta actggtagca agaggcaccc   4560
aaaaactaag gaaaaggccc aacccctaga agacctggct ggctggaaag agctcttcca   4620
gacaccagta tgcactgaca agcccacgac tcacgagaaa actaccaaaa tagcctgcag   4680
atcacaacca gacccagtgg acacaccaac aagctccaag ccacagtcca agagaagtct   4740
caggaaagtg gacgtagaag aagaattctt cgcactcagg aaacgaacac catcagcagg   4800
caaagccatg cacacaccca aaccagcagt aagtggtgag aaaaacatct acgcatttat   4860
gggaactcca gtgcagaaac tggacctgac agagaactta actggcagca agagacggct   4920
acaaactcct aaggaaaagg cccaggctct agaagacctg gctggcttta aagagctctt   4980
ccagacacga ggtcacactg aggaatcaat gactaacgat aaaactgcca aagtagcctg   5040
caaatcttca caaccagacc tagacaaaaa cccagcaagc tccaagcgac ggctcaagac   5100
atccctgggg aaagtgggcg tgaaagaaga gctcctagca gttggcaagc tcacacagac   5160
atcaggagag actacacaca cacacacaga gccaacagga gatggtaaga gcatgaaagc   5220
atttatggag tctccaaagc agatcttaga ctcagcagca agtctaactg gcagcaagag   5280
```

-continued

```
gcagctgaga actcctaagg gaaagtctga agtccctgaa gacctggccg gcttcatcga   5340
gctcttccag acaccaagtc acactaagga atcaatgact aatgaaaaaa ctaccaaagt   5400
atcctacaga gcttcacagc cagacctagt ggacacccca acaagctcca agccacagcc   5460
caagagaagt ctcaggaaag cagacactga agaagaattt ttagcattta ggaaacaaac   5520
gccatcagca ggcaaagcca tgcacacacc caaaccagca gtaggtgaag agaaagacat   5580
caacacgttt ttgggaactc cagtgcagaa actggaccag ccaggaaatt tacctggcag   5640
caatagacgg ctacaaactc gtaaggaaaa ggcccaggct ctagaagaac tgactggctt   5700
cagagagctt ttccagacac catgcactga taaccccaca gctgatgaga aaactaccaa   5760
aaaaatactc tgcaaatctc cgcaatcaga cccagcggac accccaacaa acacaaagca   5820
acggcccaag agaagcctca agaaagcaga cgtagaggaa gaatttttag cattcaggaa   5880
actaacacca tcagcaggca aagccatgca cacgcctaaa gcagcagtag gtgaagagaa   5940
agacatcaac acatttgtgg ggactccagt ggagaaactg gacctgctag gaaatttacc   6000
tggcagcaag agacggccac aaactcctaa agaaaaggcc aaggctctag aagatctggc   6060
tggcttcaaa gagctcttcc agacaccagg tcacactgag gaatcaatga ccgatgacaa   6120
aatcacagaa gtatcctgca aatctccaca accagaccca gtcaaaaccc caacaagctc   6180
caagcaacga ctcaagatat ccttggggaa agtaggtgtg aaagaagagg tcctaccagt   6240
cggcaagctc acacagacgt cagggaagac cacacagaca cacagagaga cagcaggaga   6300
tggaaagagc atcaaagcgt ttaaggaatc tgcaaagcag atgctggacc cagcaaacta   6360
tggaactggg atggagaggt ggccaagaac acctaaggaa gaggcccaat cactagaaga   6420
cctggccggc ttcaaagagc tcttccagac accagaccac actgaggaat caacaactga   6480
tgacaaaact accaaaatag cctgcaaatc tccaccacca gaatcaatgg acactccaac   6540
aagcacaagg aggcggccca aaacaccttt ggggaaaagg gatatagtgg aagagctctc   6600
agccctgaag cagctcacac agaccacaca cacagacaaa gtaccaggag atgaggataa   6660
aggcatcaac gtgttcaggg aaactgcaaa acagaaactg gacccagcag caagtgtaac   6720
tggtagcaag aggcagccaa gaactcctaa gggaaaagcc caacccctag aagacttggc   6780
tggcttgaaa gagctcttcc agacaccagt atgcactgac aagcccacga ctcacgagaa   6840
aactaccaaa atagcctgca gatctccaca accagaccca gtgggtaccc caacaatctt   6900
caagccacag tccaagagaa gtctcaggaa agcagacgta gaggaagaat ccttagcact   6960
caggaaacga acaccatcag tagggaaagc tatggacaca cccaaaccag caggaggtga   7020
tgagaaagac atgaaagcat ttatgggaac tccagtgcag aaattggacc tgccaggaaa   7080
tttacctggc agcaaaagat ggccacaaac tcctaaggaa aaggcccagg ctctagaaga   7140
cctggctggc ttcaaagagc tcttccagac accaggcact gacaagccca cgactgatga   7200
gaaaactacc aaaatagcct gcaaatctcc acaaccagac ccagtggaca ccccagcaag   7260
cacaaagcaa cggcccaaga gaaacctcag gaaagcagac gtagaggaag aatttttagc   7320
actcaggaaa cgaacaccat cagcaggcaa agccatggac accccaaaac cagcagtaag   7380
tgatgagaaa aatatcaaca catttgtgga aactccagtg cagaaactgg acctgctagg   7440
aaatttacct ggcagcaaga gacagccaca gactcctaag gaaaaggctg aggctctaga   7500
ggacctggtt ggcttcaaag aactcttcca gacaccaggt cacactgagg aatcaatgac   7560
tgatgacaaa atcacagaag tatcctgtaa atctccacag ccagagtcat tcaaaacctc   7620
```

-continued

```
aagaagctcc aagcaaaggc tcaagatacc cctggtgaaa gtggacatga aagaagagcc   7680
cctagcagtc agcaagctca cacggacatc aggggagact acgcaaacac acacagagcc   7740
aacaggagat agtaagagca tcaaagcgtt taaggagtct ccaaagcaga tcctggaccc   7800
agcagcaagt gtaactggta gcaggaggca gctgagaact cgtaaggaaa aggcccgtgc   7860
tctagaagac ctggttgact tcaaagagct cttctcagca ccaggtcaca ctgaagagtc   7920
aatgactatt gacaaaaaca caaaaattcc ctgcaaatct cccccaccag aactaacaga   7980
cactgccacg agcacaaaga gatgccccaa gacacgtccc aggaaagaag taaaagagga   8040
gctctcagca gttgagaggc tcacgcaaac atcagggcaa agcacacaca cacacaaaga   8100
accagcaagc ggtgatgagg gcatcaaagt attgaagcaa cgtgcaaaga agaaaccaaa   8160
cccagtagaa gaggaaccca gcaggagaag gccaagagca cctaaggaaa aggcccaacc   8220
cctggaagac ctggccggct tcacagagct ctctgaaaca tcaggtcaca ctcaggaatc   8280
actgactgct ggcaaagcca ctaaaatacc ctgcgaatct cccccactag aagtggtaga   8340
caccacagca agcacaaaga ggcatctcag gacacgtgtg cagaaggtac aagtaaaaga   8400
agagccttca gcagtcaagt tcacacaaac atcaggggaa accacggatg cagacaaaga   8460
accagcaggt gaagataaag gcatcaaagc attgaaggaa tctgcaaaac agacaccggc   8520
tccagcagca agtgtaactg gcagcaggag acggccaaga gcacccaggg aaagtgccca   8580
agccatagaa gacctagctg gcttcaaaga cccagcagca ggtcacactg aagaatcaat   8640
gactgatgac aaaaccacta aaataccctg caaatcatca ccagaactag aagacaccgc   8700
aacaagctca aagagacggc ccaggacacg tgcccagaaa gtagaagtga aggaggagct   8760
gttagcagtt ggcaagctca cacaaacctc aggggagacc acgcacaccg acaaagagcc   8820
ggtaggtgag ggcaaaggca cgaaagcatt taagcaacct gcaaagcgga acgtggacgc   8880
agaagatgta attggcagca ggagacagcc aagagcacct aaggaaaagg cccaacccct   8940
ggaagacctg gccagcttcc aagagctctc tcaaacacca ggccacactg aggaactggc   9000
aaatggtgct gctgatagct ttacaagcgc tccaaagcaa acacctgaca gtggaaaacc   9060
tctaaaaata tccagaagag ttcttcgggc ccctaaagta gaacccgtgg gagacgtggt   9120
aagcaccaga gaccctgtaa aatcacaaag caaaagcaac acttccctgc ccccactgcc   9180
cttcaagagg ggaggtggca aagatggaag cgtcacggga accaagaggc tgcgctgcat   9240
gccagcacca gaggaaattg tggaggagct gccagccagc aagaagcaga gggttgctcc   9300
cagggcaaga ggcaaatcat ccgaacccgt ggtcatcatg aagagaagtt tgaggacttc   9360
tgcaaaaaga attgaacctg cggaagagct gaacagcaac gacatgaaaa ccaacaaaga   9420
ggaacacaaa ttacaagact cggtccctga aaataaggga atatccctgc gctccagacg   9480
ccaagataag actgaggcag aacagcaaat aactgaggtc tttgtattag cagaaagaat   9540
agaaataaac agaaatgaaa agaagcccat gaagacctcc ccagagatgg acattcagaa   9600
tccagatgat ggagcccgga aacccatacc tagagacaaa gtcactgaga acaaaaggtg   9660
cttgaggtct gctagacaga atgagagctc ccagcctaag gtggcagagg agagcggagg   9720
gcagaagagt gcgaaggttc tcatgcagaa tcagaaaggg aaaggagaag caggaaattc   9780
agactccatg tgcctgagat caagaaagac aaaaagccag cctgcagcaa gcactttgga   9840
gagcaaatct gtgcagagag taacgcggag tgtcaagagg tgtgcagaaa atccaaagaa   9900
ggctgaggac aatgtgtgtg tcaagaaaat aacaaccaga agtcataggg acagtgaaga   9960
tatttgacag aaaaatcgaa ctgggaaaaa tataataaag ttagttttgt gataagttct  10020
```

-continued

```
agtgcagttt ttgtcataaa ttacaagtga attctgtaag taaggctgtc agtctgctta  10080
agggaagaaa actttggatt tgctgggtct gaatcggctt cataaactcc actgggagca  10140
ctgctgggct cctggactga gaatagttga acaccggggg ctttgtgaag gagtctgggc  10200
caaggtttgc cctcagcttt gcagaatgaa gccttgaggt ctgtcaccac ccacagccac  10260
cctacagcag ccttaactgt gacacttgcc acactgtgtc gtcgtttgtt tgcctatgtt  10320
ctccagggca cggtggcagg aacaactatc ctcgtctgtc ccaacactga gcaggcactc  10380
ggtaaacacg aatgaatgga taagcgcacg gatgaatgga gcttacaaga tctgtctttc  10440
caatggccgg gggcatttgg tccccaaatt aaggctattg gacatctgca caggacagtc  10500
ctatttttga tgtcctttcc tttctgaaaa taaagttttg tgctttggag aatgactcgt  10560
gagcacatct ttagggacca agagtgactt tctgtaagga gtgactcgtg gcttgccttg  10620
gtctcttggg aatacttttc taactagggt tgctctcacc tgagacattc tccacccgcg  10680
gaatctcagg gtcccaggct gtgggccatc acgacctcaa actggctcct aatctccagc  10740
tttcctgtca ttgaaagctt cggaagttta ctggctctgc tcccgcctgt tttctttctg  10800
actctatctg gcagcccgat gccacccagt acaggaagtg acaccagtac tctgtaaagc  10860
atcatcatcc ttggagagac tgagcactca gcaccttcag ccacgatttc aggatcgctt  10920
ccttgtgagc cgctgcctcc gaaatctcct ttgaagccca gacatctttc tccagcttca  10980
gacttgtaga tataactcgt tcatcttcat ttactttcca ctttgccccc tgtcctctct  11040
gtgttcccca aatcagagaa tagcccgcca tcccccagat cacctgtctg gattcctccc  11100
cattcaccca ccttgccagg tgcaggtgag gatggtgcac cagacagggt agctgtcccc  11160
caaaatgtgc cctgtgcggg cagtgccctg tctccacgtt tgtttcccca gtgtctggcg  11220
gggagccagg tgacatcata aatacttgct gaatgaatgc agaaatcagc ggtactgact  11280
tgtactatat tggctgccat gatagggttc tcacagcgtc atccatgatc gtaagggaga  11340
atgacattct gcttgaggga gggaatagaa aggggcaggg aggggacatc tgagggcttc  11400
acagggctgc aaagggtaca gggattgcac cagggcagaa caggggaggg tgttcaagga  11460
agagtggctc ttagcagagg cactttggaa ggtgtgaggc ataaatgctt ccttctacgt  11520
aggccaacct caaaactttc agtaggaatg ttgctatgat caagttgttc taacacttta  11580
gacttagtag taattatgaa cctcacatag aaaaatttca tccagccata tgcctgtgga  11640
gtggaatatt ctgtttagta gaaaaatcct ttagagttca gctctaacca gaaatcttgc  11700
tgaagtatgt cagcaccttt tctcaccctg gtaagtacag tatttcaaga gcacgctaag  11760
ggtggttttc attttacagg gctgttgatg atgggttaaa aatgttcatt taagggctac  11820
ccccgtgttt aatagatgaa caccacttct acacaaccct ccttggtact gggggaggga  11880
gagatctgac aaatactgcc cattccccta ggctgactgg atttgagaac aaatacccac  11940
ccatttccac catggtatgg taacttctct gagcttcagt ttccaagtga atttccatgt  12000
aataggacat tcccattaaa tacaagctgt ttttactttt tcgcctccca gggcctgtgc  12060
gatctggtcc cccagcctct cttgggcttt cttacactaa ctctgtacct accatctcct  12120
gcctcccta ggcaggcacc tccaaccacc acacactccc tgctgttttc cctgcctgga  12180
actttcccac cagccccacc aagatcattt catccagtcc tgagctcagc ttaagggagg  12240
cttcttgcct gtgggttccc tcacccccat gcctgtcctc caggctgggg caggttctta  12300
gtttgcctgg aattgttctg tacctctttg tagcacgtag tgttgtgaaa ctaagccact  12360
```

-continued

```
aattgagttt ctggctcccc tcctggggtt gtaagttttg ttcattcatg agggccgact  12420

gtatttcctg gttactgtat cccagtgacc agccacagga gatgtccaat aaagtatgtg  12480

atgaaatggt cttaaaaaaa aaaaaaaaaa aaaaa                             12515


<210> SEQ ID NO 314
<211> LENGTH: 2444
<212> TYPE: DNA
<213> ORGANISM: Homo sapiens

<400> SEQUENCE: 314

ggcacgaggc ggggccgggt cgcagctggg cccgcggcat ggacgaactg ttccccctca     60

tcttcccggc agagcagccc aagcagcggg gcatgcgctt ccgctacaag tgcgaggggc    120

gctccgcggg cagcatccca ggcgagagga gcacagatac caccaagacc caccccacca    180

tcaagatcaa tggctacaca ggaccaggga cagtgcgcat ctccctggtc accaaggacc    240

ctcctcaccg gcctcacccc cacgagcttg taggaaagga ctgccgggat ggcttctatg    300

aggctgagct ctgcccggac cgctgcatcc acagtttcca gaacctggga atccagtgtg    360

tgaagaagcg ggacctggag caggctatca gtcagcgcat ccagaccaac aacaacccct    420

tccaagttcc tatagaagag cagcgtgggg actacgacct gaatgctgtg cggctctgct    480

tccaggtgac agtgcgggac ccatcaggca ggcccctccg cctgccgcct gtcctttctc    540

atcccatctt tgacaatcgt gcccccaaca ctgccgagct caagatctgc cgagtgaacc    600

gaaactctgg cagctgcctc ggtggggatg agatcttcct actgtgtgac aaggtgcaga    660

aagaggacat tgaggtgtat ttcacgggac caggctggga ggcccgaggc tccttttcgc    720

aagctgatgt gcaccgacaa gtggccattg tgttccggac ccctccctac gcagacccca    780

gcctgcaggc tcctgtgcgt gtctccatgc agctgcggcg gccttccgac cgggagctca    840

gtgagcccat ggaattccag tacctgccag atacagacga tcgtcaccgg attgaggaga    900

aacgtaaaag gacatatgag accttcaaga gcatcatgaa gaagagtcct ttcagcggac    960

ccaccgaccc ccggcctcca cctcgacgca ttgctgtgcc ttcccgcagc tcagcttctg   1020

tccccaagcc agcaccccag ccctatccct ttacgtcatc cctgagcacc atcaactatg   1080

atgagtttcc caccatggtg tttccttctg ggcagatcag ccaggcctcg gccttggccc   1140

cggcccctcc ccaagtcctg ccccaggctc cagcccctgc ccctgctcca gccatggtat   1200

cagctctggc ccaggcccca gcccctgtcc cagtcctagc cccaggccct cctcaggctg   1260

tggccccacc tgcccccaag cccacccagg ctggggaagg aacgctgtca gaggccctgc   1320

tgcagctgca gtttgatgat gaagacctgg gggccttgct tggcaacagc acagacccag   1380

ctgtgttcac agacctggca tccgtcgaca actccgagtt tcagcagctg ctgaaccagg   1440

gcatacctgt ggcccccac acaactgagc ccatgctgat ggagtaccct gaggctataa   1500

ctcgcctagt gacagcccag aggccccccg acccagctcc tgctccactg gggcccccgg   1560

ggctccccaa tggcctcctt tcaggagatg aagacttctc ctccattgcg gacatggact   1620

tctcagccct gctgagtcag atcagctcct aagggggtga cgcctgccct ccccagagca   1680

ctggttgcag gggattgaag ccctccaaaa gcacttacgg attctggtgg ggtgtgttcc   1740

aactgccccc aactttgtgg atgtcttcct tggagggggg agccatattt tattctttta   1800

ttgtcagtat ctgtatctct ctctcttttt ggaggtgctt aagcagaagc attaacttct   1860

ctggaaaggg gggagctggg gaaactcaaa cttttcccct gtcctgatgg tcagctccct   1920

tctctgtagg gaactgtggg gtcccccatc cccatcctcc agcttctggt actctcctag   1980
```

-continued

```
agacagaagc aggctggagg taaggccttt gagcccacaa agccttatca agtgtcttcc   2040
atcatggatt cattacagct taatcaaaat aacgccccag ataccagccc ctgtatggca   2100
ctggcattgt ccctgtgcct aacaccagcg tttgaggggc tgccttcctg ccctacagag   2160
gtctctgccg gctctttcct tgctcaacca tggctgaagg aaacagtgca acagcactgg   2220
ctctctccag gatccagaag ggtttggtc tggacttcct tgctctcccc tcttctcaag   2280
tgccttaata gtagggtaag ttgttaagag tgggggagag caggctggca gctctccagt   2340
caggaggcat agtttttagt gaacaatcaa agcacttgga ctcttgctct ttctactctg   2400
aactaataaa gctgttgcca agctggacgg cacgagctcg tgcc                     2444
```

<210> SEQ ID NO 315
<211> LENGTH: 732
<212> TYPE: DNA
<213> ORGANISM: Homo sapiens

<400> SEQUENCE: 315

```
tgctgcgaac cacgtgggtc ccgggcgcgt ttcgggtgct ggcggctgca gccggagttc     60
aaacctaagc agctggaagg aaccatggcc aactgtgagc gtaccttcat tgcgatcaaa    120
ccagatgggg tccagcgggg tcttgtggga gagattatca agcgttttga gcagaaagga    180
ttccgccttg ttggtctgaa attcatgcaa gcttccgaag atcttctcaa ggaacactac    240
gttgacctga aggaccgtcc attctttgcc ggcctggtga aatacatgca ctcagggccg    300
gtagttgcca tggtctggga ggggctgaat gtggtgaaga cgggccgagt catgctcggg    360
gagaccaacc ctgcagactc caagcctggg accatccgtg gagacttctg catacaagtt    420
ggcaggaaca ttatacatgg cagtgattct gtggagagtg cagagaagga gatcggcttg    480
tggtttcacc ctgaggaact ggtagattac acgagctgtg ctcagaactg gatctatgaa    540
tgacaggagg gcagaccaca ttgcttttca catccatttc ccctccttcc catgggcaga    600
ggaccaggct gtaggaaatc tagttattta caggaacttc atcataattt ggagggaagc    660
tcttggagct gtgagttctc cctgtacagt gttaccatcc ccgaccatct gattaaaatg    720
cttcctccca gc                                                        732
```

<210> SEQ ID NO 316
<211> LENGTH: 2422
<212> TYPE: DNA
<213> ORGANISM: Homo sapiens

<400> SEQUENCE: 316

```
gtcagcctcc cttccaccgc catattgggc cactaaaaaa agggggctcg tcttttcggg     60
gtgtttttct ccccctcccc tgtccccgct tgctcacggc tctgcgactc cgacgccggc    120
aaggtttgga gagcggctgg gttcgcggga cccgcgggct tgcacccgcc cagactcgga    180
cgggctttgc caccctctcc gcttgcctgg tcccctctcc tctccgccct cccgctcgcc    240
agtccatttg atcagcggag actcggcggc cgggccgggg cttccccgca gcccctgcgc    300
gctcctagag ctcgggccgt ggctcgtcgg ggtctgtgtc ttttggctcc gagggcagtc    360
gctgggcttc cgagaggggt tcgggccgcg taggggcgct ttgttttgtt cggttttgtt    420
tttttgagag tgcgagagag gcggtcgtgc agacccggga gaaagatgtc aaacgtgcga    480
gtgtctaacg ggagccctag cctggagcgg atggacgcca ggcaggcgga gcaccccaag    540
ccctcggcct gcaggaacct cttcggcccg gtggaccacg aagagttaac ccgggacttg    600
```

-continued

```
gagaagcact gcagagacat ggaagaggcg agccagcgca agtggaattt cgattttcag    660

aatcacaaac ccctagaggg caagtacgag tggcaagagg tggagaaggg cagcttgccc    720

gagttctact acagaccccc gcggcccccc aaaggtgcct gcaaggtgcc ggcgcaggag    780

agccaggatg tcagcgggag ccgcccggcg gcgcctttaa ttggggctcc ggctaactct    840

gaggacacgc atttggtgga cccaaagact gatccgtcgg acagccagac ggggttagcg    900

gagcaatgcg caggaataag gaagcgacct gcaaccgacg attcttctac tcaaaacaaa    960

agagccaaca gaacagaaga aaatgtttca gacggttccc caaatgccgg ttctgtggag   1020

cagacgccca agaagcctgg cctcagaaga cgtcaaacgt aaacagctcg aattaagaat   1080

atgtttcctt gtttatcaga tacatcactg cttgatgaag caaggaagat atacatgaaa   1140

attttaaaaa tacatatcgc tgacttcatg gaatggacat cctgtataag cactgaaaaa   1200

caacaacaca ataacactaa aattttaggc actcttaaat gatctgcctc taaaagcgtt   1260

ggatgtagca ttatgcaatt aggtttttcc ttatttgctt cattgtacta cctgtgtata   1320

tagtttttac cttttatgta gcacataaac tttggggaag ggagggcagg gtggggctga   1380

ggaactgacg tggagcgggg tatgaagagc ttgctttgat ttacagcaag tagataaata   1440

tttgacttgc atgaagagaa gcaattttgg ggaagggttt gaattgtttt ctttaaagat   1500

gtaatgtccc tttcagagac agctgatact tcatttaaaa aaatcacaaa aatttgaaca   1560

ctggctaaag ataattgcta tttattttta caagaagttt attctcattt gggagatctg   1620

gtgatctccc aagctatcta aagtttgtta gatagctgca tgtggctttt ttaaaaaagc   1680

aacagaaacc tatcctcact gccctcccca gtctctctta aagttggaat ttaccagtta   1740

attactcagc agaatggtga tcactccagg tagtttgggg caaaaatccg aggtgcttgg   1800

gagttttgaa tgttaagaat tgaccatctg cttttattaa atttgttgac aaaatttttct   1860

cattttcttt tcacttcggg ctgtgtaaac acagtcaaaa taattctaaa tccctcgata   1920

tttttaaaga tctgtaagta acttcacatt aaaaaatgaa atattttttta atttaaagct   1980

tactctgtcc atttatccac aggaaagtgt tatttttaaa ggaaggttca tgtagagaaa   2040

agcacacttg taggataagt gaaatggata ctacatcttt aaacagtatt tcattgcctg   2100

tgtatggaaa aaccatttga agtgtacctg tgtacataac tctgtaaaaa cactgaaaaa   2160

ttatactaac ttatttatgt taaaagattt tttttaatct agacaatata caagccaaag   2220

tggcatgttt tgtgcatttg taaatgctgt gttgggtaga ataggttttc ccctcttttg   2280

ttaaataata tggctatgct taaaaggttg catactgagc caagtataat tttttgtaat   2340

gtgtgaaaaa gatgccaatt attgttacac attaagtaat caataaagaa aacttccata   2400

gctaaaaaaa aaaaaaaaaa aa                                             2422
```

<210> SEQ ID NO 317
<211> LENGTH: 5061
<212> TYPE: DNA
<213> ORGANISM: Homo sapiens

<400> SEQUENCE: 317

```
atggctcaga tatttagcaa cagcggattt aaagaatgtc cattttcaca tccggaacca     60

acaagagcaa aagatgtgga caaagaagaa gcattacaga tggaagcaga ggctttagca    120

aaactgcaaa aggatagaca agtgactgac aatcagagag gctttgagtt gtcaagcagc    180

accagaaaaa aagcacaggt ttataacaag caggattatg atctcatggt gtttcctgaa    240

tcagattccc aaaaaagagc attagatatt gatgtagaaa agctcaccca agctgaactt    300
```

-continued

```
gagaaactat tgctggatga cagtttcgag actaaaaaaa cacctgtatt accagttact    360
cctattctga gcccttcctt ttcagcacag ctctatttta gacctactat tcagagagga    420
cagtggccac ctggattacc tgggccttcc acttatgctt taccttctat ttatccttct    480
acttacagta aacaggctgc attccaaaat ggcttcaatc caagaatgcc cacttttcca    540
tctacagaac ctatatattt aagtcttccg ggacaatctc catatttctc atatcctttg    600
acacctgcca caccctttca tccacaagga agcttaccta tctatcgtcc agtagtcagt    660
actgacatgg caaaactatt tgacaaaata gctagtacat cagaattttt aaaaaatggg    720
aaagcaagga ctgatttgga gataacagat tcaaaagtca gcaatctaca ggtatctcca    780
aagtctgagg atatcagtaa atttgactgg ttagacttgg atcctctaag taagcctaag    840
gtggataatg tggaggtatt agaccatgag gaagagaaaa atgtttcaag tttgctagca    900
aaggatcctt gggatgctgt tcttcttgaa gagagatcga cagcaaattg tcatcttgaa    960
agaaaggtga atggaaaatc cctttctgtg gcaactgtta caagaagcca gtctttaaat   1020
attcgaacaa ctcagcttgc aaaagcccag ggccatatat ctcagaaaga cccaaatggg   1080
accagtagtt tgccaactgg aagttctctt cttcaagaag ttgaagtaca gaatgaggag   1140
atggcagctt tttgtcgatc cattacaaaa ttgaagacca aatttccata taccaatcac   1200
cgcacaaacc caggctattt gttaagtcca gtcacagcgc aaagaaacat atgcggagaa   1260
aatgctagtg tgaaggtctc cattgacatt gaaggatttc agctaccagt tacttttacg   1320
tgtgatgtga gttctactgt agaaatcatt ataatgcaag ccctttgctg ggtacatgat   1380
gacttgaatc aagtagatgt tggcagctat gttctaaaag tttgtggtca agaggaagtg   1440
ctgcagaata atcattgcct tggaagtcat gagcatattc aaaactgtcg aaaatgggac   1500
acagaaatta gactacaact cttgaccttc agtgcaatgt gtcaaaatct ggcccgaaca   1560
gcagaagatg atgaaacacc cgtggattta aacaaacacc tgtatcaaat agaaaaacct   1620
tgcaaagaag ccatgacgag acaccctgtt gaagaactct tagattctta tcacaaccaa   1680
gtagaactgg ctcttcaaat tgaaaaccaa caccgagcag tagatcaagt aattaaagct   1740
gtaagaaaaa tctgtagtgc tttagatggt gtcgagactc ttgccattac agaatcagta   1800
aagaagctaa agagagcagt taatcttcca aggagtaaaa ctgctgatgt gacttctttg   1860
tttggaggag aagacactag caggagttca actaggggct cacttaatcc tgaaaatcct   1920
gttcaagtaa gcataaacca attaactgca gcaatttatg atcttctcag actccatgca   1980
aattctggta ggagtcctac agactgtgcc caaagtagca agagtgtcaa ggaagcatgg   2040
actacaacag agcagctcca gtttactatt tttgctgctc atggaatttc aagtaattgg   2100
gtatcaaatt atgaaaaata ctacttgata tgttcactgt ctcacaatgg aaaggatctt   2160
tttaaaccta ttcaatcaaa gaaggttggc acttacaaga atttcttcta tcttattaaa   2220
tgggatgaac taatcatttt tcctatccag atatcacaat tgccattaga atcagttctt   2280
caccttactc tttttggaat tttaaatcag agcagtggaa gttcccctga ttctaataag   2340
cagagaaagg gaccagaagc tttgggcaaa gtttctttac ctctttgtga ctttagacgg   2400
tttttaacat gtggaactaa acttctatat ctttggactt catcacatac aaattctgtt   2460
cctggaacag ttaccaaaaa aggatatgtc atggaaagaa tagtgctaca ggttgatttt   2520
ccttctcctg catttgatat tatttataca actcctcaag ttgacagaag cattatacag   2580
caacataact tagaaacact agagaatgat ataaaaggga aacttcttga tattcttcat   2640
```

-continued

```
aaagactcat cacttggact ttctaaagaa gataaagctt ttttatggga gaaacgttat   2700
tattgcttca aacacccaaa ttgtcttcct aaaatattag caagcgcccc aaactggaaa   2760
tggggtaatc ttgccaaaac ttactcattg cttcaccagt ggcctgcatt gtacccacta   2820
attgcattgg aacttcttga ttcaaaattt gctgatcagg aagtaagatc cctagctgtg   2880
acctggattg aggccattag tgatgatgag ctaacagatc ttcttccaca gtttgtacaa   2940
gctttgaaat atgaaattta cttgaatagt tcattagtgc aattcctttt gtccagggca   3000
ttgggaaata tccagatagc acacaattta tattggcttc tcaaagatgc cctgcatgat   3060
gtacagttta gtacccgata cgaacatgtt ttgggtgctc tcctgtcagt aggaggaaaa   3120
cgacttagag aagaacttct aaaacagacg aaacttgtac agcttttagg aggagtagca   3180
gaaaaagtaa ggcaggctag tggatcagcc agacaggttg ttctccaaag aagtatggaa   3240
cgagtacagt cctttttca gaaaaataaa tgccgtctcc ctctcaagcc aagtctagtg   3300
gcaaaagaat taaatattaa gtcgtgttcc ttcttcagtt ctaatgctgt ccccctaaaa   3360
gtcacaatgg tgaatgctga ccctctggga gaagaaatta atgtcatgtt taaggttggt   3420
gaagatcttc ggcaagatat gttagcttta cagatgataa agattatgga taagatctgg   3480
cttaaagaag gactagatct gaggatggta attttcaaat gtctctcaac tggcagagat   3540
cgaggcatgg tggagctggt tcctgcttcc gataccctca ggaaaatcca agtggaatat   3600
ggtgtgacag gatcctttaa agataaacca cttgcagagt ggctaaggaa atacaatccc   3660
tctgaagaag aatatgaaaa ggcttcagag aactttatct attcctgtgc tggatgctgt   3720
gtagccacct atgttttagg catctgtgat cgacacaatg acaatataat gcttcgaagc   3780
acgggacaca tgtttcacat tgactttgga aagtttttgg gacatgcaca gatgtttggc   3840
agcttcaaaa gggatcgggc tccttttgtg ctgacctctg atatggcata tgtcattaat   3900
gggggtgaaa agcccaccat tcgttttcag ttgtttgtgg acctctgctg tcaggcctac   3960
aacttgataa gaaagcagac aaaccttttt cttaacctcc tttcactgat gattccttca   4020
gggttaccag aacttacaag tattcaagat ttgaaatacg ttagagatgc acttcaaccc   4080
caaactacag acgcagaagc tacaattttc tttactaggc ttattgaatc aagtttggga   4140
agcattgcca caaagtttaa cttcttcatt cacaaccttg ctcagcttcg tttttctggt   4200
cttccttcta atgatgagcc catcctttca ttttcaccta aaacatactc ctttagacaa   4260
gatggtcgaa tcaaggaagt ctctgttttt acatatcata agaaatacaa cccagataaa   4320
cattatattt atgtagtccg aattttgtgg gaaggacaga ttgaaccatc atttgtcttc   4380
cgaacatttg tcgaatttca ggaacttcac aataagctca gtattatttt tccactttgg   4440
aagttaccag gctttcctaa taggatggtt ctaggaagaa cacacataaa agatgtagca   4500
gccaaaagga aaattgagtt aaacagttac ttacagagtt tgatgaatgc ttcaacggat   4560
gtagcagagt gtgatcttgt ttgtactttc ttccaccctt tacttcgtga tgagaaagct   4620
gaagggatag ctaggtctgc agatgcaggt tccttcagtc ctactccagg ccaaatagga   4680
ggagctgtga aattatccat ctcttaccga aatggtactc ttttcatcat ggtgatgcat   4740
atcaaagatc ttgttactga agatggagct gacccaaatc catatgtcaa aacataccta   4800
cttccagata accacaaaac atccaaacgt aaaaccaaaa tttcacgaaa aacgaggaat   4860
ccgacattca atgaaatgct tgtatacagt ggatatagca aagaaaccct aagacagcga   4920
gaacttcaac taagtgtact cagtgcagaa tctctgcggg agaatttttt cttgggtgga   4980
gtaaccctgc ctttgaaaga tttcaacttg agcaaagaga cggttaaatg gtatcagctg   5040
```

actgcggcaa catacttgta a 5061

<210> SEQ ID NO 318
<211> LENGTH: 3014
<212> TYPE: DNA
<213> ORGANISM: Homo sapiens

<400> SEQUENCE: 318

```
ctgaccagcg ccgccctccc ccgcccccga cccaggaggt ggagatccct ccggtccagc     60
cacattcaac acccactttc tcctccctct gcccctatat tcccgaaacc ccctcctcct    120
tccctttcc ctcctccctg gagacggggg aggagaaaag gggagtccag tcgtcatgac    180
tgagctgaag gcaaagggtc cccgggctcc ccacgtggcg ggcggcccgc cctcccccga    240
ggtcggatcc ccactgctgt gtcgcccagc cgcaggtccg ttcccgggga gccagacctc    300
ggacaccttg cctgaagttt cggccatacc tatctccctg gacgggctac tcttccctcg    360
gccctgccag ggacaggacc cctccgacga aaagacgcag gaccagcagt cgctgtcgga    420
cgtggagggc gcatattcca gagctgaagc tacaaggggt gctggaggca gcagttctag    480
tcccccagaa aaggacagcg gactgctgga cagtgtcttg gacactctgt tggcgccctc    540
aggtcccggg cagagccaac ccagccctcc cgcctgcgag gtcaccagct cttggtgcct    600
gtttggcccc gaacttcccg aagatccacc ggctgccccc gccacccagc gggtgttgtc    660
cccgctcatg agccggtccg ggtgcaaggt tggagacagc tccgggacgg cagctgccca    720
taaagtgctg ccccggggcc tgtcaccagc ccggcagctg ctgctcccgg cctctgagag    780
ccctcactgg tccggggccc cagtgaagcc gtctccgcag gccgctgcgg tggaggttga    840
ggaggaggat ggctctgagt ccgaggagtc tgcgggtccg cttctgaagg gcaaacctcg    900
ggctctgggt ggcgcggcgg ctggaggagg agccgcggct gtcccgccgg gggcggcagc    960
aggaggcgtc gccctggtcc ccaaggaaga ttcccgcttc tcagcgccca gggtcgccct   1020
ggtggagcag gacgcgccga tggcgcccgg gcgctccccg ctggccacca cggtgatgga   1080
tttcatccac gtgcctatcc tgcctctcaa tcacgcctta ttggcagccc gcactcggca   1140
gctgctggaa gacgaaagtt acgacggcgg ggccggggct gccagcgcct ttgccccgcc   1200
gcggagttca ccctgtgcct cgtccacccc ggtcgctgta ggcgacttcc ccgactgcgc   1260
gtacccgccc gacgccgagc ccaaggacga cgcgtaccct ctctatagcg acttccagcc   1320
gcccgctcta aagataaagg aggaggagga aggcgcggag gcctccgcgc gctccccgcg   1380
ttcctacctt gtggccggtg ccaaccccgc agccttcccg gatttcccgt tggggccacc   1440
gcccccgctg ccgccgcgag cgaccccatc cagacccggg gaagcggcgg tgacggccgc   1500
acccgccagt gcctcagtct cgtctgcgtc ctcctcgggg tcgaccctgg agtgcatcct   1560
gtacaaagcg gagggcgcgc cgccccagca gggcccgttc gcgccgccgc cctgcaaggc   1620
gccgggcgcg agcggctgcc tgctcccgcg ggacggcctg ccctccacct ccgcctctgc   1680
cgccgccgcc ggggcggccc ccgcgctcta ccctgcactc ggcctcaacg ggctcccgca   1740
gctcggctac caggccgccg tgctcaagga gggcctgccg caggtctacc cgccctatct   1800
caactacctg aggccggatt cagaagccag ccagagccca caatacagct tcgagtcatt   1860
acctcagaag atttgtttaa tctgtgggga tgaagcatca ggctgtcatt atggtgtcct   1920
tacctgtggg agctgtaagg tcttctttaa gagggcaatg gaagggcagc acaactactt   1980
atgtgctgga agaaatgact gcatcgttga taaaatccgc agaaaaaact gcccagcatg   2040
```

-continued

```
tcgccttaga aagtgctgtc aggctggcat ggtccttgga ggtcgaaaat ttaaaaagtt   2100

caataaagtc agagttgtga gagcactgga tgctgttgct ctcccacagc cagtgggcgt   2160

tccaaatgaa agccaagccc taagccagag attcactttt tcaccaggtc aagacataca   2220

gttgattcca ccactgatca acctgttaat gagcattgaa ccagatgtga tctatgcagg   2280

acatgacaac acaaaacctg acacctccag ttctttgctg acaagtctta atcaactagg   2340

cgagaggcaa cttctttcag tagtcaagtg gtctaaatca ttgccaggtt ttcgaaactt   2400

acatattgat gaccagataa ctctcattca gtattcttgg atgagcttaa tggtgtttgg   2460

tctaggatgg agatcctaca aacacgtcag tgggcagatg ctgtattttg cacctgatct   2520

aatactaaat gaacagcgga tgaaagaatc atcattctat tcattatgcc ttaccatgtg   2580

gcagatccca caggagtttg tcaagcttca agttagccaa gaagagttcc tctgtatgaa   2640

agtattgtta cttcttaata caattccttt ggaagggcta cgaagtcaaa cccagtttga   2700

ggagatgagg tcaagctaca ttagagagct catcaaggca attggtttga ggcaaaaagg   2760

agttgtgtcg agctcacagc gtttctatca acttacaaaa cttcttgata acttgcatga   2820

tcttgtcaaa caacttcatc tgtactgctt gaatacattt atccagtccc gggcactgag   2880

tgttgaattt ccagaaatga tgtctgaagt tattgctgca caattaccca agatattggc   2940

agggatggtg aaaccccttc tctttcataa aaagtgaatg tcatcttttt cttttaaaga   3000

attaaatttt gtgg                                                     3014
```

<210> SEQ ID NO 319
<211> LENGTH: 2148
<212> TYPE: DNA
<213> ORGANISM: Homo sapiens

<400> SEQUENCE: 319

```
gcttcagggt acagctcccc cgcagccaga agccgggcct gcagcgcctc agcaccgctc     60

cgggacaccc cacccgcttc ccaggcgtga cctgtcaaca gcaacttcgc ggtgtggtga    120

actctctgag gaaaaaccat tttgattatt actctcagac gtgcgtggca acaagtgact    180

gagacctaga aatccaagcg ttggaggtcc tgaggccagc ctaagtcgct tcaaaatgga    240

acgaaggcgt ttgtggggtt ccattcagag ccgatacatc agcatgagtg tgtggacaag    300

cccacggaga cttgtggagc tggcagggca gagcctgctg aaggatgagg ccctggccat    360

tgccgccctg gagttgctgc ccagggagct cttcccgcca ctcttcatgg cagcctttga    420

cgggagacac agccagaccc tgaaggcaat ggtgcaggcc tggcccttca cctgcctccc    480

tctgggagtg ctgatgaagg gacaacatct tcacctggag accttcaaag ctgtgcttga    540

tggacttgat gtgctccttg cccaggaggt tcgccccagg aggtggaaac ttcaagtgct    600

ggatttacgg aagaactctc atcaggactt ctggactgta tggtctggaa acagggccag    660

tctgtactca tttccagagc cagaagcagc tcagcccatg acaaagaagc gaaaagtaga    720

tggtttgagc acagaggcag agcagccctt cattccagta gaggtgctcg tagacctgtt    780

cctcaaggaa ggtgcctgtg atgaattgtt ctcctacctc attgagaaag tgaagcgaaa    840

gaaaaatgta ctacgcctgt gctgtaagaa gctgaagatt tttgcaatgc ccatgcagga    900

tatcaagatg atcctgaaaa tggtgcagct ggactctatt gaagatttgg aagtgacttg    960

tacctggaag ctacccacct tggcgaaatt ttctccttac ctgggccaga tgattaatct   1020

gcgtagactc ctcctctccc acatccatgc atcttcctac atttccccgg agaaggaaga   1080

gcagtatatc gcccagttca cctctcagtt cctcagtctg cagtgcctgc aggctctcta   1140
```

-continued

```
tgtggactct ttatttttcc ttagaggccg cctggatcag ttgctcaggc acgtgatgaa   1200
ccccttggaa accctctcaa taactaactg ccggctttcg gaaggggatg tgatgcatct   1260
gtcccagagt cccagcgtca gtcagctaag tgtcctgagt ctaagtgggg tcatgctgac   1320
cgatgtaagt cccgagcccc tccaagctct gctggagaga gcctctgcca ccctccagga   1380
cctggtcttt gatgagtgtg ggatcacgga tgatcagctc cttgccctcc tgccttccct   1440
gagccactgc tcccagctta caaccttaag cttctacggg aattccatct ccatatctgc   1500
cttgcagagt ctcctgcagc acctcatcgg gctgagcaat ctgacccacg tgctgtatcc   1560
tgtcccccctg gagagttatg aggacatcca tggtaccctc cacctggaga ggcttgccta   1620
tctgcatgcc aggctcaggg agttgctgtg tgagttgggg cggcccagca tggtctggct   1680
tagtgccaac ccctgtcctc actgtgggga cagaaccttc tatgacccgg agcccatcct   1740
gtgcccctgt ttcatgccta actagctggg tgcacatatc aaatgcttca ttctgcatac   1800
ttggacacta aagccaggat gtgcatgcat cttgaagcaa caaagcagcc acagtttcag   1860
acaaatgttc agtgtgagtg aggaaaacat gttcagtgag gaaaaaacat tcagacaaat   1920
gttcagtgag gaaaaaaagg ggaagttggg gataggcaga tgttgacttg aggagttaat   1980
gtgatctttg gggagataca tcttatagag ttagaaatag aatctgaatt tctaaaggga   2040
gattctggct tgggaagtac atgtaggagt taatccctgt gtagactgtt gtaaagaaac   2100
tgttgaaaat aaagagaagc aatgtgaagc aaaaaaaaaa aaaaaaaa               2148
```

<210> SEQ ID NO 320
<211> LENGTH: 540
<212> TYPE: DNA
<213> ORGANISM: Homo sapiens

<400> SEQUENCE: 320

```
atccctgact cggggtcgcc tttggagcag agaggaggca atggccacca tggagaacaa     60
ggtgatctgc gccctggtcc tggtgtccat gctggccctc ggcaccctgg ccgaggccca    120
gacagagacg tgtacagtgg ccccccgtga aagacagaat tgtggttttc ctggtgtcac    180
gccctcccag tgtgcaaata agggctgctg tttcgacgac accgttcgtg gggtcccctg    240
gtgcttctat cctaatacca tcgacgtccc tccagaagag gagtgtgaat tttagacact    300
tctgcaggga tctgcctgca tcctgacggg gtgccgtccc cagcacggtg attagtccca    360
gagctcggct gccacctcca ccggacacct cagacacgct tctgcagctg tgcctcggct    420
cacaacacag attgactgct ctgactttga ctactcaaaa ttggcctaaa aattaaaaga    480
gatcgatatt aaaaaaaaaa aaaaaaaaaa aaaaaaaaaa aaaaaaaaaa aaaaaaaaaa    540
```

<210> SEQ ID NO 321
<211> LENGTH: 2346
<212> TYPE: DNA
<213> ORGANISM: Homo sapiens

<400> SEQUENCE: 321

```
gcacgaggct gcggcgggtc cgggcccatg aggcgacgaa ggaggcggga cggcttttac     60
ccagccccgg acttccgaga cagggaagct gaggacatgg caggagtgtt tgacatagac    120
ctggaccagc cagaggacgc gggctctgag gatgagctgg aggagggggg tcagttaaat    180
gaaagcatgg accatggggg agttggacca tatgaacttg gcatggaaca ttgtgagaaa    240
tttgaaatct cagaaactag tgtgaacaga gggccagaaa aaatcagacc agaatgtttt    300
```

```
gagctacttc gggtacttgg taaagggggc tatggaaagg tttttcaagt acgaaaagta    360

acaggagcaa atactgggaa aatatttgcc atgaaggtgc ttaaaaaggc aatgatagta    420

agaaatgcta aagatacagc tcatacaaaa gcagaacgga atattctgga ggaagtaaag    480

catcccttca tcgtggattt aatttatgcc tttcagactg gtggaaaact ctacctcatc    540

cttgagtatc tcagtggagg agaactattt atgcagttag aaagagaggg aatatttatg    600

gaagacactg cctgctttta cttggcagaa atctccatgg ctttggggca tttacatcaa    660

aaggggatca tctacagaga cctgaagccg gagaatatca tgcttaatca ccaaggtcat    720

gtgaaactaa cagactttgg actatgcaaa gaatctattc atgatggaac agtcacacac    780

acattttgtg gaacaataga atacatggcc cctgaaatct tgatgagaag tggccacaat    840

cgtgctgtgg attggtggag tttgggagca ttaatgtatg acatgctgac tggagcaccc    900

ccattcactg gggagaatag aaagaaaaca attgacaaaa tcctcaaatg taaactcaat    960

ttgcctccct acctcacaca agaagccaga gatctgctta aaagctgct gaaaagaaat   1020

gctgcttctc gtctgggagc tggtcctggg gacgctggag aagttcaagc tcatccattc   1080

tttagacaca ttaactggga agaacttctg gctcgaaagg tggagccccc ctttaaacct   1140

ctgttgcaat ctgaagagga tgtaagtcag tttgattcca agtttacacg tcagacacct   1200

gtcgacagcc cagatgactc aactctcagt gaaagtgcca atcaggtctt tctgggtttt   1260

acatatgtgg ctccatctgt acttgaaagt gtgaaagaaa agttttcctt tgaaccaaaa   1320

atccgatcac ctcgaagatt tattggcagc ccacgaacac ctgtcagccc agtcaaattt   1380

tctcctgggg atttctgggg aagaggtgct tcggccagca cagcaaatcc tcagacacct   1440

gtggaatacc caatggaaac aagtggcata gagcagatgg atgtgacaat gagtggggaa   1500

gcatcggcac cacttccaat acgacagccg aactctgggc catacaaaaa acaagctttt   1560

cccatgatct ccaaacggcc agagcacctg cgtatgaatc tatgacagag caatgctttt   1620

aatgaattta aggcaaaaag gtggagaggg agatgtgtga gcatcctgca aggtgaaaca   1680

agactcaaaa tgacagtttc agagagtcaa tgtcattaca tagaacactt cggacacagg   1740

aaaaataaac gtggatttta aaaaatcaat caatggtgca aaaaaaaact taaagcaaaa   1800

tagtattgct gaactcttag gcacatcaat taattgattc ctcgcgacat ctttctcaac   1860

cttatcaagg attttcatgt tgatgactcg aaactgacag tattaagggt aggatgttgc   1920

tctgaatcac tgtgagtctg atgtgtgaag aagggtatcc tttcattagg caagtacaaa   1980

ttgcctataa tacttgcaac taaggacaaa ttagcatgca agcttggtca aacttttccc   2040

aggcaaaatg ggaaggcaaa gacaaaagaa acttaccaat tgatgtttta cgtgcaaaca   2100

acctgaatct ttttttata taaatatata tttttcaaat agatttttga ttcagctcat   2160

tatgaaaaac atcccaaact ttaaaatgcg aaattattgg ttggtgtgaa gaaagccaga   2220

caacttctgt ttcttctctt ggtgaaataa taaaatgcaa atgaatcatt gttaacacag   2280

ctgtggctcg tttgagggat tggggtggac ctggggttta ttttcagtaa cccagctgcg   2340

gagcct                                                                2346
```

```
<210> SEQ ID NO 322
<211> LENGTH: 2420
<212> TYPE: DNA
<213> ORGANISM: Homo sapiens

<400> SEQUENCE: 322

tccggggcgg cccccggcag ccagcgcgac gttccaaaat cgaacctcag tggcggcgct     60
```

-continued

```
cggaagcgga actctgccgg ggccgcgccg gctacattgt ttcctccccc cgactccctc    120
ccgccccctt cccccgcctt tcttccctcc gcgacccggg ccgtgcgtcc gtccccctgc    180
ctctgcctgg cggtccctcc tcccctctcc ttgcacccat acctctttgt accgcacccc    240
ctggggaccc ctgcgcccct cccctccccc ctgaccgcat ggaccgtccc gcaggccgct    300
gatgccgccc gcggcgaggt ggcccggacc gcagtgcccc aagagagctc taatggtacc    360
aagtgacagg ttggctttac tgtgactcgg ggacgccaga gctcctgaga agatgtcagc    420
aatacaggcc gcctggccat ccggtacaga atgtattgcc aagtacaact tccacggcac    480
tgccgagcag gacctgccct tctgcaaagg agacgtgctc accattgtgg ccgtcaccaa    540
ggaccccaac tggtacaaag ccaaaaacaa ggtgggccgt gagggcatca tcccagccaa    600
ctacgtccag aagcgggagg gcgtgaaggc gggtaccaaa ctcagcctca tgccttggtt    660
ccacggcaag atcacacggg agcaggctga gcggcttctg tacccgccgg agacaggcct    720
gttcctggtg cgggagagca ccaactaccc cggagactac acgctgtgcg tgagctgcga    780
cggcaaggtg gagcactacc gcatcatgta ccatgccagc aagctcagca tcgacgagga    840
ggtgtacttt gagaacctca tgcagctggt ggagcactac acctcagacg cagatggact    900
ctgtacgcgc ctcattaaac caaaggtcat ggagggcaca gtggcggccc aggatgagtt    960
ctaccgcagc ggctgggccc tgaacatgaa ggagctgaag ctgctgcaga ccatcgggaa   1020
gggggagttc ggagacgtga tgctgggcga ttaccgaggg aacaaagtcg ccgtcaagtg   1080
cattaagaac gacgccactg cccaggcctt cctggctgaa gcctcagtca tgacgcaact   1140
gcggcatagc aacctggtgc agctcctggg cgtgatcgtg gaggagaagg gcgggctcta   1200
catcgtcact gagtacatgg ccaaggggag ccttgtggac tacctgcggt ctaggggtcg   1260
gtcagtgctg ggcggagact gtctcctcaa gttctcgcta gatgtctgcg aggccatgga   1320
atacctggag ggcaacaatt tcgtgcatcg agacctggct gcccgcaatg tgctggtgtc   1380
tgaggacaac gtggccaagg tcagcgactt tggtctcacc aaggaggcgt ccagcaccca   1440
ggacacgggc aagctgccag tcaagtggac agcccctgag gccctgagag agaagaaatt   1500
ctccactaag tctgacgtgt ggagtttcgg aatccttctc tgggaaatct actcctttgg   1560
gcgagtgcct tatccaagaa ttcccctgaa ggacgtcgtc cctcgggtgg agaagggcta   1620
caagatggat gcccccgacg gctgcccgcc cgcagtctat gaagtcatga agaactgctg   1680
gcacctggac gccgccatgc ggccctcctt cctacagctc cgagagcagc ttgagcacat   1740
caaaacccac gagctgcacc tgtgacggct ggcctccgcc tgggtcatgg gcctgtgggg   1800
actgaacctg gaagatcatg gacctggtgc ccctgctcac tgggcccgag cctgaactga   1860
gccccagcgg gctggcgggc ctttttcctg cgtcccagcc tgcacccctc cggccccgtc   1920
tctcttggac ccacctgtgg ggcctgggga gcccactgag gggccaggga ggaaggaggc   1980
cacggagcgg gcggcagcgc cccaccacgt cgggcttccc tggcctcccg ccactcgcct   2040
tcttagagtt ttattccttt cctttttga gatttttttt ccgtgtgttt atttttttatt   2100
atttttcaag ataaggagaa agaaagtacc cagcaaatgg gcattttaca agaagtacga   2160
atcttatttt tcctgtcctg cccgtgaggt gggggggacc gggcccctct ctagggaccc   2220
ctcgccccag cctcattccc cattctgtgt cccatgtccc gtgtctcctc ggtcgccccg   2280
tgtttgcgct tgaccatgtt gcactgtttg catgcgcccg aggcagacgt ctgtcagggg   2340
cttggatttc gtgtgccgct gccacccgcc cacccgcctt gtgagatgga atcgtaataa   2400
```

-continued

```
accacgccat gaggaaaaaa                                              2420


<210> SEQ ID NO 323
<211> LENGTH: 2253
<212> TYPE: DNA
<213> ORGANISM: Homo sapiens

<400> SEQUENCE: 323

ggaagacttg ggtccttggg tcgcaggtgg gagccgacgg gtgggtagac cgtgggggat     60

atctcagtgg cggacgagga cggcggggac aaggggcggc tggtcggagt ggcggagcgt    120

caagtcccct gtcggttcct ccgtccctga gtgtccttgg cgctgccttg tgcccgccca    180

gcgcctttgc atccgctcct gggcaccgag gcgccctgta ggatactgct tgttacttat    240

tacagctaga ggcatcatgg accgatctaa agaaaactgc atttcaggac ctgttaaggc    300

tacagctcca gttggaggtc caaaacgtgt tctcgtgact cagcaaattc cttgtcagaa    360

tccattacct gtaaatagtg gccaggctca gcgggtcttg tgtccttcaa attcttccca    420

gcgcgttcct ttgcaagcac aaaagcttgt ctccagtcac aagccggttc agaatcagaa    480

gcagaagcaa ttgcaggcaa ccagtgtacc tcatcctgtc tccaggccac tgaataacac    540

ccaaaagagc aagcagcccc tgccatcggc acctgaaaat aatcctgagg aggaactggc    600

atcaaaacag aaaaatgaag aatcaaaaaa gaggcagtgg gctttggaag actttgaaat    660

tggtcgccct ctgggtaaag gaaagtttgg taatgtttat ttggcaagag aaaagcaaag    720

caagtttatt ctggctctta aagtgttatt taaagctcag ctggagaaag ccggagtgga    780

gcatcagctc agaagagaag tagaaataca gtcccacctt cggcatccta atattcttag    840

actgtatggt tatttccatg atgctaccag agtctaccta attctggaat atgcaccact    900

tggaacagtt tatagagaac ttcagaaact ttcaaagttt gatgagcaga gaactgctac    960

ttatataaca gaattggcaa atgccctgtc ttactgtcat tcgaagagag ttattcatag   1020

agacattaag ccagagaact tacttcttgg atcagctgga gagcttaaaa ttgcagattt   1080

tgggtggtca gtacatgctc catcttccag gaggaccact ctctgtggca ccctggacta   1140

cctgccccct gaaatgattg aaggtcggat gcatgatgag aaggtggatc tctggagcct   1200

tggagttctt tgctatgaat ttttagttgg gaagcctcct tttgaggcaa acacatacca   1260

agagacctac aaaagaatat cacgggttga attcacattc cctgactttg taacagaggg   1320

agccagggac ctcatttcaa gactgttgaa gcataatccc agccagaggc caatgctcag   1380

agaagtactt gaacacccct ggatcacagc aaattcatca aaaccatcaa attgccaaaa   1440

caaagaatca gctagcaaac agtcttagga atcgtgcagg gggagaaatc cttgagccag   1500

ggctgccata taacctgaca ggaacatgct actgaagttt attttaccat tgactgctgc   1560

cctcaatcta gaacgctaca caagaaatat ttgttttact cagcaggtgt gccttaacct   1620

ccctattcag aaagctccac atcaataaac atgacactct gaagtgaaag tagccacgag   1680

aattgtgcta cttatactgg ttcataatct ggaggcaagg ttcgactgca gccgccccgt   1740

cagcctgtgc taggcatggt gtcttcacag gaggcaaatc cagagcctgg ctgtggggaa   1800

agtgaccact ctgccctgac cccgatcagt taaggagctg tgcaataacc ttcctagtac   1860

ctgagtgagt gtgtaactta ttgggttggc gaagcctggt aaagctgttg gaatgagtat   1920

gtgattcttt ttaagtatga aaataaagat atatgtacag acttgtattt tttctctggt   1980

ggcattcctt taggaatgct gtgtgtctgt ccggcacccc ggtaggcctg attgggtttc   2040

tagtcctcct taaccactta tctcccatat gagagtgtga aaaataggaa cacgtgctct   2100
```

```
acctccattt agggatttgc ttgggataca gaagaggcca tgtgtctcag agctgttaag   2160

ggcttatttt tttaaaacat tggagtcata gcatgtgtgt aaactttaaa tatgcaaata   2220

aataagtatc tatgtctaaa aaaaaaaaaa aaa                                2253
```

<210> SEQ ID NO 324
<211> LENGTH: 1619
<212> TYPE: DNA
<213> ORGANISM: Homo sapiens

<400> SEQUENCE: 324

```
ccgccagatt tgaatcgcgg gacccgttgg cagaggtggc ggcggcggca tgggtgcccc     60

gacgttgccc cctgcctggc agccctttct caaggaccac cgcatctcta cattcaagaa    120

ctggcccttc ttggagggct gcgcctgcac cccggagcgg atggccgagg ctggcttcat    180

ccactgcccc actgagaacg agccagactt ggcccagtgt ttcttctgct tcaaggagct    240

ggaaggctgg gagccagatg acgaccccat agaggaacat aaaaagcatt cgtccggttg    300

cgctttcctt tctgtcaaga agcagtttga agaattaacc cttggtgaat ttttgaaact    360

ggacagagaa agagccaaga acaaaattgc aaaggaaacc aacaataaga agaaagaatt    420

tgaggaaact gcgaagaaag tgcgccgtgc catcgagcag ctggctgcca tggattgagg    480

cctctggccg gagctgcctg gtcccagagt ggctgcacca cttccagggt ttattccctg    540

gtgccaccag ccttcctgtg ggccccttag caatgtctta ggaaaggaga tcaacatttt    600

caaattagat gtttcaactg tgctcctgtt ttgtcttgaa agtggcacca gaggtgcttc    660

tgcctgtgca gcgggtgctg ctggtaacag tggctgcttc tctctctctc tctctttttt    720

gggggctcat ttttgctgtt ttgattcccg ggcttaccag gtgagaagtg agggaggaag    780

aaggcagtgt ccccttttgct agagctgaca gctttgttcg cgtgggcaga gccttccaca    840

gtgaatgtgt ctggacctca tgttgttgag gctgtcacag tcctgagtgt ggacttggca    900

ggtgcctgtt gaatctgagc tgcaggttcc ttatctgtca cacctgtgcc tcctcagagg    960

acagtttttt tgttgttgtg ttttttgtt ttttttttt ggtagatgca tgacttgtgt     1020

gtgatgagag aatggagaca gagtccctgg ctcctctact gtttaacaac atggctttct   1080

tattttgttt gaattgttaa ttcacagaat agcacaaact acaattaaaa ctaagcacaa   1140

agccattcta agtcattggg gaaacggggt gaacttcagg tggatgagga gacagaatag   1200

agtgatagga agcgtctggc agatactcct tttgccactg ctgtgtgatt agacaggccc   1260

agtgagccgc ggggcacatg ctggccgctc ctccctcaga aaaaggcagt ggcctaaatc   1320

ctttttaaat gacttggctc gatgctgtgg gggactggct gggctgctgc aggccgtgtg   1380

tctgtcagcc caaccttcac atctgtcacg ttctccacac gggggagaga cgcagtccgc   1440

ccaggtcccc gctttctttg gaggcagcag ctcccgcagg gctgaagtct ggcgtaagat   1500

gatggatttg attcgccctc ctccctgtca tagagctgca gggtggattg ttacagcttc   1560

gctggaaacc tctggaggtc atctcggctg ttcctgagaa ataaaaagcc tgtcatttc    1619
```

<210> SEQ ID NO 325
<211> LENGTH: 5010
<212> TYPE: DNA
<213> ORGANISM: Homo sapiens

<400> SEQUENCE: 325

```
ggcggctcgg gacggaggac gcgctagtgt gagtgcgggc ttctagaact acaccgaccc     60
```

-continued

```
tcgtgtcctc ccttcatcct gcggggctgg ctggagcggc cgctccggtg ctgtccagca    120
gccataggga gccgcacggg gagcgggaaa gcggtcgcgg ccccaggcgg ggcggccggg    180
atggagcggg gccgcgagcc tgtggggaag ggcgctgtggc ggcgcctcga gcggctgcag   240
gttcttctgt gtggcagttc agaatgatgg atcaagctag atcagcattc tctaacttgt    300
ttggtggaga accattgtca tatacccggt tcagcctggc tcggcaagta gatggcgata    360
acagtcatgt ggagatgaaa cttgctgtag atgaagaaga aaatgctgac aataacacaa    420
aggccaatgt cacaaaacca aaaaggtgta gtggaagtat ctgctatggg actattgctg    480
tgatcgtctt tttcttgatt ggatttatga ttggctactt gggctattgt aaaggggtag    540
aaccaaaaac tgagtgtgag agactggcag gaaccgagtc tccagtgagg gaggagccag    600
gagaggactt ccctgcagca cgtcgcttat attgggatga cctgaagaga aagttgtcgg    660
agaaactgga cagcacagac ttcaccagca ccatcaagct gctgaatgaa aattcatatg    720
tccctcgtga ggctggatct caaaaagatg aaaatcttgc gttgtatgtt gaaaatcaat    780
ttcgtgaatt taaactcagc aaagtctggc gtgatcaaca ttttgttaag attcaggtca    840
aagacagcgc tcaaaactcg gtgatcatag ttgataagaa cggtagactt gtttacctgg    900
tggagaatcc tgggggttat gtggcgtata gtaaggctgc aacagttact ggtaaactgg    960
tccatgctaa ttttggtact aaaaaagatt ttgaggattt atacactcct gtgaatggat   1020
ctatagtgat tgtcagagca gggaaaatca cctttgcaga aaaggttgca aatgctgaaa   1080
gcttaaatgc aattggtgtg ttgatataca tggaccagac taaatttccc attgttaacg   1140
cagaactttc attctttgga catgctcatc tggggacagg tgacccttac acacctggat   1200
tcccttcctt caatcacact cagtttccac catctcggtc atcaggattg cctaatatac   1260
ctgtccagac aatctccaga gctgctgcag aaaagctgtt tgggaatatg gaaggagact   1320
gtccctctga ctggaaaaca gactctacat gtaggatggt aacctcagaa agcaagaatg   1380
tgaagctcac tgtgagcaat gtgctgaaag agataaaaat tcttaacatc tttggagtta   1440
ttaaaggctt tgtagaacca gatcactatg ttgtagttgg ggcccagaga gatgcatggg   1500
gccctggagc tgcaaaatcc ggtgtaggca cagctctcct attgaaactt gcccagatgt   1560
tctcagatat ggtcttaaaa gatgggtttc agcccagcag aagcattatc tttgccagtt   1620
ggagtgctgg agactttgga tcggttggtg ccactgaatg gctagaggga tacctttcgt   1680
ccctgcattt aaaggctttc acttatatta atctggataa agcggttctt ggtaccagca   1740
acttcaaggt ttctgccagc ccactgttgt atacgcttat tgagaaaaca atgcaaaatg   1800
tgaagcatcc ggttactggg caatttctat atcaggacag caactgggcc agcaaagttg   1860
agaaactcac tttagacaat gctgctttcc ctttccttgc atattctgga atcccagcag   1920
tttctttctg tttttgcgag gacacagatt atccttattt gggtaccacc atggacacct   1980
ataaggaact gattgagagg attcctgagt tgaacaaagt ggcacgagca gctgcagagg   2040
tcgctggtca gttcgtgatt aaactaaccc atgatgttga attgaacctg gactatgaga   2100
ggtacaacag ccaactgctt tcatttgtga gggatctgaa ccaatacaga gcagacataa   2160
aggaaatggg cctgagttta cagtggctgt attctgctcg tggagacttc ttccgtgcta   2220
cttccagact aacaacagat ttcgggaatg ctgagaaaac agacagattt gtcatgaaga   2280
aactcaatga tcgtgtcatg agagtggagt atcacttcct ctctccctac gtatctccaa   2340
aagagtctcc tttccgacat gtcttctggg gctccggctc tcacacgctg ccagctttac   2400
tggagaactt gaaactgcgt aaacaaaata acggtgcttt taatgaaacg ctgttcagaa   2460
```

```
accagttggc tctagctact tggactattc agggagctgc aaatgccctc tctggtgacg   2520
tttgggacat tgacaatgag ttttaaatgt gatacccata gcttccatga gaacagcagg   2580
gtagtctggt ttctagactt gtgctgatcg tgctaaattt tcagtagggc tacaaaacct   2640
gatgttaaaa ttccatccca tcatcttggt actactagat gtctttaggc agcagctttt   2700
aatacagggt agataacctg tacttcaagt taaagtgaat aaccacttaa aaaatgtcca   2760
tgatggaata ttcccctatc tctagaattt taagtgcttt gtaatgggaa ctgcctcttt   2820
cctgttgttg ttaatgaaaa tgtcagaaac cagttatgtg aatgatctct ctgaatccta   2880
agggctggtc tctgctgaag gttgtaagtg gttcgcttac tttgagtgat cctccaactt   2940
catttgatgc taaataggag ataccaggtt gaaagacctc tccaaatgag atctaagcct   3000
ttccataagg aatgtagcag gtttcctcat tcctgaaaga aacagttaac tttcagaaga   3060
gatgggcttg ttttcttgcc aatgaggtct gaaatggagg tccttctgct ggataaaatg   3120
aggttcaact gttgattgca ggaataaggc cttaatatgt taacctcagt gtcatttatg   3180
aaaagagggg accagaagcc aaagacttag tatattttct tttcctctgt cccttccccc   3240
ataagcctcc atttagttct ttgttatttt tgtttcttcc aaagcacatt gaaagagaac   3300
cagtttcagg tgtttagttg cagactcagt ttgtcagact ttaaagaata atatgctgcc   3360
aaattttggc caaagtgtta atcttagggg agagctttct gtccttttgg cactgagata   3420
tttattgttt atttatcagt gacagagttc actataaatg gtgttttttt aatagaatat   3480
aattatcgga agcagtgcct tccataatta tgacagttat actgtcggtt ttttttaaat   3540
aaaagcagca tctgctaata aaacccaaca gatactggaa gttttgcatt tatggtcaac   3600
acttaagggt tttagaaaac agccgtcagc caaatgtaat tgaataaagt tgaagctaag   3660
atttagagat gaattaaatt taattagggg ttgctaagaa gcgagcactg accagataag   3720
aatgctggtt ttcctaaatg cagtgaattg tgaccaagtt ataaatcaat gtcacttaaa   3780
ggctgtggta gtactcctgc aaaattttat agctcagttt atccaaggtg taactctaat   3840
tcccatttgc aaaatttcca gtacctttgt cacaatccta acacattatc gggagcagtg   3900
tcttccataa tgtataaaga acaaggtagt tttacctac cacagtgtct gtatcggaga   3960
cagtgatctc catatgttac actaagggtg taagtaatta tcgggaacag tgtttcccat   4020
aattttcttc atgcaatgac atcttcaaag cttgaagatc gttagtatct aacatgtatc   4080
ccaactccta taattcccta tcttttagtt ttagttgcag aaacattttg tggtcattaa   4140
gcattgggtg ggtaaattca accactgtaa aatgaaatta ctacaaaatt tgaaatttag   4200
cttgggtttt tgttaccttt atggtttctc caggtcctct acttaatgag atagcagcat   4260
acatttataa tgtttgctat tgacaagtca ttttaattta tcacattatt tgcatgttac   4320
ctcctataaa cttagtgcgg acaagtttta atccagaatt gaccttttga cttaaagcag   4380
agggactttg tatagaaggt ttgggggctg tggggaagga gagtcccctg aaggtctgac   4440
acgtctgcct acccattcgt ggtgatcaat taaatgtagg tatgaataag ttcgaagctc   4500
cgtgagtgaa ccatcatata aacgtgtagt acagctgttt gtcatagggc agttggaaac   4560
ggcctcctag ggaaaagttc atagggtctc ttcaggttct tagtgtcact tacctagatt   4620
tacagcctca cttgaatgtg tcactactca cagtctcttt aatcttcagt tttatcttta   4680
atctcctctt ttatcttgga ctgacattta gcgtagctaa gtgaaaaggt catagctgag   4740
attcctggtt cgggtgttac gcacacgtac ttaaatgaaa gcatgtggca tgttcatcgt   4800
```

-continued

```
ataacacaat atgaatacag ggcatgcatt ttgcagcagt gagtctcttc agaaaaccct   4860

tttctacagt tagggttgag ttacttccta tcaagccagt acgtgctaac aggctcaata   4920

ttcctgaatg aaatatcaga ctagtgacaa gctcctggtc ttgagatgtc ttctcgttaa   4980

ggagtagggc cttttggagg taaaggtata                                    5010
```

```
<210> SEQ ID NO 326
<211> LENGTH: 2574
<212> TYPE: DNA
<213> ORGANISM: Homo sapiens

<400> SEQUENCE: 326

cctgtttaga cacatggaca acaatcccag cgctacaagg cacacagtcc gcttcttcgt     60

cctcagggtt gccagcgctt cctggaagtc ctgaagctct cgcagtgcag tgagttcatg    120

caccttcttg ccaagcctca gtctttggga tctggggagg ccgcctggtt ttcctccctc    180

cttctgcacg tctgctgggg tctcttcctc tccaggcctt gccgtccccc tggcctctct    240

tcccagctca cacatgaaga tgcacttgca aagggctctg gtggtcctgg ccctgctgaa    300

ctttgccacg gtcagcctct ctctgtccac ttgcaccacc ttggacttcg gccacatcaa    360

gaagaagagg gtggaagcca ttaggggaca gatcttgagc aagctcaggc tcaccagccc    420

ccctgagcca acggtgatga cccacgtccc ctatcaggtc ctggcccttt acaacagcac    480

ccgggagctg ctggaggaga tgcatgggga gagggaggaa ggctgcaccc aggaaaacac    540

cgagtcggaa tactatgcca aagaaatcca taaattcgac atgatccagg ggctggcgga    600

gcacaacgaa ctggctgtct gccctaaagg aattacctcc aaggttttcc gcttcaatgt    660

gtcctcagtg gagaaaaata gaaccaacct attccgagca gaattccggg tcttgcgggt    720

gcccaacccc agctctaagc ggaatgagca gaggatcgag ctcttccaga tccttcggcc    780

agatgagcac attgccaaac agcgctatat cggtggcaag aatctgccca cacggggcac    840

tgccgagtgg ctgtcctttg atgtcactga cactgtgcgt gagtggctgt tgagaagaga    900

gtccaactta ggtctagaaa tcagcattca ctgtccatgt cacacctttc agcccaatgg    960

agatatcctg gaaaacattc acgaggtgat ggaaatcaaa ttcaaaggcg tggacaatga   1020

ggatgaccat ggccgtggag atctggggcg cctcaagaag cagaaggatc accacaaccc   1080

tcatctaatc ctcatgatga ttcccccaca ccggctcgac aacccgggcc agggggggtca   1140

gaggaagaag cgggctttgg acaccaatta ctgcttccgc aacttggagg agaactgctg   1200

tgtgcgcccc ctctacattg acttccgaca ggatctgggc tggaagtggg tccatgaacc   1260

taagggctac tatgccaact tctgctcagg cccttgccca tacctccgca gtgcagacac   1320

aacccacagc acggtgctgg gactgtacaa cactctgaac cctgaagcat ctgcctcgcc   1380

ttgctgcgtg ccccaggacc tggagcccct gaccatcctg tactatgttg ggaggacccc   1440

caaagtggag cagctctcca acatggtggt gaagtcttgt aaatgtagct gagaccccac   1500

gtgcgacaga gagaggggag agagaaccac cactgcctga ctgcccgctc ctcgggaaac   1560

acacaagcaa caaacctcac tgagaggcct ggagcccaca accttcggct ccgggcaaat   1620

ggctgagatg gaggtttcct tttggaacat ttctttcttg ctggctctga gaatcacggt   1680

ggtaaagaaa gtgtgggttt ggttagagga aggctgaact cttcagaaca cacagacttt   1740

ctgtgacgca gacagagggg atggggatag aggaaaggga tggtaagttg agatgttgtg   1800

tggcaatggg atttgggcta ccctaaaggg agaaggaagg gcagagaatg gctgggtcag   1860

ggccagactg gaagacactt cagatctgag gttggatttg ctcattgctg taccacatct   1920
```

```
gctctaggga atctggatta tgttatacaa ggcaagcatt ttttttttta aagacaggtt   1980

acgaagacaa agtcccagaa ttgtatctca tactgtctgg gattaagggc aaatctatta   2040

cttttgcaaa ctgtcctcta catcaattaa catcgtgggt cactacaggg agaaaatcca   2100

ggtcatgcag ttcctggccc atcaactgta ttgggccttt tggatatgct gaacgcagaa   2160

gaaagggtgg aaatcaaccc tctcctgtct gccctctggg tccctcctct cacctctccc   2220

tcgatcatat ttccccttgg acacttggtt agacgccttc caggtcagga tgcacatttc   2280

tggattgtgg ttccatgcag ccttggggca ttatgggtct tcccccactt cccctccaag   2340

accctgtgtt catttggtgt tcctggaagc aggtgctaca acatgtgagg cattcgggga   2400

agctgcacat gtgccacaca gtgacttggc cccagacgca tagactgagg tataaagaca   2460

agtatgaata ttactctcaa aatctttgta taaataaata tttttggggc atcctggatg   2520

atttcatctt ctggaatatt gtttctagaa cagtaaaagc cttattctaa ggtg         2574
```

<210> SEQ ID NO 327
<211> LENGTH: 1421
<212> TYPE: DNA
<213> ORGANISM: Homo sapiens

<400> SEQUENCE: 327

```
acttactgcg ggacggcctt ggagagtact cgggttcgtg aacttcccgg aggcgcaatg     60

agctgcatta acctgcccac tgtgctgccc ggctccccca gcaagacccg ggggcagatc    120

caggtgattc tcgggccgat gttctcagga aaaagcacag agttgatgag acgcgtccgt    180

cgcttccaga ttgctcagta caagtgcctg gtgatcaagt atgccaaaga cactcgctac    240

agcagcagct tctgcacaca tgaccggaac accatggagg cgctgcccgc ctgcctgctc    300

cgagacgtgg cccaggaggc cctgggcgtg gctgtcatag gcatcgacga ggggcagttt    360

ttccctgaca tcatggagtt ctgcgaggcc atggccaacg ccgggaagac cgtaattgtg    420

gctgcactgg atgggacctt ccagaggaag ccatttgggg ccatcctgaa cctggtgccg    480

ctggccgaga gcgtggtgaa gctgacggcg gtgtgcatgg agtgcttccg ggaagccgcc    540

tataccaaga ggctcggcac agagaaggag gtcgaggtga ttgggggagc agacaagtac    600

cactccgtgt gtcggctctg ctacttcaag aaggcctcag gccagcctgc cgggccggac    660

aacaaagaga actgcccagt gccaggaaag ccaggggaag ccgtggctgc caggaagctc    720

tttgccccac agcagattct gcaatgcagc cctgccaact gagggacctg caagggccgc    780

ccgctccctt cctgccactg ccgcctactg gacgctgccc tgcatgctgc ccagccactc    840

caggaggaag tcgggaggcg tggagggtga ccacaccttg gccttctggg aactctcctt    900

tgtgtggctg ccccacctgc cgcatgctcc ctcctctcct acccactggt ctgcttaaag    960

cttccctctc agctgctggg acgatcgccc aggctggagc tggccccgct tggtggcctg   1020

ggatctggca cactccctct ccttggggtg agggacagag ccccacgctg ttgacatcag   1080

cctgcttctt cccctctgcg gctttcactg ctgagtttct gttctccctg ggaagcctgt   1140

gccagcacct ttgagccttg gcccacactg aggcttaggc ctctctgcct gggatgggct   1200

cccaccctcc cctgaggatg gcctggattc acgccctctt gtttcctttt gggctcaaag   1260

cccttcctac ctctggtgat ggtttccaca ggaacaacag catctttcac caagatgggt   1320

ggcaccaacc ttgctgggac ttggatccca ggggcttatc tcttcaagtg tggagagggc   1380

agggtccacg cctctgctgt agcttatgaa attaactaat t                       1421
```

<210> SEQ ID NO 328
<211> LENGTH: 4604
<212> TYPE: DNA
<213> ORGANISM: Homo sapiens

<400> SEQUENCE: 328

```
ggaacagctt gtccacccgc cggccggacc agaagccttt gggtctgaag tgtctgtgag     60
acctcacaga agagcacccc tgggctccac ttacctgccc cctgctcctt cagggatgga    120
ggcaatggcg gccagcactt ccctgcctga ccctggagac tttgaccgga acgtgccccg    180
gatctgtggg gtgtgtggag accgagccac tggctttcac ttcaatgcta tgacctgtga    240
aggctgcaaa ggcttcttca ggcgaagcat gaagcggaag gcactattca cctgcccctt    300
caacggggac tgccgcatca ccaaggacaa ccgacgccac tgccaggcct gccggctcaa    360
acgctgtgtg gacatcggca tgatgaagga gttcattctg acagatgagg aagtgcagag    420
gaagcgggag atgatcctga agcggaagga ggaggaggcc ttgaaggaca gtctgcggcc    480
caagctgtct gaggagcagc agcgcatcat tgccatactg ctggacgccc accataagac    540
ctacgacccc acctactccg acttctgcca gttccggcct ccagttcgtg tgaatgatgg    600
tggagggagc catccttcca ggcccaactc cagacacact cccagcttct ctggggactc    660
ctcctcctcc tgctcagatc actgtatcac ctcttcagac atgatggact cgtccagctt    720
ctccaatctg gatctgagtg aagaagattc agatgaccct tctgtgaccc tagagctgtc    780
ccagctctcc atgctgcccc acctggctga cctggtcagt tacagcatcc aaaaggtcat    840
tggctttgct aagatgatac caggattcag agacctcacc tctgaggacc agatcgtact    900
gctgaagtca agtgccattg aggtcatcat gttgcgctcc aatgagtcct tcaccatgga    960
cgacatgtcc tggacctgtg gcaaccaaga ctacaagtac cgcgtcagtg acgtgaccaa   1020
agccggacac agcctggagc tgattgagcc cctcatcaag ttccaggtgg gactgaagaa   1080
gctgaacttg catgaggagg agcatgtcct gctcatggcc atctgcatcg tctccccaga   1140
tcgtcctggg gtgcaggacg ccgcgctgat tgaggccatc caggaccgcc tgtccaacac   1200
actgcagacg tacatccgct gccgccaccc gcccccgggc agccacctgc tctatgccaa   1260
gatgatccag aagctagccg acctgcgcag cctcaatgag gagcactcca agcagtaccg   1320
ctgcctctcc ttccagcctg agtgcagcat gaagctaacg ccccttgtgc tcgaagtgtt   1380
tggcaatgag atctcctgac taggacagcc tgtgcggtgc ctgggtgggg ctgctcctcc   1440
agggccacgt gccaggcccg gggctggcgg ctactcagca gccctcctca cccgtctggg   1500
gttcagcccc tcctctgcca cctcccctat ccacccagcc cattctctct cctgtccaac   1560
ctaacccctt tcctgcgggc ttttccccgg tcccttgaga cctcagccat gaggagttgc   1620
tgtttgtttg acaaagaaac ccaagtgggg gcagagggca gaggctggag gcaggccttg   1680
cccagagatg cctccaccgc tgcctaagtg gctgctgact gatgttgagg gaacagacag   1740
gagaaatgca tccattcctc agggacagag acacctgcac ctcccccac tgcaggcccc   1800
gcttgtccag cgcctagtgg ggtctccctc tcctgcctta ctcacgataa ataatcggcc   1860
cacagctccc accccacccc cttcagtgcc caccaacatc ccattgccct ggttatattc   1920
tcacgggcag tagctgtggt gaggtgggtt ttcttcccat cactggagca ccaggcacga   1980
acccacctgc tgagagaccc aaggaggaaa aacagacaaa aacagcctca cagaagaata   2040
tgacagctgt ccctgtcacc aagctcacag ttcctcgccc tgggtctaag ggttggttg   2100
aggtggaagc cctccttcca cggatccatg tagcaggact gaattgtccc cagtttgcag   2160
```

-continued

```
aaaagcacct gccgacctcg tcctccccct gccagtgcct tacctcctgc ccaggagagc   2220
cagccctccc tgtcctcctc ggatcaccga gagtagccga gagcctgctc ccccaccccc   2280
tccccagggg agagggtctg gagaagcagt gagccgcatc ttctccatct ggcagggtgg   2340
gatggaggag aagaattttc agaccccagc ggctgagtca tgatctccct gccgcctcaa   2400
tgtggttgca aggccgctgt tcaccacagg gctaagagct aggctgccgc accccagagt   2460
gtgggaaggg agagcggggc agtctcgggt ggctagtcag agagagtgtt tgggggttcc   2520
gtgatgtagg gtaaggtgcc ttcttattct cactccacca cccaaaagtc aaaaggtgcc   2580
tgtgaggcag gggcggagtg atacaacttc aagtgcatgc tctctgcagg tcgagcccag   2640
cccagctggt gggaagcgtc tgtccgttta ctccaaggtg ggtctttgtg agagtgagct   2700
gtaggtgtgc gggaccggta cagaaaggcg ttcttcgagg tggatcacag aggcttcttc   2760
agatcaatgc ttgagtttgg aatcggccgc attccctgag tcaccaggaa tgttaaagtc   2820
agtgggaacg tgactgcccc aactcctgga agctgtgtcc ttgcacctgc atccgtagtt   2880
ccctgaaaac ccagagagga atcagacttc acactgcaag agccttggtg tccacctggc   2940
cccatgtctc tcagaattct tcaggtggaa aaacatctga aagccacgtt ccttactgca   3000
gaatagcata tatatcgctt aatcttaaat ttattagata tgagttgttt tcagactcag   3060
actccatttg tattatagtc taatatacag ggtagcaggt accactgatt tggagatatt   3120
tatgggggga gaacttacat tgtgaaactt ctgtacatta attattattg ctgttgttat   3180
tttacaaggg tctagggaga gacccttgtt tgattttagc tgcagaactg tattggtcca   3240
gcttgctctt cagtgggaga aaaacacttg taagttgcta aacgagtcaa tcccctcatt   3300
caggaaaact gacagaggag ggcgtgactc acccaagcca tatataacta gctagaagtg   3360
ggccaggaca ggccgggcgc ggtggctcac gcctgtaatc ccagcagttt gggaggtcga   3420
ggtaggtgga tcacctgagg tcgggagttc gagaccaacc tgaccaacat ggagaaaccc   3480
tgtctctatt aaaaatacaa aaaaaaaaaa aaaaaaaaat agccgggcat ggtggcgcaa   3540
gcctgtaatc ccagctactc aggaggctga ggcagaagaa ttgaacccag gaggtggagg   3600
ttgcagtgag ctgagatcgt gccgttactc tccaacctgg acaacaagag cgaaactccg   3660
tcttagaagt ggaccaggac aggaccagat tttggagtca tggtccggtg tccttttcac   3720
tacaccatgt ttgagctcag acccccactc tcattcccca ggtggctgac ccagtccctg   3780
ggggaagccc tggatttcag aaagagccaa gtctggatct gggacccttt ccttccttcc   3840
ctggcttgta actccaccaa gcccatcaga aggagaagga aggagactca cctctgcctc   3900
aatgtgaatc agaccctacc ccaccacgat gtgccctggc tgctgggctc tccacctcag   3960
gccttggata atgctgttgc ctcatctata acatgcattt gtctttgtaa tgtcaccacc   4020
ttcccagctc tccctctggc cctgcttctt cggggaactc ctgaaatatc agttactcag   4080
ccctgggccc caccacctag gccactcctc caaaggaagt ctaggagctg ggaggaaaag   4140
aaaagagggg aaaatgagtt tttatggggc tgaacgggga gaaaaggtca tcatcgattc   4200
tactttagaa tgagagtgtg aaatagacat ttgtaaatgt aaaactttta aggtatatca   4260
ttataactga aggagaaggt gccccaaaat gcaagatttt ccacaagatt cccagagaca   4320
ggaaaatcct ctggctggct aactggaagc atgtaggaga atccaagcga ggtcaacaga   4380
gaaggcagga atgtgtggca gatttagtga aagctagaga tatggcagcg aaaggatgta   4440
aacagtgcct gctgaatgat ttccaaagag aaaaaaagtt tgccagaagt ttgtcaagtc   4500
```

-continued

```
aaccaatgta gaaagctttg cttatggtaa taaaaatggc tcatacttat atagcactta   4560

ctttgtttgc aagtactgct gtaaataaat gctttatgca aacc                     4604


<210> SEQ ID NO 329
<211> LENGTH: 2076
<212> TYPE: DNA
<213> ORGANISM: Homo sapiens

<400> SEQUENCE: 329

cggggaaggg gagggaggag ggggacgagg gctctggcgg gtttggaggg gctgaacatc     60

gcggggtgtt ctggtgtccc ccgccccgcc tctccaaaaa gctacaccga cgcggaccgc    120

ggcggcgtcc tccctcgccc tcgcttcacc tcgcgggctc cgaatgcggg gagctcggat    180

gtccggtttc ctgtgaggct tttacctgac acccgccgcc tttccccggc actggctggg    240

agggcgccct gcaaagttgg gaacgcggag ccccggaccc gctcccgccg cctccggctc    300

gcccaggggg ggtcgccggg aggagcccgg gggagaggga ccaggagggg cccgcggcct    360

cgcaggggcg cccgcgcccc cacccctgcc cccgccagcg gaccggtccc ccaccccccgg   420

tccttccacc atgcacttgc tgggcttctt ctctgtggcg tgttctctgc tcgccgctgc    480

gctgctcccg ggtcctcgcg aggcgcccgc cgccgccgcc gccttcgagt ccggactcga    540

cctctcggac gcggagcccg acgcgggcga ggccacggct tatgcaagca aagatctgga    600

ggagcagtta cggtctgtgt ccagtgtaga tgaactcatg actgtactct acccagaata    660

ttggaaaatg tacaagtgtc agctaaggaa aggaggctgg caacataaca gagaacaggc    720

caacctcaac tcaaggacag aagagactat aaaatttgct gcagcacatt ataatacaga    780

gatcttgaaa agtattgata atgagtggag aaagactcaa tgcatgccac gggaggtgtg    840

tatagatgtg gggaaggagt ttggagtcgc gacaaacacc ttctttaaac ctccatgtgt    900

gtccgtctac agatgtgggg gttgctgcaa tagtgagggg ctgcagtgca tgaacaccag    960

cacgagctac ctcagcaaga cgttatttga aattacagtg cctctctctc aaggccccaa   1020

accagtaaca atcagttttg ccaatcacac ttcctgccga tgcatgtcta aactggatgt   1080

ttacagacaa gttcattcca ttattagacg ttccctgcca gcaacactac cacagtgtca   1140

ggcagcgaac aagacctgcc ccaccaatta catgtggaat aatcacatct gcagatgcct   1200

ggctcaggaa gattttatgt tttcctcgga tgctggagat gactcaacag atggattcca   1260

tgacatctgt ggaccaaaca aggagctgga tgaagagacc tgtcagtgtg tctgcagagc   1320

ggggcttcgg cctgccagct gtggacccca caaagaacta gacagaaact catgccagtg   1380

tgtctgtaaa aacaaactct tccccagcca atgtggggcc aaccgagaat ttgatgaaaa   1440

cacatgccag tgtgtatgta aaagaacctg ccccagaaat caacccctaa atcctggaaa   1500

atgtgcctgt gaatgtacag aaagtccaca gaaatgcttg ttaaaaggaa agaagttcca   1560

ccaccaaaca tgcagctgtt acagacggcc atgtacgaac cgccagaagg cttgtgagcc   1620

aggattttca tatagtgaag aagtgtgtcg ttgtgtccct tcatattgga aaagaccaca   1680

aatgagctaa gattgtactg ttttccagtt catcgatttt ctattatgga aaactgtgtt   1740

gccacagtag aactgtctgt gaacagagag acccttgtgg gtccatgcta acaaagacaa   1800

aagtctgtct ttcctgaacc atgtggataa ctttacagaa atggactgga gctcatctgc   1860

aaaaggcctc ttgtaaagac tggttttctg ccaatgacca aacagccaag attttcctct   1920

tgtgatttct ttaaaagaat gactatataa tttatttcca ctaaaaatat tgtttctgca   1980

ttcattttta tagcaacaac aattggtaaa actcactgtg atcaatattt ttatatcatg   2040
```

caaaatatgt ttaaaataaa atgaaaattg tattat 2076

<210> SEQ ID NO 330
<211> LENGTH: 2819
<212> TYPE: DNA
<213> ORGANISM: Homo sapiens

<400> SEQUENCE: 330
ctgggcccag ctcccccgag aggtggtcgg atcctctggg ctgctcggtc gatgcctgtg 60
ccactgacgt ccaggcatga ggtggttcct gccctggacg ctggcagcag tgacagcagc 120
agccgccagc accgtcctgg ccacggccct ctctccagcc cctacgacca tggactttac 180
cccagctcca ctggaggaca cctcctcacg cccccaattc tgcaagtggc catgtgagtg 240
cccgccatcc ccaccccgct gcccgctggg ggtcagcctc atcacagatg gctgtgagtg 300
ctgtaagatg tgcgctcagc agcttgggga caactgcacg gaggctgcca tctgtgaccc 360
ccaccggggc ctctactgtg actacagcgg ggaccgcccg aggtacgcaa taggagtgtg 420
tgcacaggtg gtcggtgtgg gctgcgtcct ggatggggtg cgctacaaca acggccagtc 480
cttccagcct aactgcaagt acaactgcac gtgcatcgac ggcgcggtgg gctgcacacc 540
actgtgcctc cgagtgcgcc ccccgcgtct ctggtgcccc cacccgcggc gcgtgagcat 600
acctggccac tgctgtgagc agtgggtatg tgaggacgac gccaagaggc cacgcaagac 660
cgcaccccgt gacacaggag ccttcgatgc tgtgggtgag gtggaggcat ggcacaggaa 720
ctgcatagcc tacacaagcc cctggagccc ttgctccacc agctgcggcc tgggggtctc 780
cactcggatc tccaatgtta acgcccagtg ctggcctgag caagagagcc gcctctgcaa 840
cttgcggcca tgcgatgtgg acatccatac actcattaag gcagggaaga agtgtctggc 900
tgtgtaccag ccagaggcat ccatgaactt cacacttgcg ggctgcatca gcacacgctc 960
ctatcaaccc aagtactgtg gagtttgcat ggacaatagg tgctgcatcc cctacaagtc 1020
taagactatc gacgtgtcct tccagtgtcc tgatgggctt ggcttctccc gccaggtcct 1080
atggattaat gcctgcttct gtaacctgag ctgtaggaat cccaatgaca tctttgctga 1140
cttggaatcc taccctgact tctcagaaat tgccaactag gcaggcacaa atcttgggtc 1200
ttggggacta acccaatgcc tgtgaagcag tcagccctta tggccaataa cttttcacca 1260
atgagcctta gttaccctga tctggaccct tggcctccat ttctgtctct aaccattcaa 1320
atgacgcctg atggtgctgc tcaggcccat gctatgagtt ttctccttga tatcattcag 1380
catctactct aaagaaaaat gcctgtctct agctgttctg gactacaccc aagcctgatc 1440
cagcctttcc aagtcactag aagtcctgct ggatcttgcc taaatcccaa gaaatggaat 1500
caggtagact tttaatatca ctaatttctt ctttagatgc caaaccacaa gactctttgg 1560
gtccattcag atgaatagat ggaatttgga acaatagaat aatctattat ttggagcctg 1620
ccaagaggta ctgtaatggg taattctgac gtcagcgcac caaaactatc ctgattccaa 1680
atatgtatgc acctcaaggt catcaaacat ttgccaagtg agttgaatag ttgcttaatt 1740
ttgattttta atggaaagtt gtatccatta acctgggcat tgttgaggtt aagtttctct 1800
tcacccctac actgtgaagg gtacagatta ggtttgtccc agtcagaaat aaaatttgat 1860
aaacattcct gttgatggga aaagccccca gttaatactc cagagacagg gaaaggtcag 1920
cccgtttcag aaggaccaat tgactctcac actgaatcag ctgctgactg gcagggcttt 1980
gggcagttgg ccaggctctt ccttgaatct tctcccttgt cctgcttggg gttcatagga 2040

-continued

```
attggtaagg cctctggact ggcctgtctg gcccctgaga gtggtgccct ggaacactcc   2100
tctactctta cagagccttg agagacccag ctgcagacca tgccagaccc actgaaatga   2160
ccaagacagg ttcaggtagg ggtgtgggtc aaaccaagaa gtgggtgccc ttggtagcag   2220
cctggggtga cctctagagc tggaggctgt gggactccag gggcccccgt gttcaggaca   2280
catctattgc agagactcat ttcacagcct ttcgttctgc tgaccaaatg gccagttttc   2340
tggtaggaag atggaggttt accggttgtt tagaaacaga aatagactta ataaaggttt   2400
aaagctgaag aggttgaagc taaaaggaaa aggttgttgt taatgaatat caggctatta   2460
tttattgtat taggaaaata taatatttac tgttagaatt cttttattta gggccttttc   2520
tgtgccagac attgctctca gtgctttgca tgtattagct cactgaatct tcacgacaat   2580
gttgagaagt tcccattatt atttctgttc ttacaaatgt gaaacggaag ctcatagagg   2640
tgagaaaact caaccagagt cacccagttg gtgactggga aagttaggat tcagatcgaa   2700
attggactgt ctttataacc catattttcc ccctgttttt agagcttcca aatgtgtcag   2760
aataggaaaa cattgcaata aatggcttga ttttttaaaa aaaaaaaaaa aaaaaaaaa    2819
```

<210> SEQ ID NO 331
<211> LENGTH: 2540
<212> TYPE: DNA
<213> ORGANISM: Homo sapiens

<400> SEQUENCE: 331

```
gaaaaggtgg acaagtccta ttttcaagag aagatgactt ttaacagttt tgaaggatct     60
aaaacttgtg tacctgcaga catcaataag gaagaagaat ttgtagaaga gtttaataga    120
ttaaaaactt ttgctaattt tccaagtggt agtcctgttt cagcatcaac actggcacga    180
gcagggtttc tttatactgg tgaaggagat accgtgcggt gctttagttg tcatgcagct    240
gtagatagat ggcaatatgg agactcagca gttggaagac acaggaaagt atccccaaat    300
tgcagattta tcaacggctt ttatcttgaa aatagtgcca cgcagtctac aaattctggt    360
atccagaatg gtcagtacaa agttgaaaac tatctgggaa gcagagatca ttttgcctta    420
gacaggccat ctgagacaca tgcagactat cttttgagaa ctgggcaggt tgtagatata    480
tcagacacca tatacccgag gaaccctgcc atgtattgtg aagaagctag attaaagtcc    540
tttcagaact ggccagacta tgctcaccta accccaagag agttagcaag tgctggactc    600
tactacacag gtattggtga ccaagtgcag tgcttttgtt gtggtggaaa actgaaaaat    660
tgggaacctt gtgatcgtgc ctggtcagaa cacaggcgac actttcctaa ttgcttcttt    720
gttttgggcc ggaatcttaa tattcgaagt gaatctgatg ctgtgagttc tgataggaat    780
ttcccaaatt caacaaatct tccaagaaat ccatccatgg cagattatga agcacggatc    840
tttacttttg ggacatggat atactcagtt aacaaggagc agcttgcaag agctggattt    900
tatgctttag gtgaaggtga taaagtaaag tgctttcact gtggaggagg gctaactgat    960
tggaagccca gtgaagaccc ttgggaacaa catgctaaat ggtatccagg gtgcaaatat   1020
ctgttagaac agaagggaca agaatatata aacaatattc atttaactca ttcacttgag   1080
gagtgtctgg taagaactac tgagaaaaca ccatcactaa ctagaagaat tgatgatacc   1140
atcttccaaa atcctatggt acaagaagct atacgaatgg ggttcagttt caaggacatt   1200
aagaaaataa tggaggaaaa aattcagata tctgggagca actataaatc acttgaggtt   1260
ctggttgcag atctagtgaa tgctcagaaa gacagtatgc aagatgagtc aagtcagact   1320
tcattacaga aagagattag tactgaagag cagctaaggc gcctgcaaga ggagaagctt   1380
```

```
tgcaaaatct gtatggatag aaatattgct atcgtttttg ttccttgtgg acatctagtc   1440

acttgtaaac aatgtgctga agcagttgac aagtgtccca tgtgctacac agtcattact   1500

ttcaagcaaa aaatttttat gtcttaatct aactctatag taggcatgtt atgttgttct   1560

tattaccctg attgaatgtg tgatgtgaac tgactttaag taatcaggat tgaattccat   1620

tagcatttgc taccaagtag gaaaaaaaat gtacatggca gtgttttagt tggcaatata   1680

atctttgaat ttcttgattt ttcagggtat tagctgtatt atccattttt tttactgtta   1740

tttaattgaa accatagact aagaataaga agcatcatac tataactgaa cacaatgtgt   1800

attcatagta tactgattta atttctaagt gtaagtgaat taatcatctg gatttttttat   1860

tcttttcaga taggcttaac aaatggagct ttctgtatat aaatgtggag attagagtta   1920

atctccccaa tcacataatt tgttttgtgt gaaaaaggaa taaattgttc catgctggtg   1980

gaaagataga gattgttttt agaggttggt tgttgtgttt taggattctg tccattttct   2040

tgtaaaggga taaacacgga cgtgtgcgaa atatgtttgt aaagtgattt gccattgttg   2100

aaagcgtatt taatgataga atactatcga gccaacatgt actgacatgg aaagatgtca   2160

gagatatgtt aagtgtaaaa tgcaagtggc gggacactat gtatagtctg agccagatca   2220

aagtatgtat gttgttaata tgcatagaac gagagatttg gaaagatata caccaaactg   2280

ttaaatgtgg tttctcttcg gggagggggg gattggggga ggggccccag aggggtttta   2340

gaggggcctt ttcactttcg acttttttca ttttgttctg ttcggatttt ttataagtat   2400

gtagaccccg aagggtttta tggaactaa catcagtaac ctaacccccg tgactatcct   2460

gtgctcttcc tagggagctg tgttgtttcc cacccaccac ccttccctct gaacaaatgc   2520

ctgagtgctg gggcactttg                                               2540
```

<210> SEQ ID NO 332
<211> LENGTH: 1474
<212> TYPE: DNA
<213> ORGANISM: Homo sapiens

<400> SEQUENCE: 332

```
aaaaagaaat caagaatgca attttattta caatagtcac gccggaaata cctagaaata     60

aatttaactg aggatgtaaa agacctctac aaggagagtt caatgcgtag cgggagcgga    120

gagctgaccc cagagagccc tgggcagccc cacctccgcc gccggcctag ttaccatcac    180

accccggaga gcccgcagct gccgcagccg gccccagtca ccatcaccgc aaccatgagc    240

agcgaggccg agacccagca gccgcccgcc gcccccccg ccgcccccgc cctcagcgcc    300

gccgacacca agcccggcac taccggagcg gcgcagggag cggtggcccg ggcggctcac    360

atcggcggcg ctggcgcggg cgacaagaag gtcatcgcaa cgaaggtttt gggaacagta    420

aaatggttca atgtaaggaa cggatatggt ttcatcaaca ggaatgacac caaggaagat    480

gtatttgtac accagactgc cataaagaag aataacccca ggaagtacct tcgcagtgta    540

ggagatggag agactgtgga gtttgatgtt gttgaaggag aaaagggtgc ggaggcagca    600

aatgttacag gtcctggtgg tgttccagtt caaggcagta aatatgcagc agaccgtaac    660

cattatagac gctatccacg tcgtaggggt cctccacgca attaccagca aaattaccag    720

aatagtgaga gtggggaaaa gaacgaggga tcggagagtg ctcccgaagc caggcccaac    780

aacgccggcc ctacgcaggc gaaggttccc accttactac atgcggagac ctatgggcgt    840

cgaccacagt attccaaccc tcctgtgcag ggagaagtga tggagggtgc tgacaaccag    900
```

-continued

```
ggtgcaggag aacaaggtag accagtgagg cagatatgta tcggggatat agaccacgat    960
tccgcagggg ccctcctcgc caaaagacag cctagagagg acggcaatga agaagataaa   1020
gaaaatcaag gagatgagac ccaaggtcag cagccacctc aagctcggta ccgccgcaac   1080
ttcaattacc gacgcagacg cccagaaaac cctaaaccac aagatggcaa agagacaaaa   1140
gcagccgatc caccagctga gaattcgtcc gctcccgagg ctgagcaggg cggggctgag   1200
taaatgccgg cttaccatct ctaccatcat ccggtttagt catccaacaa gaagaaatat   1260
gaaattccag caataagaaa tgaacaaaag attggagctg aagacctaaa gtgcttgctt   1320
tttgcccgtt gaccagataa atagaactat ctgcattatc tatgcagcat ggggtttttta  1380
ttatgtttta cctaaagacg tctctttttg gtaataacaa accgtgtttt ttaaaaaagc   1440
ctggtttttc tcaatacgcc tttaaaggaa ttcc                               1474
```

<210> SEQ ID NO 333
<211> LENGTH: 4079
<212> TYPE: DNA
<213> ORGANISM: Homo sapiens

<400> SEQUENCE: 333

```
ggagcggcgg gcgggcggga gggctggcgg ggcgaacgtc tgggagacgt ctgaaagacc     60
aacgagactt tggagaccag agacgcgcct ggggggacct ggggcttggg gcgtgcgaga    120
tttcccttgc attcgctggg agctcgcgca gggatcgtcc catggccggg gctcggagcc    180
gcgacccttg gggggcctcc gggatttgct accttttttgg ctccctgctc gtcgaactgc   240
tcttctcacg ggctgtcgcc ttcaatctgg acgtgatggg tgccttgcgc aaggagggcg    300
agccaggcag cctcttcggc ttctctgtgg ccctgcaccg gcagttgcag ccccgacccc    360
agagctggct gctggtgggt gctccccagg ccctggctct tcctgggcag caggcgaatc    420
gcactggagg cctcttcgct tgcccgttga gcctggagga gactgactgc tacagagtgg    480
acatcgacca gggagctgat atgcaaaagg aaagcaagga gaaccagtgg ttgggagtca    540
gtgttcggag ccaggggcct gggggcaaga ttgttacctg tgcacaccga tatgaggcaa    600
ggcagcgagt ggaccagatc ctggagacgc gggatatgat tggtcgctgc tttgtgctca    660
gccaggacct ggccatccgg gatgagttgg atggtgggga atggaagttc tgtgagggac    720
gccccccaagg ccatgaacaa tttgggttct gccagcaggg cacagctgcc gccttctccc   780
ctgatagcca ctacctcctc tttggggccc caggaaccta taattggaag ggggttgcttt   840
ttgtgaccaa cattgatagc tcagaccccg accagctggt gtataaaact ttggaccctg    900
ctgaccggct cccaggacca gccggagact tggccctcaa tagctactta ggcttctcta    960
ttgactcggg gaaaggtctg gtgcgtgcag aagagctgag ctttgtggct ggagcccccc   1020
gcgccaacca caagggtgct gtggttatcc tgcgcaagga cagcgccagt cgcctggtgc   1080
ccgaggttat gctgtctggg gagcgcctga cctccggctt tggctactca ctggctgtgg   1140
ctgacctcaa cagtgatggc tggccagacc tgatagtggg tgccccctac ttctttgagc   1200
gccaagaaga gctgggggggt gctgtgtatg tgtacttgaa ccagggggggt cactgggctg  1260
ggatctcccc tctccggctc tgcggctccc ctgactccat gttcgggatc agcctggctg   1320
tcctggggga cctcaaccaa gatggctttc cagatattgc agtgggtgcc ccctttgatg   1380
gtgatgggaa agtcttcatc taccatggga gcagcctggg ggttgtcgcc aaaccttcac   1440
aggtgctgga gggcgaggct gtgggcatca agagcttcgg ctactccctg tcaggcagct   1500
tggatatgga tgggaaccaa taccctgacc tgctggtggg ctccctggct gacaccgcag   1560
```

-continued

```
tgctcttcag ggccagaccc atcctccatg tctcccatga ggtctctatt gctccacgaa   1620
gcatcgacct ggagcagccc aactgtgctg gcggccactc ggtctgtgtg gacctaaggg   1680
tctgtttcag ctacattgca gtccccagca gctatagccc tactgtggcc ctggactatg   1740
tgttagatgc ggacacagac cggaggctcc ggggccaggt tccccgtgtg acgttcctga   1800
gccgtaacct ggaagaaccc aagcaccagg cctcgggcac cgtgtggctg aagcaccagc   1860
atgaccgagt ctgtggagac gccatgttcc agctccagga aaatgtcaaa gacaagcttc   1920
gggccattgt agtgaccttg tcctacagtc tccagacccc tcggctccgg cgacaggctc   1980
ctggccaggg gctgcctcca gtggccccca tcctcaatgc ccaccagccc agcacccagc   2040
gggcagagat ccacttcctg aagcaaggct gtggtgaaga caagatctgc cagagcaatc   2100
tgcagctggt ccacgcccgc ttctgtaccc gggtcagcga cacggaattc caacctctgc   2160
ccatggatgt ggatggaaca acagccctgt ttgcactgag tgggcagcca gtcattggcc   2220
tggagctgat ggtcaccaac ctgccatcgg acccagccca gccccaggct gatggggatg   2280
atgcccatga agcccagctc ctggtcatgc ttcctgactc actgcactac tcaggggtcc   2340
gggccctgga ccctgcggag aagccactct gcctgtccaa tgagaatgcc tcccatgttg   2400
agtgtgagct ggggaacccc atgaagagag gtgcccaggt caccttctac ctcatcctta   2460
gcacctccgg gatcagcatt gagaccacgg aactggaggt agagctgctg ttggccacga   2520
tcagtgagca ggagctgcat ccagtctctg cacgagcccg tgtcttcatt gagctgccac   2580
tgtccattgc aggaatggcc attccccagc aactcttctt ctctggtgtg gtgaggggcg   2640
agagagccat gcagtctgag cgggatgtgg gcagcaaggt caagtatgag gtcacggttt   2700
ccaaccaagg ccagtcgctc agaaccctgg gctctgcctt cctcaacatc atgtggcctc   2760
atgagattgc caatgggaag tggttgctgt acccaatgca ggttgagctg gagggcgggc   2820
aggggcctgg gcagaaaggg ctttgctctc ccaggcccaa catcctccac ctggatgtgg   2880
acagtaggga taggaggcgg cgggagctgg agccacctga gcagcaggag cctggtgagc   2940
ggcaggagcc cagcatgtcc tggtggccag tgtcctctgc tgagaagaag aaaaacatca   3000
ccctggactg cgcccggggc acggccaact gtgtggtgtt cagctgccca ctctacagct   3060
ttgaccgcgc ggctgtgctg catgtctggg gccgtctctg gaacagcacc tttctggagg   3120
agtactcagc tgtgaagtcc ctggaagtga ttgtccgggc caacatcaca gtgaagtcct   3180
ccataaagaa cttgatgctc cgagatgcct ccacagtgat cccagtgatg gtatacttgg   3240
accccatggc tgtggtggca gaaggagtgc cctggtgggt catcctcctg gctgtactgg   3300
ctgggctgct ggtgctagca ctgctggtgc tgctcctgtg gaagatggga ttcttcaaac   3360
gggcgaagca ccccgaggcc accgtgcccc agtaccatgc ggtgaagatt cctcgggaag   3420
accgacagca gttcaaggag gagaagacgg gcaccatcct gaggaacaac tggggcagcc   3480
cccggcggga gggcccggat gcacacccca tcctggctgc tgacgggcat cccgagctgg   3540
gccccgatgg gcatccaggg ccaggcaccg cctaggttcc catgtcccag cctggcctgt   3600
ggctgccctc catcccttcc ccagagatgg ctccttggga tgaagagggt agagtgggct   3660
gctggtgtcg catcaagatt tggcaggatc ggcttcctca ggggcacaga cctctcccac   3720
ccacaagaac tcctcccacc caacttcccc ttagagtgct gtgagatgag agtgggtaaa   3780
tcagggacag ggccatgggg tagggtgaga agggcagggg tgtcctgatg caaaggtggg   3840
gagaagggat cctaatccct tcctctccca ttcaccctgt gtaacaggac cccaaggacc   3900
```

-continued tgcctccccg gaagtgcctt aacctagagg gtcggggagg aggttgtgtc actgactcag 3960
gctgctcctt ctctagtttc ccctctcatc tgaccttagt ttgctgccat cagtctagtg 4020
gtttcgtggt ttcgtctatt tattaaaaaa tatttgagaa caaaaaaaaa aaaaaaaaa 4079

<210> SEQ ID NO 334
<211> LENGTH: 3373
<212> TYPE: DNA
<213> ORGANISM: Homo sapiens

<400> SEQUENCE: 334
ggtggcaact tctcctcctg cggccgggag cggcctgcct gcctccctgc gcacccgcag 60
cctcccccgc tgcctcccta gggctcccct ccggccgcca gcgcccattt ttcattccct 120
agatagagat actttgcgcg cacacacata catacgcgcg caaaaaggaa aaaaaaaaaa 180
aaaagcccac cctccagcct cgctgcaaag agaaaaccgg agcagccgca gctcgcagct 240
cgcagctcgc agcccgcagc ccgcagagga cgcccagagc ggcgagcagg cgggcagacg 300
gaccgacgga ctcgcgccgc gtccacctgt cggccgggcc cagccgagcg cgcagcgggc 360
acgccgcgcg cgcggagcag ccgtgcccgc cgcccgggcc cgccgccagg gcgcacacgc 420
tcccgccccc ctacccggcc cgggcgggag tttgcacctc tccctgcccg ggtgctcgag 480
ctgccgttgc aaagccaact ttggaaaaag ttttttgggg gagacttggg ccttgaggtg 540
cccagctccg cgctttccga ttttgggggc ctttccagaa aatgttgcaa aaaagctaag 600
ccggcgggca gaggaaaacg cctgtagccg gcgagtgaag acgaaccatc gactgccgtg 660
ttccttttcc tcttggaggt tggagtcccc tgggcgcccc cacacggcta gacgcctcgg 720
ctggttcgcg acgcagcccc ccggccgtgg atgctgcact cgggctcggg atccgcccag 780
gtagccggcc tcggacccag gtcctgcgcc caggtcctcc cctgcccccc agcgacggag 840
ccggggccgg gggcggcggc gccgggggca tgcgggtgag ccgcggctgc agaggcctga 900
gcgcctgatc gccgcggacc tgagccgagc ccaccccccct ccccagcccc ccaccctggc 960
cgcgggggcg gcgcgctcga tctacgcgtc cggggccccg cggggccggg cccggagtcg 1020
gcatgaatcg ctgctgggcg ctcttcctgt ctctctgctg ctacctgcgt ctggtcagcg 1080
ccgaggggga ccccattccc gaggagcttt atgagatgct gagtgaccac tcgatccgct 1140
cctttgatga tctccaacgc ctgctgcacg gagaccccgg agaggaagat ggggccgagt 1200
tggacctgaa catgacccgc tcccactctg gaggcgagct ggagagcttg gctcgtggaa 1260
gaaggagcct gggttccctg accattgctg agccggccat gatcgccgag tgcaagacgc 1320
gcaccgaggt gttcgagatc tcccggcgcc tcatagaccg caccaacgcc aacttcctgg 1380
tgtggccgcc ctgtgtggag gtgcagcgct gctccggctg ctgcaacaac cgcaacgtgc 1440
agtgccgccc cacccaggtg cagctgcgac ctgtccaggt gagaaagatc gagattgtgc 1500
ggaagaagcc aatctttaag aaggccacgg tgacgctgga agaccacctg gcatgcaagt 1560
gtgagacagt ggcagctgca cggcctgtga cccgaagccc gggggggttcc caggagcagc 1620 gagccaaaac gccccaaact cgggtgacca ttcggacggt gcgagtccgc cggcccccca 1680
agggcaagca ccggaaattc aagcacacgc atgacaagac ggcactgaag gagacccttg 1740
gagcctaggg gcatcggcag gagagtgtgt gggcagggtt atttaatatg gtatttgctg 1800
tattgccccc atggggtcct tggagtgata atattgtttc cctcgtccgt ctgtctcgat 1860
gcctgattcg gacggccaat ggtgcttccc ccacccctcc acgtgtccgt ccacccttcc 1920
atcagcgggt ctcctcccag cggcctccgg tcttgcccag cagctcaaag aagaaaaaga 1980

```
aggactgaac tccatcgcca tcttcttccc ttaactccaa gaacttggga taagagtgtg   2040
agagagactg atggggtcgc tctttggggg aaacgggttc cttcccctgc acctggcctg   2100
ggccacacct gagcgctgtg gactgtcctg aggagccctg aggacctctc agcatagcct   2160
gcctgatccc tgaacccctg gccagctctg aggggaggca cctccaggca ggccaggctg   2220
cctcggactc catggctaag accacagacg ggcacacaga ctggagaaaa cccctcccac   2280
ggtgcccaaa caccagtcac ctcgtctccc tggtgcctct gtgcacagtg gcttcttttc   2340
gttttcgttt tgaagacgtg gactcctctt ggtgggtgtg gccagcacac caagtggctg   2400
ggtgccctct caggtgggtt agagatggag tttgctgttg aggtggtgta gatggtgacc   2460
tgggtatccc ctgcctcctg ccacccccttc ctccccatac tccactctga ttcacctctt   2520
cctctggttc ctttcatctc tctacctcca ccctgcattt tcctcttgtc ctggcccttc   2580
agtctgctcc accaaggggc tcttgaaccc cttattaagg ccccagatga ccccagtcac   2640
tcctctctag ggcagaagac tagaggccag ggcagcaagg gacctgctca tcatattcca   2700
acccagccac gactgccatg taaggttgtg cagggtgtgt actgcacaag gacattgtat   2760
gcagggagca ctgttcacat catagataaa gctgatttgt atatttatta tgacaatttc   2820
tggcagatgt aggtaaagag gaaaaggatc cttttcctaa ttcacacaaa gactccttgt   2880
ggactggctg tgcccctgat gcagcctgtg gctggagtgg ccaaatagga gggagactgt   2940
ggtaggggca gggaggcaac actgctgtcc acatgacctc catttcccaa agtcctctgc   3000
tccagcaact gcccttccag gtgggtgtgg gacacctggg agaaggtctc caagggaggg   3060
tgcagccctc ttgcccgcac ccctccctgc ttgcacactt ccccatcttt gatccttctg   3120
agctccacct ctggtggctc ctcctaggaa accagctcgt gggctgggaa tgggggagag   3180
aagggaaaag atccccaaga ccccctgggg tgggatctga gctcccacct cccttcccac   3240
ctactgcact ttcccccttc ccgccttcca aaacctgctt ccttcagttt gtaaagtcgg   3300
tgattatatt tttgggggct ttccttttat tttttaaatg taaaatttat ttatattccg   3360
tatttaaagt tgt                                                      3373
```

<210> SEQ ID NO 335
<211> LENGTH: 2304
<212> TYPE: DNA
<213> ORGANISM: Homo sapiens

<400> SEQUENCE: 335

```
gtccccgcag cgccgtcgcg ccctcctgcc gcaggccacc gaggccgccg ccgtctagcg     60
ccccgacctc gccaccatga gagccctgct ggcgcgcctg cttctctgcg tcctggtcgt    120
gagcgactcc aaaggcagca atgaacttca tcaagttcca tcgaactgtg actgtctaaa    180
tggaggaaca tgtgtgtcca acaagtactt ctccaacatt cactggtgca actgcccaaa    240
gaaattcgga gggcagcact gtgaaataga taagtcaaaa acctgctatg aggggaatgg    300
tcacttttac cgaggaaagg ccagcactga caccatgggc cggccctgcc tgccctggaa    360
ctctgccact gtccttcagc aaacgtacca tgcccacaga tctgatgctc ttcagctggg    420
cctggggaaa cataattact gcaggaaccc agacaaccgg aggcgaccct ggtgctatgt    480
gcaggtgggc ctaaagccgc ttgtccaaga gtgcatggtg catgactgcg cagatggaaa    540
aaagccctcc tctcctccag aagaattaaa atttcagtgt ggccaaaaga ctctgaggcc    600
ccgctttaag attattgggg gagaattcac caccatcgag aaccagccct ggtttgcggc    660
```

-continued

```
catctacagg aggcaccggg ggggctctgt cacctacgtg tgtggaggca gcctcatcag    720
cccttgctgg gtgatcagcg ccacacactg cttcattgat tacccaaaga aggaggacta    780
catcgtctac ctgggtcgct caaggcttaa ctccaacacg caaggggaga tgaagtttga    840
ggtggaaaac ctcatcctac acaaggacta cagcgctgac acgcttgctc accacaacga    900
cattgccttg ctgaagatcc gttccaagga gggcaggtgt gcgcagccat cccggactat    960
acagaccatc tgcctgccct cgatgtataa cgatccccag tttggcacaa gctgtgagat   1020
cactggcttt ggaaaagaga attctaccga ctatctctat ccggagcagc tgaaaatgac   1080
tgttgtgaag ctgatttccc accgggagtg tcagcagccc cactactacg gctctgaagt   1140
caccaccaaa atgctatgtg ctgctgaccc ccaatggaaa acagattcct gccagggaga   1200
ctcaggggga cccctcgtct gttccctcca aggccgcatg actttgactg gaattgtgag   1260
ctggggccgt ggatgtgccc tgaaggacaa gccaggcgtc tacacgagag tctcacactt   1320
cttaccctgg atccgcagtc acaccaagga agagaatggc ctggccctct gagggtcccc   1380
agggaggaaa cgggcaccac ccgctttctt gctggttgtc atttttgcag tagagtcatc   1440
tccatcagct gtaagaagag actgggaaga taggctctgc acagatggat ttgcctgtgg   1500
caccaccagg gtgaacgaca atagctttac cctcacggat aggcctgggt gctggctgcc   1560
cagaccctct ggccaggatg gaggggtggt cctgactcaa catgttactg accagcaact   1620
tgtctttttc tggactgaag cctgcaggag ttaaaaaggg cagggcatct cctgtgcatg   1680
ggctcgaagg gagagccagc tcccccgacc ggtgggcatt tgtgaggccc atggttgaga   1740
aatgaataat ttcccaatta ggaagtgtaa gcagctgagg tctcttgagg gagcttagcc   1800
aatgtgggag cagcggtttg gggagcagag acactaacga cttcagggca gggctctgat   1860
attccatgaa tgtatcagga aatatatatg tgtgtgtatg tttgcacact tgttgtgtgg   1920
gctgtgagtg taagtgtgag taagagctgg tgtctgattg ttaagtctaa atatttcctt   1980
aaactgtgtg gactgtgatg ccacacagag tggtctttct ggagaggtta taggtcactc   2040
ctggggcctc ttgggtcccc cacgtgacag tgcctgggaa tgtacttatt ctgcagcatg   2100
acctgtgacc agcactgtct cagtttcact ttcacataga tgtccctttc ttggccagtt   2160
atcccttcct tttagcctag ttcatccaat cctcactggg tggggtgagg accactcctt   2220
acactgaata tttatatttc actattttta tttatatttt tgtaatttta aataaaagtg   2280
atcaataaaa tgtgattttt ctga                                          2304
```

<210> SEQ ID NO 336
<211> LENGTH: 1876
<212> TYPE: DNA
<213> ORGANISM: Homo sapiens

<400> SEQUENCE: 336

```
cgcggccgcg gttcgctgtg gcgggcgcct gggccgccgg ctgtttaact tcgcttccgc     60
tggcccatag tgatctttgc agtgacccag cagcatcact gtttcttggc gtgtgaagat    120
aacccaagga attgaggaag ttgctgagaa gagtgtgctg gagatgctct aggaaaaaat    180
tgaatagtga gacgagttcc agcgcaaggg tttctggttt gccaagaaga aagtgaacat    240
catggatcag aacaacagcc tgccacctta cgctcagggc ttggcctccc ctcagggtgc    300
catgactccc ggaatcccta tctttagtcc aatgatgcct tatggcactg gactgacccc    360
acagcctatt cagaacacca atagtctgtc tattttggaa gagcaacaaa ggcagcagca    420
gcaacaacaa cagcagcagc agcagcagca gcagcagcaa cagcaacagc agcagcagca    480
```

```
gcagcagcag cagcagcagc agcagcagca gcagcagcag caacaggcag tggcagctgc    540
agccgttcag cagtcaacgt cccagcaggc aacacaggga acctcaggcc aggcaccaca    600
gctcttccac tcacagactc tcacaactgc acccttgccg ggcaccactc cactgtatcc    660
ctcccccatg actcccatga cccccatcac tcctgccacg ccagcttcgg agagttctgg    720
gattgtaccg cagctgcaaa atattgtatc cacagtgaat cttggttgta aacttgacct    780
aaagaccatt gcacttcgtg cccgaaacgc cgaatataat cccaagcggt ttgctgcggt    840
aatcatgagg ataagagagc cacgaaccac ggcactgatt ttcagttctg ggaaaatggt    900
gtgcacagga gccaagagtg aagaacagtc cagactggca gcaagaaaat atgctagagt    960
tgtacagaag ttgggttttc cagctaagtt cttggacttc aagattcaga acatggtggg   1020
gagctgtgat gtgaagtttc ctataaggtt agaaggcctt gtgctcaccc accaacaatt   1080
tagtagttat gagccagagt tatttcctgg tttaatctac agaatgatca aacccagaat   1140
tgttctcctt atttttgttt ctggaaaagt tgtattaaca ggtgctaaag tcagagcaga   1200
aatttatgaa gcatttgaaa acatctaccc tattctaaag ggattcagga agacgacgta   1260
atggctctca tgtacccttg cctcccccac cccctttcttt tttttttttt aaacaaatca   1320
gtttgttttg gtacctttaa atggtggtgt tgtgagaaga tggatgttga gttgcagggt   1380
gtggcaccag gtgatgccct tctgtaagtg cccaccgcgg gatgccggga aggggcatta   1440
tttgtgcact gagaacaccg cgcagcgtga ctgtgagttg ctcataccgt gctgctatct   1500
gggcagcgct gcccatttat ttatatgtag attttaaaca ctgctgttga caagttggtt   1560
tgagggagaa aactttaagt gttaaagcca cctctataat tgattggact ttttaatttt   1620
aatgtttttc cccatgaacc acagttttta tatttctacc agaaaagtaa aaatcttttt   1680
taaaagtgtt gtttttctaa tttataactc ctaggggtta tttctgtgcc agacacattc   1740
cacctctcca gtattgcagg acggaatata tgtgttaatg aaaatgaatg gctgtacata   1800
tttttttctt tcttcagagt actctgtaca ataaatgcag tttataaaag tgttaaaaaa   1860
aaaaaaaaaa aaaaaa                                                  1876
```

<210> SEQ ID NO 337
<211> LENGTH: 6633
<212> TYPE: DNA
<213> ORGANISM: Homo sapiens

<400> SEQUENCE: 337

```
ttctccccgc cccccagttg ttgtcgaagt ctgggggttg ggactggacc ccctgattgc     60
gtaagagcaa aaagcgaagg cgcaatctgg acactgggag attcggagcg cagggagttt    120
gagagaaact tttattttga agagaccaag gttgaggggg ggcttatttc ctgacagcta    180
tttacttaga gcaaatgatt agttttagaa ggatggacta taacattgaa tcaattacaa    240
aacgcggttt ttgagcccat tactgttgga gctacaggga gagaaacagg aggagactgc    300
aagagatcat ttgggaaggc cgtgggcacg ctctttactc catgtgtggg acattcattg    360
cggaataaca tcggaggaga agtttcccag agctatgggg acttcccatc cggcgttcct    420
ggtcttaggc tgtcttctca cagggctgag cctaatcctc tgccagcttt cattaccctc    480
tatccttcca aatgaaaatg aaaaggttgt gcagctgaat tcatcctttt ctctgagatg    540
ctttggggag agtgaagtga gctggcagta ccccatgtct gaagaagaga gctccgatgt    600
ggaaatcaga aatgaagaaa acaacagcgg cctttttgtg acggtcttgg aagtgagcag    660
```

-continued

```
tgcctcggcg gcccacacag ggttgtacac ttgctattac aaccacactc agacagaaga    720
gaatgagctt gaaggcaggc acatttacat ctatgtgcca gacccagatg tagcctttgt    780
acctctagga atgacggatt atttagtcat cgtggaggat gatgattctg ccattatacc    840
ttgtcgcaca actgatcccg agactcctgt aaccttacac aacagtgagg gggtggtacc    900
tgcctcctac gacagcagac agggctttaa tgggaccttc actgtagggc cctatatctg    960
tgaggccacc gtcaaaggaa agaagttcca gaccatccca tttaatgttt atgctttaaa   1020
agcaacatca gagctggatc tagaaatgga agctcttaaa accgtgtata agtcagggga   1080
aacgattgtg gtcacctgtg ctgtttttaa caatgaggtg gttgaccttc aatggactta   1140
ccctggagaa gtgaaaggca aaggcatcac aatgctggaa gaaatcaaag tcccatccat   1200
caaattggtg tacactttga cggtccccga ggccacggtg aaagacagtg gagattacga   1260
atgtgctgcc cgccaggcta ccagggaggt caaagaaatg aagaaagtca ctatttctgt   1320
ccatgagaaa ggtttcattg aaatcaaacc caccttcagc cagttggaag ctgtcaacct   1380
gcatgaagtc aaacattttg ttgtagaggt gcgggcctac ccacctccca ggatatcctg   1440
gctgaaaaac aatctgactc tgattgaaaa tctcactgag atcaccactg atgtggaaaa   1500
gattcaggaa ataaggtatc gaagcaaatt aaagctgatc cgtgctaagg aagaagacag   1560
tggccattat actattgtag ctcaaaatga agatgctgtg aagagctata cttttgaact   1620
gttaactcaa gttccttcat ccattctgga cttggtcgat gatcaccatg gctcaactgg   1680
gggacagacg gtgaggtgca cagctgaagg cacgccgctt cctgatattg agtggatgat   1740
atgcaaagat attaagaaat gtaataatga aacttcctgg actattttgg ccaacaatgt   1800
ctcaaacatc atcacggaga tccactcccg agacaggagt accgtggagg gccgtgtgac   1860
tttcgccaaa gtggaggaga ccatcgccgt gcgatgcctg gctaagaatc tccttggagc   1920
tgagaaccga gagctgaagc tggtggctcc caccctgcgt tctgaactca cggtggctgc   1980
tgcagtcctg gtgctgttgg tgattgtgat catctcactt attgtcctgg ttgtcatttg   2040
gaaacagaaa ccgaggtatg aaattcgctg gagggtcatt gaatcaatca gcccggatgg   2100
acatgaatat atttatgtgg acccgatgca gctgccttat gactcaagat gggagtttcc   2160
aagagatgga ctagtgcttg gtcgggtctt ggggtctgga gcgtttggga aggtggttga   2220
aggaacagcc tatggattaa gccggtccca acctgtcatg aaagttgcag tgaagatgct   2280
aaaacccacg gccagatcca gtgaaaaaca agctctcatg tctgaactga agataatgac   2340
tcacctgggg ccacatttga acattgtaaa cttgctggga gcctgcacca agtcaggccc   2400
catttacatc atcacagagt attgcttcta tggagatttg gtcaactatt tgcataagaa   2460
tagggatagc ttcctgagcc accacccaga gaagccaaag aaagagctgg atatctttgg   2520
attgaaccct gctgatgaaa gcacacggag ctatgttatt ttatcttttg aaaacaatgg   2580
tgactacatg gacatgaagc aggctgatac tacacagtat gtccccatgc tagaaaggaa   2640
agaggtttct aaatattccg acatccagag atcactctat gatcgtccag cctcatataa   2700
gaagaaatct atgttagact cagaagtcaa aaacctcctt tcagatgata actcagaagg   2760
ccttacttta ttggatttgt tgagcttcac ctatcaagtt gcccgaggaa tggagttttt   2820
ggcttcaaaa aattgtgtcc accgtgatct ggctgctcgc aacgtcctcc tggcacaagg   2880
aaaaattgtg aagatctgtg actttggcct ggccagagac atcatgcatg attcgaacta   2940
tgtgtcgaaa ggcagtacct ttctgcccgt gaagtggatg gctcctgaga gcatctttga   3000
caacctctac accacactga gtgatgtctg gtcttatggc attctgctct gggagatctt   3060
```

-continued

```
ttcccttggt ggcacccctt accccggcat gatggtggat tctactttct acaataagat   3120
caagagtggg taccggatgg ccaagcctga ccacgctacc agtgaagtct acgagatcat   3180
ggtgaaatgc tggaacagtg agccggagaa gagaccctcc ttttaccacc tgagtgagat   3240
tgtggagaat ctgctgcctg gacaatataa aaagagttat gaaaaaattc acctggactt   3300
cctgaagagt gaccatcctg ctgtggcacg catgcgtgtg gactcagaca atgcatacat   3360
tggtgtcacc tacaaaaacg aggaagacaa gctgaaggac tgggagggtg gtctggatga   3420
gcagagactg agcgctgaca gtggctacat cattcctctg cctgacattg accctgtccc   3480
tgaggaggag gacctgggca agaggaacag acacagctcg cagacctctg aagagagtgc   3540
cattgagacg ggttccagca gttccacctt catcaagaga gaggacgaga ccattgaaga   3600
catcgacatg atggacgaca tcggcataga ctcttcagac ctggtggaag acagcttcct   3660
gtaactggcg gattcgaggg gttccttcca cttctggggc cacctctgga tcccgttcag   3720
aaaaccactt tattgcaatg cggaggttga gaggaggact tggttgatgt ttaaagagaa   3780
gttcccagcc aagggcctcg gggagcgttc taaatatgaa tgaatgggat attttgaaat   3840
gaactttgtc agtgttgcct ctcgcaatgc ctcagtagca tctcagtggt gtgtgaagtt   3900
tggagataga tggataaggg aataataggc cacagaaggt gaactttgtg cttcaaggac   3960
attggtgaga gtccaacaga cacaatttat actgcgacag aacttcagca ttgtaattat   4020
gtaaataact ctaaccaagg ctgtgtttag attgtattaa ctatcttctt tggacttctg   4080
aagagaccac tcaatccatc catgtacttc cctcttgaaa cctgatgtca gctgctgttg   4140
aactttttaa agaagtgcat gaaaaaccat ttttgaacct taaaaggtac tggtactata   4200
gcattttgct atcttttttta gtgttaagag ataaagaata ataattaacc aaccttgttt   4260
aatagatttg ggtcatttag aagcctgaca actcattttc atattgtaat ctatgtttat   4320
aatactacta ctgttatcag taatgctaaa tgtgtaataa tgtaacatga tttccctcca   4380
gagaaagcac aatttaaaac aatccttact aagtaggtga tgagtttgac agtttttgac   4440
atttatatta aataacatgt ttctctataa agtatggtaa tagctttagt gaattaaatt   4500
tagttgagca tagagaacaa agtaaaagta gtgttgtcca ggaagtcaga atttttaact   4560
gtactgaata ggttccccaa tccatcgtat taaaaaacaa ttaactgccc tctgaaataa   4620
tgggattaga aacaaacaaa actcttaagt cctaaaagtt ctcaatgtag aggcataaac   4680
ctgtgctgaa cataacttct catgtatatt acccaatgga aaatataatg atcagcaaaa   4740
agactggatt tgcagaagtt tttttttttt ttcttcatgc ctgatgaaag ctttggcaac   4800
cccaatatat gtatttttttg aatctatgaa cctgaaaagg gtcagaagga tgcccagaca   4860
tcagcctcct tctttcaccc cttaccccaa agagaaagag tttgaaactc gagaccataa   4920
agatattctt tagtggaggc tggatgtgca ttagcctgga tcctcagttc tcaaatgtgt   4980
gtggcagcca ggatgactag atcctgggtt tccatccttg agattctgaa gtatgaagtc   5040
tgagggaaac cagagtctgt atttttctaa actccctggc tgttctgatc ggccagtttt   5100
cggaaacact gacttaggtt tcaggaagtt gccatgggaa acaaataatt tgaactttgg   5160
aacagggttg gaattcaacc acgcaggaag cctactattt aaatccttgg cttcaggtta   5220
gtgacattta atgccatcta gctagcaatt gcgaccttaa tttaactttc cagtcttagc   5280
tgaggctgag aaagctaaag tttggttttg acaggttttc caaaagtaaa gatgctactt   5340
cccactgtat gggggagatt gaactttccc cgtctcccgt cttctgcctc ccactccata   5400
```

-continued

```
ccccgccaag gaaaggcatg tacaaaaatt atgcaattca gtgttccaag tctctgtgta   5460

accagctcag tgttttggtg gaaaaaacat tttaagtttt actgataatt tgaggttaga   5520

tgggaggatg aattgtcaca tctatccaca ctgtcaaaca ggttggtgtg ggttcattgg   5580

cattctttgc aatactgctt aattgctgat accatatgaa tgaaacatgg gctgtgatta   5640

ctgcaatcac tgtgctatcg gcagatgatg ctttggaaga tgcagaagca ataataaagt   5700

acttgactac ctactggtgt aatctcaatg caagccccaa ctttcttatc caactttttc   5760

atagtaagtg cgaagactga gccagattgg ccaattaaaa acgaaaacct gactaggttc   5820

tgtagagcca attagacttg aaatacgttt gtgtttctag aatcacagct caagcattct   5880

gtttatcgct cactctccct tgtacagcct tattttgttg gtgctttgca ttttgatatt   5940

gctgtgagcc ttgcatgaca tcatgaggcc ggatgaaact tctcagtcca gcagtttcca   6000

gtcctaacaa atgctcccac ctgaatttgt atatgactgc atttgtgggt gtgtgtgtgt   6060

tttcagcaaa ttccagattt gtttcctttt ggcctcctgc aaagtctcca gaagaaaatt   6120

tgccaatctt tcctactttc tatttttatg atgacaatca aagccggcct gagaaacact   6180

atttgtgact ttttaaacga ttagtgatgt ccttaaaatg tggtctgcca atctgtacaa   6240

aatggtccta tttttgtgaa gagggacata agataaaatg atgttataca tcaatatgta   6300

tatatgtatt tctatataga cttggagaat actgccaaaa catttatgac aagctgtatc   6360

actgccttcg tttatatttt tttaactgtg ataatcccca caggcacatt aactgttgca   6420

cttttgaatg tccaaaattt atattttaga aataataaaa agaaagatac ttacatgttc   6480

ccaaaacaat ggtgtggtga atgtgtgaga aaaactaact tgatagggtc taccaataca   6540

aaatgtatta cgaatgcccc tgttcatgtt tttgttttaa aacgtgtaaa tgaagatctt   6600

tatatttcaa taaatgatat ataatttaaa gtt                                6633
```

<210> SEQ ID NO 338
<211> LENGTH: 994
<212> TYPE: DNA
<213> ORGANISM: Homo sapiens

<400> SEQUENCE: 338

```
tgctggccag cacctcgagg gaagatggcg gacgaggaga agctgccgcc cggctgggag     60

aagcgcatga gccgcagctc aggccgagtg tactacttca accacatcac taacgccagc    120

cagtgggagc ggcccagcgg caacagcagc agtggtggca aaaacgggca gggggagcct    180

gccagggtcc gctgctcgca cctgctggtg aagcacagcc agtcacggcg gccctcgtcc    240

tggcggcagg agaagatcac ccggaccaag gaggaggccc tggagctgat caacggctac    300

atccagaaga tcaagtcggg agaggaggac tttgagtctc tggcctcaca gttcagcgac    360

tgcagctcag ccaaggccag gggagacctg ggtgccttca gcagaggtca gatgcagaag    420

ccatttgaag acgcctcgtt tgcgctgcgg acgggggaga tgagcgggcc cgtgttcacg    480

gattccggca tccacatcat cctccgcact gagtgagggt ggggagccca ggcctggcct    540

cggggcaggg cagggcggct aggccggcca gctccccctt gcccgccagc cagtggccga    600

accccccact ccctgccacc gtcacacagt atttattgtt cccacaatgg ctgggagggg    660

gcccttccag attgggggcc ctggggtccc cactccctgt ccatccccag ttggggctgc    720

gaccgccaga ttctccctta aggaattgac ttcagcaggg gtgggaggct cccagaccca    780

gggcagtgtg gtgggagggg tgttccaaag agaaggcctg gtcagcagag ccgccccgtg    840

tccccccagg tgctggaggc agactcgagg gccgaattgt ttctagttag gccacgctcc    900
```

tctgttcagt cgcaaaggtg aacactcatg cggcagccat gggccctctg agcaactgtg 960
cagacccttt cacccccaat taaacccaga acca 994

<210> SEQ ID NO 339
<211> LENGTH: 772
<212> TYPE: DNA
<213> ORGANISM: Homo sapiens

<400> SEQUENCE: 339
agctcgtgcc gaattcggca cgagccgggt cggagccatg gcggtggcaa attcaagtcc 60
tgttaacccc gtggtgttct ttgatgtcag tattggcggt caggaagttg gccgcatgaa 120
gatcgagctc tttgcagacg ttgtgcctaa gacggccgag aactttaggc agttctgcac 180
cggagaattc aggaaagatg ggggttccaat aggatacaaa ggaagcacct tccacagggt 240
cataaaggat ttcatgattc agggtggaga ttttgttaat ggagatggta ctggagtcgc 300
cagtatttac cgggggccat ttgcagatga aaattttaaa cttagacact cagctccagg 360
cctgctttcc atggcgaaca gtggtccaag tacaaatggc tgtcagttct ttatcacctg 420
ctctaagtgc gattggctgg atgggaagca tgtggtgttt ggaaaaatca tcgatggact 480
tctagtgatg agaaagattg agaatgttcc cacaggcccc aacaataagc ccaagctacc 540
tgtggtgatc tcgcagtgtg gggagatgta gtccagacaa agactgaatc aggccttccc 600
ttcttcttgg tggtgttctt gagtaagata atctggactg gccccccgtct ttgcttccct 660 gcctgctgct gccccatttg atcaagagac catggaagtg tcagagattc agaatccaag 720
attgtcttta agttttcaac tgtaaataaa gttttttttgt atgcgtaaaa aa 772

<210> SEQ ID NO 340
<211> LENGTH: 919
<212> TYPE: DNA
<213> ORGANISM: Homo sapiens

<400> SEQUENCE: 340
cgctcgcctc cctcgctcca cgcgcgcccg gacgcggcgg ccaggcttgc gcgtggttcc 60
cctcccggtg ggcggattcc tggcaagat gaagtgggtg tgggcgctct tgctgttggc 120
ggcgtgggca gcggccgagc gcgactgccg agtgagcagc ttccgagtca aggagaactt 180
cgacaaggct cgcttctctg ggacctggta cgccatggcc aagaaggacc ccgagggcct 240
ctttctgcag gacaacatcg tcgcggagtt ctcggtggac gagaccggcc agatgagcgc 300
cacagccaag ggccgagtcc gtcttttgaa taactgggac gtgtgcgcag acatggtggg 360
caccttcaca gacaccgagg accctgccaa gttcaagatg aagtactggg gcgtagcctc 420
ctttctgcag aaaggaaatg atgaccactg gatcgtcgac acagactacg acacgtatgc 480
cgtacagtac tcctgccgcc tcctgaacct cgatggcacc tgtgctgaca gctactcctt 540
cgtgttttcc cgggaccccca acggcctgcc cccagaagcg cagaagattg taaggcagcg 600
gcaggaggag ctgtgcctgg ccaggcagta caggctgatc gtccacaacg gttactgcga 660
tggcagatca gaaagaaacc ttttgtagca atatcaagaa tctagtttca tctgagaact 720
tctgattagc tctcagtctt cagctctatt tatcttagga gtttaatttg cccttctctc 780
cccatcttcc ctcagttccc ataaaacctt cattacacat aaagatacac gtgggggtca 840
gtgaatctgc ttgcctttcc tgaaagtttc tggggcttaa gattccagac tctgattcat 900
taaactatag tcacccgtg 919

<210> SEQ ID NO 341
<211> LENGTH: 7365
<212> TYPE: DNA
<213> ORGANISM: Homo sapiens

<400> SEQUENCE: 341

```
ggcagtttgt aggtcgcgag ggaagcgctg aggatcagga agggggcact gagtgtccgt     60
gggggaatcc tcgtgatagg aactggaata tgccttgagg gggacactat gtctttaaaa    120
acgtcggctg gtcatgaggt caggagttcc agaccagcct gaccaacgtg gtgaaactcc    180
gtctctacta aaaatacaaa aattagccgg gcgtggtgcc gctccagcta ctcaggaggc    240
tgaggcagga gaatcgctag aacccgggag gcggaggttg cagtgagccg agatcgcgcc    300
attgcactcc agcctgggcg acagagcgag actgtctcaa aacaaaacaa aacaaaacaa    360
aacaaaaaac accggctgtt cattggaaca gaaagaaatg gatttatctg ctcttcgcgt    420
tgaagaagta caaaatgtca ttaatgctat gcagaaaatc ttagagtgtc ccatctgtct    480
ggagttgatc aaggaacctg tctccacaaa gtgtgaccac atattttgca aattttgcat    540
gctgaaactt ctcaaccaga agaaagggcc ttcacagtgt cctttatgta agaatgatat    600
aaccaaaagg agcctacaag aaagtacgag atttagtcaa cttgttgaag agctattgaa    660
aatcatttgt gcttttcagc ttgacacagg tttggagtat gcaaacagct ataattttgc    720
aaaaaaggaa aataactctc ctgaacatct aaaagatgaa gtttctatca tccaaagtat    780
gggctacaga aaccgtgcca aaagacttct acagagtgaa cccgaaaatc cttccttgca    840
ggaaaccagt ctcagtgtcc aactctctaa ccttggaact gtgagaactc tgaggacaaa    900
gcagcggata caacctcaaa agacgtctgt ctacattgaa ttgggatctg attcttctga    960
agataccgtt aataaggcaa cttattgcag tgtgggagat caagaattgt tacaaatcac   1020
ccctcaagga accagggatg aaatcagttt ggattctgca aaaaaggctg cttgtgaatt   1080
ttctgagacg gatgtaacaa atactgaaca tcatcaaccc agtaataatg atttgaacac   1140
cactgagaag cgtgcagctg agaggcatcc agaaaagtat cagggtagtt ctgtttcaaa   1200
cttgcatgtg gagccatgtg gcacaaatac tcatgccagc tcattacagc atgagaacag   1260
cagtttatta ctcactaaag acagaatgaa tgtagaaaag gctgaattct gtaataaaag   1320
caaacagcct ggcttagcaa ggagccaaca taacagatgg gctggaagta aggaaacatg   1380
taatgatagg cggactccca gcacagaaaa aaaggtagat ctgaatgctg atcccctgtg   1440
tgagagaaaa gaatggaata agcagaaact gccatgctca gagaatccta gagatactga   1500
agatgttcct tggataacac taaatagcag cattcagaaa gttaatgagt ggttttccag   1560
aagtgatgaa ctgttaggtt ctgatgactc acatgatggg gagtctgaat caaatgccaa   1620
agtagctgat gtattggacg ttctaaatga ggtagatgaa tattctggtt cttcagagaa   1680
aatagactta ctggccagtg atcctcatga ggctttaata tgtaaaagtg aaagagttca   1740
ctccaaatca gtagagagta atattgaaga caaaatattt gggaaaacct atcggaagaa   1800
ggcaagcctc cccaacttaa gccatgtaac tgaaaatcta attataggag catttgttac   1860
tgagccacag ataatacaag agcgtcccct cacaaataaa ttaaagcgta aaaggagacc   1920
tacatcaggc cttcatcctg aggattttat caagaaagca gatttggcag ttcaaaagac   1980
tcctgaaatg ataaatcagg gaactaacca aacggagcag aatggtcaag tgatgaatat   2040
tactaatagt ggtcatgaga ataaaacaaa aggtgattct attcagaatg agaaaaatcc   2100
taacccaata gaatcactcg aaaaagaatc tgctttcaaa acgaaagctg aacctataag   2160
```

-continued

```
cagcagtata agcaatatgg aactcgaatt aaatatccac aattcaaaag cacctaaaaa   2220
gaataggctg aggaggaagt cttctaccag gcatattcat gcgcttgaac tagtagtcag   2280
tagaaatcta agcccaccta attgtactga attgcaaatt gatagttgtt ctagcagtga   2340
agagataaag aaaaaaaagt acaaccaaat gccagtcagg cacagcagaa acctacaact   2400
catggaaggt aaagaacctg caactggagc caagaagagt aacaagccaa atgaacagac   2460
aagtaaaaga catgacagcg atactttccc agagctgaag ttaacaaatg cacctggttc   2520
ttttactaag tgttcaaata ccagtgaact taaagaattt gtcaatccta gccttccaag   2580
agaagaaaaa gaagagaaac tagaaacagt taaagtgtct aataatgctg aagaccccaa   2640
agatctcatg ttaagtggag aaagggtttt gcaaactgaa agatctgtag agagtagcag   2700
tatttcattg gtacctggta ctgattatgg cactcaggaa agtatctcgt tactggaagt   2760
tagcactcta gggaaggcaa aaacagaacc aaataaatgt gtgagtcagt gtgcagcatt   2820
tgaaaacccc aagggactaa ttcatggttg ttccaaagat aatagaaatg acacagaagg   2880
ctttaagtat ccattgggac atgaagttaa ccacagtcgg gaaacaagca tagaaatgga   2940
agaaagtgaa cttgatgctc agtatttgca gaatacattc aaggtttcaa agcgccagtc   3000
atttgctccg ttttcaaatc caggaaatgc agaagaggaa tgtgcaacat tctctgccca   3060
ctctgggtcc ttaaagaaac aaagtccaaa agtcactttt gaatgtgaac aaaaggaaga   3120
aaatcaagga aagaatgagt ctaatatcaa gcctgtacag acagttaata tcactgcagg   3180
ctttcctgtg gttggtcaga aagataagcc agttgataat gccaaatgta gtatcaaagg   3240
aggctctagg ttttgtctat catctcagtt cagaggcaac gaaactggac tcattactcc   3300
aaataaacat ggacttttac aaaacccata tcgtatacca ccactttttc ccatcaagtc   3360
atttgttaaa actaaatgta agaaaaatct gctagaggaa aactttgagg aacattcaat   3420
gtcacctgaa agagaaatgg gaaatgagaa cattccaagt acagtgagca caattagccg   3480
taataacatt agagaaaatg tttttaaaga agccagctca agcaatatta atgaagtagg   3540
ttccagtact aatgaagtgg gctccagtat taatgaaata ggttccagtg atgaaaacat   3600
tcaagcagaa ctaggtagaa acagagggcc aaaattgaat gctatgctta gattaggggt   3660
tttgcaacct gaggtctata aacaaagtct tcctggaagt aattgtaagc atcctgaaat   3720
aaaaaagcaa gaatatgaag aagtagttca gactgttaat acagatttct ctccatatct   3780
gatttcagat aacttagaac agcctatggg aagtagtcat gcatctcagg tttgttctga   3840
gacacctgat gacctgttag atgatggtga aataaaggaa gatactagtt ttgctgaaaa   3900
tgacattaag gaaagttctg ctgtttttag caaaagcgtc cagaaaggag agcttagcag   3960
gagtcctagc cctttcaccc atacacattt ggctcagggt taccgaagag ggccaagaa    4020
attagagtcc tcagaagaga acttatctag tgaggatgaa gagcttccct gcttccaaca   4080
cttgttattt ggtaaagtaa acaatatacc ttctcagtct actaggcata gcaccgttgc   4140
taccgagtgt ctgtctaaga acacagagga gaatttatta tcattgaaga atagcttaaa   4200
tgactgcagt aaccaggtaa tattggcaaa ggcatctcag gaacatcacc ttagtgagga   4260
aacaaaatgt tctgctagct tgttttcttc acagtgcagt gaattggaag acttgactgc   4320
aaatacaaac acccaggatc ctttcttgat tggttcttcc aaacaaatga ggcatcagtc   4380
tgaaagccag ggagttggtc tgagtgacaa ggaattggtt tcagatgatg aagaaagagg   4440
aacgggcttg gaagaaaata atcaagaaga gcaaagcatg gattcaaact taggtgaagc   4500
```

-continued

```
agcatctggg tgtgagagtg aaacaagcgt ctctgaagac tgctcagggc tatcctctca   4560
gagtgacatt ttaaccactc agcagaggga taccatgcaa cataacctga taaagctcca   4620
gcaggaaatg gctgaactag aagctgtgtt agaacagcat gggagccagc cttctaacag   4680
ctacccttcc atcataagtg actcttctgc ccttgaggac ctgcgaaatc cagaacaaag   4740
cacatcagaa aaagcagtat taacttcaca gaaaagtagt gaatacccta taagccagaa   4800
tccagaaggc ctttctgctg acaagtttga ggtgtctgca gatagttcta ccagtaaaaa   4860
taaagaacca ggagtggaaa ggtcatcccc ttctaaatgc ccatcattag atgataggtg   4920
gtacatgcac agttgctctg ggagtcttca gaatagaaac tacccatctc aagaggagct   4980
cattaaggtt gttgatgtgg aggagcaaca gctggaagag tctgggccac acgatttgac   5040
ggaaacatct tacttgccaa ggcaagatct agagggaacc ccttacctgg aatctggaat   5100
cagcctcttc tctgatgacc ctgaatctga tccttctgaa gacagagccc cagagtcagc   5160
tcgtgttggc aacataccat cttcaacctc tgcattgaaa gttccccaat tgaaagttgc   5220
agaatctgcc cagagtccag ctgctgctca tactactgat actgctgggt ataatgcaat   5280
ggaagaaagt gtgagcaggg agaagccaga attgacagct tcaacagaaa gggtcaacaa   5340
aagaatgtcc atggtggtgt ctggcctgac cccagaagaa tttatgctcg tgtacaagtt   5400
tgccagaaaa caccacatca ctttaactaa tctaattact gaagagacta ctcatgttgt   5460
tatgaaaaca gatgctgagt ttgtgtgtga acggacactg aaatattttc taggaattgc   5520
gggaggaaaa tgggtagtta gctatttctg ggtgacccag tctattaaag aaagaaaaat   5580
gctgaatgag catgattttg aagtcagagg agatgtggtc aatggaagaa accaccaagg   5640
tccaaagcga gcaagagaat cccaggacag aaagatcttc agggggctag aaatctgttg   5700
ctatgggccc ttcaccaaca tgcccacaga tcaactggaa tggatggtac agctgtgtgg   5760
tgcttctgtg gtgaaggagc tttcatcatt caccettggc acaggtgtcc acccaattgt   5820
ggttgtgcag ccagatgcct ggacagagga caatggcttc catgcaattg ggcagatgtg   5880
tgaggcacct gtggtgaccc gagagtgggt gttggacagt gtagcactct accagtgcca   5940
ggagctggac acctacctga taccccagat cccccacagc cactactgac tgcagccagc   6000
cacaggtaca gagccacagg accccaagaa tgagcttaca aagtggcctt tccaggccct   6060
gggagctcct ctcactcttc agtccttcta ctgtcctggc tactaaatat tttatgtaca   6120
tcagcctgaa aaggacttct ggctatgcaa gggtccctta aagattttct gcttgaagtc   6180
tcccttggaa atctgccatg agcacaaaat tatggtaatt tttcacctga gaagatttta   6240
aaaccattta aacgccacca attgagcaag atgctgattc attatttatc agccctattc   6300
tttctattca ggctgttgtt ggcttagggc tggaagcaca gagtggcttg gcctcaagag   6360
aatagctggt ttccctaagt ttacttctct aaaaccctgt gttcacaaag gcagagagtc   6420
agacccttca atggaaggag agtgcttggg atcgattatg tgacttaaag tcagaatagt   6480
ccttgggcag ttctcaaatg ttggagtgga acattgggga ggaaattctg aggcaggtat   6540
tagaaatgaa aaggaaactt gaaacctggg catggtggct cacgcctgta atcccagcac   6600
tttgggaggc caaggtgggc agatcactgg aggtcaggag ttcgaaacca gcctggccaa   6660
catggtgaaa ccccatctct actaaaaata cagaaattag ccggtcatgg tggtggacac   6720
ctgtaatccc agctactcag gtggctaagg caggagaatc acttcagccc gggaggtgga   6780
ggttgcagtg agccaagatc ataccacggc actccagcct gggtgacagt gagactgtgg   6840
ctcaaaaaaa aaaaaaaaaa aggaaaatga aactaggaaa ggtttcttaa agtctgagat   6900
```

```
atatttgcta gatttctaaa gaatgtgttc taaaacagca gaagattttc aagaaccggt   6960

ttccaaagac agtcttctaa ttcctcatta gtaataagta aaatgtttat tgttgtagct   7020

ctggtatata atccattcct cttaaaatat aagacctctg gcatgaatat ttcatatcta   7080

taaaatgaca gatcccacca ggaaggaagc tgttgctttc tttgaggtga ttttttttcct  7140

ttgctccctg ttgctgaaac catacagctt cataaataat tttgcttgct gaaggaagaa   7200

aaagtgtttt tcataaaccc attatccagg actgtttata gctgttggaa ggactaggtc   7260

ttccctagcc cccccagtgt gcaagggcag tgaagacttg attgtacaaa atacgttttg   7320

taaatgttgt gctgttaaca ctgcaaataa acttggtagc aaaca                   7365
```

```
<210> SEQ ID NO 342
<211> LENGTH: 10386
<212> TYPE: DNA
<213> ORGANISM: Homo sapiens
<220> FEATURE:
<221> NAME/KEY: unsure
<222> LOCATION: (0)...(0)
<223> OTHER INFORMATION: n = a, t, c or g

<400> SEQUENCE: 342
```

```
attgaggact cggaaatgag gtccaagggt agccaaggat ggctgcagct tcatatgatc     60

agttgttaaa gcaagttgag gcactgaaga tggagaactc aaatcttcga caagagctag    120

aagataattc caatcatctt acaaaactgg aaactgaggc atctaatatg aaggaagtac    180

ttaaacaact acaaggaagt attgaagatg aagctatggc ttcttctgga cagattgatt    240

tattagagcg tcttaaagag cttaacttag atagcagtaa tttccctgga gtaaaactgc    300

ggtcaaaaat gtccctccgt tcttatggaa gccgggaagg atctgtatca agccgttctg    360

gagagtgcag tcctgttcct atgggttcat ttccaagaag agggtttgta aatggaagca    420

gagaaagtac tggatattta gaagaacttg agaaagagag gtcattgctt cttgctgatc    480

ttgacaaaga agaaaaggaa aaagactggt attacgctca acttcagaat ctcactaaaa    540

gaatagatag tcttccttta actgaaaatt tttccttaca aacagatatg accagaaggc    600

aattggaata tgaagcaagg caaatcagag ttgcgatgga agaacaacta ggtacctgcc    660

aggatatgga aaaacgagca cagcgaagaa tagccagaat tcagcaaatc gaaaaggaca    720

tacttcgtat acgacagctt ttacagtccc aagcaacaga agcagagagg tcatctcaga    780

acaagcatga aaccggctca catgatgctg agcggcagaa tgaaggtcaa ggagtgggag    840

aaatcaacat ggcaacttct ggtaatggtc agggttcaac tacacgaatg gaccatgaaa    900

cagccagtgt tttgagttct agtagcacac actctgcacc tcgaaggctg acaagtcatc    960

tgggaaccaa ggtggaaatg gtgtattcat tgttgtcaat gcttggtact catgataagg   1020

atgatatgtc gcgaactttg ctagctatgt ctagctccca agacagctgt atatccatgc   1080

gacagtctgg atgtcttcct ctcctcatcc agcttttaca tggcaatgac aaagactctg   1140

tattgttggg aaattcccgg ggcagtaaag aggctcgggc cagggccagt gcagcactcc   1200

acaacatcat tcactcacag cctgatgaca agagaggcag gcgtgaaatc cgagtccttc   1260

atcttttgga acagatacgc gcttactgtg aaacctgttg ggagtggcag gaagctcatg   1320

aaccaggcat ggaccaggac aaaaatccaa tgccagctcc tgttgaacat cagatctgtc   1380

ctgctgtgtg tgttctaatg aaactttcat ttgatgaaga gcatagacat gcaatgaatg   1440

aactaggggg actacaggcc attgcagaat tattgcaagt ggactgtgaa atgtacgggc   1500
```

-continued

```
ttactaatga ccactacagt attacactaa gacgatatgc tggaatggct ttgacaaact   1560
tgacttttgg agatgtagcc aacaaggcta cgctatgctc tatgaaaggc tgcatgagag   1620
cacttgtggc ccaactaaaa tctgaaagtg aagacttaca gcaggttatt gcaagtgttt   1680
tgaggaattt gtcttggcga gcagatgtaa atagtaaaaa gacgttgcga gaagttggaa   1740
gtgtgaaagc attgatggaa tgtgctttag aagttaaaaa ggaatcaacc ctcaaaagcg   1800
tattgagtgc cttatggaat ttgtcagcac attgcactga gaataaagct gatatatgtg   1860
ctgtagatgg tgcacttgca tttttggttg gcactcttac ttaccggagc cagacaaaca   1920
ctttagccat tattgaaagt ggaggtggga tattacggaa tgtgtccagc ttgatagcta   1980
caaatgagga ccacaggcaa atcctaagag agaacaactg tctacaaact ttattacaac   2040
acttaaaatc tcatagtttg acaatagtca gtaatgcatg tggaactttg tggaatctct   2100
cagcaagaaa tcctaaagac caggaagcat tatgggacat gggggcagtt agcatgctca   2160
agaacctcat tcattcaaag cacaaaatga ttgctatggg aagtgctgca gctttaagga   2220
atctcatggc aaataggcct gcgaagtaca aggatgccaa tattatgtct cctggctcaa   2280
gcttgccatc tcttcatgtt aggaaacaaa aagccctaga agcagaatta gatgctcagc   2340
acttatcaga aacttttgac aatatagaca atttaagtcc caaggcatct catcgtagta   2400
agcagagaca caagcaaagt ctctatggtg attatgtttt tgacaccaat cgacatgatg   2460
ataataggtc agacaatttt aatactggca acatgactgt cctttcacca tatttgaata   2520
ctacagtgtt acccagctcc tcttcatcaa gaggaagctt agatagttct cgttctgaaa   2580
aagatagaag tttggagaga gaacgcggaa ttggtctagg caactaccat ccagcaacag   2640
aaaatccagg aacttcttca aagcgaggtt tgcagatctc caccactgca gcccagattg   2700
ccaaagtcat ggaagaagtg tcagccattc atacctctca ggaagacaga agttctgggt   2760
ctaccactga attacattgt gtgacagatg agagaaatgc acttagaaga agctctgctg   2820
cccatacaca ttcaaacact tacaatttca ctaagtcgga aaattcaaat aggacatgtt   2880
ctatgcctta tgccaaatta gaatacaaga gatcttcaaa tgatagttta aatagtgtca   2940
gtagtagtga tggttatggt aaaagaggtc aaatgaaacc ctcgattgaa tcctattctg   3000
aagatgatga aagtaagttt tgcagttatg gtcaataccc agccgaccta gcccataaaa   3060
tacatagtgc aaatcatatg gatgataatg atggagaact agatacacca ataaattata   3120
gtcttaaata ttcagatgag cagttgaact ctggaaggca aagtccttca cagaatgaaa   3180
gatgggcaag acccaaacac ataatagaag atgaaataaa acaaagtgag caaagacaat   3240
caaggaatca aagtacaact tatcctgttt atactgagag cactgatgat aaacacctca   3300
agttccaacc acattttgga cagcaggaat gtgtttctcc atacaggtca cggggagcca   3360
atggttcaga aacaaatcga gtgggttcta atcatggaat taatcaaaat gtaagccagt   3420
ctttgtgtca agaagatgac tatgaagatg ataagcctac caattatagt gaacgttact   3480
ctgaagaaga acagcatgaa gaagaagaga gaccaacaaa ttatagcata aaatataatg   3540
aagagaaacg tcatgtggat cagcctattg attatagttt aaaatatgcc acagatattc   3600
cttcatcaca gaaacagtca ttttcattct caaagagttc atctggacaa agcagtaaaa   3660
ccgaacatat gtcttcaagc agtgagaata cgtccacacc ttcatctaat gccaagaggc   3720
agaatcagct ccatccaagt tctgcacaga gtagaagtgg tcagcctcaa aaggctgcca   3780
cttgcaaagt ttcttctatt aaccaagaaa caatacagac ttattgtgta gaagatactc   3840
caatatgttt ttcaagatgt agttcattat catctttgtc atcagctgaa gatgaaatag   3900
```

```
gatgtaatca gacgacacag gaagcagatt ctgctaatac cctgcaaata gcagaaataa   3960
aagaaaagat tggaactagg tcagctgaag atcctgtgag cgaagttcca gcagtgtcac   4020
agcaccctag aaccaaatcc agcagactgc agggttctag tttatcttca gaatcagcca   4080
ggcacaaagc tgttgaattt tcttcaggag cgaaatctcc ctccaaaagt ggtgctcaga   4140
cacccaaaag tccacctgaa cactatgttc aggagacccc actcatgttt agcagatgta   4200
cttctgtcag ttcacttgat agttttgaga gtcgttcgat tgccagctcc gttcagagtg   4260
aaccatgcag tggaatggta agtggcatta taagccccag tgatcttcca gatagccctg   4320
gacaaaccat gccaccaagc agaagtaaaa cacctccacc acctcctcaa acagctcaaa   4380
ccaagcgaga agtacctaaa aataaagcac ctactgctga aaagagagag agtggaccta   4440
agcaagctgc agtaaatgct gcagttcaga gggtccaggt tcttccagat gctgatactt   4500
tattacattt tgccacggaa agtactccag atggattttc ttgttcatcc agcctgagtg   4560
ctctgagcct cgatgagcca tttatacaga aagatgtgga attaagaata atgcctccag   4620
ttcaggaaaa tgacaatggg aatgaaacag aatcagagca gcctaaagaa tcaaatgaaa   4680
accaagagaa agaggcagaa aaaactattg attctgaaaa ggacctatta gatgattcag   4740
atgatgatga tattgaaata ctagaagaat gtattatttc tgccatgcca acaaagtcat   4800
cacgtaaagc aaaaaagcca gcccagactg cttcaaaatt acctccacct gtggcaagga   4860
aaccaagtca gctgcctgtg tacaaacttc taccatcaca aaacaggttg caaccccaaa   4920
agcatgttag ttttacaccg gggggatgata tgccacgggt gtattgtgtt gaagggacac   4980
ctataaactt ttccacagct acatctctaa gtgatctaac aatcgaatcc cctccaaatg   5040
agttagctgc tggagaagga gttagaggag gagcacagtc aggtgaattt gaaaaacgag   5100
ataccattcc tacagaaggc agaagtacag atgaggctca aggaggaaaa acctcatctg   5160
taaccatacc tgaattggat gacaataaag cagaggaagg tgatattctt gcagaatgca   5220
ttaattctgc tatgcccaaa gggaaaagtc acaagccttt ccgtgtgaaa aagataatgg   5280
accaggtcca gcaagcatct gcgtcgtctt ctgcacccaa caaaaatcag ttagatggta   5340
agaaaaagaa accaacttca ccagtaaaac ctataccaca aaatactgaa tataggacac   5400
gtgtaagaaa aaatgcagac tcaaaaaata atttaaatgc tgagagagtt ttctcagaca   5460
acaaagattc aaagaaacag aatttgaaaa ataattccaa ggacttcaat gataagctcc   5520
caaataatga agatagagtc agaggaagtt ttgcttttga ttcacctcat cattacacgc   5580
ctattgaagg aactccttac tgtttttcac gaaatgattc tttgagttct ctagattttg   5640
atgatgatga tgttgacctt tccagggaaa aggctgaatt aagaaaggca aaagaaaata   5700
aggaatcaga ggctaaagtt accagccaca cagaactaac ctccaaccaa caatcagcta   5760
ataagacaca agctattgca aagcagccaa taaatcgagg tcagcctaaa cccatacttc   5820
agaaacaatc cacttttccc cagtcatcca aagacatacc agacagaggg gcagcaactg   5880
atgaaaagtt acagaatttt gctattgaaa atactccagt ttgcttttct cataattcct   5940
ctctgagttc tctcagtgac attgaccaag aaaacaacaa taaagaaaat gaacctatca   6000
aagagactga gccccctgac tcacagggag aaccaagtaa acctcaagca tcaggctatg   6060
ctcctaaatc atttcatgtt gaagataccc cagtttgttt ctcaagaaac agttctctca   6120
gttctcttag tattgactct gaagatgacc tgttgcagga atgtataagc tccgcaatgc   6180
caaaaaagaa aaagccttca agactcaagg gtgataatga aaaacatagt cccagaaata   6240
```

-continued

```
tgggtggcat attaggtgaa gatctgacac ttgatttgaa agatatacag agaccagatt   6300
cagaacatgg tctatcccct gattcagaaa attttgattg gaaagctatt caggaaggtg   6360
caaattccat agtaagtagt ttacatcaag ctgctgctgc tgcatgttta tctagacaag   6420
cttcgtctga ttcagattcc atcctttccc tgaaatcagg aatctctctg ggatcaccat   6480
ttcatcttac acctgatcaa gaagaaaaac cctttacaag taataaaggc ccacgaattc   6540
taaaaccagg ggagaaaagt acattggaaa ctaaaaagat agaatctgaa agtaaaggaa   6600
tcaaaggagg aaaaaaagtt tataaaagtt tgattactgg aaaagttcga tctaattcag   6660
aaatttcagg ccaaatgaaa cagcccctte aagcaaacat gccttcaatc tctcgaggca   6720
ggacaatgat tcatattcca ggagttcgaa atagctcctc aagtacaagt cctgtttcta   6780
aaaaaggccc accccttaag actccagcct ccaaaagccc tagtgaaggt caaacagcca   6840
ccacttctcc tagaggagcc aagccatctg tgaaatcaga attaagccct gttgccaggc   6900
agacatccca aataggtggg tcaagtaaag caccttctag atcaggatct agagattcga   6960
ccccttcaag acctgcccag caaccattaa gtagacctat acagtctcct ggccgaaact   7020
caatttcccc tggtagaaat ggaataagtc ctcctaacaa attatctcaa cttccaagga   7080
catcatcccc tagtactgct tcaactaagt cctcaggttc tggaaaaatg tcatatacat   7140
ctccaggtag acagatgagc caacagaacc ttaccaaaca aacaggttta tccaagaatg   7200
ccagtagtat tccaagaagt gagtctgcct ccaaaggact aaatcagatg aataatggta   7260
atggagccaa taaaaaggta gaactttcta gaatgtcttc aactaaatca agtggaagtg   7320
aatctgatag atcagaaaga cctgtattag tacgccagtc aactttcatc aaagaagctc   7380
caagcccaac cttaagaaga aaattggagg aatctgcttc atttgaatct ctttctccat   7440
catctagacc agcttctccc actaggtccc aggcacaaac tccagtttta agtccttccc   7500
ttcctgatat gtctctatcc acacattcgt ctgttcaggc tggtggatgg cgaaaactcc   7560
cacctaatct cagtcccact atagagtata atgatggaag accagcaaag cgccatgata   7620
ttgcacggtc tcattctgaa agtccttcta gacttccaat caataggtca ggaacctgga   7680
aacgtgagca cagcaaacat tcatcatccc ttcctcgagt aagcacttgg agaagaactg   7740
gaagttcatc ttcaattctt tctgcttcat cagaatccag tgaaaaagca aaaagtgagg   7800
atgaaaaaca tgtgaactct atttcaggaa ccaaacaaag taaagaaaac caagtatccg   7860
caaaaggaac atggagaaaa ataaaagaaa atgaattttc tcccacaaat agtacttctc   7920
agaccgtttc ctcaggtgct acaaatggtg ctgaatcaaa gactctaatt tatcaaatgg   7980
cacctgctgt ttctaaaaca gaggatgttt gggtgagaat tgaggactgt cccattaaca   8040
atcctagatc tggaagatct cccacaggta atactccccc ggtgattgac agtgtttcag   8100
aaaaggcaaa tccaaacatt aaagattcaa aagataatca ggcaaaacaa aatgtgggta   8160
atggcagtgt tcccatgcgt accgtgggtt tggaaaatcg cctgaactcc tttattcagg   8220
tggatgcccc tgaccaaaaa ggaactgaga taaaaccagg acaaaataat cctgtccctg   8280
tatcagagac taatgaaagt tctatagtgg aacgtacccc attcagttct agcagctcaa   8340
gcaaacacag ttcacctagt gggactgttg ctgccagagt gactcctttt aattacaacc   8400
caagccctag gaaaagcagc gcagatagca cttcagctcg gccatctcag atcccaactc   8460
cagtgaataa caacacaaag aagcgagatt ccaaaactga cagcacagaa tccagtggaa   8520
cccaaagtcc taagcgccat tctgggtctt accttgtgac atctgtttaa aagagaggaa   8580
gaatgaaact aagaaaattc tatgttaatt acaactgcta tatagacatt ttgtttcaaa   8640
```

```
tgaaacttta aaagactgaa aaattttgta aataggtttg attcttgtta gagggttttt   8700

gttctggaag ccatatttga tagtatactt tgtcttcact ggtcttattt tgggaggcac   8760

tcttgatggt taggaaaaaa atagtaaagc caagtatgtt tgtacagtat gttttacatg   8820

tatttaaagt agcatcccat cccaacttcc tttaattatt gcttgtctta aaataatgaa   8880

cactacagat agaaaatatg atatattgct gttatcaatc atttctagat tataaactga   8940

ctaaacttac atcagggaaa aattggtatt tatgcaaaaa aaaatgtttt tgtccttgtg   9000

agtccatcta acatcataat taatcatgtg gctgtgaaat tcacagtaat atggttcccg   9060

atgaacaagc tttacccagc ctgtttgctt tactgcatga atgaaactga tggttcaatt   9120

tcagaagtaa tgattaacag ttatgtggtc acatgatgtg catagagata gctacagtgt   9180

aataatttac actattttgt gctccaaaca aaacaaaaat ctgtgtaact gtaaaacatt   9240

gaatgaaact attttacctg aactagattt tatctgaaag taggtagaat ttttgctatg   9300

ctgtaatttg ttgtatattc tggtatttga ggtgagatgg ctgctctttt attaatgaga   9360

catgaattgt gtctcaacag aaactaaatg aacatttcag aataaattat tgctgtatgt   9420

aaactgttac tgaaattggt atttgtttga agggtcttgt ttcacatttg tattaataat   9480

tgtttaaaat gcctctttta aaagcttata taaatttttt ncttcagctt ctatgcatta   9540

agagtaaaat tcctcttact gtaataaaaa caattgaaga agactgttgc cacttaacca   9600

ttccatgcgt tggcacttat ctattcctga aattctttta tgtgattagc tcatcttgat   9660

ttttaacatt tttccactta aacttttttt tcttactcca ctggagctca gtaaaagtaa   9720

attcatgtaa tagcaatgca agcagcctag cacagactaa gcattgagca taataggccc   9780

acataatttc ctctttctta atattataga aattctgtac ttgaaattga ttcttagaca   9840

ttgcagtctc ttcgaggctt tacagtgtaa actgtcttgc cccttcatct tcttgttgca   9900

actgggtctg acatgaacac tttttatcac cctgtatgtt agggcaagat ctcagcagtg   9960

aagtataatc agcactttgc catgctcaga aaattcaaat cacatggaac tttagaggta  10020

gatttaatac gattaagata ttcagaagta tattttagaa tccctgcctg ttaaggaaac  10080

tttatttgtg gtaggtacag ttctggggta catgttaagt gtccccttat acagtggagg  10140

gaagtcttcc ttcctgaagg aaaataaact gacacttatt aactaagata atttacttaa  10200

tatatcttcc ctgatttgtt ttaaaagatc agagggtgac tgatgataca tgcatacata  10260

tttgttgaat aaatgaaaat ttatttttag tgataagatt catacactct gtatttgggg  10320

agagaaaacc tttttaagca tggtggggca ctcagatagg agtgaataca cctacctggt  10380

ggtcat                                                             10386
```

<210> SEQ ID NO 343
<211> LENGTH: 2191
<212> TYPE: DNA
<213> ORGANISM: Homo sapiens

<400> SEQUENCE: 343

```
ggtggccgag cgggggaccg ggaagcatgg cccgggggtc ggcggttgcc tgggcggcgc     60

tcgggccgtt gttgtggggc tgcgcgctgg ggctgcaggg cgggatgctg tacccccagg    120

agagcccgtc gcgggagtgc aaggagctgg acggcctctg gagcttccgc gccgacttct    180

ctgacaaccg acgccggggc ttcgaggagc agtggtaccg gcggccgctg tgggagtcag    240

gccccaccgt ggacatgcca gttccctcca gcttcaatga catcagccag gactggcgtc    300
```

-continued

```
tgcggcattt tgtcggctgg gtgtggtacg aacgggaggt gatcctgccg gagcgatgga    360
cccaggacct gcgcacaaga gtggtgctga ggattggcag tgcccattcc tatgccatcg    420
tgtgggtgaa tggggtcgac acgctagagc atgagggggg ctacctcccc ttcgaggccg    480
acatcagcaa cctggtccag gtggggcccc tgccctcccg gctccgaatc actatcgcca    540
tcaacaacac actcaccccc accaccctgc caccagggac catccaatac ctgactgaca    600
cctccaagta tcccaagggt tactttgtcc agaacacata ttttgacttt ttcaactacg    660
ctggactgca gcggtctgta cttctgtaca cgacacccac cacctacatc gatgacatca    720
ccgtcaccac cagcgtggag caagacagtg ggctggtgaa ttaccagatc tctgtcaagg    780
gcagtaacct gttcaagttg gaagtgcgtc ttttggatgc agaaaacaaa gtcgtggcga    840
atgggactgg gacccagggc caacttaagg tgccaggtgt cagcctctgg tggccgtacc    900
tgatgcacga acgccctgcc tatctgtatt cattggaggt gcagctgact gcacagacgt    960
cactggggcc tgtgtctgac ttctacacac tccctgtggg gatccgcact gtggctgtca   1020
ccaagagcca gttcctcatc aatgggaaac ctttctattt ccacggtgtc aacaagcatg   1080
aggatgcgga catccgaggg aagggcttcg actggccgct gctggtgaag gacttcaacc   1140
tgcttcgctg gcttggtgcc aacgctttcc gtaccagcca ctacccctat gcagaggaag   1200
tgatgcagat gtgtgaccgc tatgggattg tggtcatcga tgagtgtccc ggcgtgggcc   1260
tggcgctgcc gcagttcttc aacaacgttt ctctgcatca ccacatgcag gtgatggaag   1320
aagtggtgcg tagggacaag aaccaccccg cggtcgtgat gtggtctgtg gccaacgagc   1380
ctgcgtccca cctagaatct gctggctact acttgaagat ggtgatcgct cacaccaaat   1440
ccttggaccc ctcccggcct gtgacctttg tgagcaactc taactatgca gcagacaagg   1500
gggctccgta tgtggatgtg atctgtttga acagctacta ctcttggtat cacgactacg   1560
ggcacctgga gttgattcag ctgcagctgg ccacccagtt tgagaactgg tataagaagt   1620
atcagaagcc cattattcag agcgagtatg gagcagaaac gattgcaggg tttcaccagg   1680
atccacctct gatgttcact gaagagtacc agaaaagtct gctagagcag taccatctgg   1740
gtctggatca aaaacgcaga aaatatgtgg ttggagagct catttggaat tttgccgatt   1800
tcatgactga acagtcaccg acgagagtgc tggggaataa aaaggggatc ttcactcggc   1860
agagacaacc aaaaagtgca gcgttccttt tgcgagagag atactggaag attgccaatg   1920
aaaccaggta tccccactca gtagccaagt cacaatgttt ggaaaacagc ccgtttactt   1980
gagcaagact gataccacct gcgtgtccct tcctccccga gtcagggcga cttccacagc   2040
agcagaacaa gtgcctcctg gactgttcac ggcagaccag aacgtttctg gcctgggttt   2100
tgtggtcatc tattctagca gggaacacta aaggtggaaa taaaagattt tctattatgg   2160
aaataaagag ttggcatgaa agtcgctact g                                   2191
```

```
<210> SEQ ID NO 344
<211> LENGTH: 2776
<212> TYPE: DNA
<213> ORGANISM: Homo sapiens

<400> SEQUENCE: 344

cagggcagac tggtagcaaa gcccccacgc ccagccagga gcaccgccgc ggactccagc     60
acaccgaggg acatgctggg cctgcgcccc ccactgctcg ccctggtggg gctgctctcc    120
ctcgggtgcg tcctctctca ggagtgcacg aagttcaagg tcagcagctg ccgggaatgc    180
atcgagtcgg ggcccggctg cacctggtgc cagaagctga acttcacagg gccgggggat    240
```

-continued

```
cctgactcca ttcgctgcga cacccggcca cagctgctca tgaggggctg tgcggctgac    300
gacatcatgg accccacaag cctcgctgaa acccaggaag accacaatgg gggccagaag    360
cagctgtccc cacaaaaagt gacgctttac ctgcgaccag gccaggcagc agcgttcaac    420
gtgaccttcc ggcgggccaa gggctacccc atcgacctgt actatctgat ggacctctcc    480
tactccatgc ttgatgacct caggaatgtc aagaagctag gtggcgacct gctccgggcc    540
ctcaacgaga tcaccgagtc cggccgcatt ggcttcgggt ccttcgtgga caagaccgtg    600
ctgccgttcg tgaacacgca ccctgataag ctgcgaaacc catgccccaa caaggagaaa    660
gagtgccagc ccccgtttgc cttcaggcac gtgctgaagc tgaccaacaa ctccaaccag    720
tttcagaccg aggtcgggaa gcagctgatt tccggaaacc tggatgcacc cgagggtggg    780
ctggacgcca tgatgcaggt cgccgcctgc ccggaggaaa tcggctggcg caacgtcacg    840
cggctgctgg tgtttgccac tgatgacggc ttccatttcg cgggcgacgg aaagctgggc    900
gccatcctga cccccaacga cggccgctgt cacctggagg acaacttgta caagaggagc    960
aacgaattcg actacccatc ggtgggccag ctggcgcaca agctggctga aaacaacatc   1020
cagcccatct tcgcggtgac cagtaggatg gtgaagacct acgagaaact caccgagatc   1080
atccccaagt cagccgtggg ggagctgtct gaggactcca gcaatgtggt ccatctcatt   1140
aagaatgctt acaataaact ctcctccagg gtcttcctgg atcacaacgc cctccccgac   1200
accctgaaag tcacctacga ctccttctgc agcaatggag tgacgcacag gaaccagccc   1260
agaggtgact gtgatggcgt gcagatcaat gtcccgatca ccttccaggt gaaggtcacg   1320
gccacagagt gcatccagga gcagtcgttt gtcatccggg cgctgggctt cacggacata   1380
gtgaccgtgc aggttcttcc ccagtgtgag tgccggtgcc gggaccagag cagagaccgc   1440
agcctctgcc atggcaaggg cttcttggag tgcggcatct gcaggtgtga cactggctac   1500
attgggaaaa actgtgagtg ccagacacag ggccggagca gccaggagct ggaaggaagc   1560
tgccggaagg acaacaactc catcatctgc tcagggctgg gggactgtgt ctgcgggcag   1620
tgcctgtgcc acaccagcga cgtccccggc aagctgatat acgggcagta ctgcgagtgt   1680
gacaccatca actgtgagcg ctacaacggc caggtctgcg gcggcccggg gagggggctc   1740
tgcttctgcg ggaagtgccg ctgccacccg ggctttgagg gctcagcgtg ccagtgcgag   1800
aggaccactg agggctgcct gaacccgcgg cgtgttgagt gtagtggtcg tggccggtgc   1860
cgctgcaacg tatgcgagtg ccattcaggc taccagctgc ctctgtgcca ggagtgcccc   1920
ggctgcccct caccctgtgg caagtacatc tcctgcgccg agtgcctgaa gttcgaaaag   1980
ggcccctttg ggaagaactg cagcgcggcg tgtccgggcc tgcagctgtc gaacaacccc   2040
gtgaagggca ggacctgcaa ggagagggac tcagagggct gctgggtggc ctacacgctg   2100
gagcagcagg acgggatgga ccgctacctc atctatgtgg atgagagccg agagtgtgtg   2160
gcaggcccca acatcgccgc catcgtcggg ggcaccgtgg caggcatcgt gctgatcggc   2220
attctcctgc tggtcatctg gaaggctctg atccacctga gcgacctccg ggagtacagg   2280
cgctttgaga aggagaagct caagtcccag tggaacaatg ataatcccct tttcaagagc   2340
gccaccacga cggtcatgaa ccccaagttt gctgagagtt aggagcactt ggtgaagaca   2400
aggccgtcag gacccaccat gtctgcccca tcacgcggcc gagacatggc ttggccacag   2460
ctcttgagga tgtcaccaat taaccagaaa tccagttatt ttccgccctc aaaatgacag   2520
ccatggccgg ccggtgcttc tgggggctcg tcggggggac agctccactc tgactggcac   2580
```

```
agtctttgca tggagacttg aggagggctt gaggttggtg aggttaggtg cgtgtttcct   2640

gtgcaagtca ggacatcagt ctgattaaag gtggtgccaa tttatttaca tttaaacttg   2700

tcagggtata aaatgacatc ccattaatta tattgttaat caatcacgtg tatagaaaaa   2760

aaaataaaac ttcaat                                                   2776
```

<210> SEQ ID NO 345
<211> LENGTH: 3160
<212> TYPE: DNA
<213> ORGANISM: Homo sapiens

<400> SEQUENCE: 345

```
cctcccctcg cccggcgcgg tcccgtccgc ctctcgctcg cctcccgcct cccctcggtc     60

ttccgaggcg cccgggctcc cggcgcggcg gcggaggggg cgggcaggcc ggcgggcggt    120

gatgtggcag gactctttat gcgctgcggc aggatacgcg ctcggcgctg ggacgcgact    180

gcgctcagtt ctctcctctc ggaagctgca gccatgatgg aagtttgaga gttgagccgc    240

tgtgaggcga ggccgggctc aggcgaggga gatgagagac ggcggcggcc gcggcccgga    300

gcccctctca gcgcctgtga gcagccgcgg gggcagcgcc ctcggggagc cggccggcct    360

gcggcggcgg cagcggcggc gtttctcgcc tcctcttcgt cttttctaac cgtgcagcct    420

cttcctcggc ttctcctgaa agggaaggtg gaagccgtgg gctcgggcgg gagccggctg    480

aggcgcggcg gcggcggcgg cggcacctcc cgctcctgga gcggggggga gaagcggcgg    540

cggcggcggc cgcggcggct gcagctccag ggagggggtc tgagtcgcct gtcaccattt    600

ccagggctgg gaacgccgga gagttggtct ctccccttct actgcctcca acacggcggc    660

ggcggcggcg gcacatccag ggacccgggc cggttttaaa cctcccgtcc gccgccgccg    720

cacccccgt ggcccgggct ccggaggccg ccggcggagg cagccgttcg gaggattatt     780

cgtcttctcc ccattccgct gccgccgctg ccaggcctct ggctgctgag gagaagcagg    840

cccagtcgct gcaaccatcc agcagccgcc gcagcagcca ttacccggct gcggtccaga    900

gccaagcggc ggcagagcga ggggcatcag ctaccgccaa gtccagagcc atttccatcc    960

tgcagaagaa gccccgccac cagcagcttc tgccatctct ctcctccttt ttcttcagcc   1020

acaggctccc agacatgaca gccatcatca aagagatcgt tagcagaaac aaaaggagat   1080

atcaagagga tggattcgac ttagacttga cctatattta tccaaacatt attgctatgg   1140

gatttcctgc agaaagactt gaaggcgtat acaggaacaa tattgatgat gtagtaaggt   1200

tttggattc  aaagcataaa aaccattaca agatatacaa tctttgtgct gaaagacatt   1260

atgacaccgc caaatttaat tgcagagttg cacaatatcc ttttgaagac cataacccac   1320

cacagctaga acttatcaaa cccttttgtg aagatcttga ccaatggcta agtgaagatg   1380

acaatcatgt tgcagcaatt cactgtaaag ctggaaaggg acgaactggt gtaatgatat   1440

gtgcatattt attacatcgg ggcaaatttt taaaggcaca agaggcccta gatttctatg   1500

gggaagtaag gaccagagac aaaaagggag taactattcc cagtcagagg cgctatgtgt   1560

attattatag ctacctgtta aagaatcatc tggattatag accagtggca ctgttgtttc   1620

acaagatgat gtttgaaact attccaatgt tcagtggcgg aacttgcaat cctcagtttg   1680

tggtctgcca gctaaaggtg aagatatatt cctccaattc aggacccaca cgacgggaag   1740

acaagttcat gtactttgag ttccctcagc cgttacctgt gtgtggtgat atcaaagtag   1800

agttcttcca caaacagaac aagatgctaa aaaaggacaa aatgtttcac ttttgggtaa   1860

atacattctt cataccagga ccagaggaaa cctcagaaaa agtagaaaat ggaagtctat   1920
```

```
gtgatcaaga aatcgatagc atttgcagta tagagcgtgc agataatgac aaggaatatc   1980
tagtacttac tttaacaaaa aatgatcttg acaaagcaaa taaagacaaa gccaaccgat   2040
acttttctcc aaattttaag gtgaagctgt acttcacaaa aacagtagag gagccgtcaa   2100
atccagaggc tagcagttca acttctgtaa caccagatgt tagtgacaat gaacctgatc   2160
attatagata ttctgacacc actgactctg atccagagaa tgaacctttt gatgaagatc   2220
agcatacaca aattacaaaa gtctgaattt ttttttatca agagggataa aacaccatga   2280
aaataaactt gaataaactg aaaatggacc tttttttttt taatggcaat aggacattgt   2340
gtcagattac cagttatagg aacaattctc ttttcctgac caatcttgtt ttaccctata   2400
catccacagg gttttgacac ttgttgtcca gttgaaaaaa ggttgtgtag ctgtgtcatg   2460
tatatacctt tttgtgtcaa aaggacattt aaaattcaat taggattaat aaagatggca   2520
ctttcccgtt ttattccagt tttataaaaa gtggagacag actgatgtgt atacgtagga   2580
attttttcct tttgtgttct gtcaccaact gaagtggcta aagagctttg tgatatactg   2640
gttcacatcc taccccttg cacttgtggc aacagataag tttgcagttg gctaagagag   2700
gtttccgaaa ggttttgcta ccattctaat gcatgtattc gggttagggc aatggagggg   2760
aatgctcaga aaggaaataa ttttatgctg gactctggac catataccat ctccagctat   2820
ttacacacac ctttctttag catgctacag ttattaatct ggacattcga ggaattggcc   2880
gctgtcactg cttgttgttt gcgcattttt ttttaaagca tattggtgct agaaaaggca   2940
gctaaaggaa gtgaatctgt attggggtac aggaatgaac cttctgcaac atcttaagat   3000
ccacaaatga agggatataa aaataatgtc ataggtaaga aacacagcaa caatgactta   3060
accatataaa tgtggaggct atcaacaaag aatgggcttg aaacattata aaaattgaca   3120
atgatttatt aaatatgttt tctcaattgt aaaaaaaaaa                         3160
```

<210> SEQ ID NO 346
<211> LENGTH: 2629
<212> TYPE: DNA
<213> ORGANISM: Homo sapiens

<400> SEQUENCE: 346

```
acttgtcatg gcgactgtcc agctttgtgc caggagcctc gcaggggttg atgggattgg     60
ggttttcccc tcccatgtgc tcaagactgg cgctaaaagt tttgagcttc tcaaaagtct    120
agagccaccg tccagggagc aggtagctgc tgggctccgg ggacactttg cgttcgggct    180
gggagcgtgc tttccacgac ggtgacacgc ttccctggat tggcagccag actgccttcc    240
gggtcactgc catggaggag ccgcagtcag atcctagcgt cgagccccct ctgagtcagg    300
aaacattttc agacctatgg aaactacttc ctgaaaacaa cgttctgtcc cccttgccgt    360
cccaagcaat ggatgatttg atgctgtccc cggacgatat tgaacaatgg ttcactgaag    420
acccaggtcc agatgaagct cccagaatgc cagaggctgc tccccgcgtg gcccctgcac    480
cagcagctcc tacaccggcg gcccctgcac cagccccctc ctggcccctg tcatcttctg    540
tcccttccca gaaaacctac cagggcagct acggtttccg tctgggcttc ttgcattctg    600
ggacagccaa gtctgtgact tgcacgtact cccctgccct caacaagatg ttttgccaac    660
tggccaagac ctgccctgtg cagctgtggg ttgattccac acccccgccc ggcacccgcg    720
tccgcgccat ggccatctac aagcagtcac agcacatgac ggaggttgtg aggcgctgcc    780
cccaccatga gcgctgctca gatagcgatg gtctggcccc tcctcagcat cttatccgag    840
```

-continued

```
tggaaggaaa tttgcgtgtg gagtatttgg atgacagaaa cacttttcga catagtgtgg    900

tggtgcccta tgagccgcct gaggttggct ctgactgtac caccatccac tacaactaca    960

tgtgtaacag ttcctgcatg ggcggcatga accggaggcc catcctcacc atcatcacac   1020

tggaagactc cagtggtaat ctactgggac ggaacagctt tgaggtgcgt gtttgtgcct   1080

gtcctgggag agaccggcgc acagaggaag agaatctccg caagaaaggg gagcctcacc   1140

acgagctgcc cccagggagc actaagcgag cactgcccaa caacaccagc tcctctcccc   1200

agccaaagaa gaaaccactg gatggagaat atttcaccct tcagatccgt gggcgtgagc   1260

gcttcgagat gttccgagag ctgaatgagg ccttggaact caaggatgcc caggctggga   1320

aggagccagg ggggagcagg gctcactcca gccacctgaa gtccaaaaag ggtcagtcta   1380

cctcccgcca taaaaaactc atgttcaaga cagaagggcc tgactcagac tgacattctc   1440

cacttcttgt tccccactga cagcctccca cccccatctc tccctcccct gccattttgg   1500

gttttgggtc tttgaaccct tgcttgcaat aggtgtgcgt cagaagcacc caggacttcc   1560

atttgctttg tcccggggct ccactgaaca agttggcctg cactggtgtt ttgttgtggg   1620

gaggaggatg gggagtagga cataccagct tagattttaa ggtttttact gtgagggatg   1680

tttgggagat gtaagaaatg ttcttgcagt taagggttag tttacaatca gccacattct   1740

aggtaggtag gggcccactt caccgtacta accagggaag ctgtccctca tgttgaattt   1800

tctctaactt caaggcccat atctgtgaaa tgctggcatt tgcacctacc tcacagagtg   1860

cattgtgagg gttaatgaaa taatgtacat ctggccttga aaccaccttt tattacatgg   1920

ggtctaaaac ttgaccccct tgagggtgcc tgttccctct ccctctccct gttggctggt   1980

gggttggtag tttctacagt tgggcagctg gttaggtaga gggagttgtc aagtcttgct   2040

ggcccagcca aaccctgtct gacaacctct tggtcgacct tagtacctaa aaggaaatct   2100

caccccatcc cacaccctgg aggatttcat ctcttgtata tgatgatctg gatccaccaa   2160

gacttgtttt atgctcaggg tcaatttctt ttttcttttt tttttttttt tttctttttc   2220

tttgagactg ggtctcgctt tgttgcccag gctggagtgg agtggcgtga tcttggctta   2280

ctgcagcctt tgcctccccg gctcgagcag tcctgcctca gcctccggag tagctgggac   2340

cacaggttca tgccaccatg gccagccaac ttttgcatgt tttgtagaga tggggtctca   2400

cagtgttgcc caggctggtc tcaaactcct gggctcaggc gatccacctg tctcagcctc   2460

ccagagtgct gggattacaa ttgtgagcca ccacgtggag ctggaagggt caacatcttt   2520

tacattctgc aagcacatct gcattttcac ccccaccttc ccctccttct cccttttat    2580

atcccatttt tatatcgatc tcttatttta caataaaact ttgctgcca               2629
```

<210> SEQ ID NO 347
<211> LENGTH: 3442
<212> TYPE: DNA
<213> ORGANISM: Homo sapiens

<400> SEQUENCE: 347

```
agccggtgcg ccgcagacta gggcgcctcg ggccagggag cgcggaggag ccatggccac     60

cgctaacggg gccgtggaaa acgggcagcc ggacgggaag ccgccggccc tgccgcgccc    120

catccgcaac ctggaggtca agttcaccaa gatatttatc aacaatgaat ggcacgaatc    180

caagagtggg aaaaagtttg ctacatgtaa cccttcaact cgggagcaaa tatgtgaagt    240

ggaagaagga gataagcccg acgtggacaa ggctgtggag gctgcacagg ttgccttcca    300

gaggggctcg ccatggcgcc ggctggatgc cctgagtcgt gggcggctgc tgcaccagct    360
```

-continued

```
ggctgacctg gtggagaggg accgcgccac cttggccgcc ctggagacga tggatacagg    420
gaagccattt cttcatgctt ttttcatcga cctggagggc tgtattagaa ccctcagata    480
ctttgcaggg tgggcagaca aaatccaggg caagaccatc cccacagatg acaacgtcgt    540
atgcttcacc aggcatgagc ccattggtgt ctgtggggcc atcactccat ggaacttccc    600
cctgctgatg ctggtgtgga agctggcacc cgccctctgc tgtgggaaca ccatggtcct    660
gaagcctgcg gagcagacac ctctcaccgc cctttatctc ggctctctga tcaaagaggc    720
cgggttccct ccaggagtgg tgaacattgt gccaggattc gggcccacag tgggagcagc    780
aatttcttct caccctcaga tcaacaagat cgccttcacc ggctccacag aggttggaaa    840
actggttaaa gaagctgcgt cccggagcaa tctgaagcgg gtgacgctgg agctgggggg    900
gaagaacccc tgcatcgtgt gtgcggacgc tgacttggac ttggcagtgg agtgtgccca    960
tcagggagtg ttcttcaacc aaggccagtg ttgcacggca gcctccaggg tgttcgtgga   1020
ggagcaggtc tactctgagt ttgtcaggcg gagcgtggag tatgccaaga aacggcccgt   1080
gggagacccc ttcgatgtca aaacagaaca ggggcctcag attgatcaaa agcagttcga   1140
caaaatctta gagctgatcg agagtgggaa gaaggaaggg gccaagctgg aatgcggggg   1200
ctcagccatg gaagacaagg ggctcttcat caaacccact gtcttctcag aagtcacaga   1260
caacatgcgg attgccaaag aggagatttt cgggccagtg caaccaatac tgaagttcaa   1320
aagtatcgaa gaagtgataa aaagagcgaa tagcaccgac tatggactca cagcagccgt   1380
gttcacaaaa aatctcgaca aagccctgaa gttggcttct gccttagagt ctggaacggt   1440
ctggatcaac tgctacaacg ccctctatgc acaggctcca tttggtggct ttaaaatgtc   1500
aggaaatggc agagaactag gtgaatacgc tttggccgaa tacacagaag tgaaaactgt   1560
caccatcaaa cttggcgaca agaacccctg aaggaaaggc ggggctcctt cctcaaacat   1620
cggacggcgg aatgtggcag atgaaatgtg ctggaggaaa aaaatgacat ttctgacctt   1680
cccgggacac attcttctgg aggctttaca tctactggag ttgaatgatt gctgttttcc   1740
tctcactctc ctgtttattc accagactgg ggatgcctat aggttgtctg tgaaatcgca   1800
gtcctgcctg gggagggagc tgttggccat ttctgtgttt ccctttaaac cagatcctgg   1860
agacagtgag atactcaggg cgttgttaac agggagtggt atttgaagtg tccagcagtt   1920
gcttgaaatg ctttgccgaa tctgactcca gtaagaatgt gggaaaaccc cctgtgtgtt   1980
ctgcaagcag ggctcttgca ccagcggtct cctcagggtg gacctgctta cagagcaagc   2040
cacgcctctt tccgaggtga aggtgggacc attccttggg aaaggattca cagtaaggtt   2100
ttttggtttt tgttttttgt tttcttgttt ttaaaaaaag gatttcacag tgagaaagtt   2160
ttggttagtg cataccgtgg aagggcgcca gggtctttgt ggattgcatg ttgacattga   2220
ccgtgagatt cggcttcaaa ccaatactgc ctttggaata tgacagaatc aatagcccag   2280
agagcttagt caaagacgat atcacggtct accttaacca aggcactttc ttaagcagaa   2340
aatattgttg aggttacctt tgctgctaaa gatccaatct tctaacgcca caacagcata   2400
gcaaatccta ggataattca cctcctcatt tgacaaatca gagctgtaat tcactttaac   2460
aaattacgca tttctatcac gttcactaac agcttatgat aagtctgtgt agtcttcctt   2520
ttctccagtt ctgttaccca atttagatta gtaaagcgta cacaactgga aagactgctg   2580
taataacaca gccttgttat ttttaagtcc tattttgata ttaatttctg attagttagt   2640
aaataacacc tggattctat ggaggacctc ggtcttcatc caagtggcct gagtatttca   2700
```

-continued

```
ctggcaggtt gtgaattttt cttttcctct ttgggaatcc aaatgatgat gtgcaatttc   2760

atgttttaac ttgggaaact gaaagtgttc ccatatagct tcaaaaacaa aaacaaatgt   2820

gttatccgac ggatactttt atggttacta actagtactt tcctaattgg gaaagtagtg   2880

cttaagtttg caaattaagt tggggagggc aataataaaa tgagggcccg taacagaacc   2940

agtgtgtgta taacgaaaac catgtataaa atgggcctat cacccttgtc agagatataa   3000

attaccacat ttggcttccc ttcatcagct aacacttatc acttatacta ccaataactt   3060

gttaaatcag gatttggctt catacactga attttcagta ttttatctca agtagatata   3120

gacactaacc ttgatagtga tacgttagag ggttcctatt cttccattgt acgataatgt   3180

ctttaatatg aaatgctaca ttatttataa ttggtagagt tattgtatct ttttatagtt   3240

gtaagtacac agaggtggta tatttaaact tctgtaatat actgtattta gaaatggaaa   3300

tatatatagt gttaggtttc acttctttta aggtttaccc ctgtggtgtg gtttaaaaat   3360

ctataggcct gggaattccg atcctagctg cagatcgcat cccacaatgc gagaatgata   3420

aaataaaatt ggatatttga ga                                            3442
```

<210> SEQ ID NO 348
<211> LENGTH: 737
<212> TYPE: DNA
<213> ORGANISM: Homo sapiens

<400> SEQUENCE: 348

```
ggagtttcgc cgccgcagtc ttcgccacca tgccgcccta caccgtggtc tatttcccag     60

ttcgaggccg ctgcgcggcc ctgcgcatgc tgctggcaga tcagggccag agctggaagg    120

aggaggtggt gaccgtggag acgtggcagg agggctcact caaagcctcc tgcctatacg    180

ggcagctccc caagttccag gacggagacc tcaccctgta ccagtccaat accatcctgc    240

gtcacctggg ccgcaccctt gggctctatg ggaaggacca gcaggaggca gccctggtgg    300

acatggtgaa tgacggcgtg gaggacctcc gctgcaaata catctccctc atctacacca    360

actatgaggc gggcaaggat gactatgtga aggcactgcc cgggcaactg aagccttttg    420

agaccctgct gtcccagaac cagggaggca agaccttcat tgtgggagac cagatctcct    480

tcgctgacta caacctgctg gacttgctgc tgatccatga ggtcctagcc cctggctgcc    540

tggatgcgtt cccccctgctc tcagcatatg tggggcgcct cagcgcccgg cccaagctca    600

aggccttcct ggcctcccct gagtacgtga acctccccat caatggcaac gggaaacagt    660

gagggttggg gggactctga gcgggaggca gagtttgcct tcctttctcc aggaccaata    720

aaatttctaa gagagct                                                   737
```

<210> SEQ ID NO 349
<211> LENGTH: 5189
<212> TYPE: DNA
<213> ORGANISM: Homo sapiens

<400> SEQUENCE: 349

```
atggccaagt cgggtggctg cggcgcggga gccggcgtgg gcggcggcaa cggggcactg     60

acctgggtga acaatgctgc aaaaaaagaa gagtcagaaa ctgccaacaa aaatgattct    120

tcaaagaagt tgtctgttga gagagtgtat cagaagaaga cacaacttga acacattctt    180

cttcgtcctg atacatatat tgggtcagtg gagccattga cgcagttcat gtgggtgtat    240

gatgaagatg taggaatgaa ttgcagggag gttacctttg tgccaggttt atacaagatc    300

tttgatgaaa ttttggttaa tgctgctgac aataaacaga gggataagaa catgacttgt    360
```

```
attaaagttt ctattgatcc tgaatctaac attataagca tttggaataa tgggaaaggc    420
attccagtag tagaacacaa ggtagagaaa gtttatgttc ctgctttaat ttttggacag    480
cttttaacat ccagtaacta tgatgatgat gagaaaaaag ttacaggtgg tcgtaatggt    540
tatggtgcaa aactttgtaa tattttcagt acaaagttta cagtagaaac agcttgcaaa    600
gaatacaaac acagttttaa gcagacatgg atgaataata tgatgaagac ttctgaagcc    660
aaaattaaac attttgatgg tgaagattac acatgcataa cattccaacc agatctgtcc    720
aaatttaaga tggaaaaact tgacaaggat attgtggccc tcatgactag aagggcatat    780
gatttggctg gttcgtgtag aggggtcaag gtcatgttta atggaaagaa attgcctgta    840
aatggatttc gcagttatgt agatctttat gtgaaagaca aattggatga aactggggtg    900
gccctgaaag ttattcatga gcttgcaaat gaaagatggg atgtttgtct cacattgagt    960
gaaaaaggat tccagcaaat cagctttgta aatagtattg caactacaaa aggtggacgg   1020
cacgtggatt atgtggtaga tcaagttgtt ggtaaactga ttgaagtagt taagaaaaag   1080
aacaaagctg gtgtatcagt gaaaccattt caagtaaaaa accatatatg ggtttttatt   1140
aattgcctta ttgaaaatcc aacttttgat tctcagacta aggaaaacat gactctgcag   1200
cccaaaagtt ttgggtctaa atgccagctg tcagaaaaat tttttaaagc agcctctaat   1260
tgtggcattg tagaaagtat cctgaactgg gtgaaattta aggctcagac tcagctgaat   1320
aagaagtgtt catcagtaaa atacagtaaa atcaaaggta ttcccaaact ggatgatgct   1380
aatgatgctg gtggtaaaca ttccctggag tgtacactga tattaacaga gggagactct   1440
gccaaatcac tggctgtgtc tggattaggt gtgattggac gagacagata cggagttttt   1500
ccactcaggg gcaaaattct taatgtacgg gaagcttctc ataaacagat catggaaaat   1560
gctgaaataa ataatattat taaaatagtt ggtctacaat ataagaaaag ttacgatgat   1620
gcagaatctc tgaaaacctt acgctatgga aagattatga ttatgaccga tcaggatcaa   1680
gatggttctc acataaaagg cctgcttatt aatttcatcc atcacaattg gccatcactt   1740
ttgaagcatg gttttcttga agagttcatt actcctattg taaaggcaag caaaaataag   1800
caggaacttt ccttctacag tattcctgaa tttgacgaat ggaaaaaaca tatagaaaac   1860
cagaaagcct ggaaaataaa gtactataaa ggattgggta ctagtacagc taaagaagca   1920
aaggaatatt ttgctgatat ggaaaggcat cgcatcttgt ttagatatgc tggtcctgaa   1980
gatgatgctg ccattacctt ggcatttagt aagaagaaga ttgatgacag aaaagaatgg   2040
ttaacaaatt ttatggaaga ccggagacag cgtaggctac atggcttacc agagcaattt   2100
ttatatggta ctgcaacaaa gcatttgact tataatgatt tcatcaacaa ggaattgatt   2160
ctcttctcaa actcagacaa tgaaagatct ataccatctc ttgttgatgg ctttaaacct   2220
ggccagcgga aagttttatt tacctgtttc aagaggaatg ataaacgtga agtaaaagtt   2280
gcccagttgg ctggctctgt tgctgagatg tcggcttatc atcatggaga acaagcattg   2340
atgatgacta ttgtgaattt ggctcagaac tttgtgggaa gtaacaacat taacttgctt   2400
cagcctattg gtcagtttgg aactcggctt catggtggca aagatgctgc aagccctcgt   2460
tatattttca caatgttaag cactttagca aggctacttt ttcctgctgt ggatgacaac   2520
ctccttaagt tcctttatga tgataatcaa cgtgtagagc ctgagtggta tattcctata   2580
attcccatgg ttttaataaa tggtgctgag ggcattggta ctggatgggc ttgtaaacta   2640
cccaactatg atgctaggga aattgtgaac aatgtcagac gaatgctaga tggcctggat   2700
```

-continued

```
cctcatccca tgcttccaaa ctacaaaaac tttaaaggca cgattcaaga acttggtcaa   2760
aaccagtatg cagtcagtgg tgaaatattt gtagtggaca gaaacacagt agaaattaca   2820
gagcttccag ttagaacttg gacacaggta tataaagaac aggttttaga acctatgcta   2880
aatggaacag ataaaacacc agcattaatt tctgattata aagaatatca tactgacaca   2940
actgtgaaat ttgtggtgaa aatgactgaa gagaaactag cacaagcaga agctgctgga   3000
ctgcataaag tttttaaact tcaaactact cttacttgta attccatggt actttttgat   3060
catatgggat gtctgaagaa atatgaaact gtgcaagaca ttctgaaaga attctttgat   3120
ttacgattaa gttattacgg tttacgtaag gagtggcttg tgggaatgtt gggagcagaa   3180
tctacaaagc ttaacaatca agcccgtttc attttagaga agatacaagg gaaaattact   3240
atagagaata ggtcaaagaa agatttgatt caaatgttag tccagagagg ttatgaatct   3300
gacccagtga aagcctggaa agaagcacaa gaaaaggcag cagaagagga tgaaacacaa   3360
aaccagcatg atgatagttc ctccgattca ggaactcctt caggcccaga ttttaattat   3420
attttaaata tgtctctgtg gtctcttact aaagaaaaag ttgaagaact gattaaacag   3480
agagatgcaa aagggcgaga ggtcaatgat cttaaaagaa aatctccttc agatctttgg   3540
aaagaggatt tagcggcatt tgttgaagaa ctggataaag tggaatctca agaacgagaa   3600
gatgttctgg ctggaatgtc tggaaaagca attaaaggta aagttggcaa acctaaggtg   3660
aagaaactcc agttggaaga gacaatgccc tcaccttatg gcagaagaat aattcctgaa   3720
attacagcta tgaaggcaga tgccagcaaa aagttgctga agaagaagaa gggtgatctt   3780
gatactgcag cagtaaaagt ggaatttgat gaagaattca gtggagcacc agtagaaggt   3840
gcaggagaag aggcattgac tccatcagtt cctataaata aaggtcccaa acctaagagg   3900
gagaagaagg agcctggtac cagagtgaga aaaacaccta catcatctgg taaacctagt   3960
gcaaagaaag tgaagaaacg gaatccttgg tcagatgatg aatccaagtc agaaagtgat   4020
ttggaagaaa cagaacctgt ggttattcca agagattctt tgcttaggag agcagcagcc   4080
gaaagaccta aatacacatt tgatttctca gaagaagagg atgatgatgc tgatgatgat   4140
gatgatgaca ataatgattt agaggaattg aaagttaaag catctcccat aacaaatgat   4200
ggggaagatg aatttgttcc ttcagatggg ttagataaag atgaatatac attttcacca   4260
ggcaaatcaa aagccactcc agaaaaatct ttgcatgaca aaaaaagtca ggattttgga   4320
aatctcttct catttccttc atattctcag aagtcagaag atgattcagc taaatttgac   4380
agtaatgaag aagattctgc ttctgttttt tcaccatcat ttggtctgaa acagacagat   4440
aaagttccaa gtaaaacggt agctgctaaa aagggaaaac cgtcttcaga tacagtccct   4500
aagcccaaga gagccccaaa acagaagaaa gtagtagagg ctgtaaactc tgactcggat   4560
tcagaatttg gcattccaaa gaagactaca acaccaaaag gtaaaggccg aggggcaaag   4620
aaaaggaaag catctggctc tgaaaatgaa ggcgattata accctggcag gaaaacatcc   4680
aaaacaacaa gcaagaaacc gaagaagaca tcttttgatc aggattcaga tgtggacatc   4740
ttcccctcag acttccctac tgagccacct tctctgccac gaaccggtcg ggctaggaaa   4800
gaagtaaaat attttgcaga gtctgatgaa gaagaagatg atgttgattt tgcaatgttt   4860
aattaagtgc ccaaagagca caaacatttt tcaacaaata tcttgtgttg tccttttgtc   4920
ttctctgtct cagacttttg tacatctggc ttattttaat gtgatgatgt aattgacggt   4980
tttttattat tgtggtaggc cttttaacat tttgttctta cacatacagt tttatgctct   5040
tttttactca ttgaaatgtc acgtactgtc tgattggctt gtagaattgt tatagactgc   5100
```

cgtgcattag cacagatttt aattgtcatg gttacaaact acagacctgc tttttgaaat 5160
gaaatttaaa cattaaaaat ggaactgtg 5189

<210> SEQ ID NO 350
<211> LENGTH: 1536
<212> TYPE: DNA
<213> ORGANISM: Homo sapiens

<400> SEQUENCE: 350
gggggggggg ggaccacttg gcctgcctcc gtcccgccgc gccacttggc ctgcctccgt 60
cccgccgcgc cacttcgcct gcctccgtcc cccgcccgcc gcgccatgcc tgtggccggc 120
tcggagctgc cgcgccggcc cttgcccccc gccgcacagg agcgggacgc cgagccgcgt 180
ccgccgcacg gggagctgca gtacctgggg cagatccaac acatcctccg ctgcggcgtc 240
aggaaggacg accgcacggg caccggcacc ctgtcggtat tcggcatgca ggcgcgctac 300
agcctgagag atgaattccc tctgctgaca accaaacgtg tgttctggaa gggtgttttg 360
gaggagttgc tgtggtttat caagggatcc acaaatgcta aagagctgtc ttccaaggga 420
gtgaaaatct gggatgccaa tggatcccga gactttttgg acagcctggg attctccacc 480
agagaagaag gggacttggg cccagtttat ggcttccagt ggaggcattt tggggcagaa 540
tacagagata tggaatcaga ttattcagga cagggagttg accaactgca aagagtgatt 600
gacaccatca aaaccaaccc tgacgacaga agaatcatca tgtgcgcttg gaatccaaga 660
gatcttcctc tgatggcgct gcctccatgc catgccctct gccagttcta tgtggtgaac 720
agtgagctgt cctgccagct gtaccagaga tcgggagaca tgggcctcgg tgtgcctttc 780
aacatcgcca gctacgccct gctcacgtac atgattgcgc acatcacggg cctgaagcca 840
ggtgacttta tacacacttt gggagatgca catatttacc tgaatcacat cgagccactg 900
aaaattcagc ttcagcgaga acccagacct ttcccaaagc tcaggattct tcgaaaagtt 960
gagaaaattg atgacttcaa agctgaagac tttcagattg aagggtacaa tccgcatcca 1020
actattaaaa tggaaatggc tgtttagggt gctttcaaag gagcttgaag gatattgtca 1080
gtctttaggg gttgggctgg atgccgaggt aaaagttctt tttgctctaa aagaaaaagg 1140
aactaggtca aaaatctgtc cgtgacctat cagttattaa tttttaagga tgttgccact 1200
ggcaaatgta actgtgccag ttctttccat aataaaaggc tttgagttaa ctcactgagg 1260
gtatctgaca atgctgaggt tatgaacaaa gtgaggagaa tgaaatgtat gtgctcttag 1320
caaaaacatg tatgtgcatt tcaatcccac gtacttataa agaaggttgg tgaatttcac 1380
aagctatttt tggaatattt ttagaatatt ttaagaattt cacaagctat tccctcaaat 1440
ctgagggagc tgagtaacac catcgatcat gatgtagagt gtggttatga actttatagt 1500
tgttttatat gttgctataa taaagaagtg ttctgc 1536

<210> SEQ ID NO 351
<211> LENGTH: 2386
<212> TYPE: DNA
<213> ORGANISM: Homo sapiens

<400> SEQUENCE: 351
ggaggaggaa gcaagcgagg gggctggttc ctgagcttcg caattcctgt gtcgccttct 60
gggctcccag cctgccgggt cgcatgatcc ctccggccgg agctggtttt tttgccagcc 120
accgcgaggc cggctgagtt accggcatcc ccgcagccac ctcctctccc gacctgtgat 180

-continued

```
acaaaagatc ttccgggggc tgcacctgcc tgcctttgcc taaggcggat ttgaatctct    240

ttctctccct tcagaatctt atcttggctt tggatcttag aagagaatca ctaaccagag    300

acgagactca gtgagtgagc aggtgttttg gacaatggac tggttgagcc catccctatt    360

ataaaaatgt ctcagagcaa ccgggagctg gtggttgact ttctctccta caagctttcc    420

cagaaaggat acagctggag tcagtttagt gatgtggaag agaacaggac tgaggcccca    480

gaagggactg aatcggagat ggagaccccc agtgccatca atggcaaccc atcctggcac    540

ctggcagaca gccccgcggt gaatggagcc actggccaca gcagcagttt ggatgcccgg    600

gaggtgatcc ccatggcagc agtaaagcaa gcgctgaggg aggcaggcga cgagtttgaa    660

ctgcggtacc ggcgggcatt cagtgacctg acatcccagc tccacatcac cccagggaca    720

gcatatcaga gctttgaaca ggatactttt gtggaactct atgggaacaa tgcagcagcc    780

gagagccgaa agggccagga acgcttcaac cgctggttcc tgacgggcat gactgtggcc    840

ggcgtggttc tgctgggctc actcttcagt cggaaatgac cagacactga ccatccactc    900

taccctccca ccccttctc tgctccacca catcctccgt ccagccgcca ttgccaccag    960

gagaaccact acatgcagcc catgcccacc tgcccatcac agggttgggc ccagatctgg   1020

tcccttgcag ctagttttct agaatttatc acacttctgt gagaccccca cacctcagtt   1080

cccttggcct cagaattcac aaaatttcca caaaatctgt ccaaaggagg ctggcaggta   1140

tggaagggtt tgtggctggg ggcaggaggg ccctacctga ttggtgcaac ccttacccct   1200

tagcctccct gaaaatgttt ttctgccagg gagcttgaaa gttttcagaa cctcttcccc   1260

agaaaggaga ctagattgcc tttgttttga tgtttgtggc ctcagaattg atcattttcc   1320

ccccactctc cccacactaa cctgggttcc ctttccttcc atccctaccc cctaagagcc   1380

atttaggggc cacttttgac tagggattca ggctgcttgg gataaagatg caaggaccag   1440

gactccctcc tcacctctgg actggctaga gtcctcactc ccagtccaaa tgtcctccag   1500

aagcctctgg ctagaggcca gccccaccca ggagggaggg ggctatagct acaggaagca   1560

ccccatgcca aagctagggt ggcccttgca gttcagcacc accctagtcc cttcccctcc   1620

ctggctccca tgaccatact gagggaccaa ctgggcccaa gacagatgcc ccagagctgt   1680

ttatggcctc agctgcctca cttcctacaa gagcagcctg tggcatcttt gccttgggct   1740

gctcctcatg gtgggttcag ggactcagc cctgaggtga aagggagcta tcaggaacag   1800

ctatgggagc cccagggtct tccctacctc aggcaggaag ggcaggaagg agagcctgct   1860

gcatggggtg gggtagggct gactagaagg gccagtcctg cctggccagg cagatctgtg   1920

ccccatgcct gtccagcctg ggcagccagg ctgccaaggc cagagtggcc tggccaggag   1980

ctcttcaggc ctccctctct cttctgctcc acccttggcc tgtctcatcc ccaggggtcc   2040

cagccacccc gggctctctg ctgtacatat ttgagactag tttttattcc ttgtgaagat   2100

gatatactat ttttgttaag cgtgtctgta tttatgtgtg aggagctgct ggcttgcagt   2160

gcgcgtgcac gtggagagct ggtgcccgga gattggacgg cctgatgctc cctcccctgc   2220

cctggtccag ggaagctggc cgagggtcct ggctcctgag ggcatctgc ccctcccca    2280

acccccaccc cacacttgtt ccagctcttt gaaatagtct gtgtgaaggt gaaagtgcag   2340

ttcagtaata aactgtgttt actcagtgaa aaaaaaaaaa aaaaaa                  2386
```

<210> SEQ ID NO 352
<211> LENGTH: 1270
<212> TYPE: DNA
<213> ORGANISM: Homo sapiens

<400> SEQUENCE: 352

```
agacgttcgc acacctgggt gccagcgccc cagaggtccc gggacagccc gaggcgccgc      60
gcccgccgcc ccgagctccc caagccttcg agagcggcgc acactcccgg tctccactcg     120
ctcttccaac acccgctcgt tttggcggca gctcgtgtcc cagagaccga gttgccccag     180
agaccgagac gccgccgctg cgaaggacca atgagagccc cgctgctacc gccggcgccg     240
gtggtgctgt cgctcttgat actcggctca ggccattatg ctgctggatt ggacctcaat     300
gacacctact ctgggaagcg tgaaccattt tctggggacc acagtgctga tggatttgag     360
gttacctcaa gaagtgagat gtcttcaggg agtgagattt cccctgtgag tgaaatgcct     420
tctagtagtg aaccgtcctc gggagccgac tatgactact cagaagagta tgataacgaa     480
ccacaaatac ctggctatat tgtcgatgat tcagtcagag ttgaacaggt agttaagccc     540
ccccaaaaca agacggaaag tgaaaatact tcagataaac ccaaaagaaa gaaaaaggga     600
ggcaaaaatg gaaaaaatag aagaaacaga aagaagaaaa atccatgtaa tgcagaattt     660
caaaatttct gcattcacgg agaatgcaaa tatatagagc acctggaagc agtaacatgc     720
aaatgtcagc aagaatattt cggtgaacgg tgtggggaaa agtccatgaa aactcacagc     780
atgattgaca gtagtttatc aaaaattgca ttagcagcca tagctgcctt tatgtctgct     840
gtgatcctca cagctgttgc tgttattaca gtccagctta gaagacaata cgtcaggaaa     900
tatgaaggag aagctgagga acgaaagaaa cttcgacaag agaatggaaa tgtacatgct     960
atagcataac tgaagataaa attacaggat atcacattgg agtcactgcc aagtcatagc    1020
cataaatgat gagtcggtcc tctttccagt ggatcataag acaatggacc ctttttgtta    1080
tgatggtttt aaactttcaa ttgtcacttt ttatgctatt tctgtatata aaggtgcacg    1140
aaggtaaaaa gtatttttc aagttgtaaa taatttattt aatatttaat ggaagtgtat    1200
ttattttaca gctcattaaa ctttttaac caaacagaaa aaaaaaaaaa aaaaaaaaaa    1260
aaaaaaaaaa                                                           1270
```

<210> SEQ ID NO 353
<211> LENGTH: 1600
<212> TYPE: DNA
<213> ORGANISM: Homo sapiens

<400> SEQUENCE: 353

```
gccccgccgc cggcagtgga ccgctgtgcg cgaaccctga accctacggt cccgacccgc      60
gggcgaggcc gggtacctgg gctgggatcc ggagcaagcg ggcgagggca gcgccctaag     120
caggcccgga gcgatggcag ccttgatgac cccgggaacc ggggccccac ccgcgcctgg     180
tgacttctcc ggggaaggga gccagggact tcccgaccct tcgccagagc ccaagcagct     240
cccggagctg atccgcatga agcgagacgg aggccgcctg agcgaagcgg acatcagggg     300
cttcgtggcc gctgtggtga atgggagcgc gcagggcgca cagatcgggg ccatgctgat     360
ggccatccga cttcggggca tggatctgga ggagacctcg gtgctgaccc aggccctggc     420
tcagtcggga cagcagctgg agtggccaga ggcctggcgc cagcagcttg tggacaagca     480
ttccacaggg ggtgtgggtg acaaggtcag cctggtcctc gcacctgccc tggcggcatg     540
tggctgcaag gtgccaatga tcagcggacg tggtctgggg cacacaggag gcaccttgga     600
taagctggag tctattcctg gattcaatgt catccagagc ccagagcaga tgcaagtgct     660
gctggaccag gcgggctgct gtatcgtggg tcagagtgag cagctggttc ctgcggacgg     720
```

-continued

```
aatcctatat gcagccagag atgtgacagc caccgtggac agcctgccac tcatcacagc    780
ctccattctc agtaagaaac tcgtggaggg gctgtccgct ctggtggtgg acgttaagtt    840
cggaggggcc gccgtcttcc ccaaccagga gcaggcccgg gagctggcaa agacgctggt    900
tggcgtggga gccagcctag ggcttcgggt cgcggcagcg ctgaccgcca tggacaagcc    960
cctgggtcgc tgcgtgggcc acgccctgga ggtggaggag gcgctgctct gcatggacgg   1020
cgcaggcccg ccagacttaa gggacctggt caccacgctc gggggcgccc tgctctggct   1080
cagcggacac gcggggactc aggctcaggg cgctgcccgg gtggccgcgg cgctggacga   1140
cggctcggcc cttggccgct tcgagcggat gctggcggcg cagggcgtgg atcccggtct   1200
ggcccgagcc ctgtgctcgg gaagtcccgc agaacgccgg cagctgctgc ctcgcgcccg   1260
ggagcaggag gagctgctgg cgcccgcaga tggcaccgtg gagctggtcc gggcgctgcc   1320
gctggcgctg gtgctgcacg agctcggggc cgggcgcagc cgcgctgggg agccgctccg   1380
cctgggggtg ggcgcagagc tgctggtcga cgtgggtcag aggctgcgcc gtgggacccc   1440
ctggctccgc gtgcaccggg acggccccgc gctcagcggc ccgcagagcc gcgccctgca   1500
ggaggcgctc gtactctccg accgcgcgcc attcgccgcc ccctcgccct tcgcagagct   1560
cgttctgccg ccgcagcaat aaagctcctt tgccgcgaaa                         1600
```

<210> SEQ ID NO 354
<211> LENGTH: 1842
<212> TYPE: DNA
<213> ORGANISM: Homo sapiens

<400> SEQUENCE: 354

```
cgatcagatc gatctaagat ggcgactgtc gaaccggaaa ccacccctac tcctaatccc     60
ccgactacag aagaggagaa aacggaatct aatcaggagg ttgctaaccc agaacactat    120
attaaacatc ccctacagaa cagatgggca ctctggtttt ttaaaaatga taaaagcaaa    180
acttggcaag caaacctgcg gctgatctcc aagtttgata ctgttgaaga cttttgggct    240
ctgtacaacc atatccagtt gtctagtaat ttaatgcctg gctgtgacta ctcacttttt    300
aaggatggta ttgagcctat gtgggaagat gagaaaaaca aacggggagg acgatggcta    360
attacattga acaaacagca gagacgaagt gacctcgatc gcttttggct agagacactt    420
ctgtgcctta ttggagaatc ttttgatgac tacagtgatg atgtatgtgg cgctgttgtt    480
aatgttagag ctaaaggtga taagatagca atatggacta ctgaatgtga aaacagagaa    540
gctgttacac atatagggag ggtatacaag gaaaggttag gacttcctcc aaagatagtg    600
attggttatc agtcccacgc agacacagct actaagagcg gctccaccac taaaaatagg    660
tttgttgttt aagaagacac cttctgagta ttctcatagg agactgcgtc aagcaatcga    720
gatttgggag ctgaaccaaa gcctcttcaa aaagcagagt ggactgcatt taaatttgat    780
ttccatctta atgttactca gatataagag aagtctcatt cgcctttgtc ttgtacttct    840
gtgttcattt tttttttttt tttttggcta gagtttccac tatcccaatc aaagaattac    900
agtacacatc cccagaatcc ataaatgtgt tcctggccca ctctgtaata gttcagtaga    960
attaccatta attacataca gattttacct atccacaata gtcagaaaac aacttggcat   1020
ttctatactt tacaggaaaa aaaattctgt tgttccattt tatgcagaag catattttgc   1080
tggtttgaaa gattatgatg catacagttt tctagcaatt ttctttgttt ctttttacag   1140
cattgtcttt gctgtactct tgctgatggc tgctagattt taatttattt gtttccctac   1200
ttgataatat tagtgattct gatttcagtt tttcatttgt tttgcttaaa tttttttttt   1260
```

```
tttttcctc atgtaacatt ggtgaaggat ccaggaatat gacacaaagg tggaataaac   1320

attaattttg tgcattcttt ggtaattttt tttgtttttt gtaactacaa agctttgcta   1380

caaatttatg catttcattc aaatcagtga tctatgtttg tgtgatttcc taaacataat   1440

tgtggattat aaaaaatgta acatcataat tacattccta actagaatta gtatgtctgt   1500

ttttgtatct ttatgctgta ttttaacact ttgtattact taggttattt tgctttggtt   1560

aaaaatggct caagtagaaa agcagtccca ttcatattaa gacagtgtac aaaactgtaa   1620

ataaaatgtg tacagtgaat tgtcttttag acaactagat ttgtcctttt atttctccat   1680

ctttatagaa ggaatttgta cttcttattg caggcaagtc tctatattat gtcctctttt   1740

gtggtgtctt ccatgtgaac agcataagtt tggagcacta gtttgattat tatgtttatt   1800

acaattttta ataaattgaa taggtagtat catatatatg ga                      1842
```

```
<210> SEQ ID NO 355
<211> LENGTH: 4975
<212> TYPE: DNA
<213> ORGANISM: Homo sapiens

<400> SEQUENCE: 355

ctctcacaca cacacacccc tcccctgcca tccctccccg gactccggct ccggctccga     60

ttgcaatttg caacctccgc tgccgtcgcc gcagcagcca ccaattcgcc agcggttcag    120

gtggctcttg cctcgatgtc ctagcctagg ggcccccggg ccggacttgg ctgggctccc    180

ttcaccctct gcggagtcat gagggcgaac gacgctctgc aggtgctggg cttgcttttc    240

agcctggccc ggggctccga ggtgggcaac tctcaggcag tgtgtcctgg gactctgaat    300

ggcctgagtg tgaccggcga tgctgagaac caataccaga cactgtacaa gctctacgag    360

aggtgtgagg tggtgatggg gaaccttgag attgtgctca cgggacacaa tgccgacctc    420

tccttcctgc agtggattcg agaagtgaca ggctatgtcc tcgtggccat gaatgaattc    480

tctactctac cattgcccaa cctccgcgtg gtgcgaggga cccaggtcta cgatgggaag    540

tttgccatct tcgtcatgtt gaactataac accaactcca gccacgctct gcgccagctc    600

cgcttgactc agctcaccga gattctgtca gggggtgttt atattgagaa gaacgataag    660

ctttgtcaca tggacacaat tgactggagg gacatcgtga gggaccgaga tgctgagata    720

gtggtgaagg acaatggcag aagctgtccc ccctgtcatg aggtttgcaa ggggcgatgc    780

tggggtcctg gatcagaaga ctgccagaca ttgaccaaga ccatctgtgc tcctcagtgt    840

aatggtcact gctttgggcc caaccccaac cagtgctgcc atgatgagtg tgccgggggc    900

tgctcaggcc ctcaggacac agactgcttt gcctgccggc acttcaatga cagtggagcc    960

tgtgtacctc gctgtccaca gcctcttgtc tacaacaagc taactttcca gctggaaccc   1020

aatccccaca ccaagtatca gtatggagga gtttgtgtag ccagctgtcc ccataacttt   1080

gtggtggatc aaacatcctg tgtcagggcc tgtcctcctg acaagatgga agtagataaa   1140

aatgggctca agatgtgtga gccttgtggg ggactatgtc ccaaagcctg tgagggaaca   1200

ggctctggga gccgcttcca gactgtggac tcgagcaaca ttgatggatt tgtgaactgc   1260

accaagatcc tgggcaacct ggactttctg atcaccggcc tcaatggaga cccctggcac   1320

aagatccctg ccctggaccc agagaagctc aatgtcttcc ggacagtacg ggagatcaca   1380

ggttacctga acatccagtc ctggccgccc cacatgcaca acttcagtgt tttttccaat   1440

ttgacaacca ttggaggcag aagcctctac aaccggggct tctcattgtt gatcatgaag   1500
```

-continued

```
aacttgaatg tcacatctct gggcttccga tccctgaagg aaattagtgc tgggcgtatc   1560
tatataagtg ccaataggca gctctgctac caccactctt tgaactggac caaggtgctt   1620
cgggggccta cggaagagcg actagacatc aagcataatc ggccgcgcag agactgcgtg   1680
gcagagggca aagtgtgtga cccactgtgc tcctctgggg gatgctgggg cccaggccct   1740
ggtcagtgct tgtcctgtcg aaattatagc cgaggaggtg tctgtgtgac ccactgcaac   1800
tttctgaatg ggagcctcg agaatttgcc catgaggccg aatgcttctc ctgccacccg   1860
gaatgccaac ccatgggggg cactgccaca tgcaatggct cgggctctga tacttgtgct   1920
caatgtgccc attttcgaga tgggccccac tgtgtgagca gctgccccca tggagtccta   1980
ggtgccaagg gcccaatcta caagtaccca gatgttcaga atgaatgtcg gccctgccat   2040
gagaactgca cccaggggtg taaaggacca gagcttcaag actgtttagg acaaacactg   2100
gtgctgatcg gcaaaaccca tctgacaatg gctttgacag tgatagcagg attggtagtg   2160
attttcatga tgctgggcgg cacttttctc tactggcgtg ggcgccggat tcagaataaa   2220
agggctatga ggcgatactt ggaacggggt gagagcatag agcctctgga ccccagtgag   2280
aaggctaaca aagtcttggc cagaatcttc aaagagacag agctaaggaa gcttaaagtg   2340
cttggctcgg gtgtctttgg aactgtgcac aaaggagtgt ggatccctga gggtgaatca   2400
atcaagattc cagtctgcat taaagtcatt gaggacaaga gtggacggca gagttttcaa   2460
gctgtgacag atcatatgct ggccattggc agcctggacc atgcccacat tgtaaggctg   2520
ctgggactat gcccagggtc atctctgcag cttgtcactc aatatttgcc tctgggttct   2580
ctgctggatc atgtgagaca acaccggggg gcactggggc cacagctgct gctcaactgg   2640
ggagtacaaa ttgccaaggg aatgtactac cttgaggaac atggtatggt gcatagaaac   2700
ctggctgccc gaaacgtgct actcaagtca cccagtcagg ttcaggtggc agattttggt   2760
gtggctgacc tgctgcctcc tgatgataag cagctgctat acagtgaggc caagactcca   2820
attaagtgga tggcccttga gagtatccac tttgggaaat acacacacca gagtgatgtc   2880
tggagctatg gtgtgacagt ttgggagttg atgaccttcg ggcagagcc ctatgcaggg   2940
ctacgattgg ctgaagtacc agacctgcta gagaaggggg agcggttggc acagccccag   3000
atctgcacaa ttgatgtcta catggtgatg gtcaagtgtt ggatgattga tgagaacatt   3060
cgcccaacct ttaaagaact agccaatgag ttcaccagga tggcccgaga cccaccacgg   3120
tatctggtca taaagagaga gagtgggcct ggaatagccc ctgggccaga gccccatggt   3180
ctgacaaaca agaagctaga ggaagtagag ctggagccag aactagacct agacctagac   3240
ttggaagcag aggaggacaa cctggcaacc accacactgg gctccgccct cagcctacca   3300
gttggaacac ttaatcggcc acgtgggagc cagagccttt taagtccatc atctggatac   3360
atgcccatga accagggtaa tcttgggggg tcttgccagg agtctgcagt ttctgggagc   3420
agtgaacggt gccccgtcc agtctctcta cacccaatgc cacggggatg cctggcatca   3480
gagtcatcag aggggcatgt aacaggctct gaggctgagc tccaggagaa agtgtcaatg   3540
tgtagaagcc ggagcaggag ccggagccca cggccacgcg gagatagcgc ctaccattcc   3600
cagcgccaca gtctgctgac tcctgttacc ccactctccc cacccgggtt agaggaagag   3660
gatgtcaacg gttatgtcat gccagataca cacctcaaag gtactccctc ctcccgggaa   3720
ggcacccttt cttcagtggg tctcagttct gtcctgggta ctgaagaaga agatgaagat   3780
gaggagtatg aatacatgaa ccggaggaga aggcacagtc cacctcatcc ccctaggcca   3840
agttcccttg aggagctggg ttatgagtac atggatgtgg ggtcagacct cagtgcctct   3900
```

```
ctgggcagca cacagagttg cccactccac cctgtaccca tcatgcccac tgcaggcaca   3960
actccagatg aagactatga atatatgaat cggcaacgag atggaggtgg tcctgggggt   4020
gattatgcag ccatgggggc ctgcccagca tctgagcaag ggtatgaaga gatgagagct   4080
tttcaggggc ctggacatca ggccccccat gtccattatg cccgcctaaa aactctacgt   4140
agcttagagg ctacagactc tgcctttgat aaccctgatt actggcatag caggcttttc   4200
cccaaggcta atgcccagag aacgtaactc ctgctccctg tggcactcag ggagcattta   4260
atggcagcta gtgcctttag agggtaccgt cttctcccta ttccctctct ctcccaggtc   4320
ccagcccctt ttccccagtc ccagacaatt ccattcaatc tttggaggct tttaaacatt   4380
ttgacacaaa attcttatgg tatgtagcca gctgtgcact ttcttctctt tcccaacccc   4440
aggaaaggtt ttccttattt tgtgtgcttt cccagtccca ttcctcagct tcttcacagg   4500
cactcctgga gatatgaagg attactctcc atatcccttc ctctcaggct cttgactact   4560
tggaactagg ctcttatgtg tgcctttgtt tcccatcaga ctgtcaagaa gaggaaaggg   4620
aggaaaccta gcagaggaaa gtgtaatttt ggtttatgac tcttaacccc ctagaaagac   4680
agaagcttaa aatctgtgaa gaaagaggtt aggagtagat attgattact atcataattc   4740
agcacttaac tatgagccag gcatcatact aaacttcacc tacattatct cacttagtcc   4800
tttatcatcc ttaaaacaat tctgtgacat acatattatc tcattttaca caaagggaag   4860
tcgggcatgg tggctcatgc ctgtaatctc agcactttgg gaggctgagg cagaaggatt   4920
acctgaggca aggagtttga gaccagctta gccaacatag taagaccccc atctc        4975
```

<210> SEQ ID NO 356
<211> LENGTH: 4627
<212> TYPE: DNA
<213> ORGANISM: Homo sapiens

<400> SEQUENCE: 356

```
tcacttgcct gatatttcca gtgtcagagg gacacagcca acgtggggtc ccttctaggc     60
tgacagccgc tctccagcca ctgccgcgag cccgtctgct cccgccctgc ccgtgcactc    120
tccgcagccg ccctccgcca agccccagcg cccgctccca tcgccgatga ccgcggggag    180
gaggatggag atgctctgtg ccggcagggt ccctgcgctg ctgctctgcc tgggtttcca    240
tcttctacag gcagtcctca gtacaactgt gattccatca tgtatcccag gagagtccag    300
tgataactgc acagctttag ttcagacaga agacaatcca cgtgtggctc aagtgtcaat    360
aacaaagtgt agctctgaca tgaatggcta ttgtttgcat ggacagtgca tctatctggt    420
ggacatgagt caaaactact gcaggtgtga agtgggttat actggtgtcc gatgtgaaca    480
cttcttttta accgtccacc aacctttaag caaagagtat gtggctttga ccgtgattct    540
tattattttg tttcttatca cagtcgtcgg ttccacatat tatttctgca gatggtacag    600
aaatcgaaaa agtaaagaac caaagaagga atatgagaga gttacctcag gggatccaga    660
gttgccgcaa gtctgaatgg cgccatcaaa cttatgggca gggataacag tgtgcctggt    720
taatattaat attccatttt attaataata tttatgttgg gtcaagtgtt aggtcaataa    780
cactgtattt taatgtactt gaaaaatgtt tttatttttg ttttattttt gacagactat    840
ttgctaatgt ataatgtgca gaaaatattt aatatcaaaa gaaaattgat atttttatac    900
aagtaatttc ctgagctaaa tgcttcattg aaagcttcaa agtttatatg cctggtgcac    960
agtgcttaga agtaagcaat tcccaggtca tagctcaaga attgttagca aatgacagat   1020
```

-continued

```
ttctgtaagc ctatatatat agtcaaatcg atttagtaag tatgtttttt atgttcctca   1080
aatcagtgat aattggtttg actgtaccat ggtttgatat gtagttggca ccatggtatc   1140
atatattaaa acaataatgc aattagaatt tgggagaagc aaatataggt cctgtgttaa   1200
acactacaca tttgaaacaa gctaaccctg gggagtctat ggtctcttca ctcaggtctc   1260
agctataatt ctgttatatg aggggcagtg gacagttccc tatgccaact cacgactcct   1320
acaggtacta gtcactcatc taccagattc tgcctatgta aaatgaattg aaaaacaatt   1380
ttctgtaatc ttttatttaa gtagtgggca tttcatagct tcacaatgtt cctttttttgt  1440
atattacaac atttatgtga ggtaattatt gctcaacaga caattagaaa aaagtccaca   1500
cttgaagcct aaatttgtgc tttttaagaa tatttttaga ctatttcttt ttataggggc   1560
tttgctgaat tctaacatta aatcacagcc caaaatttga tggactaatt attattttaa   1620
aatatatgaa gacaataatt ctacatgttg tcttaagatg gaaatacagt tatttcatct   1680
tttattcaag gaagttttaa ctttaataca gctcagtaaa tggcttcttc tagaatgtaa   1740
agttatgtat ttaaagttgt atcttgacac aggaaatggg aaaaaactta aaaattaata   1800
tggtgtattt ttccaaatga aaaatctcaa ttgaaagctt ttaaaatgta gaaacttaaa   1860
cacaccttcc tgtggaggct gagatgaaaa ctagggctca ttttcctgac atttgtttat   1920
tttttggaag agacaaagat ttcttctgca ctctgagccc ataggtctca gagagttaat   1980
aggagtattt ttgggctatt gcataaggag ccactgctgc caccactttt ggattttatg   2040
ggaggctcct tcatcgaatg ctaaaccttt gagtagagtc tccctggatc acataccagg   2100
tcagggagga tctgttcttc ctctacgttt atcctggcat gtgctagggt aaacgaaggc   2160
ataataagcc atggctgacc tctggagcac caggtgccag gacttgtctc catgtgtatc   2220
catgcattat ataccctggt gcaatcacac gactgtcatc taaagtcctg gccctggccc   2280
ttactattag gaaaataaac agacaaaaac aagtaaatat atatggtcct atacatattg   2340
tatatatatt catatacaaa catgtatgta tacatgacct taatggatca tagaattgca   2400
gtcatttggt gctctgctaa ccatttatat aaaacttaaa aacaagagaa aagaaaaatc   2460
aattagatct aaacagttat ttctgtttcc tatttaatat agctgaagtc aaaatatgta   2520
agaacacatt ttaaatactc tacttacagt tggccctctg tggttagttc cacatctgtg   2580
gattcaacca accaaggacg gaaaatgctt aaaaaaataat acaacaacaa caaaaaaatac  2640
attataacaa ctatttactt tttttttttt ctttttgaga tggagtctcg ctctgttgcc   2700
caggttggag tgcagtggca cgatctcggc tcactgcaac ctcacctccc gggttcaaga   2760
gatcctcctg cctcagcctc ctgagcagct gggactacag gcgcatgcca ccatgcccag   2820
ctaatttttg tatttttagt agaggcgggg tttcaccatg ttggccagga tggtctcaat   2880
ctcctaacct tgagatccac cctccacagc ctcccaaact gctgggatta caggcgtgag   2940
ccaccgcacg tagcatttac attaggtatt acaagtaatg taaagatgat ttaagtatac   3000
aggaggatgt gaataggtta tatgcaagca ctatgccctt ttatataagt gacttgaaca   3060
tctgtgcccg attttagtat gtgcaggggg gcgatctggg aatcagtccc ctgtggatac   3120
caaggtacaa ctgtatttat taacgcttac tagatgtgag gagagtctga atattttcag   3180
tgatcttggc tgtttcaaaa aaatctattg acttttcaat aaatcagctg caatccattt   3240
atttcattta caaaagattt attgtaagcc tctcaatctt ggtttttcag ttgatcttaa   3300
gcatgtcaat tcataaaaac aagtcatttt tgtatttttc atctttaaga atgcttaaaa   3360
aagctaatcc ctaaaatagt tagatctttg taaatgcata ttaaataata aagtatgacc   3420
```

-continued

```
cacattactt tttatgggtg aaaataagac aaaaataata gttttagtga ggatggtgct   3480

gagtaaacat aaaaactgat ttgctctcag ctgatgtgtc ctgtacacag tgggaagatt   3540

ttagttcaca cttagtctaa ctcccccatt ttacagattt ctcactatat atatttctag   3600

aaggggctat gcatattcaa tgtattgaga accaaagcaa ccacaaatgc ataaatgcat   3660

aatttatggt cttcaaccaa ggccacataa taacccagtt aacttactct ttaaccagga   3720

atattaagtt ctataactag tactcaaggt ttaaccttaa aattaagatt tccttaacct   3780

taaccttaaa attgatatta tattaaacat acataataca atgtaactcc actgttctcc   3840

tgaatatttt ttgctctaat ctctctgccg aaagtcaaag tgatgggaga attggtatac   3900

tggtatgact acgtcttaag tcagattttt atttatgagt ctttgagact aaattcaatc   3960

accaccaggt atcaaatcaa cttttatgca gcaaatatat gattctagtg tctgactttt   4020

gttaaattca gtaatgcagt ttttaaaaac ctgtatctga cccactttgt aatttttgct   4080

ccaatatcca ttctgtagac ttttgaaaaa aaagttttta atttgatgcc caatatattc   4140

tgaccgttaa aaaattcttg ttcatatggg agaaggggga gtaatgactt gtacaaacag   4200

tatttctggt gtatatttta atgtttttaa aaagagtaat ttcatttaaa tatctgttat   4260

tcaaatttga tgatgttaaa tgtaatataa tgtattttct ttttattttg cactctgtaa   4320

ttgcactttt taagtttgaa gagccatttt ggtaaacggt ttttattaaa gatgctatgg   4380

aacataaagt tgtattgcat gcaatttaaa gtaacttatt tgactatgaa tattatcgga   4440

ttactgaatt gtatcaattt gtttgtgttc aatatcagct ttgataattg tgtaccttaa   4500

gatattgaag gagaaaatag ataatttaca agatattatt aatttttatt tatttttctt   4560

gggaattgaa aaaaattgaa ataaataaaa atgcattgaa catcttgcat tcaaaatctt   4620

cactgac                                                              4627
```

<210> SEQ ID NO 357
<211> LENGTH: 2634
<212> TYPE: DNA
<213> ORGANISM: Homo sapiens

<400> SEQUENCE: 357

```
ggcacgaggc tgagtgtccg tctcgcgccc ggaagcgggc gaccgccgtc agcccggagg     60

aggaggagga ggaggaggag gagggggcgg ccatggggct gctgtcccag ggctcgccgc    120

tgagctggga ggaaaccaag cgccatgccg accacgtgcg gcggcacggg atcctccagt    180

tcctgcacat ctaccacgcc gtcaaggacc ggcacaagga cgttctcaag tggggcgatg    240

aggtggaata catgttggta tcttttgatc atgaaaataa aaaagtccgg ttggtcctgt    300

ctggggagaa agttcttgaa actctgcaag agaaggggga aaggacaaac ccaaaccatc    360

ctaccctttg gagaccagag tatgggagtt acatgattga agggacacca ggacagccct    420

acggaggaac aatgtccgag ttcaatacag ttgaggccaa catgcgaaaa cgccggaagg    480

aggctacttc tatattagaa gaaaatcagg ctctttgcac aataacttca tttcccagat    540

taggctgtcc tgggttcaca ctgcccgagg tcaaacccaa cccagtggaa ggaggagctt    600

ccaagtccct cttctttcca gatgaagcaa taaacaagca ccctcgcttc agtaccttaa    660

caagaaatat ccgacatagg agaggagaaa aggttgtcat caatgtacca atatttaagg    720

acaagaatac accatctcca tttatagaaa catttactga ggatgatgaa gcttcaaggg    780

cttctaagcc ggatcatatt tacatggatg ccatgggatt tggaatgggc aattgctgtc    840
```

-continued

```
tccaggtgac attccaagcc tgcagtatat ctgaggccag atacctttat gatcagttgg    900

ctactatctg tccaattgtt atggctttga gtgctgcatc tccctttttac cgaggctatg    960

tgtcagacat tgattgtcgc tggggagtga tttctgcatc tgtagatgat agaactcggg   1020

aggagcgagg actggagcca ttgaagaaca ataactatag gatcagtaaa tcccgatatg   1080

actcaataga cagctattta tctaagtgtg gtgagaaata taatgacatc gacttgacga   1140

tagataaaga gatctacgaa cagctgttgc aggaaggcat tgatcatctc ctggcccagc   1200

atgttgctca tctctttatt agagacccac tgacactgtt tgaagagaaa atacacctgg   1260

atgatgctaa tgagtctgac cattttgaga atattcagtc cacaaattgg cagacaatga   1320

gatttaagcc ccctcctcca aactcagaca ttggatggag agtagaattt cgacccatgg   1380

aggtgcaatt aacagacttt gagaactctg cctatgtggt gtttgtggta ctgctcacca   1440

gagtgatcct ttcctacaaa ttggattttc tcattccact gtcaaaggtt gatgagaaca   1500

tgaaggtagc acagaaaaga gatgctgtct tgcagggaat gttttatttc aggaaagata   1560

tttgcaaagg tggcaatgca gtggtggatg gttgtggcaa ggcccagaac agcacggagc   1620

tcgctgcaga ggagtacacc ctcatgagca tagacaccat catcaatggg aaggaaggtg   1680

tgtttcctgg actgatccca attctgaact cttaccttga aaacatggaa gtggatgtgg   1740

acaccagatg tagtattctg aactacctaa agctaattaa gaagagagca tctggagaac   1800

taatgacagt tgccagatgg atgagggagt ttatcgcaaa ccatcctgac tacaagcaag   1860

acagtgtcat aactgatgaa atgaattata gccttatttt gaagtgtaac caaattgcaa   1920

atgaattatg tgaatgccca gagttacttg gatcagcatt taggaaagta aaatatagtg   1980

gaagtaaaac tgactcatcc aactagacat tctacagaaa gaaaaatgca ttattgacga   2040

actggctaca gtaccatgcc tctcagcccg tgtgtataat atgaagacca aatgatagaa   2100

ctgtactgtt ttctgggcca gtgagccaga aattgattaa ggctttcttt ggtaggtaaa   2160

tctagagttt atacagtgta catgtacata gtaaagtatt tttgattaac aatgtatttt   2220

aataacatat ctaaagtcat catgaactgg cttgtacatt tttaaattct tactctggag   2280

caacctactg tctaagcagt tttgtaaatg tactggtaat tgtacaatac ttgcattcca   2340

gagttaaaat gtttactgta aatttttgtt cttttaaaga ctacctggga cctgatttat   2400

tgaaattttt ctctttaaaa acattttctc tcgttaattt tcctttgtca tttcctttgt   2460

tgtctacatt aaatcacttg aatccattga aagtgcttca agggtaatct tgggtttcta   2520

gcaccttatc tatgatgttt cttttgcaat tggaataatc acttggtcac cttgccccaa   2580

gctttcccct ctgaataaat acccattgaa ctctgaaaaa aaaaaaaaaa aaaa         2634
```

<210> SEQ ID NO 358
<211> LENGTH: 1246
<212> TYPE: DNA
<213> ORGANISM: Homo sapiens

<400> SEQUENCE: 358

```
gaccagccta cagccgcctg catctgtatc cagcgccagg tcccgccagt cccagctgcg     60

cgcgcccccc agtcccgcac ccgttcggcc caggctaagt tagccctcac catgccggtc    120

aaaggaggca ccaagtgcat caaatacctg ctgttcggat ttaacttcat cttctggctt    180

gccgggattg ctgtccttgc cattggacta tggctccgat tcgactctca gaccaagagc    240

atcttcgagc aagaaactaa taataataat tccagcttct acacaggagt ctatattctg    300

atcggagccg gcgccctcat gatgctggtg ggcttcctgg gctgctgcgg ggctgtgcag    360
```

-continued

```
gagtcccagt gcatgctggg actgttcttc ggcttcctct tggtgatatt cgccattgaa    420

atagctgcgg ccatctgggg atattcccac aaggatgagg tgattaagga agtccaggag    480

ttttacaagg acacctacaa caagctgaaa accaaggatg agccccagcg ggaaacgctg    540

aaagccatcc actatgcgtt gaactgctgt ggtttggctg gggggcgtgga acagtttatc    600

tcagacatct gccccaagaa ggacgtactc gaaaccttca ccgtgaagtc ctgtcctgat    660

gccatcaaag aggtcttcga caataaattc cacatcatcg gcgcagtggg catcggcatt    720

gccgtggtca tgatatttgg catgatcttc agtatgatct tgtgctgtgc tatccgcagg    780

aaccgcgaga tggtctagag tcagcttaca tccctgagca ggaaagttta cccatgaaga    840

ttggtgggat tttttgtttg tttgttttgt tttgtttgtt gtttgttgtt tgttttttttg    900

ccactaattt tagtattcat tctgcattgc tagataaaag ctgaagttac tttatgtttg    960

tcttttaatg cttcattcaa tattgacatt tgtagttgag cgggggggttt ggtttgcttt   1020

ggtttatatt ttttcagttg tttgtttttg cttgttatat taagcagaaa tcctgcaatg   1080

aaaggtacta tatttgctag actctagaca agatattgta cataaaagaa ttttttttgtc   1140

tttaaataga tacaaatgtc tatcaacttt aatcaagttg taacttatat tgaagacaat   1200

ttgatacata ataaaaaatt atgacaatgt caaaaaaaaa aaaaaa                   1246
```

<210> SEQ ID NO 359
<211> LENGTH: 2360
<212> TYPE: DNA
<213> ORGANISM: Homo sapiens

<400> SEQUENCE: 359

```
gctacgcggg ccacgctgct ggctggcctg acctaggcgc gcggggtcgg gcggccgcgc      60

gggcgggctg agtgagcaag acaagacact caagaagagc gagctgcgcc tgggtcccgg    120

ccaggcttgc acgcagaggc gggcggcaga cggtgcccgg cggaatctcc tgagctccgc    180

cgcccagctc tggtgccagc gcccagtggc cgccgcttcg aaagtgactg gtgcctcgcc    240

gcctcctctc ggtgcgggac catgaagctg ctgccgtcgg tggtgctgaa gctctttctg    300

gctgcagttc tctcggcact ggtgactggc gagagcctgg agcggcttcg gagagggcta    360

gctgctggaa ccagcaaccc ggaccctccc actgtatcca cggaccagct gctacccccta    420

ggaggcggcc gggaccggaa agtccgtgac ttgcaagagg cagatctgga ccttttgaga    480

gtcactttat cctccaagcc acaagcactg gccacaccaa acaaggagga gcacgggaaa    540

agaaagaaga aaggcaaggg gctagggaag aagagggacc catgtcttcg gaaatacaag    600

gacttctgca tccatggaga atgcaaatat gtgaaggagc tccgggctcc ctcctgcatc    660

tgccacccgg gttaccatgg agagaggtgt catgggctga gcctcccagt ggaaaatcgc    720

ttatatacct atgaccacac aaccatcctg gccgtggtgg ctgtggtgct gtcatctgtc    780

tgtctgctgg tcatcgtggg gcttctcatg tttaggtacc ataggagagg aggttatgat    840

gtggaaaatg aagagaaagt gaagttgggc atgactaatt cccactgaga gagacttgtg    900

ctcaaggaat cggctgggga ctgctacctc tgagaagaca caaggtgatt tcagactgca    960

gaggggaaag acttccatct agtcacaaag actccttcgt ccccagttgc cgtctaggat   1020

tgggcctccc ataattgctt tgccaaaata ccagagcctt caagtgccaa acagagtatg   1080

tccgatggta tctgggtaag aagaaagcaa aagcaaggga ccttcatgcc cttctgattc   1140

ccctccacca aaccccactt cccctcataa gtttgtttaa acacttatct tctggattag   1200
```

-continued

```
aatgccggtt aaattccata tgctccagga tctttgactg aaaaaaaaaa agaagaagaa   1260
gaaggagagc aagaaggaaa gatttgtgaa ctggaagaaa gcaacaaaga ttgagaagcc   1320
atgtactcaa gtaccaccaa gggatctgcc attgggaccc tccagtgctg gatttgatga   1380
gttaactgtg aaataccaca agcctgagaa ctgaattttg ggacttctac ccagatggaa   1440
aaataacaac tatttttgtt gttgttgttt gtaaatgcct cttaaattat atatttattt   1500
tattctatgt atgttaattt atttagtttt taacaatcta acaataatat ttcaagtgcc   1560
tagactgtta ctttggcaat ttcctggccc tccactcctc atccccacaa tctggcttag   1620
tgccacccac ctttgccaca aagctaggat ggttctgtga cccatctgta gtaatttatt   1680
gtctgtctac atttctgcag atcttccgtg gtcagagtgc cactgcggga gctctgtatg   1740
gtcaggatgt aggggttaac ttggtcagag ccactctatg agttggactt cagtcttgcc   1800
taggcgattt tgtctaccat ttgtgttttg aaagcccaag gtgctgatgt caaagtgtaa   1860
cagatatcag tgtctccccg tgtcctctcc ctgccaagtc tcagaagagg ttgggcttcc   1920
atgcctgtag ctttcctggt ccctcacccc catggcccca ggccacagcg tgggaactca   1980
ctttcccttg tgtcaagaca tttctctaac tcctgccatt cttctggtgc tactccatgc   2040
aggggtcagt gcagcagagg acagtctgga gaaggtatta gcaaagcaaa aggctgagaa   2100
ggaacaggga acattggagc tgactgttct tggtaactga ttacctgcca attgctaccg   2160
agaaggttgg aggtggggaa ggctttgtat aatcccaccc acctcaccaa aacgatgaag   2220
gtatgctgtc atggtccttt ctggaagttt ctggtgccat ttctgaactg ttacaacttg   2280
tatttccaaa cctggttcat atttatactt tgcaatccaa ataaagataa cccttattcc   2340
ataaaaaaaa aaaaaaaaaa                                                2360
```

<210> SEQ ID NO 360
<211> LENGTH: 1433
<212> TYPE: DNA
<213> ORGANISM: Homo sapiens

<400> SEQUENCE: 360

```
attcggggcg agggaggagg aagaagcgga ggaggcggct cccgctcgca gggccgtgca     60
cctgcccgcc cgcccgctcg ctcgctcgcc cgccgcgccg cgctgccgac cgccagcatg    120
ctgccgagag tgggctgccc cgcgctgccg ctgccgccgc cgccgctgct gccgctgctg    180
ccgctgctgc tgctgctact gggcgcgagt ggcggcggcg gcggggcgcg cgcggaggtg    240
ctgttccgct gcccgccctg cacacccgag cgcctggccg cctgcgggcc cccgccggtt    300
gcgccgcccg ccgcggtggc cgcagtggcc ggaggcgccc gcatgccatg cgcggagctc    360
gtccgggagc cgggctgcgg ctgctgctcg gtgtgcgccc ggctggaggg cgaggcgtgc    420
ggcgtctaca ccccgcgctg cggccagggg ctgcgctgct atccccaccc gggctccgag    480
ctgcccctgc aggcgctggt catgggcgag ggcacttgtg agaagcgccg ggacgccgag    540
tatggcgcca gcccggagca ggttgcagac aatggcgatg accactcaga aggaggcctg    600
gtggagaacc acgtggacag caccatgaac atgttgggcg ggggaggcag tgctggccgg    660
aagcccctca agtcgggtat gaaggagctg gccgtgttcc gggagaaggt cactgagcag    720
caccggcaga tgggcaaggg tggcaagcat caccttggcc tggaggagcc caagaagctg    780
cgaccacccc ctgccaggac tccctgccaa caggaactgg accaggtcct ggagcggatc    840
tccaccatgc gccttccgga tgagcggggc cctctggagc acctctactc cctgcacatc    900
cccaactgtg acaagcatgg cctgtacaac ctcaaacagt gcaagatgtc tctgaacggg    960
```

```
cagcgtgggg agtgctggtg tgtgaacccc aacaccggga agctgatcca gggagccccc   1020

accatccggg gggaccccga gtgtcatctc ttctacaatg agcagcagga ggcttgcggg   1080

gtgcacaccc agcggatgca gtagaccgca gccagccggt gcctggcgcc cctgcccccc   1140

gcccctctcc aaacaccggc agaaaacgga gagtgcttgg gtggtgggtg ctggaggatt   1200

ttccagttct gacacacgta tttatatttg gaaagagacc agcaccgagc tcggcacctc   1260

cccggcctct ctcttcccag ctgcagatgc cacacctgct ccttcttgct ttccccgggg   1320

gaggaagggg gttgtggtcg gggagctggg gtacaggttt ggggaggggg aagagaaatt   1380

tttatttttg aacccctgtg tcccttttgc ataagattaa aggaaggaaa agt          1433
```

```
<210> SEQ ID NO 361
<211> LENGTH: 1632
<212> TYPE: DNA
<213> ORGANISM: Homo sapiens

<400> SEQUENCE: 361

gccggccgaa cccagacccg aggttttaga agcagagtca ggcgaagctg ggccagaacc     60

gcgacctccg caaccttgag cggcatccgt ggagtgcgcc tgcgcagcta cgaccgcagc    120

aggaaagcgc cgccggccag gcccagctgt ggccggacag ggactggaag agaggacgcg    180

gtcgagtagg tgtgcaccag ccctggcaac gagagcgtct accccgaact ctgctggcct    240

tgaggtgggg aagccgggga gggcagttga ggaccccgcg gaggcgcgtg actggttgag    300

cgggcaggcc agcctccgag ccgggtggac acaggtttta aaacatgaat cctacactca    360

tccttgctgc cttttgcctg ggaattgcct cagctactct aacatttgat cacagtttag    420

aggcacagtg gaccaagtgg aaggcgatgc acaacagatt atacggcatg aatgaagaag    480

gatggaggag agcagtgtgg gagaagaaca tgaagatgat tgaactgcac aatcaggaat    540

acagggaagg gaaacacagc ttcacaatgg ccatgaacgc ctttggagac atgaccagtg    600

aagaattcag gcaggtgatg aatggctttc aaaaccgtaa gcccaggaag gggaaagtgt    660

tccaggaacc tctgttttat gaggccccca gatctgtgga ttggagagag aaaggctacg    720

tgactcctgt gaagaatcag ggtcagtgtg gttcttgttg ggcttttagt gctactggtg    780

ctcttgaagg acagatgttc cggaaaactg ggaggcttat ctcactgagt gagcagaatc    840

tggtagactg ctctgggcct caaggcaatg aaggctgcaa tggtggccta atggattatg    900

ctttccagta tgttcaggat aatggaggcc tggactctga ggaatcctat ccatatgagg    960

caacagaaga atcctgtaag tacaatccca agtattctgt tgctaatgac accggctttg   1020

tggacatccc taagcaggag aaggccctga tgaaggcagt tgcaactgtg gggcccattt   1080

ctgttgctat tgatgcaggt catgagtcct tcctgttcta taaagaaggc atttattttg   1140

agccagactg tagcagtgaa gacatggatc atggtgtgct ggtggttggc tacggatttg   1200

aaagcacaga atcagataac aataaatatt ggctggtgaa gaacagctgg ggtgaagaat   1260

ggggcatggg tggctacgta aagatggcca aagaccggag aaaccattgt ggaattgcct   1320

cagcagccag ctaccccact gtgtgagctg gtggacggtg atgaggaagg acttgactgg   1380

ggatggcgca tgcatgggag gaattcatct tcagtctacc agcccccgct gtgtcggata   1440

cacactcgaa tcattgaaga tccgagtgtg atttgaattc tgtgatattt tcacactggt   1500

aaatgttacc tctattttaa ttactgctat aaataggttt atattattga ttcacttact   1560

gactttgcat tttcgttttt aaaaggatgt ataaattttt acctgtttaa ataaaattta   1620
```

atttcaaatg ta 1632

<210> SEQ ID NO 362
<211> LENGTH: 2756
<212> TYPE: DNA
<213> ORGANISM: Homo sapiens

<400> SEQUENCE: 362
atgctgtcct tccagtaccc cgacgtgtac cgcgacgaga ccgccgtaca ggattatcat 60
ggtcataaaa tttgtgaccc ttacgcctgg cttgaagacc ccgacagtga acagactaag 120
gcctttgtgg aggcccagaa taagattact gtgccatttc ttgagcagtg tcccatcaga 180
ggtttataca aagagagaat gactgaacta tatgattatc ccaagtatag ttgccacttc 240
aagaaaggaa aacggtattt ttattttac aatacaggtt tgcagaacca gcgagtatta 300
tatgtacagg attccttaga gggtgaggcc agagtgttcc tggaccccaa catactgtct 360
gacgatggca cagtggcact ccgaggttat gcgttcagcg aagatggtga atattttgcc 420
tatggtctga gtgccagtgg ctcagactgg gtgacaatca agttcatgaa agttgatggt 480
gccaaagagc ttccagatgt gcttgaaaga gtcaagttca gctgtatggc ctggacccat 540
gatgggaagg gaatgttcta caactcatac cctcaacagg atggaaaaag tgatggcaca 600
gagacatcta ccaatctcca ccaaaagctc tactaccatg tcttgggaac cgatcagtca 660
gaagatattt tgtgtgctga gtttcctgat gaacctaaat ggatgggtgg agctgagtta 720
tctgatgatg gccgctatgt cttgttatca ataagggaag gatgtgatcc agtaaaccga 780
ctctggtact gtgacctaca gcaggaatcc agtggcatcg cgggaatcct gaagtgggta 840
aaactgattg acaactttga aggggaatat gactacgtga ccaatgaggg ggcggtgttc 900
acattcaaga cgaatcgcca gtctcccaac tatcgcgtga tcaacattga cttcagggat 960
cctgaagagt ctaagtggaa agtacttgtt cctgagcatg agaaagatgt cttagaatgg 1020
atagcttgtg tcaggtccaa cttcttggtc ttatgctacc tccatgacgt caagaacatt 1080
ctgcagctcc atgacctgac tactggtgct ctccttaaga ccttccccgct cgatgtcggc 1140 agcattgtag ggtacagcgg tcagaagaag gacactgaaa tcttctatca gtttacttcc 1200
tttttatctc caggtatcat ttatcactgt gatcttacca aagaggagct ggagccaaga 1260
gttttccgag aggtgaccgt aaaaggaatt gatgcttctg attaccagac agtccagatt 1320
ttctacccta gcaaggatgg tacgaagatt ccaatgttca ttgtgcataa aaaaagcata 1380
aaattggatg gctctcatcc agctttctta tatggctatg gcggcttcaa catatccatc 1440
acacccaact acagtgtttc caggcttatt tttgtgagac acatgggtgg tatcctggca 1500
gtggccaaca tcagaggagg tggcgaatat ggagagacgt ggcataaagg tggtatcttg 1560
gccaacaaac aaaactgctt tgatgacttt cagtgtgctg ctgagtatct gatcaaggaa 1620
ggttacacat ctcccaagag gctgactatt aatggaggtt caaatggagg cctcttagtg 1680
gctgcttgtg caaatcagag acctgacctc tttggttgtg ttattgccca agttggagta 1740
atggacatgc tgaagtttca taaatatacc atcggccatg cttggaccac tgattatggg 1800
tgctcggaca gcaaacaaca ctttgaatgg cttgtcaaat actctccatt gcataatgtg 1860
aagttaccag aagcagatga catccagtac ccgtccatgc tgctcctcac tgctgaccat 1920
gatgaccgcg tggtcccgct tcactccctg aagttcattg ccacccttca gtacatcgtg 1980
ggccgcagca ggaagcaaag caaccccctg cttatccacg tggacaccaa ggcgggccac 2040
ggggcgggga agcccacagc caaagtgata gaggaagtct cagacatgtt tgcgttcatc 2100

-continued

```
gcgcggtgcc tgaacgtcga ctggattcca taaacagttt tcgtgcttcc tcctgacagc   2160
gacagaaaac ctcaagggct ttcccacgtt gacaccaaga aaccactggg cataatgctt   2220
ccccacggga acattattcc tggactgaca ggctacagtt gaacagaact gccgtgggaa   2280
ttttatcttt tttaggcttc tcctttttag caaggccttg gtgtttcttt ttccaccctg   2340
tctaggcaca tgtggttttt tggtgttttt tttaagggca tgttgggata aatagctaaa   2400
tggcaacaaa cacattgtga atattagatt gctgaattaa ggatcatagt cgggcatact   2460
tatctatatc cataacctct atatctttaa ataaatgtga gaactgttct catggagaag   2520
acttctttgc aacaataata aatgttattt aagaatgaca gggatttact tccggtttct   2580
tcatattgag gggcaactcc agaagtggag ttttctgtga gaataaagca tttcaccttt   2640
ctgcaacaag ttagttttca agcagttaag tcatagaatg tttgttagct gtgaaaataa   2700
gttgttcatc caaaaaaaaa aaaaaaaaaa aaaaaaaaaa aaaaaaaaag gaattc       2756
```

<210> SEQ ID NO 363
<211> LENGTH: 2768
<212> TYPE: DNA
<213> ORGANISM: Homo sapiens

<400> SEQUENCE: 363

```
cactgctgtg cagggcagga aagctccatg cacatagccc agcaaagagc aacacagagc     60
tgaaaggaag actcagagga gagagataag taaggaaagt agtgatggct ctcatcccag    120
acttggccat ggaaacctgg cttctcctgg ctgtcagcct ggtgctcctc tatctatatg    180
gaacccattc acatggactt tttaagaagc ttggaattcc agggcccaca cctctgcctt    240
ttttgggaaa tattttgtcc taccataagg gcttttgtat gtttgacatg gaatgtcata    300
aaaagtatgg aaaagtgtgg ggcttttatg atggtcaaca gcctgtgctg gctatcacag    360
atcctgacat gatcaaaaca gtgctagtga aagaatgtta ttctgtcttc acaaaccgga    420
ggccttttgg tccagtggga tttatgaaaa gtgccatctc tatagctgag gatgaagaat    480
ggaagagatt acgatcattg ctgtctccaa ccttcaccag tggaaaactc aaggagatgg    540
tccctatcat tgcccagtat ggagatgtgt tggtgagaaa tctgaggcgg gaagcagaga    600
caggcaagcc tgtcaccttg aaagacgtct ttggggccta cagcatggat gtgatcacta    660
gcacatcatt tggagtgaac atcgactctc tcaacaatcc acaagacccc tttgtggaaa    720
acaccaagaa gcttttaaga tttgattttt tggatccatt ctttctctca ataacagtct    780
ttccattcct catcccaatt cttgaagtat taaatatctg tgtgtttcca agagaagtta    840
caaatttttt aagaaaatct gtaaaaagga tgaaagaaag tcgcctcgaa gatacacaaa    900
agcaccgagt ggatttcctt cagctgatga ttgactctca gaattcaaaa gaaactgagt    960
cccacaaagc tctgtccgat ctggagctcg tggcccaatc aattatcttt atttttgctg   1020
gctatgaaac cacgagcagt gttctctcct tcattatgta tgaactggcc actcaccctg   1080
atgtccagca gaaactgcag gaggaaattg atgcagtttt acccaataag gcaccaccca   1140
cctatgatac tgtgctacag atggagtatc ttgacatggt ggtgaatgaa acgctcagat   1200
tattcccaat tgctatgaga cttgagaggg tctgcaaaaa agatgttgag atcaatggga   1260
tgttcattcc caaaggggtg gtggtgatga ttccaagcta tgctcttcac cgtgacccaa   1320
agtactggac agagcctgag aagttcctcc ctgaaagatt cagcaagaag aacaaggaca   1380
acatagatcc ttacatatac acaccctttg gaagtggacc cagaaactgc attggcatga   1440
```

-continued

```
ggtttgctct catgaacatg aaacttgctc taatcagagt ccttcagaac ttctccttca   1500

aaccttgtaa agaaacacag atccccctga aattaagctt aggaggactt cttcaaccag   1560

aaaaacccgt tgttctaaag gttgagtcaa gggatggcac cgtaagtgga gcctgaattt   1620

tcctaaggac ttctgctttg ctcttcaaga aatctgtgcc tgagaacacc agagacctca   1680

aattactttg tgaatagaac tctgaaatga agatgggctt catccaatgg actgcataaa   1740

taaccgggga ttctgtacat gcattgagct ctctcattgt ctgtgtagag tgttatactt   1800

gggaatataa aggaggtgac caaatcagtg tgaggaggta gatttggctc ctctgcttct   1860

cacgggacta tttccaccac ccccagttag caccattaac tcctcctgag ctctgataag   1920

agaatcaaca tttctcaata atttcctcca caaattatta atgaaaataa gaattatttt   1980

gatggctcta acaatgacat ttatatcaca tgttttctct ggagtattct ataagtttta   2040

tgttaaatca ataaagacca ctttacaaaa gtattatcag atgctttcct gcacattaag   2100

gagaaatcta tagaactgaa tgagaaccaa caagtaaata tttttggtca ttgtaatcac   2160

tgttggcgtg gggcctttgt cagaactaga atttgattat taacataggt gaaagttaat   2220

ccactgtgac tttgcccatt gtttagaaag aatattcata gtttaattat gccttttttg   2280

atcaggcaca gtggctcacg cctgtaatcc tagcagtttg ggaggctgag ccgggtggat   2340

cgcctgaggt caggagttca agacaagcct ggcctacatg gttgaaaccc catctctact   2400

aaaaatacac aaattagcta ggcatggtgg actcgcctgt aatctcacta cacaggaggc   2460

tgaggcagga gaatcacttg aacctgggag gcggatgttg aagtgagctg agattgcacc   2520

actgcactcc agtctgggtg agagtgagac tcagtcttaa aaaaatatgc ctttttgaag   2580

cacgtacatt ttgtaacaaa gaactgaagc tcttattata ttattagttt tgatttaatg   2640

ttttcagccc atctcctttc atatttctgg gagacagaaa acatgtttcc ctacacctct   2700

tgcattccat cctcaacacc caactgtctc gatgcaatga acacttaata aaaaacagtc   2760

gattggtc                                                            2768
```

```
<210> SEQ ID NO 364
<211> LENGTH: 2984
<212> TYPE: DNA
<213> ORGANISM: Homo sapiens

<400> SEQUENCE: 364
```

```
gaggaggaac agaaaagaaa agaaaagaaa aagtgggaaa caaataatct aagaatgagg     60

agaaagcaag aagagtgacc cccttgtggg cactccattg gttttatggc gcctctactt    120

tctggagttt gtgtaaaaca aaaatattat ggtctttgtg cacatttaca tcaagctcag    180

cctgggcggc acagccagat gcgagatgcg tctctgctga tctgagtctg cctgcagcat    240

ggacctgggt cttccctgaa gcatctccag ggctggaggg acgactgcca tgcaccgagg    300

gctcatccat ccacagagca gggcagtggg aggagacgcc atgaccccca tcctcacggt    360

cctgatctgt ctcgggctga gtctgggccc ccggacccac gtgcaggcag ggcacctccc    420

caagcccacc ctctgggctg aaccaggctc tgtgatcacc caggggagtc ctgtgaccct    480

caggtgtcag gggggccagg agacccagga gtaccgtcta tatagagaaa agaaaacagc    540

accctggatt acacggatcc cacaggagct tgtgaagaag ggccagttcc ccatcccatc    600

catcacctgg gaacatgcag ggcggtatcg ctgttactat ggtagcgaca ctgcaggccg    660

ctcagagagc agtgaccccc tggagctggt ggtgacagga gcctacatca aacccaccct    720

ctcagcccag cccagccccg tggtgaactc aggagggaat gtaaccctcc agtgtgactc    780
```

-continued

```
acaggtggca tttgatggct tcattctgtg taaggaagga gaagatgaac acccacaatg    840
cctgaactcc cagccccatg cccgtgggtc gtcccgcgcc atcttctccg tgggccccgt    900
gagcccgagt cgcaggtggt ggtacaggtg ctatgcttat gactcgaact ctccctatga    960
gtggtctcta cccagtgatc tcctggagct cctggtccta ggtgtttcta agaagccatc   1020
actctcagtg cagccaggtc ctatcgtggc ccctgaggag accctgactc tgcagtgtgg   1080
ctctgatgct ggctacaaca gatttgttct gtataaggac ggggaacgtg acttccttca   1140
gctcgctggc gcacagcccc aggctgggct ctcccaggcc aacttcaccc tgggccctgt   1200
gagccgctcc tacgggggcc agtacagatg ctacggtgca cacaacctct cctccgagtg   1260
gtcggccccc agcgaccccc tggacatcct gatcgcagga cagttctatg acagagtctc   1320
cctctcggtg cagccgggcc ccacggtggc ctcaggagag aacgtgaccc tgctgtgtca   1380
gtcacaggga tggatgcaaa ctttccttct gaccaaggag ggggcagctg atgacccatg   1440
gcgtctaaga tcaacgtacc aatctcaaaa ataccaggct gaattcccca tgggtcctgt   1500
gacctcagcc catgcgggga cctacaggtg ctacggctca cagagctcca aaccctacct   1560
gctgactcac cccagtgacc ccctggagct cgtggtctca ggaccgtctg gggcccccag   1620
ctccccgaca acaggcccca cctccacatc tggccctgag gaccagcccc tcacccccac   1680
cgggtcggat ccccagagtg gtctgggaag gcacctgggg gttgtgatcg gcatcttggt   1740
ggccgtcatc ctactgctcc tcctcctcct cctcctcttc ctcatcctcc gacatcgacg   1800
tcagggcaaa cactggacat cgacccagag aaaggctgat ttccaacatc ctgcaggggc   1860
tgtggggcca gagcccacag acagaggcct gcagtggagg tccagcccag ctgccgatgc   1920
ccaggaagaa aacctctatg ctgccgtgaa gcacacacag cctgaggatg gggtggagat   1980
ggacactcgg agcccacacg atgaagaccc ccaggcagtg acgtatgccg aggtgaaaca   2040
ctccagacct aggagagaaa tggcctctcc tccttcccca ctgtctgggg aattcctgga   2100
cacaaaggac agacaggcgg aagaggacag gcagatggac actgaggctg ctgcatctga   2160
agccccccag gatgtgacct acgcccagct gcacagcttg acccttagac ggaaggcaac   2220
tgagcctcct ccatcccagg aagggccctc tccagctgtg cccagcatct acgccactct   2280
ggccatccac tagcccaggg ggggacgcag accccacact ccatggagtc tggaatgcat   2340
gggagctgcc cccccagtgg acaccattgg accccaccca gcctggatct accccaggag   2400
actctgggaa cttttagggg tcactcaatt ctgcagtata aataactaat gtctctacaa   2460
ttttgaaata aagcaacaga cttctcaata atcaatgaag tagctgagaa aactaagtca   2520
gaaagtgcat taaactgaat cacaatgtaa atattacaca tcaagcgatg aaactggaaa   2580
actacaagcc acgaatgaat gaattaggaa agaaaaaaag taggaaatga atgatcttgg   2640
ctttcctata agaaatttag ggcagggcac ggtggctcac gcctgtaatt ccagcacttt   2700
gggaggccga ggcgggcaga tcacgagttc aggagatcga gaccatcttg gccaacatgg   2760
tgaaaccctg tctctcctaa aaatacaaaa attagctgga tgtggtggca gtgcctgtaa   2820
tcccagctat ttgggaggct gaggcaggag aatcgcttga accagggagt cagaggtttc   2880
agtgagccaa gatcgcacca ctgctctcca gcctggcgac agagggagac tccatctcaa   2940
attaaaaaaa aaaaaaaaaa agaaagaaaa aaaaaaaaaa aaaa                    2984
```

<210> SEQ ID NO 365
<211> LENGTH: 3061
<212> TYPE: DNA

<213> ORGANISM: Homo sapiens

<400> SEQUENCE: 365

```
cggcacgagg cgactttggt ggaggtagtt ctttggcagc gggcatggcg ggtaccgtgg     60
tgctggacga tgtggagctg cgggaggctc agagagatta cctggacttc ctggacgacg    120
aggaagacca gggaatttat cagagcaaag ttcgggagct gatcagtgac aaccaatacc    180
ggctgattgt caatgtgaat gacctgcgca ggaaaaacga gaagagggct aaccggcttc    240
tgaacaatgc ctttgaggag ctggttgcct tccagcgggc cttaaaggat tttgtggcct    300
ccattgatgc tacctatgcc aagcagtatg aggagttcta cgtaggactg gaaggcagct    360
ttggctccaa gcacgtctcc ccgcggactc ttacctcctg cttcctcagc tgtgtggtct    420
gtgtggaggg cattgtcact aaatgttctc tagttcgtcc caaagtcgtc cgcagtgtcc    480
actactgtcc tgctactaag aagaccatag agcgacgtta ttctgatctc accaccctgg    540
tggcctttcc ctccagctct gtctatccta ccaaggatga ggagaacaat ccccttgaga    600
cagaatatgg cctttctgtc tacaaggatc accagaccat caccatccag gagatgccgg    660
agaaggcccc agccggccag ctcccccgct ctgtggacgt cattctggat gatgacttgg    720
tggataaagc gaagcctggt gaccgggttc aggtggtggg aacctaccgt tgccttcctg    780
gaaagaaggg aggctacacc tctgggacct tcaggactgt cctgattgcc tgtaatgtta    840
agcagatgag caaggatgct cagccctctt tctctgctga ggatatagcc aagatcaaga    900
agttcagtaa aacccgatcc aaggatatct ttgaccagct ggccaagtca ttggccccaa    960
gtatccatgg gcatgactat gtcaagaaag caatcctctg cttgctcttg ggaggggtgg   1020
aacgagacct agaaaatggc agccacatcc gtggggacat caatattctt ctaataggag   1080
acccatccgt tgccaagtct cagcttctgc ggtatgtgct ttgcactgca ccccgagcta   1140
tccccaccac tggccggggc tcctctggag tgggtctgac ggctgctgtc accacagacc   1200
aggaaacagg agagcgccgt ctggaagcag gggccatggt cctggctgac cgaggcgtgg   1260
tttgcattga tgaatttgac aaaatgtctg acatggatcg cacagccatc catgaagtga   1320
tggagcaggg tcgagtgacc attgccaagg ctggcatcca tgctcggctg aatgcccgct   1380
gcagtgtttt ggcagctgcc aaccctgtct acggcaggta tgaccagtat aagactccaa   1440
tggagaacat tgggctacag gactcactgc tgtcacgatt tgacttgctc ttcatcatgc   1500
tggatcagat ggatcctgag caggatcggg agatctcaga ccatgtcctt cggatgcacc   1560
gttacagagc acctggggag caggatggcg atgctatgcc cttgggtagt gctgtggata   1620
tcctggccac agatgatccc aactttagcc aggaagatca gcaggacacc cagatttatg   1680
agaagcatga caaccttcta catgggacca agaagaaaaa ggagaagatg gtgagtgcag   1740
cattcatgaa gaagtacatc catgtggcca aaatcatcaa gcctgtcctg acacaggagt   1800
cggccaccta cattgcagaa gagtattcac gcctgcgcag ccaggatagc atgagctcag   1860
acaccgccag gacatctcca gttacagccc gaacactgga aactctgatt cgactggcca   1920
cagcccatgc gaaggcccgc atgagcaaga ctgtggacct gcaggatgca gaggaagctg   1980
tggagttggt ccagtatgct tactttaaga aggttctgga gaaggagaag aaacgtaaga   2040
agcgaagtga ggatgaatca gagacagaag atgaagagga gaaaagccaa gaggaccagg   2100
agcagaagag gaagagaagg aagactcgcc agccagatgc caaagatggg gattcatacg   2160
acccctatga cttcagtgac acagaggagg aaatgcctca agtacacact ccaaagacgg   2220
cagactcaca ggagaccaag gaatcccaga aagtggagtt gagtgaatcc aggttgaagg   2280
```

```
cattcaaggt ggccctcttg gatgtgttcc gggaagctca tgcgcagtca atcggcatga   2340
atcgcctcac agaatccatc aaccgggaca gcgaagagcc cttctcttca gttgagatcc   2400
aggctgctct gagcaagatg caggatgaca atcaggtcat ggtgtctgag ggcatcatct   2460
tcctcatctg aggaggcctc gtctctgaac ttgggttgtg ccgagagagt ttgttctgtg   2520
tttcccaccc tctccctgac ccaagtcttt gcctctactc ccttaacagt gttgaattca   2580
actgaaggcg aggaatgttg gtgatgaagc tgagttcagg actcggtgga ccctttggga   2640
atgggtcatg aaagctgcca tggggtgagg aaagaggaga cagtgggaga ggacaatgac   2700
tattgcatct tcattgcaaa agcactggct catccgccct acttcccatc ccacacaaac   2760
ccaattgtaa ataacatatg acttctgagt acttttgggg gcacaactgt tttctgtttg   2820
ctgttttttt gttttgtttt ttttctccag agcactttgg tctagactag gctttgggtg   2880
gttccaattg gtggagagaa gctctgaggc acgtcatgca ggtcaagaaa gctttctttg   2940
cagtagcacc agttaaggtg aatatgtatt gtatcacaaa acaaacccaa tatccagatg   3000
aatatccgag atgttgaata aacttagcca tttcgtacaa aaaaaggggg gcccggtaaa   3060
c                                                                  3061
```

<210> SEQ ID NO 366
<211> LENGTH: 1360
<212> TYPE: DNA
<213> ORGANISM: Homo sapiens

<400> SEQUENCE: 366

```
cgggggttgc tccgtccgtg ctccgcctcg ccatgacttc ctacagctat cgccagtcgt     60
cggccacgtc gtccttcgga ggcctgggcg gcggctccgt gcgttttggg ccgggggtcg    120
cttttcgcgc gcccagcatt cacgggggct ccggcggccg cggcgtatcc gtgtcctccg    180
cccgctttgt gtcctcgtcc tcctcggggg gctacggcgg cggctacggc ggcgtcctga    240
ccgcgtccga cgggctgctg gcgggcaacg agaagctaac catgcagaac ctcaacgacc    300
gcctggcctc ctacctggac aaggtgcgcg ccctggaggc ggccaacggc gagctagagg    360
tgaagatccg cgactggtac cagaagcagg ggcctgggcc ctcccgcgac tacagccact    420
actacacgac catccaggac ctgcgggaca agattcttgg tgccaccatt gagaactcca    480
ggattgtcct gcagatcgac aacgcccgtc tggctgcaga tgacttccga accaagtttg    540
agacggaaca ggctctgcgc atgagcgtgg aggccgacat caacggcctg cgcagggtgc    600
tggatgagct gaccctggcc aggaccgacc tggagatgca gatcgaaggc ctgaaggaag    660
agctggccta cctgaagaag aaccatgagg aggaaatcag tacgctgagg ggccaagtgg    720
gaggccaggt cagtgtggag gtggattccg ctccgggcac cgatctcgcc aagatcctga    780
gtgacatgcg aagccaatat gaggtcatgg ccgagcagaa ccggaaggat gctgaagcct    840
ggttcaccag ccggactgaa gaattgaacc gggaggtcgc tggccacacg gagcagctcc    900
agatgagcag gtccgaggtt actgacctgc ggcgcaccct tcagggtctt gagattgagc    960
tgcagtcaca gctgagcatg aaagctgcct tggaagacac actggcagaa acggaggcgc   1020
gctttggagc ccagctggcg catatccagg cgctgatcag cggtattgaa gcccagctgg   1080
cggatgtgcg agctgatagt gagcggcaga atcaggagta ccagcggctc atggacatca   1140
agtcgcggct ggagcaggag attgccacct accgcagcct gctcgaggga caggaagatc   1200
actacaacaa tttgtctgcc tccaaggtcc tctgaggcag caggctctgg ggcttctgct   1260
```

gtcctttgga gggtgtcttc tgggtagagg gatgggaagg aagggaccct tacccccggc 1320
tcttctcctg acctgccaat aaaaatttat ggtccaaggg 1360

<210> SEQ ID NO 367
<211> LENGTH: 1412
<212> TYPE: DNA
<213> ORGANISM: Homo sapiens

<400> SEQUENCE: 367
cggggtcgtc cgcaaagcct gagtcctgtc ctttctctct ccccggacag catgagcttc 60
accactcgct ccaccttctc caccaactac cggtccctgg gctctgtcca ggcgcccagc 120
tacggcgccc ggccggtcag cagcgcggcc agcgtctatg caggcgctgg gggctctggt 180
tcccggatct ccgtgtcccg ctccaccagc ttcaggggcg gcatggggtc cgggggcctg 240
gccaccggga tagccggggg tctggcagga atgggaggca tccagaacga gaaggagacc 300
atgcaaagcc tgaacgaccg cctggcctct tacctggaca gagtgaggag cctggagacc 360
gagaaccgga ggctggagag caaaatccgg gagcacttgg agaagaaggg accccaggtc 420
agagactgga gccattactt caagatcatc gaggacctga gggctcagat cttcgcaaat 480
actgtggaca atgcccgcat cgttctgcag attgacaatg cccgtcttgc tgctgatgac 540
tttagagtca agtatgagac agagctggcc atgcgccagt ctgtggagaa cgacatccat 600
gggctccgca aggtcattga tgacaccaat atcacacgac tgcagctgga gacagagatc 660
gaggctctca aggaggagct gctcttcatg aagaagaacc acgaagagga agtaaaaggc 720
ctacaagccc agattgccag ctctgggttg accgtggagg tagatgcccc caaatctcag 780
gacctcgcca agatcatggc agacatccgg gcccaatatg acgagctggc tcggaagaac 840
cgagaggagc tagacaagta ctggtctcag cagattgagg agagcaccac agtggtcacc 900
acacagtctg ctgaggttgg agctgctgag acgacgctca cagagctgag acgtacagtc 960
cagtccttgg agatcgacct ggactccatg agaaatctga aggccagctt ggagaacagc 1020
ctgagggagg tggaggcccg ctacgcccta cagatggagc agctcaacgg gatcctgctg 1080
caccttgagt cagagctggc acagacccgg gcagagggac agcgccaggc ccaggagtat 1140
gaggccctgc tgaacatcaa ggtcaagctg gaggctgaga tcgccaccta ccgccgcctg 1200
ctggaagatg gcgaggactt taatcttggt gatgccttgg acagcagcaa ctccatgcaa 1260
accatccaaa agaccaccac ccgccggata gtggatggca aagtggtgtc tgagaccaat 1320
gacaccaaag ttctgaggca ttaagccagc agaagcaggg taccctttgg ggagcaggag 1380
gccaataaaa agttcagagt tcattggatg tc 1412

<210> SEQ ID NO 368
<211> LENGTH: 1075
<212> TYPE: DNA
<213> ORGANISM: Homo sapiens

<400> SEQUENCE: 368
cgcagcaaac acatccgtag aaggcagcgc ggccgccgag agccgcagcg ccgctcgccc 60
gccgcccccc accccgccgc cccgcccggc gaattgcgcc ccgcgcccct cccctcgcgc 120
ccccgagaca aagaggagag aaagtttgcg cggccgagcg gggcaggtga ggagggtgag 180
ccgcgcggga ggggcccgcc tcggccccgg ctcagccccc gcccgcgccc ccagcccgcc 240
gccgcgagca gcgcccggac cccccagcgg cggcccccgc ccgcccagcc ccccggcccg 300
ccatgggcgc cgcggcccgc accctgcggc tggcgctcgg cctcctgctg ctggcgacgc 360

```
tgcttcgccc ggccgacgcc tgcagctgct ccccggtgca cccgcaacag gcgttttgca    420

atgcagatgt agtgatcagg gccaaagcgg tcagtgagaa ggaagtggac tctggaaacg    480

acatttatgg caaccctatc aagaggatcc agtatgagat caagcagata aagatgttca    540

aagggcctga gaaggatata gagtttatct acacggcccc ctcctcggca gtgtgtgggg    600

tctcgctgga cgttggagga aagaaggaat atctcattgc aggaaaggcc gagggggacg    660

gcaagatgca catcaccctc tgtgacttca tcgtgccctg ggacaccctg agcaccaccc    720

agaagaagag cctgaaccac aggtaccaga tgggctgcga gtgcaagatc acgcgctgcc    780

ccatgatccc gtgctacatc tcctccccgg acgagtgcct ctggatggac tgggtcacag    840

agaagaacat caacgggcac caggccaagt tcttcgcctg catcaagaga agtgacggct    900

cctgtgcgtg gtaccgcggc gcggcgcccc ccaagcagga gtttctcgac atcgaggacc    960

cataagcagg cctccaacgc ccctgtggcc aactgcaaaa aaagcctcca agggtttcga   1020

ctggtccagc tctgacatcc cttcctggaa acagcatgaa taaaacactc atccc        1075
```

<210> SEQ ID NO 369
<211> LENGTH: 1127
<212> TYPE: DNA
<213> ORGANISM: Homo sapiens

<400> SEQUENCE: 369

```
cacgggcggg gcggggcctg ggtccaccgg ggttctgagg ggagactgag gtcctgagcc     60

gacagcctca gctccctgcc aggccagacc cggcagacag atgagggccc aggaggcctg    120

gcgggcctgg gggcgctacg gtgggagagg aagccagggg tacctgcctc tgccttccag    180

ggccaccgtt ggccccagct gtgccttgac tacgtaacat cttgtcctca cagcccagag    240

catgttccag atcccagagt ttgagccgag tgagcaggaa gactccagct ctgcagagag    300

gggcctgggc cccagccccg caggggacgg gccctcaggc tccggcaagc atcatcgcca    360

ggccccaggc ctcctgtggg acgccagtca ccagcaggag cagccaacca gcagcagcca    420

tcatggaggc gctggggctg tggagatccg gagtcgccac agctcctacc ccgcggggac    480

ggaggacgac gaagggatgg gggaggagcc cagccccttt cggggccgct cgcgctcggc    540

gccccccaac ctctgggcag cacagcgcta tggccgcgag ctccggagga tgagtgacga    600

gtttgtggac tcctttaaga agggacttcc tcgcccgaag agcgcgggca cagcaacgca    660

gatgcggcaa agctccagct ggacgcgagt cttccagtcc tggtgggatc ggaacttggg    720

caggggaagc tccgcccccct cccagtgacc ttcgctccac atcccgaaac tccacccgtt    780

cccactgccc tgggcagcca tcttgaatat gggcggaagt acttccctca ggcctatgca    840

aaaagaggat ccgtgctgtc tcctttggag ggagggctga cccagattcc cttccggtgc    900

gtgtgaagcc acggaaggct tggtcccatc ggaagttttg ggttttccgc ccacagccgc    960

cggaagtggc tccgtggccc cgccctcagg ctccgggctt tcccccaggc gcctgcgcta   1020

agtcgcgagc caggtttaac cgttgcgtca ccgggacccg agcccccgcg atgccctggg   1080

ggccgtgctc actaccaaat gttaataaag cccgcgtctg tgccgcc                 1127
```

<210> SEQ ID NO 370
<211> LENGTH: 1890
<212> TYPE: DNA
<213> ORGANISM: Homo sapiens

<400> SEQUENCE: 370

-continued

```
cttaataaga agagaaggct tcaatggaac cttttgtggt cctggtgctg tgtctctctt     60
ttatgcttct cttttcactc tggagacaga gctgtaggag aaggaagctc cctcctggcc    120
ccactcctct tcctattatt ggaaatatgc tacagataga tgttaaggac atctgcaaat    180
ctttcaccaa tttctcaaaa gtctatggtc ctgtgttcac cgtgtatttt ggcatgaatc    240
ccatagtggt gtttcatgga tatgaggcag tgaaggaagc cctgattgat aatggagagg    300
agttttctgg aagaggcaat tccccaatat ctcaaagaat tactaaagga cttggaatca    360
tttccagcaa tggaaagaga tggaaggaga tccggcgttt ctccctcaca aacttgcgga    420
attttgggat ggggaagagg agcattgagg accgtgttca agaggaagct cactgccttg    480
tggaggagtt gagaaaaacc aaggcttcac cctgtgatcc cactttcatc ctgggctgtg    540
ctccctgcaa tgtgatctgc tccgttgttt tccagaaacg atttgattat aaagatcaga    600
attttctcac cctgatgaaa agattcaatg aaaacttcag gattctgaac tccccatgga    660
tccaggtctg caataatttc cctctactca ttgattgttt cccaggaact cacaacaaag    720
tgcttaaaaa tgttgctctt acacgaagtt acattaggga gaaagtaaaa gaacaccaag    780
catcactgga tgttaacaat cctcgggact ttatggattg cttcctgatc aaaatggagc    840
aggaaaagga caaccaaaag tcagaattca atattgaaaa cttggttggc actgtagctg    900
atctatttgt tgctggaaca gagacaacaa gcaccactct gagatatgga ctcctgctcc    960
tgctgaagca cccagaggtc acagctaaag tccaggaaga gattgatcat gtaattggca   1020
gacacaggag cccctgcatg caggatagga gccacatgcc ttacactgat gctgtagtgc   1080
acgagatcca gagatacagt gaccttgtcc ccaccggtgt gccccatgca gtgaccactg   1140
atactaagtt cagaaactac ctcatcccca agagctttga taacaagata atgctggctg   1200
cataaaacta gggcacaacc ataatggcat tactgacttc cgtgctacat gatgacaaag   1260
aatttcctaa tccaaatatc tttgaccctg gccactttct agataagaat ggcaacttta   1320
agaaaagtga ctacttcatg cctttctcag caggaaaacg aatttgtgca ggagaaggac   1380
ttgcccgcat ggagctattt ttatttctaa ccacaatttt acagaacttt aacctgaaat   1440
ctgttgatga tttaaagaac ctcaatacta ctgcagttac caaagggatt gtttctctgc   1500
caccctcata ccagatctgc ttcatccctg tctgaagaat gctagcccat ctggctgctg   1560
atctgctatc acctgcaact cttttttat caaggacatt cccactatta tgtcttctct   1620
gacctctcat caaatcttcc cattcactca atatcccata agcatccaaa ctccattaag   1680
gagagttgtt caggtcactg cacaaatata tctgcaatta ttcatactct gtaacacttg   1740
tattaattgc tgcatatgct aatacttttc taatgctgac tttttaatat gttatcactg   1800
taaaacacag aaaagtgatt aatgaatgat aatttagtcc atttcttttg tgaatgtgct   1860
aaataaaaag tgttattaat tgctggttca                                     1890
```

<210> SEQ ID NO 371
<211> LENGTH: 4946
<212> TYPE: DNA
<213> ORGANISM: Homo sapiens

<400> SEQUENCE: 371

```
agtcagccct gctgccagcc agtgccgggt gctggggact cagggaggcc cgccgggacc     60
actgcgggac agtgagccga gcagaagctg gaacgcagga gaggaaggag agggggcggt    120
cagggctctc aggagccggg tcctgggcaa ggcgcagccg ttttcaaatt ttcaggaaag    180
cggtcggctc acactcgagc agtaaaaaga tgcctctggg gaggaggccc gtgcagctct    240
```

-continued

```
ccgggcaatg gtggtggctc ggcctagaga ggcggtagtg gaacgcagac cctggtgggg    300
gaatgacatc aagggaggag acgggcggga ccccagattt ctgcctgtgg gcgatggaag    360
tgaggttcac tggccagcgg agccggacac agaacgcgca aaacgccgtg taggcctgga    420
ggagccgaag agcaggcgga cccccctccgc gggggaacag tttccgccgg gagcacaaag    480
caacggaccg gaagtggggg gcggaagtgc agtgggctca gcgccgactg cgcgcctctg    540
cccgcgaaaa ctctgagctg gctgacagct ggggacgggt ggcggccctc gactggagtc    600
ggttgagttc ctgagggacc ccggttctgg aaggttcgcc gcggagacaa gtgagcagtc    660
tgtgccatag ggattctcga agagaacagc gttgtgtccc agtgcacatg ctcgcatcgc    720
ttaccaggag tgcccgagac cctaagatgt tcggagtggt tttttcgcac agacccgaat    780
agcctgcccc tcagccacgc tctgtgccct tctgagaaca ggctgatatg cccaagatag    840
tcctgaatgg tgtgaccgta gacttccctt tccagcccta caaatgccaa caggagtaca    900
tgaccaaggt cctggaatgt ctgcagcaga aggtgaatgg catcctggag agccctacgg    960
gtacagggaa gacgctgtgc ctgctgtgca ccacgctggc ctggcgagaa cacctccgag   1020
acggcatctc tgcccgcaag attgccgaga gggcgcaagg agagcttttc ccggatcggg   1080
ccttgtcatc ctggggcaac gctgctgctg ctgctggaga ccccatagct tgctacacgg   1140
acatcccaaa gattatttac gcctccagga cccactcgca actcacacag gtcatcaacg   1200
agcttcggaa cacctcctac cggcctaagg tgtgtgtgct gggctcccgg gagcagctgt   1260
gcatccatcc tgaggtgaag aaacaagaga gtaaccatct acagatccac ttgtgccgta   1320
agaaggtggc aagtcgctcc tgtcatttct acaacaacgt agaagaaaaa agcctggagc   1380
aggagctggc cagccccatc ctggacattg aggacttggt caagagcgga agcaagcaca   1440
gggtgtgccc ttactacctg tcccggaacc tgaagcagca agccgacatc atattcatgc   1500
cgtacaatta cttgttggat gccaagagcc gcagagcaca caacattgac ctgaagggga   1560
cagtcgtgat ctttgacgaa gctcacaacg tggagaagat gtgtgaagaa tcggcatcct   1620
ttgacctgac tccccatgac ctggcttcag gactggacgt catagaccag gtgctggagg   1680
agcagaccaa ggcagcgcag cagggtgagc cccacccgga gttcagcgcg gactccccca   1740
gcccagggct gaacatggag ctggaagaca ttgcaaagct gaagatgatc ctgctgcgcc   1800
tggagggggc catcgatgct gttgagctgc ctggagacga cagcggtgtc accaagccag   1860
ggagctacat ctttgagctg tttgctgaag cccagatcac gtttcagacc aagggctgca   1920
tcctggactc gctggaccag atcatccagc acctggcagg acgtgctgga gtgttcacca   1980
acacggccgg actgcagaag ctggcggaca ttatccagat tgtgttcagt gtggacccct   2040
ccgagggcag ccctggttcc ccagcagggc tgggggcctt acagtcctat aaggtgcaca   2100
tccatcctga tgctggtcac cggaggacgg ctcagcggtc tgatgcctgg agcaccactg   2160
cagccagaaa gcgagggaag gtgctgagct actggtgctt cagtcccggc cacagcatgc   2220
acgagctggt ccgccagggc gtccgctccc tcatccttac cagcggcacg ctggccccgg   2280
tgtcctcctt tgctctggag atgcagatcc ctttcccagt ctgcctggag aacccacaca   2340
tcatcgacaa gcaccagatc tgggtggggg tcgtccccag aggccccgat ggagcccagt   2400
tgagctccgc gtttgacaga cggttttccg aggagtgctt atcctccctg gggaaggctc   2460
tgggcaacat cgcccgcgtg gtgccctatg ggctcctgat cttcttccct tcctatcctg   2520
tcatggagaa gagcctggag ttctggcggg cccgcgactt ggccaggaag atggaggcgc   2580
```

-continued

```
tgaagccgct gtttgtggag cccaggagca aaggcagctt ctccgagacc atcagtgctt   2640
actatgcaag ggttgccgcc cctgggtcca ccggcgccac cttcctggcg gtctgccggg   2700
gcaaggccag cgaggggctg gacttctcag acacgaatgg ccgtggtgtg attgtcacgg   2760
gcctcccgta ccccccacgc atggaccccc gggttgtcct caagatgcag ttcctggatg   2820
agatgaaggg ccagggtggg gctgggggcc agttcctctc tgggcaggag tggtaccggc   2880
agcaggcgtc cagggctgtg aaccaggcca tcgggcgagt gatccggcac cgccaggact   2940
acggagctgt cttcctctgt gaccacaggt tcgcctttgc cgacgcaaga gcccaactgc   3000
cctcctgggt gcgtccccac gtcagggtgt atgacaactt tggccatgtc atccgagacg   3060
tggcccagtt cttccgtgtt gccgagcgaa ctatgccagc gccggccccc cgggctacag   3120
cacccagtgt gcgtggagaa gatgctgtca gcgaggccaa gtcgcctggc cccttcttct   3180
ccaccaggaa agctaagagt ctggacctgc atgtccccag cctgaagcag aggtcctcag   3240
ggtcaccagc tgccggggac cccgagagta gcctgtgtgt ggagtatgag caggagccag   3300
ttcctgcccg gcagaggccc agggggctgc tggccgccct ggagcacagc gaacagcggg   3360
cggggagccc tggcgaggag caggcccaca gctgctccac cctgtccctc ctgtctgaga   3420
agaggccggc agaagaaccg cgaggaggga ggaagaagat ccggctggtc agccacccgg   3480
aggagcccgt ggctggtgca cagacggaca gggccaagct cttcatggtg gccgtgaagc   3540
aggagttgag ccaagccaac tttgccacct tcacccaggc cctgcaggac tacaagggtt   3600
ccgatgactt cgccgccctg gccgcctgtc tcggccccct ctttgctgag gaccccaaga   3660
agcacaacct gctccaaggc ttctaccagt ttgtgcggcc ccaccataag cagcagtttg   3720
aggaggtctg tatccagctg acaggacgag gctgtggcta tcggcctgag cacagcattc   3780
cccgaaggca gcgggcacag ccggtcctgg accccactgg aagaacggcg ccggatccca   3840
agctgaccgt gtccacggct gcagcccagc agctggaccc ccaagagcac ctgaaccagg   3900
gcaggcccca cctgtcgccc aggccacccc caacaggaga ccctggcagc caaccacagt   3960
gggggtctgg agtgcccaga gcagggaagc agggccagca cgccgtgagc gcctacctgg   4020
ctgatgcccg cagggccctg ggtccgcgg gctgtagcca actcttggca gcgctgacag   4080
cctataagca agacgacgac ctcgacaagg tgctggctgt gttggccgcc ctgaccactg   4140
caaagccaga ggacttcccc ctgctgcaca ggttcagcat gtttgtgcgt ccacaccaca   4200
agcagcgctt ctcacagacg tgcacagacc tgaccggccg gccctacccg ggcatggagc   4260
caccgggacc ccaggaggag aggcttgccg tgcctcctgt gcttacccac agggctcccc   4320
aaccaggccc ctcacggtcc gagaagaccg ggaagaccca gagcaagatc tcgtccttcc   4380
ttagacagag gccagcaggg actgtggggg cgggcggtga ggatgcaggt cccagccagt   4440
cctcaggacc tccccacggg cctgcagcat ctgagtgggg cctctaggat gtgcccagcc   4500
tgccacaccg cctccaggaa gcagagcgtc atgcaggtct tctggccaga gccccagtga   4560
gtgcccacgg aggcccccag cacacccaac gtggcttgat cacctgcctg tccagctctg   4620
gtgggccaag aacccaccca acagaatagg ccagcccatg ccagccggct tggcccgctg   4680
caggcctcag gcaggcgggg cccatggttg gtccctgcgg tgggaccgga tctgggcctg   4740
cctctgagaa gccctgagct accttggggt ctggggtggg tttctgggaa agtgcttccc   4800
cagaacttcc ctggctcctg gcctgtgagt ggtgccacag gggcacccca gctgagcccc   4860
tcaccgggaa ggaggagacc cccgtgggca cgtgtccact tttaatcagg ggacagggct   4920
ctctaataaa gctgctggca gtgccc                                        4946
```

<210> SEQ ID NO 372
<211> LENGTH: 1743
<212> TYPE: DNA
<213> ORGANISM: Homo sapiens

<400> SEQUENCE: 372

```
cagtatccct cctgacaaaa ctaacaaaaa tcctgttagc caaataatca gccacattca     60
tatttaccgt caaagttttt atcctcattt tacagcagtg gagagcgatt gccccgggtc    120
ccacgttagg aagagagaga actgggattt gcacccaggc aatctgggga cagagctgtg    180
atcacaactc catgagtcag ggccgagcca gccccttcac caccagccgg ccgcgccccg    240
ggaaggaagt ttgtggcgga ggaggttcgt acgggaggag ggggaggcgc ccacgcatct    300
ggggctgact cgctctttcg caaaacgtct gggaggagtc cctggggcca caaaactgcc    360
tccttcctga ggccagaagg agagaagacg tgcagggacc ccgcgcacag gagctgccct    420
cgcgacatgg gtcacccgcc gctgctgccg ctgctgctgc tgctccacac ctgcgtccca    480
gcctcttggg gcctgcggtg catgcagtgt aagaccaacg gggattgccg tgtggaagag    540
tgcgccctgg gacaggacct ctgcaggacc acgatcgtgc gcttgtggga agaaggagaa    600
gagctggagc tggtggagaa aagctgtacc cactcagaga agaccaacag gaccctgagc    660
tatcggactg gcttgaagat caccagcctt accgaggttg tgtgtgggtt agacttgtgc    720
aaccagggca actctggccg ggctgtcacc tattcccgaa gccgttacct cgaatgcatt    780
tcctgtggct catcagacat gagctgtgag aggggccggc accagagcct gcagtgccgc    840
agccctgaag aacagtgcct ggatgtggtg acccactgga tccaggaagg tgaagaaggg    900
cgtccaaagg atgaccgcca cctccgtggc tgtggctacc ttcccggctg cccgggctcc    960
aatggtttcc acaacaacga caccttccac ttcctgaaat gctgcaacac caccaaatgc   1020
aacgagggcc caatcctgga gcttgaaaat ctgccgcaga atggccgcca gtgttacagc   1080
tgcaagggga acagcaccca tggatgctcc tctgaagaga ctttcctcat tgactgccga   1140
ggccccatga atcaatgtct ggtagccacc ggcactcacg aaccgaaaaa ccaaagctat   1200
atggtaagag gctgtgcaac cgcctcaatg tgccaacatg cccacctggg tgacgccttc   1260
agcatgaacc acattgatgt ctcctgctgt actaaaagtg gctgtaacca cccagacctg   1320
gatgtccagt accgcagtgg ggctgctcct cagcctggcc ctgcccatct cagcctcacc   1380
atcaccctgc taatgactgc cagactgtgg ggaggcactc tcctctggac ctaaacctga   1440
aatcccccctc tctgccctgg ctggatccgg gggacccctt tgcccttccc tcggctccca   1500
gccctacaga cttgctgtgt gacctcaggc cagtgtgccg acctctctgg gcctcagttt   1560
tcccagctat gaaaacagct atctcacaaa gttgtgtgaa gcagaagaga aaagctggag   1620
gaaggccgtg ggcaatggga gagctcttgt tattattaat attgttgccg ctgttgtgtt   1680
gttgttatta attaatattc atattattta ttttatactt acataaagat tttgtaccag   1740
tgg                                                                 1743
```

<210> SEQ ID NO 373
<211> LENGTH: 5061
<212> TYPE: DNA
<213> ORGANISM: Homo sapiens

<400> SEQUENCE: 373

```
atggctcaga tatttagcaa cagcggattt aaagaatgtc cattttcaca tccggaacca     60
```

-continued

```
acaagagcaa aagatgtgga caaagaagaa gcattacaga tggaagcaga ggctttagca    120

aaactgcaaa aggatagaca agtgactgac aatcagagag gctttgagtt gtcaagcagc    180

accagaaaaa aagcacaggt ttataacaag caggattatg atctcatggt gtttcctgaa    240

tcagattccc aaaaaagagc attagatatt gatgtagaaa agctcaccca agctgaactt    300

gagaaactat tgctggatga cagtttcgag actaaaaaaa cacctgtatt accagttact    360

cctattctga gcccttcctt ttcagcacag ctctatttta gacctactat tcagagagga    420

cagtggccac ctggattacc tgggccttcc acttatgctt taccttctat ttatccttct    480

acttacagta aacaggctgc attccaaaat ggcttcaatc caagaatgcc cacttttcca    540

tctacagaac ctatatattt aagtcttccg ggacaatctc catatttctc atatcctttg    600

acacctgcca cacccttca tccacaagga agcttaccta tctatcgtcc agtagtcagt    660

actgacatgg caaaactatt tgacaaaata gctagtacat cagaattttt aaaaaatggg    720

aaagcaagga ctgatttgga gataacagat tcaaaagtca gcaatctaca ggtatctcca    780

aagtctgagg atatcagtaa atttgactgg ttagacttgg atcctctaag taagcctaag    840

gtggataatg tggaggtatt agaccatgag gaagagaaaa atgtttcaag tttgctagca    900

aaggatcctt gggatgctgt tcttcttgaa gagagatcga cagcaaattg tcatcttgaa    960

agaaaggtga atggaaaatc cctttctgtg gcaactgtta caagaagcca gtctttaaat   1020

attcgaacaa ctcagcttgc aaaagcccag ggccatatat ctcagaaaga cccaaatggg   1080

accagtagtt tgccaactgg aagttctctt cttcaagaag ttgaagtaca gaatgaggag   1140

atggcagctt tttgtcgatc cattacaaaa ttgaagacca aatttccata taccaatcac   1200

cgcacaaacc caggctattt gttaagtcca gtcacagcgc aaagaaacat atgcggagaa   1260

aatgctagtg tgaaggtctc cattgacatt gaaggatttc agctaccagt tacttttacg   1320

tgtgatgtga gttctactgt agaaatcatt ataatgcaag ccctttgctg ggtacatgat   1380

gacttgaatc aagtagatgt tggcagctat gttctaaaag tttgtggtca agaggaagtg   1440

ctgcagaata atcattgcct tggaagtcat gagcatattc aaaactgtcg aaaatgggac   1500

acagaaatta gactacaact cttgaccttc agtgcaatgt gtcaaaatct ggcccgaaca   1560

gcagaagatg atgaaacacc cgtggattta aacaaacacc tgtatcaaat agaaaaacct   1620

tgcaaagaag ccatgacgag acaccctgtt gaagaactct tagattctta tcacaaccaa   1680

gtagaactgg ctcttcaaat tgaaaaccaa caccgagcag tagatcaagt aattaaagct   1740

gtaagaaaaa tctgtagtgc tttagatggt gtcgagactc ttgccattac agaatcagta   1800

aagaagctaa agagagcagt taatcttcca aggagtaaaa ctgctgatgt gacttctttg   1860

tttggaggag aagacactag caggagttca actaggggct cacttaatcc tgaaaatcct   1920

gttcaagtaa gcataaacca attaactgca gcaatttatg atcttctcag actccatgca   1980

aattctggta ggagtcctac agactgtgcc caaagtagca agagtgtcaa ggaagcatgg   2040

actacaacag agcagctcca gtttactatt tttgctgctc atggaatttc aagtaattgg   2100

gtatcaaatt atgaaaaata ctacttgata tgttcactgt ctcacaatgg aaaggatctt   2160

tttaaaccta ttcaatcaaa gaaggttggc acttacaaga atttcttcta tcttattaaa   2220

tgggatgaac taatcatttt tcctatccag atatcacaat tgccattaga atcagttctt   2280

caccttactc tttttggaat tttaaatcag agcagtggaa gttcccctga ttctaataag   2340

cagagaaagg gaccagaagc tttgggcaaa gtttctttac ctctttgtga ctttagacgg   2400

tttttaacat gtggaactaa acttctatat ctttggactt catcacatac aaattctgtt   2460
```

-continued

```
cctggaacag ttaccaaaaa aggatatgtc atggaaagaa tagtgctaca ggttgatttt   2520
ccttctcctg catttgatat tatttataca actcctcaag ttgacagaag cattatacag   2580
caacataact tagaaacact agagaatgat ataaaaggga aacttcttga tattcttcat   2640
aaagactcat cacttggact ttctaaagaa gataaagctt ttttatggga gaaacgttat   2700
tattgcttca aacacccaaa ttgtcttcct aaaatattag caagcgcccc aaactggaaa   2760
tggggtaatc ttgccaaaac ttactcattg cttcaccagt ggcctgcatt gtacccacta   2820
attgcattgg aacttcttga ttcaaaattt gctgatcagg aagtaagatc cctagctgtg   2880
acctggattg aggccattag tgatgatgag ctaacagatc ttcttccaca gtttgtacaa   2940
gctttgaaat atgaaattta cttgaatagt tcattagtgc aattcctttt gtccagggca   3000
ttgggaaata tccagatagc acacaattta tattggcttc tcaaagatgc cctgcatgat   3060
gtacagttta gtacccgata cgaacatgtt ttgggtgctc tcctgtcagt aggaggaaaa   3120
cgacttagag aagaacttct aaaacagacg aaacttgtac agcttttagg aggagtagca   3180
gaaaaagtaa ggcaggctag tggatcagcc agacaggttg ttctccaaag aagtatggaa   3240
cgagtacagt cctttttca gaaaaataaa tgccgtctcc ctctcaagcc aagtctagtg   3300
gcaaaagaat taaatattaa gtcgtgttcc ttcttcagtt ctaatgctgt ccccctaaaa   3360
gtcacaatgg tgaatgctga ccctctggga gaagaaatta atgtcatgtt taaggttggt   3420
gaagatcttc ggcaagatat gttagcttta cagatgataa agattatgga taagatctgg   3480
cttaaagaag gactagatct gaggatggta attttcaaat gtctctcaac tggcagagat   3540
cgaggcatgg tggagctggt tcctgcttcc gataccctca ggaaaatcca agtggaatat   3600
ggtgtgacag gatcctttaa agataaacca cttgcagagt ggctaaggaa atacaatccc   3660
tctgaagaag aatatgaaaa ggcttcagag aactttatct attcctgtgc tggatgctgt   3720
gtagccacct atgttttagg catctgtgat cgacacaatg acaatataat gcttcgaagc   3780
acgggacaca tgtttcacat tgactttgga aagtttttgg gacatgcaca gatgtttggc   3840
agcttcaaaa gggatcgggc tccttttgtg ctgacctctg atatggcata tgtcattaat   3900
gggggtgaaa agcccaccat tcgttttcag ttgtttgtgg acctctgctg tcaggcctac   3960
aacttgataa gaaagcagac aaaccttttt cttaacctcc tttcactgat gattccttca   4020
gggttaccag aacttacaag tattcaagat ttgaaatacg ttagagatgc acttcaaccc   4080
caaactacag acgcagaagc tacaattttc tttactaggc ttattgaatc aagtttggga   4140
agcattgcca caaagtttaa cttcttcatt cacaaccttg ctcagcttcg tttttctggt   4200
cttccttcta atgatgagcc catcctttca ttttcaccta aaacatactc ctttagacaa   4260
gatggtcgaa tcaaggaagt ctctgttttt acatatcata agaaatacaa cccagataaa   4320
cattatattt atgtagtccg aattttgtgg gaaggacaga ttgaaccatc atttgtcttc   4380
cgaacatttg tcgaatttca ggaacttcac aataagctca gtattatttt tccactttgg   4440
aagttaccag gctttcctaa taggatggtt ctaggaagaa cacacataaa agatgtagca   4500
gccaaaagga aaattgagtt aaacagttac ttacagagtt tgatgaatgc ttcaacggat   4560
gtagcagagt gtgatcttgt ttgtactttc ttccaccctt tacttcgtga tgagaaagct   4620
gaagggatag ctaggtctgc agatgcaggt tccttcagtc ctactccagg ccaaatagga   4680
ggagctgtga aattatccat ctcttaccga aatggtactc ttttcatcat ggtgatgcat   4740
atcaaagatc ttgttactga agatggagct gacccaaatc catatgtcaa aacataccta   4800
```

-continued

```
cttccagata accacaaaac atccaaacgt aaaaccaaaa tttcacgaaa aacgaggaat   4860

ccgacattca atgaaatgct tgtatacagt ggatatagca aagaaaccct aagacagcga   4920

gaacttcaac taagtgtact cagtgcagaa tctctgcggg agaatttttt cttgggtgga   4980

gtaaccctgc ctttgaaaga tttcaacttg agcaaagaga cggttaaatg gtatcagctg   5040

actgcggcaa catacttgta a                                             5061
```

<210> SEQ ID NO 374
<211> LENGTH: 6802
<212> TYPE: DNA
<213> ORGANISM: Homo sapiens

<400> SEQUENCE: 374

```
cggccccaga aaacccgagc gagtaggggg cggcgcgcag gagggaggag aactgggggc     60

gcgggaggct ggtgggtgtc gggggtggag atgtagaaga tgtgacgccg cggcccggcg    120

ggtgccagat tagcggacgg ctgcccgcgg ttgcaacggg atcccgggcg ctgcagcttg    180

ggaggcggct ctccccaggc ggcgtccgcg gagacaccca tccgtgaacc ccaggtcccg    240

ggccgccggc tcgccgcgca ccaggggccg gcggacagaa gagcggccga gcggctcgag    300

gctgggggac cgcgggcgcg gccgcgcgct gccgggcggg aggctggggg gccggggccg    360

gggccgtgcc ccggagcggg tcggaggccg gggccggggc cgggggacgg cggctccccg    420

cgcggctcca gcggctcggg gatcccggcc gggccccgca gggaccatgg cagccgggag    480

catcaccacg ctgcccgcct tgcccgagga tggcggcagc ggcgccttcc cgcccggcca    540

cttcaaggac cccaagcggc tgtactgcaa aaacgggggc ttcttcctgc gcatccaccc    600

cgacggccga gttgacgggg tccgggagaa gagcgaccct cacatcaagc tacaacttca    660

agcagaagag agaggagttg tgtctatcaa aggagtgtgt gctaaccgtt acctggctat    720

gaaggaagat ggaagattac tggcttctaa atgtgttacg gatgagtgtt tcttttttga    780

acgattggaa tctaataact acaatactta ccggtcaagg aaatacacca gttggtatgt    840

ggcactgaaa cgaactgggc agtataaact tggatccaaa acaggacctg ggcagaaagc    900

tatacttttt cttccaatgt ctgctaagag ctgattttaa tggccacatc taatctcatt    960

tcacatgaaa gaagaagtat attttagaaa tttgttaatg agagtaaaag aaaataaatg   1020

tgtatagctc agtttggata attggtcaaa caattttttta tccagtagta aaatatgtaa   1080

ccattgtccc agtaaagaaa aataacaaaa gttgtaaaat gtatattctc ccttttatat   1140

tgcatctgct gttacccagt gaagcttacc tagagcaatg atctttttca cgcatttgct   1200

ttattcgaaa agaggctttt aaaatgtgca tgtttagaaa caaaatttct tcatggaaat   1260

catatacatt agaaaatcac agtcagatgt ttaatcaatc caaaatgtcc actatttctt   1320

atgtcattcg ttagtctaca tgtttctaaa catataaatg tgaatttaat caattccttt   1380

catagtttta taattctctg gcagttcctt atgatagagt ttataaaaca gtcctgtgta   1440

aactgctgga agttcttcca cagtcaggtc aattttgtca aacccttctc tgtacccata   1500

cagcagcagc ctagcaactc tgctggtgat gggagttgta ttttcagtct tcgccaggtc   1560

attgagatcc atccactcac atcttaagca ttcttcctgg caaaaattta tggtgaatga   1620

atatggcttt aggcggcaga tgatatacat atctgacttc ccaaaagctc caggatttgt   1680

gtgctgttgc cgaatactca ggacggacct gaattctgat tttataccag tctcttcaaa   1740

aacttctcga accgctgtgt ctcctacgta aaaaaagaga tgtacaaatc aataataatt   1800

acacttttag aaactgtatc atcaaagatt ttcagttaaa gtagcattat gtaaaggctc   1860
```

-continued

```
aaaacattac cctaacaaag taaagttttc aatacaaatt ctttgccttg tggatatcaa   1920
gaaatcccaa aatattttct taccactgta aattcaagaa gcttttgaaa tgctgaatat   1980
ttctttggct gctacttgga ggcttatcta cctgtacatt tttggggtca gctcttttta   2040
acttcttgct gctcttttc ccaaaaggta aaaatataga ttgaaaagtt aaaacatttt   2100
gcatggctgc agttcctttg tttcttgaga taagattcca aagaacttag attcatttct   2160
tcaacaccga aatgctggag gtgtttgatc agttttcaag aaacttggaa tataaataat   2220
tttataattc aacaaaggtt ttcacatttt ataaggttga tttttcaatt aaatgcaaat   2280
ttgtgtggca ggatttttat tgccattaac atatttttgt ggctgctttt tctacacatc   2340
cagatggtcc ctctaactgg gctttctcta attttgtgat gttctgtcat tgtctcccaa   2400
agtatttagg agaagccctt taaaaagctg ccttcctcta ccactttgct ggaaagcttc   2460
acaattgtca cagacaaaga tttttgttcc aatactcgtt ttgcctctat ttttcttgtt   2520
tgtcaaatag taaatgatat ttgcccttgc agtaattcta ctggtgaaaa acatgcaaag   2580
aagaggaagt cacagaaaca tgtctcaatt cccatgtgct gtgactgtag actgtcttac   2640
catagactgt cttacccatc ccctggatat gctcttgttt tttccctcta atagctatgg   2700
aaagatgcat agaaagagta taatgtttta aaacataagg cattcatctg ccatttttca   2760
attacatgct gacttccctt acaattgaga tttgcccata ggttaaacat ggttagaaac   2820
aactgaaagc ataaaagaaa aatctaggcc gggtgcagtg gctcatgcct atattccctg   2880
cactttggga ggccaaagca ggaggatcgc ttgagcccag gagttcaaga ccaacctggt   2940
gaaaccccgt ctctacaaaa aaacacaaaa aatagccagg catggtggcg tgtacatgtg   3000
gtctcagata cttgggaggc tgaggtggga gggttgatca cttgaggctg agaggtcaag   3060
gttgcagtga gccataatcg tgccactgca gtccagccta ggcaacagag tgagactttg   3120
tctcaaaaaa agagaaattt tccttaataa gaaaagtaat tttactctg atgtgcaata   3180
catttgttat taaatttatt atttaagatg gtagcactag tcttaaattg tataaaatat   3240
cccctaacat gtttaaatgt ccatttttat tcattatgct ttgaaaaata attatgggga   3300
aatacatgtt tgttattaaa tttattatta aagatagtag cactagtctt aaatttgata   3360
taacatctcc taacttgttt aaatgtccat ttttattctt tatgcttgaa aataaattat   3420
ggggatccta tttagctctt agtaccacta atcaaaagtt cggcatgtag ctcatgatct   3480
atgctgtttc tatgtcgtgg aagcaccgga tgggggtagt gagcaaatct gccctgctca   3540
gcagtcacca tagcagctga ctgaaaatca gcactgcctg agtagttttg atcagtttaa   3600
cttgaatcac taactgactg aaaattgaat gggcaaataa gtgcttttgt ctccagagta   3660
tgcgggagac ccttccacct caagatggat atttcttccc caaggatttc aagatgaatt   3720
gaaattttta atcaagatag tgtgctttat tctgttgtat tttttattat tttaatatac   3780
tgtaagccaa actgaaataa catttgctgt tttataggtt tgaagaacat aggaaaaact   3840
aagaggtttt gtttttattt ttgctgatga agagatatgt ttaaatatgt tgtattgttt   3900
tgtttagtta caggacaata atgaaatgga gtttatattt gttatttcta ttttgttata   3960
tttaataata gaattagatt gaaataaaat ataatgggaa ataatctgca gaatgtgggt   4020
ttcctggtgt ttcctctgac tctagtgcac tgatgatctc tgataaggct cagctgcttt   4080
atagttctct ggctaatgca gcagatactc ttcctgccag tggtaatacg attttttaag   4140
aaggcagttt gtcaatttta atcttgtgga tacctttata ctcttagggt attattttat   4200
```

-continued

```
acaaaagcct tgaggattgc attctatttt ctatatgacc ctcttgatat ttaaaaaaca   4260
ctatggataa caattcttca tttacctagt attatgaaag aatgaaggag ttcaaacaaa   4320
tgtgtttccc agttaactag ggtttactgt ttgagccaat ataaatgttt aactgtttgt   4380
gatggcagta ttcctaaagt acattgcatg ttttcctaaa tacagagttt aaataatttc   4440
agtaattctt agatgattca gcttcatcat taagaatatc ttttgtttta tgttgagtta   4500
gaaatgcctt catatagaca tagtctttca gacctctact gtcagttttc atttctagct   4560
gctttcaggg ttttatgaat tttcaggcaa agctttaatt tatactaagc ttaggaagta   4620
tggctaatgc caacggcagt ttttttcttc ttaattccac atgactgagg catatatgat   4680
ctctgggtag gtgagttgtt gtgacaacca caagcacttt tttttttttt aaagaaaaaa   4740
aggtagtgaa tttttaatca tctggacttt aagaaggatt ctggagtata cttaggcctg   4800
aaattatata tatttggctt ggaaatgtgt ttttcttcaa ttacatctac aagtaagtac   4860
agctgaaatt cagaggaccc ataagagttc acatgaaaaa aatcaattca tttgaaaagg   4920
caagatgcag gagagaggaa gccttgcaaa cctgcagact gctttttgcc caatatagat   4980
tgggtaaggc tgcaaaacat aagcttaatt agctcacatg ctctgctctc acgtggcacc   5040
agtggatagt gtgagagaat taggctgtag aacaaatggc cttctctttc agcattcaca   5100
ccactacaaa atcatctttt atatcaacag aagaataagc ataaactaag caaaaggtca   5160
ataagtacct gaaaccaaga ttggctagag atatatctta atgcaatcca ttttctgatg   5220
gattgttacg agttggctat ataatgtatg tatggtattt tgatttgtgt aaaagtttta   5280
aaaatcaagc tttaagtaca tggacatttt taaataaaat atttaaagac aatttagaaa   5340
attgccttaa tatcattgtt ggctaaatag aatagggcac atgcatatta aggaaaaggt   5400
catggagaaa taatattggt atcaaacaaa tacattgatt tgtcatgata cacattgaat   5460
ttgatccaat agtttaagga ataggtagga aaatttggtt tctatttttc gatttcctgt   5520
aaatcagtga cataaataat tcttagctta ttttatattt ccttgtctta aatactgagc   5580
tcagtaagtt gtgttagggg attatttctc agttgagact ttcttatatg acattttact   5640
atgttttgac ttcctgacta ttaaaaataa atagtagaaa caattttcat aaagtgaaga   5700
attatataat cactgcttta taactgactt tattatattt atttcaaagt tcatttaaag   5760
gctactattc atcctctgtg atggaatggt caggaatttg ttttctcata gtttaattcc   5820
aacaacaata ttagtcgtat ccaaaataac ctttaatgct aaactttact gatgtatatc   5880
caaagcttct ccttttcaga cagattaatc cagaagcagt cataaacaga agaataggtg   5940
gtatgttcct aatgatatta tttctactaa tggaataaac tgtaatatta gaaattatgc   6000
tgctaattat atcagctctg aggtaatttc tgaaatgttc agactcagtc ggaacaaatt   6060
ggaaaattta aatttttatt cttagctata aagcaagaaa gtaaacacat taatttcctc   6120
aacattttta agccaattaa aaatataaaa gatacacacc aatatcttct tcaggctctg   6180
acaggcctcc tggaaacttc cacatatttt tcaactgcag tataaagtca gaaaataaag   6240
ttaacataac tttcactaac acacacatat gtagatttca caaaatccac ctataattgg   6300
tcaaagtggt tgagaatata ttttttagta attgcatgca aaatttttct agcttccatc   6360
ctttctccct cgtttcttct ttttttgggg gagctggtaa ctgatgaaat cttttcccac   6420
cttttctctt caggaaatat aagtggtttt gtttggttaa cgtgatacat tctgtatgaa   6480
tgaaacattg gagggaaaca tctactgaat ttctgtaatt taaaatattt tgctgctagt   6540
taactatgaa cagatagaag aatcttacag atgctgctat aaataagtag aaaatataaa   6600
```

```
tttcatcact aaaatatgct attttaaaat ctatttccta tattgtattt ctaatcagat   6660

gtattactct tattatttct attgtatgtg ttaatgattt tatgtaaaaa tgtaattgct   6720

tttcatgagt agtatgaata aaattgatta gtttgtgttt tcttgtctcc cgaaaaaaaa   6780

aaaaaaaaaa aaaaaaaaaa aa                                             6802
```

<210> SEQ ID NO 375
<211> LENGTH: 1840
<212> TYPE: DNA
<213> ORGANISM: Homo sapiens

<400> SEQUENCE: 375

```
cccattaggt gacaggtttt tagagaagcc aatcacgtcg ccgcggtcct ggttctaaag     60

tcctcgctca cccacccgga ctcattctcc ccagacgcca aggatggtgg tcatggcgcc    120

ccgaaccctc ttcctgctgc tctcgggggc cctgaccctg accgagacct gggcgggctc    180

ccactccatg aggtatttca gcgccgccgt gtcccggccc ggccgcgggg agccccgctt    240

catcgccatg ggctacgtgg acgacacgca gttcgtgcgg ttcgacagcg actcggcgtg    300

tccgaggatg gagccgcggg cgccgtgggt ggagcaggag gggccggagt attgggaaga    360

ggagacacgg aacaccaagg cccacgcaca gactgacaga atgaacctgc agaccctgcg    420

cggctactac aaccagagcg aggccagttc tcacaccctc cagtggatga ttggctgcga    480

cctggggtcc gacggacgcc tcctccgcgg gtatgaacag tatgcctacg atggcaagga    540

ttacctcgcc ctgaacgagg acctgcgctc ctggaccgca gcggacactg cggctcagat    600

ctccaagcgc aagtgtgagg cggccaatgt ggctgaacaa aggagagcct acctggaggg    660

cacgtgcgtg gagtggctcc acagatacct ggagaacggg aaggagatgc tgcagcgcgc    720

ggaccccccc aagacacacg tgacccacca ccctgtcttt gactatgagg ccaccctgag    780

gtgctgggcc ctgggcttct accctgcgga gatcatactg acctggcagc gggatgggga    840

ggaccagacc caggacgtgg agctcgtgga gaccaggcct gcaggggatg gaaccttcca    900

gaagtgggca gctgtggtgg tgccttctgg agaggagcag agatacacgt gccatgtgca    960

gcatgagggg ctgccggagc ccctcatgct gagatggaag cagtcttccc tgcccaccat   1020

ccccatcatg ggtatcgttg ctggcctggt tgtccttgca gctgtagtca ctggagctgc   1080

ggtcgctgct gtgctgtgga gaaagaagag ctcagattga aaggagggga gctactctca   1140

ggctgcaagt aagtatgaag gaggctgatc cctgagatcc ttgggatctt gtgtttggga   1200

gccatggggg agctcaccca ccccacaatt cctcctctgg ccacatctcc tgtggtctct   1260

gaccaggtgc tgtttttgtt ctactctagg cagtgacagt gcccagggct ctaatgtgtc   1320

tctcacggct tgtaaatgtg acaccccggg ggcctgatg tgtgtgggtt gttgagggga    1380

acaggggaca tagctgtgct atgaggtttc tttgacttca atgtattgag catgtgatgg   1440

gctgtttaaa gtgtcacccc tcactgtgac tgatatgaat ttgttcatga atatttttct   1500

gtagtgtgaa acagctgccc tgtgtgggac tgagtggcaa gtccctttgt gacttcaaga   1560

accctgactt ctctttgtgc agagaccagc ccacccctgt gcccaccatg accctcttcc   1620

tcatgctgaa ctgcattcct tccccaatca cctttcctgt tccagaaaag ggctgggat    1680

gtctccgtct ctgtctcaaa tttgtggtcc actgagctat aacttacttc tgtattaaaa   1740

ttagaatctg agtgtaaatt tactttttca aattatttcc aagagagatt gatgggttaa   1800

ttaaaggaga agattcctga aatttgagag acaaaataaa                          1840
```

-continued

<210> SEQ ID NO 376
<211> LENGTH: 6754
<212> TYPE: DNA
<213> ORGANISM: Homo sapiens

<400> SEQUENCE: 376
gtcgacgtgg cggccggcgg cggctgcggg ctgagcggcg agtttccgat ttaaagctga 60
gctgcgagga aaatggcggc gggaggatca aaatacttgc tggatggtgg actcagagac 120
caataaaaat aaactgcttg aacatccttt gactggttag ccagttgctg atgtatattc 180
aagatgagtg gattaggaga aaacttggat ccactggcca gtgattcacg aaaacgcaaa 240
ttgccatgtg atactccagg acaaggtctt acctgcagtg gtgaaaaacg gagacgggag 300
caggaaagta aatatattga agaattggct gagctgatat ctgccaatct tagtgatatt 360
gacaatttca atgtcaaacc agataaatgt gcgattttaa aggaaacagt aagacagata 420
cgtcaaataa aagagcaagg aaaaactatt tccaatgatg atgatgttca aaaagccgat 480
gtatcttcta cagggcaggg agttattgat aaagactcct taggaccgct tttacttcag 540
gcattggatg gtttcctatt tgtggtgaat cgagacggaa acattgtatt tgtatcagaa 600
aatgtcacac aatacctgca atataagcaa gaggacctgg ttaacacaag tgtttacaat 660
atcttacatg aagaagacag aaaggatttt cttaagaatt taccaaaatc tacagttaat 720
ggagtttcct ggacaaatga gacccaaaga caaaaaagcc atacatttaa ttgccgtatg 780
ttgatgaaaa caccacatga tattctggaa gacataaacg ccagtcctga aatgcgccag 840
agatatgaaa caatgcagtg ctttgccctg tctcagccac gagctatgat ggaggaaggg 900
gaagatttgc aatcttgtat gatctgtgtg gcacgccgca ttactacagg agaaagaaca 960
tttccatcaa ccctgagag ctttattacc agacatgatc tttcaggaaa ggttgtcaat 1020
atagatacaa attcactgag atcctccatg aggcctggct ttgaagatat aatccgaagg 1080
tgtattcaga gattttttag tctaaatgat gggcagtcat ggtcccagaa acgtcactat 1140
caagaagtta ccagtgatgg gatattttcc ccaacagctt atcttaatgg ccatgcagaa 1200
accccagtat atcgattctc gttggctgat ggaactatag tgactgcaca gacaaaaagc 1260
aaactcttcc gaaatcctgt aacaaatgat cgacatggct ttgtctcaac ccacttcctt 1320
cagagagaac agaatggata tagaccaaac ccaaatcctg ttggacaagg gattagacca 1380
cctatggctg gatgcaacag ttcggtaggc ggcatgagta tgtcgccaaa ccaaggctta 1440
cagatgccga gcagcagggc ctatggcttg gcagacccta gcaccacagg gcagatgagt 1500
ggagctaggt atgggggttc cagtaacata gcttcattga cccctgggcc aggcatgcaa 1560
tcaccatctt cctaccagaa caacaactat aggctcaaca tgagtagccc cccacatggg 1620
agtcctggtc ttgccccaaa ccagcagaat atcatgattt ctcctcgtaa tcgtgggagt 1680
ccaaagatag cctcacatca gttttctcct gttgcaggtg tgcactctcc catggcatct 1740
tctggcaata ctgggaacca cagcttttcc agcagctctc tcagtgccct gcaagccatc 1800
agtgaaggtg tggggacttc ccttttatct actctgtcat caccaggccc caaattggat 1860
aactctccca atatgaatat tacccaacca agtaaagtaa gcaatcagga ttccaagagt 1920
cctctgggct tttattgcga ccaaaatcca gtggagagtt caatgtgtca gtcaaatagc 1980
agagatcacc tcagtgacaa agaaagtaag gagagcagtg ttgagggggc agagaatcaa 2040
aggggtcctt tggaaagcaa aggtcataaa aaattactgc agttacttac ctgttcttct 2100
gatgaccggg gtcattcctc cttgaccaac tccccctag attcaagttg taaagaatct 2160

```
tctgttagtg tcaccagccc ctctggagtc tcctcctcta catctggagg agtatcctct   2220
acatccaata tgcatgggtc actgttacaa gagaagcacc ggattttgca caagttgctg   2280
cagaatggga attcaccagc tgaggtagcc aagattactg cagaagccac tgggaaagac   2340
accagcagta taacttcttg tggggacgga aatgttgtca agcaggagca gctaagtcct   2400
aagaagaagg agaataatgc acttcttaga tacctgctgg acagggatga tcctagtgat   2460
gcactctcta aagaactaca gccccaagtg gaaggagtgg ataataaaat gagtcagtgc   2520
accagctcca ccattcctag ctcaagtcaa gagaaagacc ctaaaattaa gacagagaca   2580
agtgaagagg gatctggaga cttggataat ctagatgcta ttcttggtga tctgactagt   2640
tctgactttt acaataattc catatcctca aatggtagtc atctggggac taagcaacag   2700
gtgtttcaag gaactaattc tctgggtttg aaaagttcac agtctgtgca gtctattcgt   2760
cctccatata accgagcagt gtctctggat agccctgttt ctgttggctc aagtcctcca   2820
gtaaaaaata tcagtgcttt ccccatgtta ccaaagcaac ccatgttggg tgggaatcca   2880
agaatgatgg atagtcagga aaattatggc tcaagtatgg gagactgggg cttaccaaac   2940
tcaaaggccg gcagaatgga acctatgaat tcaaactcca tgggaagacc aggaggagat   3000
tataatactt ctttacccag acctgcactg ggtggctcta ttcccacatt gcctcttcgg   3060
tctaatagca taccaggtgc gagaccagta ttgcaacagc agcagcagat gcttcaaatg   3120
aggcctggtg aaatccccat gggaatgggg gctaatccct atggccaagc agcagcatct   3180
aaccaactgg gttcctggcc cgatggcatg ttgtccatgg aacaagtttc tcatggcact   3240
caaaataggc ctcttcttag gaattccctg gatgatcttg ttgggccacc ttccaacctg   3300
gaaggccaga gtgacgaaag agcattattg gaccagctgc acactcttct cagcaacaca   3360
gatgccacag gcctggaaga aattgacaga gctttgggca ttcctgaact tgtcaatcag   3420
ggacaggcat tagagcccaa acaggatgct ttccaaggcc aagaagcagc agtaatgatg   3480
gatcagaagg caggattata tggacagaca tacccagcac aggggcctcc aatgcaagga   3540
ggctttcatc ttcagggaca atcaccatct tttaactcta tgatgaatca gatgaaccag   3600
caaggcaatt ttcctctcca aggaatgcac ccacgagcca acatcatgag accccggaca   3660
aacaccccca agcaacttag aatgcagctt cagcagaggc tgcagggcca gcagtttttg   3720
aatcagagcc gacaggcact tgaattgaaa atggaaaacc ctactgctgg tggtgctgcg   3780
gtgatgaggc ctatgatgca gccccagcag ggttttctta atgctcaaat ggtcgcccaa   3840
cgcagcagag agctgctaag tcatcacttc cgacaacaga gggtggctat gatgatgcag   3900
cagcagcaac agcagcagca gcagcagcag cagcagcaac agcaacagca acagcaacag   3960
cagcaacagc agcaaaccca ggccttcagc ccacctccta atgtgactgc ttcccccagc   4020
atggatgggc ttttggcagg acccacaatg ccacaagctc ctccgcaaca gtttccatat   4080
caaccaaatt atggaatggg acaacaacca gatccagcct ttggtcgagt gtctagtcct   4140
cccaatgcaa tgatgtcgtc aagaatgggt ccctcccaga atcccatgat gcaacacccg   4200
caggctgcat ccatctatca gtcctcagaa atgaagggct ggccatcagg aaatttggcc   4260
aggaacagct ccttttccca gcagcagttt gcccaccagg ggaatcctgc agtgtatagt   4320
atggtgcaca tgaatggcag cagtggtcac atgggacaga tgaacatgaa ccccatgccc   4380
atgtctggca tgcctatggg tcctgatcag aaatactgct gacatctctg caccaggacc   4440
tcttaaggaa accactgtac aaatgacact gcactaggat tattgggaag gaatcattgt   4500
```

-continued

```
tccaggcatc catcttggaa gaaaggacca gctttgagct ccatcaaggg tattttaagt   4560
gatgtcattt gagcaggact ggattttaag ccgaagggca atatctacgt gtttttcccc   4620
cctccttctg ctgtgtatca tggtgttcaa aacagaaatg ttttttggca ttccacctcc   4680
tagggatata attctggaga catggagtgt tactgatcat aaaacttttg tgtcactttt   4740
ttctgccttg ctagccaaaa tctcttaaat acacgtaggt gggccagaga acattggaag   4800
aatcaagaga gattagaata tctggtttct ctagttgcag tattggacaa agagcatagt   4860
cccagccttc aggtgtagta gttctgtgtt gaccctttgt ccagtggaat tggtgattct   4920
gaattgtcct ttactaatgg tgttgagttg ctctgtccct attatttgcc ctaggctttc   4980
tcctaatgaa ggttttcatt tgccattcat gtcctgtaat acttcacctc caggaactgt   5040
catggatgtc caaatggctt tgcagaaagg aaatgagatg acagtattta atcgcagcag   5100
tagcaaactt ttcacatgct aatgtgcagc tgagtgcact ttatttaaaa agaatggata   5160
aatgcaatat tcttgaggtc ttgagggaat agtgaaacac attcctggtt tttgcctaca   5220
cttacgtgtt agacaagaac tatgattttt ttttttaaag tactggtgtc accctttgcc   5280
tatatggtag agcaataatg ctttttaaaa ataaacttct gaaaacccaa ggccaggtac   5340
tgcattctga atcagaatct cgcagtgttt ctgtgaatag atttttttgt aaatatgacc   5400
tttaagatat tgtattatgt aaaatatgta tataccttttt tttgtaggtc acaacaactc   5460
atttttacag agtttgtgaa gctaaatatt taacattgtt gatttcagta agctgtgtgg   5520
tgaggctacc agtggaagag acatcccttg acttttgtgg cctgggggag gggtagtgca   5580
ccacagcttt tccttcccca ccccccagcc ttagatgcct cgctcttttc aatctcttaa   5640
tctaaatgct ttttaaagag attatttgtt tagatgtagg cattttaatt ttttaaaaat   5700
tcctctacca gaactaagca ctttgttaat ttggggggaa agaatagata tggggaaata   5760
aacttaaaaa aaaatcagga atttaaaaaa aacgagcaat ttgaagagaa tcttttggat   5820
tttaagcagt ccgaaataat agcaattcat gggctgtgtg tgtgtgtgta tgtgtgtgtg   5880
tgtgtgtgta tgtttaatta tgttaccttt tcatcccctt taggagcgtt ttcagatttt   5940
ggttcgtaag acctgaatcc catattgaga tctcgagtag aatccttggt gtggtttctg   6000
gtgtctgctc agctgtcccc tcattctact aatgtgatgc tttcattatg tccctgtgga   6060
ttagaatagt gtcagttatt tcttaagtaa ctcagtaccc agaacagcca gttttactgt   6120
gattcagagc cacagtctaa ctgagcacct tttaaacccc tccctcttct gccccctacc   6180
acttttctgc tgttgcctct ctttgacacc tgttttagtc agttgggagg aagggaaaaa   6240
tcaagtttaa ttccctttat ctgggttaat tcatttggtt caaatagttg acggaattgg   6300
gtttctgaat gtctgtgaat ttcagaggtc tctgctagcc ttggtatcat tttctagcaa   6360
taactgagag ccagttaatt ttaagaattt cacacattta gccaatcttt ctagatgtct   6420
ctgaaggtaa gatcatttaa tatctttgat atgcttacga gtaagtgaat cctgattatt   6480
tccagaccca ccaccagagt ggatcttatt ttcaaagcag tatagacaat tatgagtttg   6540
ccctctttcc cctaccaagt tcaaaatata tctaagaaag attgtaaatc cgaaaacttc   6600
cattgtagtg gcctgtgctt ttcagatagt atactctcct gtttggagac agaggaagaa   6660
ccaggtcagt ctgtctcttt ttcagctcaa ttgtatctga cccttcttta agttatgtgt   6720
gtggggagaa atagaatggt gctcttatgt cgac                               6754
```

<210> SEQ ID NO 377
<211> LENGTH: 757

<212> TYPE: DNA
<213> ORGANISM: Homo sapiens

<400> SEQUENCE: 377

```
ggaaccgaga ggctgagact aacccagaaa catccaattc tcaaactgaa gctcgcactc     60
tcgcctccag catgaaagtc tctgccgccc ttctgtgcct gctgctcata gcagccacct    120
tcattcccca agggctcgct cagccagatg caatcaatgc cccagtcacc tgctgttata    180
acttcaccaa taggaagatc tcagtgcaga ggctcgcgag ctatagaaga atcaccagca    240
gcaagtgtcc caaagaagct gtgatcttca agaccattgt ggccaaggag atctgtgctg    300
accccaagca gaagtgggtt caggattcca tggaccacct ggacaagcaa acccaaactc    360
cgaagacttg aacactcact ccacaaccca agaatctgca gctaacttat tttcccctag    420
ctttccccag acaccctgtt ttattttatt ataatgaatt ttgtttgttg atgtgaaaca    480
ttatgcctta agtaatgtta attcttattt aagttattga tgttttaagt ttatctttca    540
tggtactagt gtttttttaga tacagagact tggggaaatt gcttttcctc ttgaaccaca    600
gttctacccc tgggatgttt tgagggtctt tgcaagaatc attaatacaa agaatttttt    660
ttaacattcc aatgcattgc taaaatatta ttgtggaaat gaatattttg taactattac    720
accaaataaa tatatttttg tacaaaaaaa aaaaaaa                             757
```

<210> SEQ ID NO 378
<211> LENGTH: 476
<212> TYPE: DNA
<213> ORGANISM: Homo sapiens

<400> SEQUENCE: 378

```
taaaggcaaa gaaggttttt atttaagtga caacatttga gagctaaaaa ccagctcaca     60
tcaaaatcaa gacccagttg taaaaatctt ttaactccat aatgctgttt ttgtcttgtt    120
agaaatctga tatcttacat tagcgtttct aacggatttt gtacaaggca gccataagga    180
atataataaa cctttttcac cacagaacca tctgtcacag ataatactga aagttacaca    240
cttaggaaca gtcagaccac agacaaggtc agactggctg ccaccaccaa gtaaacaact    300
agaaaaggac agcggggtcc aagggtgggg gtccctgtgc acgagtcgcc ctcctctggc    360
ctgccccccc tcgggtcacc tgtttctcct ttgccccaaa gagggtggag tcaaatgcag    420
attttcctcc caactgcctg ttagtgtctc aacaaggaga gcagagccca ggtcag        476
```

<210> SEQ ID NO 379
<211> LENGTH: 2518
<212> TYPE: DNA
<213> ORGANISM: Homo sapiens

<400> SEQUENCE: 379

```
gggtgcgctc ggccgtggcg cacctggtga gctccggggg cgctccgcct ccgcgcccca     60
aatccccgga cctgcccaac gccgcctcgg cgccgcccgc cgccgctcca gaagcgccca    120
ggagccctcc cgcgaaggct gggagcggga gcgcgacgcc cgcgaaggct gttgaggctc    180
gagcgagctt ctccagaccg acctttctgc agctgagccc cggggggctg cgacgcgccg    240
atgaccacgc gggccgggct gtgcaaagcc ccccggacac gggccgccgc ctgccctgga    300
gcacaggcta cgccgagtga gcgccccctg gggcacccaa accaggatgg ggctcccacc    360
cctctcccca gctccgcatc cccggcgcta ggacgcgttc ccccacgccgc gtccgggcca    420
ggagctccct tttccgtgga cctttgctat cctctggtct tcgggccgca ccccctccca    480
```

-continued

```
acccattttc cagtgggggg cagcctgtgt caccttcttc acgtccttcc cgctcattga    540

ctgccctcgc ccacgccgcc tcaggaccct gttctgcccc agagcccgga gggcggagag    600

cccggcgaag gatgagttgg ccagttcccc gtcgcggccc ggcagcttaa aggctaaggg    660

aaaaggggtt tcacgaagga gcggggttct ttttaatagg ggacatagcg gttgggaaga    720

ctcgctcacc cgcttcccgg ctccagcgcc ccagttccct gtccctctta ccgtagttcc    780

cctccccctc cacacccaga aatagcccgc gacaccagga ggccgccagc ttccccagga    840

gcggggaggg ggacgcccgg ggtagaggag ggtcccattt agatgccctt cagcctgcca    900

actcgtgctg gcctggcaaa gaagcggacc ccctgcccgg agcggccggc tggcccccgg    960

gctgtgtgta ttttaaatgc atctgccggg aacgcagagc accgagggag atgggggcgc   1020

tcagttcgct gaggaaggtg gctggtggcc catggaccca ccaccacctc ccttagcctc   1080

ctgtgtggga ggagtttatg ggtatgtggc tcctgcccag tccaggtggg ctttcacttc   1140

tactctattt cagttcctct ttcccgatct gggctggaga gcttcctcat tgttaaggca   1200

gcagaaactt tcgctggatg gttttaggat aaggggtcat caatgctggc aagagtcggc   1260

acaatgagga ccaggcttgc tgtgaagtgg tgtatgtgga aggtcggagg agtgttacag   1320

gagtacctag ggagcctagc cgaggccagg gactctgctt ctactactgg ggcctatttg   1380

atgggcatgc agggggcgga gctgctgaaa tggcctcacg gctcctgcat cgccatatcc   1440

gagagcagct aaaggacctg aaggaagtga gccacgagag cctggtagtg gggccattg    1500

agaatgcctt ccagctcatg gatgagcaga tggcccggga gcggcgtggc caccaagtgg   1560

aggggggctg ctgtgcactg gttgtgatct acctgctagg caaggtgtac gtggccaatg   1620

caggcgatag cagggccatc attgtccgga atggtgaaat cattccaatg tcccgggagt   1680

ttaccccgga gactgagcgc cagcgtcttc agctgcttgg cttcctgaaa ccagagctgc   1740

taggcagtga attcacccac cttgagttcc cccgcagagt tctgcccaag gagctggggc   1800

agaggatgtt gtaccgggac cagaacatga ccggctgggc ctacaaaaag atcgagctgg   1860

aggatctcag gtttcctctg gtctgtgggg agggcaaaaa ggctcgggtg atggccacca   1920

ttggggtgac ccgaggcttg ggagaccaca gccttaaggt ctgcagttcc accctgccca   1980

tcaagccctt tctctcctgc ttccctgagg tacgagtgta tgacctgaca caatatgagc   2040

actgcccaga tgatgtgcta gtcctgggaa cagatggcct gtgggatgtc actactgact   2100

gtgaggtagc tgccactgtg gacagggtgc tgtcggccta tgagcctaat gaccacagca   2160

ggtatacagc tctggcccaa gctctggtcc tgggggcccg gggtaccccc cgagaccgtg   2220

gctggcgtct ccccaacaac aagctgggtt ccggggatga catctctgtc ttcgtcatcc   2280

ccctgggagg gccaggcagt tactcctgag ggctgaaca ccatccctcc cactagcctc   2340

tccatactta ctcctctcac agcccaaatt ctgaagttgt ctccctgacc cttctttagt   2400

ggcaacttaa ctgaagaagg gatgtccgct atatccaaaa ttacagctat tggcaaataa   2460

acgagatgga taaaaaaaaa aaaaaaaaaa aaaaaaaaaa aaaaaaaaaa aaaaaaaa     2518
```

<210> SEQ ID NO 380
<211> LENGTH: 4160
<212> TYPE: DNA
<213> ORGANISM: Homo sapiens

<400> SEQUENCE: 380

```
gcgcttgcgg aggattgcgt tgacgagact cttatttatt gtcaccaacc tgtggtggaa     60

tttgcagttg cacattggat ctgattcgcc ccgccccgaa tgacgcctgc ccggaggcag    120
```

```
tgaaagtaca gccgcgccgc cccaagtcag cctggacaca taaatcagca cgcggccgga    180
gaaccccgca atctctgcgc ccacaaaata caccgacgat gcccgatcta ctttaagggc    240
tgaaacccac gggcctgaga gactataaga gcgttcccta ccgccatgga acaacgggga    300
cagaacgccc cggccgcttc gggggcccgg aaaaggcacg gcccaggacc cagggaggcg    360
cggggagcca ggcctgggct ccgggtcccc aagacccttg tgctcgttgt cgccgcggtc    420
ctgctgttgg tctcagctga gtctgctctg atcacccaac aagacctagc tccccagcag    480
agagcggccc cacaacaaaa gaggtccagc ccctcagagg gattgtgtcc acctggacac    540
catatctcag aagacggtag agattgcatc tcctgcaaat atggacagga ctatagcact    600
cactggaatg acctcctttt ctgcttgcgc tgcaccaggt gtgattcagg tgaagtggag    660
ctaagtccct gcaccacgac cagaaacaca gtgtgtcagt gcgaagaagg caccttccgg    720
gaagaagatt ctcctgagat gtgccggaag tgccgcacag ggtgtcccag agggatggtc    780
aaggtcggtg attgtacacc ctggagtgac atcgaatgtg tccacaaaga atcaggtaca    840
aagcacagtg gggaagcccc agctgtggag gagacggtga cctccagccc agggactcct    900
gcctctccct gttctctctc aggcatcatc ataggagtca cagttgcagc cgtagtcttg    960
attgtggctg tgtttgtttg caagtcttta ctgtggaaga aagtccttcc ttacctgaaa   1020
ggcatctgct caggtggtgg tggggaccct gagcgtgtgg acagaagctc acaacgacct   1080
ggggctgagg acaatgtcct caatgagatc gtgagtatct tgcagcccac ccaggtccct   1140
gagcaggaaa tggaagtcca ggagccagca gagccaacag gtgtcaacat gttgtccccc   1200
ggggagtcag agcatctgct ggaaccggca gaagctgaaa ggtctcagag gaggaggctg   1260
ctggttccag caaatgaagg tgatcccact gagactctga gacagtgctt cgatgacttt   1320
gcagacttgg tgccctttga ctcctgggag ccgctcatga ggaagttggg cctcatggac   1380
aatgagataa aggtggctaa agctgaggca gcgggccaca gggacacctt gtacacgatg   1440
ctgataaagt gggtcaacaa aaccgggcga gatgcctctg tccacaccct gctggatgcc   1500
ttggagacgc tgggagagag acttgccaag cagaagattg aggaccactt gttgagctct   1560
ggaaagttca tgtatctaga aggtaatgca gactctgcca tgtcctaagt gtgattctct   1620
tcaggaagtc agaccttccc tggtttacct tttttctgga aaaagcccaa ctggactcca   1680
gtcagtagga aagtgccaca attgtcacat gaccggtact ggaagaaact ctcccatcca   1740
acatcaccca gtggatggaa catcctgtaa cttttcactg cacttggcat tatttttata   1800
agctgaatgt gataataagg acactatgga aatgtctgga tcattccgtt tgtgcgtact   1860
ttgagatttg gtttgggatg tcattgtttt cacagcactt ttttatccta atgtaaatgc   1920
tttatttatt tatttgggct acattgtaag atccatctac acagtcgttg tccgacttca   1980
cttgatacta tatgatatga accttttttg ggtggggggt gcggggcagt tcactctgtc   2040
tcccaggctg gagtgcaatg gtgcaatctt ggctcactat agccttgacc tctcaggctc   2100
aagcgattct cccacctcag ccatccaaat agctgggacc acaggtgtgc accaccacgc   2160
ccggctaatt ttttgtattt tgtctagata taggggctct ctatgttgct cagggtggtc   2220
tcgaattcct ggactcaagc agtctgccca cctcagactc ccaaagcggt ggaattagag   2280
gcgtgagccc ccatgcttgg ccttaccttt ctacttttat aattctgtat gttattattt   2340
tatgaacatg aagaaacttt agtaaatgta cttgtttaca tagttatgtg aatagattag   2400
ataaacataa aaggaggaga catacaatgg gggaagaaga agaagtcccc tgtaagatgt   2460
```

-continued

```
cactgtctgg gttccagccc tccctcagat gtactttggc ttcaatgatt ggcaacttct   2520

acaggggcca gtcttttgaa ctggacaacc ttacaagtat atgagtatta tttataggta   2580

gttgtttaca tatgagtcgg gaccaaagag aactggatcc acgtgaagtc ctgtgtgtgg   2640

ctggtcccta cctgggcagt ctcatttgca cccatagccc ccatctatgg acaggctggg   2700

acagaggcag atgggttaga tcacacataa caatagggtc tatgtcatat cccaagtgaa   2760

cttgagccct gtttgggctc aggagataga agacaaaatc tgtctcccac gtctgccatg   2820

gcatcaaggg ggaagagtag atggtgcttg agaatggtgt gaaatggttg ccatctcagg   2880

agtagatggc ccggctcact tctggttatc tgtcaccctg agcccatgag ctgcctttta   2940

gggtacagat tgcctacttg aggaccttgg ccgctctgta agcatctgac tcatctcaga   3000

aatgtcaatt cttaaacact gtggcaacag gacctagaat ggctgacgca ttaaggtttt   3060

cttcttgtgt cctgttctat tattgtttta agacctcagt aaccatttca gcctctttcc   3120

agcaaaccct tctccatagt atttcagtca tggaaggatc atttatgcag gtagtcattc   3180

caggagtttt tggtcttttc tgtctcaagg cattgtgtgt tttgttccgg gactggtttg   3240

ggtgggacaa agttagaatt gcctgaagat cacacattca gactgttgtg tctgtggagt   3300

tttaggagtg gggggtgacc tttctggtct ttgcacttcc atcctctccc acttccatct   3360

ggcatcccac gcgttgtccc ctgcacttct ggaaggcaca gggtgctgct gcctcctggt   3420

ctttgccttt gctgggcctt ctgtgcagga cgctcagcct cagggctcag aaggtgccag   3480

tccggtccca ggtcccttgt cccttccaca gaggccttcc tagaagatgc atctagagtg   3540

tcagccttat cagtgtttaa gatttgtctt ttatttttaa ttttttgag acagaatctc   3600

actctctcgc ccaggctgga gtgcaacggt acgatcttgg ctcagtgcaa cctccgcctc   3660

ctgggttcaa gcgattctcg tgcctcagcc tccggagtag ctgggattgc aggcacccgc   3720

caccacgcct ggctaatttt tgtattttta gtagagacgg ggtttcacca tgttggtcag   3780

gctggtctcg aactcctgac ctcaggtgat ccaccttggc ctccgaaagt gctgggatta   3840

caggcgtgag ccaccagcca ggccaagcta ttcttttaaa gtaagcttcc tgacgacatg   3900

aaataattgg gggttttgtt gtttagttac attaggcttt gctatatccc caggccaaat   3960

agcatgtgac acaggacagc catagtatag tgtgtcactc gtggttggtg tcctttcatg   4020

cttctgccct gtcaaaggtc cctatttgaa atgtgttata atacaaacaa ggaagcacat   4080

tgtgtacaaa atacttatgt atttatgaat ccatgaccaa attaaatatg aaaccttata   4140

taaaaaaaaa aaaaaaaaaa                                               4160
```

<210> SEQ ID NO 381
<211> LENGTH: 1295
<212> TYPE: DNA
<213> ORGANISM: Homo sapiens

<400> SEQUENCE: 381

```
gtgcggagtt tggctgctcc ggggttagca ggtgagcctg cgatgcgcgg gaagacgttc     60

cgctttgaaa tgcagcggga tttggtgagt ttcccgctgt ctccagcggt gcgggtgaag    120

ctggtgtctg cggggttcca gactgctgag gaactcctag aggtgaaacc ctccgagctt    180

agcaaagaag ttgggatatc taaagcagaa gccttagaaa ctctgcaaat tatcagaaga    240

gaatgtctca caaataaacc aagatatgct ggtacatctg agtcacacaa gaagtgtaca    300

gcactggaac ttcttgagca ggagcatacc cagggcttca taatcacctt ctgttcagca    360

ctagatgata ttcttggggg tggagtgccc ttaatgaaaa caacagaaat ttgtggtgca    420
```

ccaggtgttg gaaaaacaca attatgtatg cagttggcag tagatgtgca gataccagaa 480
tgttttggag gagtggcagg tgaagcagtt tttattgata cagagggaag ttttatggtt 540
gatagagtgg tagaccttgc tactgcctgc attcagcacc ttcagcttat agcagaaaaa 600
cacaagggag aggaacaccg aaaagctttg gaggatttca ctcttgataa tattctttct 660
catatttatt attttcgctg tcgtgactac acagagttac tggcacaagt ttatcttctt 720
ccagatttcc tttcagaaca ctcaaaggtt cgactagtga tagtggatgg tattgctttt 780
ccatttcgtc atgacctaga tgacctgtct cttcgtactc ggttattaaa tggcctagcc 840
cagcaaatga tcagccttgc aaataatcac agattagctg taattttaac caatcagatg 900
acaacaaaga ttgatagaaa tcaggccttg cttgttcctg cattagggga aagttgggga 960
catgctgcta caatacggct aatctttcat tgggaccgaa agcaaaggtt ggcaacattg 1020
tacaagtcac ccagccagaa ggaatgcaca gtactgtttc aaatcaaacc tcagggattt 1080
agagatactg ttgttacttc tgcatgttca ttgcaaacag aaggttcctt gagcacccgg 1140
aaacggtcac gagacccaga ggaagaatta taacccagaa acaaatctca aagtgtacaa 1200
atttattgat gttgtgaaat caatgtgtac aagtggactt gttaccttaa agtataaata 1260
aacacactat ggcatgaatg aaaaaaaaaa aaaaa 1295

<210> SEQ ID NO 382
<211> LENGTH: 2210
<212> TYPE: DNA
<213> ORGANISM: Homo sapiens

<400> SEQUENCE: 382
cgcgcccctc cctcctcgcg gacctggcgg tgccggcgcc cggagtggcc ctttaaaagg 60
cagcttattg tccggagggg gcgggcgggg ggcgccgacc gcggcctgag gcccggcccc 120
tcccctctcc ctccctctgt ccccgcgtcg ctcgctggct agctcgctgg ctcgctcgcc 180
cgtccggcgc acgctccgcc tccgtcagtt ggctccgctg tcgggtgcgc ggcgtggagc 240
ggcagccggt ctggacgcgc ggccggggct gggggctggg agcgcggcgc gcaagatctc 300
cccgcgcgag agcggcccct gccaccgggc gaggcctgcg ccgcgatggc agagatgggc 360
agtaaagggg tgacggcggg aaagatcgcc agcaacgtgc agaagaagct cacccgcgcg 420
caggagaagg ttctccagaa gctggggaag gcagatgaga ccaaggatga gcagtttgag 480
cagtgcgtcc agaatttcaa caagcagctg acggagggca cccggctgca gaaggatctc 540
cggacctacc tggcctccgt caaagccatg cacgaggctt ccaagaagct gaatgagtgt 600
ctgcaggagg tgtatgagcc cgattggccc ggcagggatg aggcaaacaa gatcgcagag 660
aacaacgacc tgctgtggat ggattaccac cagaagctgg tggaccaggc gctgctgacc 720
atggacacgt acctgggcca gttccccgac atcaagtcac gcattgccaa gcgggggcgc 780
aagctggtgg actacgacag tgcccggcac cactacgagt cccttcaaac tgccaaaaag 840
aaggatgaag ccaaaattgc caaggccgag gaggagctca tcaaagccca gaaggtgttt 900
gaggagatga atgtggatct gcaggaggag ctgccgtccc tgtggaacag ccgcgtaggt 960
ttctacgtca acacgttcca gagcatcgcg ggcctggagg aaaacttcca caaggagatg 1020
agcaagctca accagaacct caatgatgtg ctggtcggcc tggagaagca acacgggagc 1080
aacaccttca cggtcaaggc ccagcccaga aagaaaagta aactgttttc gcggctgcgc 1140
agaaagaaga acagtgacaa cgcgcctgca aaagggaaca agagcccttc gcctccagat 1200
ggctcccctg ccgccacccc cgagatcaga gtcaaccacg agccagagcc ggccggcggg 1260
gccacgcccg gggccaccct ccccaagtcc ccatctcagc cagcagaggc ctcggaggtg 1320
gcgggtggga cccaacctgc ggctggagcc caggagccag gggagacggc ggcaagtgaa 1380
gcagcctcca gctctcttcc tgctgtcgtg gtggagacct tcccagcaac tgtgaatggc 1440
accgtggagg gcggcagtgg ggccgggcgc ttggacctgc ccccaggttt catgttcaag 1500
gtacaggccc agcacgacta cacggccact gacacagacg agctgcagct caaggctggt 1560
gatgtggtgc tggtgatccc cttccagaac cctgaagagc aggatgaagg ctggctcatg 1620
ggcgtgaagg agagcgactg gaaccagcac aaggagctgg agaagtgccg tggcgtcttc 1680
cccgagaact tcactgagag ggtcccatga cggcggggcc caggcagcct ccgggcgtgt 1740
gaagaacacc tcctcccgaa aaatgtgtgg ttcttttttt tgttttgttt tcgtttttca 1800
tcttttgaag agcaaaggga aatcaagagg agacccccag gcagaggggc gttctcccaa 1860
agattaggtc gttttccaaa gagccgcgtc ccggcaagtc cggcggaatt caccagtgtt 1920
cctgaagctg ctgtgtcctc tagttgagtt tctggcgccc ctgcctgtgc ccgcatgtgt 1980
gcctggccgc agggcggggc tgggggctgc cgagccacca tgcttgcctg aagcttcggc 2040
cgcgccaccc gggcaagggt cctcttttcc tggcagctgc tgtgggtggg gcccagacac 2100
cagcctagcc tggctctgcc ccgcagacgg tctgtgtgct gtttgaaaat aaatcttagt 2160
gttcaaaaca aaatgaaaca aaaaaaaaat gataaaaact ctcaaaaaaa 2210

<210> SEQ ID NO 383
<211> LENGTH: 4604
<212> TYPE: DNA
<213> ORGANISM: Homo sapiens

<400> SEQUENCE: 383
ggaacagctt gtccacccgc cggccggacc agaagccttt gggtctgaag tgtctgtgag 60
acctcacaga agagcacccc tgggctccac ttacctgccc cctgctcctt cagggatgga 120
ggcaatggcg gccagcactt ccctgcctga ccctggagac tttgaccgga acgtgccccg 180
gatctgtggg gtgtgtggag accgagccac tggctttcac ttcaatgcta tgacctgtga 240
aggctgcaaa ggcttcttca ggcgaagcat gaagcggaag gcactattca cctgcccctt 300
caacggggac tgccgcatca ccaaggacaa ccgacgccac tgccaggcct gccggctcaa 360
acgctgtgtg gacatcggca tgatgaagga gttcattctg acagatgagg aagtgcagag 420
gaagcgggag atgatcctga agcggaagga ggaggaggcc ttgaaggaca gtctgcggcc 480
caagctgtct gaggagcagc agcgcatcat tgccatactg ctggacgccc accataagac 540
ctacgacccc acctactccg acttctgcca gttccggcct ccagttcgtg tgaatgatgg 600
tggagggagc catccttcca ggcccaactc cagacacact cccagcttct ctggggactc 660
ctcctcctcc tgctcagatc actgtatcac ctcttcagac atgatggact cgtccagctt 720
ctccaatctg gatctgagtg aagaagattc agatgaccct tctgtgaccc tagagctgtc 780
ccagctctcc atgctgcccc acctggctga cctggtcagt tacagcatcc aaaaggtcat 840
tggctttgct aagatgatac caggattcag agacctcacc tctgaggacc agatcgtact 900
gctgaagtca agtgccattg aggtcatcat gttgcgctcc aatgagtcct tcaccatgga 960
cgacatgtcc tggacctgtg gcaaccaaga ctacaagtac cgcgtcagtg acgtgaccaa 1020
agccggacac agcctggagc tgattgagcc cctcatcaag ttccaggtgg gactgaagaa 1080
gctgaacttg catgaggagg agcatgtcct gctcatggcc atctgcatcg tctccccaga 1140

-continued

```
tcgtcctggg gtgcaggacg ccgcgctgat tgaggccatc caggaccgcc tgtccaacac   1200
actgcagacg tacatccgct gccgccaccc gcccccgggc agccacctgc tctatgccaa   1260
gatgatccag aagctagccg acctgcgcag cctcaatgag gagcactcca agcagtaccg   1320
ctgcctctcc ttccagcctg agtgcagcat gaagctaacg ccccttgtgc tcgaagtgtt   1380
tggcaatgag atctcctgac taggacagcc tgtgcggtgc ctgggtgggg ctgctcctcc   1440
agggccacgt gccaggcccg gggctggcgg ctactcagca gccctcctca cccgtctggg   1500
gttcagcccc tcctctgcca cctcccctat ccacccagcc cattctctct cctgtccaac   1560
ctaacccctt tcctgcgggc ttttccccgg tcccttgaga cctcagccat gaggagttgc   1620
tgtttgtttg acaaagaaac ccaagtgggg gcagagggca gaggctggag gcaggccttg   1680
cccagagatg cctccaccgc tgcctaagtg gctgctgact gatgttgagg gaacagacag   1740
gagaaatgca tccattcctc agggacagag acacctgcac ctcccccac tgcaggcccc   1800
gcttgtccag cgcctagtgg ggtctccctc tcctgcctta ctcacgataa ataatcggcc   1860
cacagctccc accccacccc cttcagtgcc caccaacatc ccattgccct ggttatattc   1920
tcacgggcag tagctgtggt gaggtgggtt ttcttcccat cactggagca ccaggcacga   1980
acccacctgc tgagagaccc aaggaggaaa aacagacaaa aacagcctca cagaagaata   2040
tgacagctgt ccctgtcacc aagctcacag ttcctcgccc tgggtctaag ggttggttg   2100
aggtggaagc cctccttcca cggatccatg tagcaggact gaattgtccc cagtttgcag   2160
aaaagcacct gccgacctcg tcctccccct gccagtgcct tacctcctgc ccaggagagc   2220
cagccctccc tgtcctcctc ggatcaccga gagtagccga gagcctgctc ccccaccccc   2280
tccccagggg agagggtctg gagaagcagt gagccgcatc ttctccatct ggcagggtgg   2340
gatggaggag aagaatttc agaccccagc ggctgagtca tgatctccct gccgcctcaa   2400
tgtggttgca aggccgctgt tcaccacagg gctaagagct aggctgccgc accccagagt   2460
gtgggaaggg agagcggggc agtctcgggt ggctagtcag agagagtgtt tgggggttcc   2520
gtgatgtagg gtaaggtgcc ttcttattct cactccacca cccaaaagtc aaaaggtgcc   2580
tgtgaggcag gggcggagtg atacaacttc aagtgcatgc tctctgcagg tcgagcccag   2640
cccagctggt gggaagcgtc tgtccgttta ctccaaggtg ggtctttgtg agagtgagct   2700
gtaggtgtgc gggaccggta cagaaaggcg ttcttcgagg tggatcacag aggcttcttc   2760
agatcaatgc ttgagtttgg aatcggccgc attccctgag tcaccaggaa tgttaaagtc   2820
agtgggaacg tgactgcccc aactcctgga agctgtgtcc ttgcacctgc atccgtagtt   2880
ccctgaaaac ccagagagga atcagacttc acactgcaag agccttggtg tccacctggc   2940
cccatgtctc tcagaattct tcaggtggaa aaacatctga aagccacgtt ccttactgca   3000
gaatagcata tatatcgctt aatcttaaat ttattagata tgagttgttt tcagactcag   3060
actccatttg tattatagtc taatatacag ggtagcaggt accactgatt tggagatatt   3120
tatgggggga gaacttacat tgtgaaactt ctgtacatta attattattg ctgttgttat   3180
tttacaaggg tctagggaga gacccttgtt tgattttagc tgcagaactg tattggtcca   3240
gcttgctctt cagtgggaga aaaacacttg taagttgcta aacgagtcaa tcccctcatt   3300
caggaaaact gacagaggag ggcgtgactc acccaagcca tatataacta gctagaagtg   3360
ggccaggaca ggccgggcgc ggtggctcac gcctgtaatc ccagcagttt gggaggtcga   3420
ggtaggtgga tcacctgagg tcgggagttc gagaccaacc tgaccaacat ggagaaaccc   3480
```

-continued

```
tgtctctatt aaaaatacaa aaaaaaaaaa aaaaaaaaat agccgggcat ggtggcgcaa   3540

gcctgtaatc ccagctactc aggaggctga ggcagaagaa ttgaacccag gaggtggagg   3600

ttgcagtgag ctgagatcgt gccgttactc tccaacctgg acaacaagag cgaaactccg   3660

tcttagaagt ggaccaggac aggaccagat tttggagtca tggtccggtg tccttttcac   3720

tacaccatgt ttgagctcag acccccactc tcattcccca ggtggctgac ccagtccctg   3780

ggggaagccc tggatttcag aaagagccaa gtctggatct gggacccttt ccttccttcc   3840

ctggcttgta actccaccaa gcccatcaga aggagaagga aggagactca cctctgcctc   3900

aatgtgaatc agaccctacc ccaccacgat gtgccctggc tgctgggctc tccacctcag   3960

gccttggata atgctgttgc ctcatctata acatgcattt gtctttgtaa tgtcaccacc   4020

ttcccagctc tccctctggc cctgcttctt cggggaactc ctgaaatatc agttactcag   4080

ccctgggccc caccacctag gccactcctc caaaggaagt ctaggagctg ggaggaaaag   4140

aaaagagggg aaaatgagtt tttatggggc tgaacgggga gaaaaggtca tcatcgattc   4200

tactttagaa tgagagtgtg aaatagacat ttgtaaatgt aaaactttta aggtatatca   4260

ttataactga aggagaaggt gccccaaaat gcaagatttt ccacaagatt cccagagaca   4320

ggaaaatcct ctggctggct aactggaagc atgtaggaga atccaagcga ggtcaacaga   4380

gaaggcagga atgtgtggca gatttagtga aagctagaga tatggcagcg aaaggatgta   4440

aacagtgcct gctgaatgat ttccaaagag aaaaaaagtt tgccagaagt ttgtcaagtc   4500

aaccaatgta gaaagctttg cttatggtaa taaaaatggc tcatacttat atagcactta   4560

ctttgtttgc aagtactgct gtaaataaat gctttatgca aacc                    4604


<210> SEQ ID NO 384
<211> LENGTH: 545
<212> TYPE: DNA
<213> ORGANISM: Homo sapiens

<400> SEQUENCE: 384

gagtgactct cacgagagcc gcgagagtca gcttggccaa tccgtgcggt cggcggccgc     60

tccctttata agccgactcg cccggcagcg caccgggttg cggagggtgg gcctgggagg    120

ggtggtggcc attttttgtc taaccctaac tgagaagggc gtaggcgccg tgcttttgct    180

ccccgcgcgc tgtttttctc gctgactttc agcgggcgga aaagcctcgg cctgccgcct    240

tccaccgttc attctagagc aaacaaaaaa tgtcagctgc tggcccgttc gcccctcccg    300

gggacctgcg gcgggtcgcc tgcccagccc ccgaaccccg cctggaggcc gcggtcggcc    360

cggggcttct ccggaggcac ccactgccac cgcgaagagt tgggctctgt cagccgcggg    420

tctctcgggg gcgagggcga ggttcaggcc tttcaggccg caggaagagg aacggagcga    480

gtccccgcgc gcggcgcgat tccctgagct gtgggacgtg cacccaggac tcggctcaca    540

catgc                                                                545
```